(12) United States Patent
Schwammenthal et al.

(10) Patent No.: US 11,883,274 B2
(45) Date of Patent: Jan. 30, 2024

(54) VENA-CAVAL BLOOD PUMP

(71) Applicant: Magenta Medical Ltd., Kadima (IL)

(72) Inventors: Ehud Schwammenthal, Ra'anana (IL); Yosi Tuval, Even Yehuda (IL); Daniel Glozman, Kfar Yona (IL)

(73) Assignee: Magenta Medical Ltd., Kadima (IL)

( * ) Notice: Subject to any disclaimer, the term of this patent is extended or adjusted under 35 U.S.C. 154(b) by 392 days.

(21) Appl. No.: 16/677,893

(22) Filed: Nov. 8, 2019

(65) Prior Publication Data
US 2020/0069857 A1 Mar. 5, 2020

Related U.S. Application Data

(63) Continuation of application No. 16/278,323, filed on Feb. 18, 2019, now Pat. No. 10,864,310, which is a (Continued)

(51) Int. Cl.
*A61M 1/12* (2006.01)
*A61F 2/07* (2013.01)
(Continued)

(52) U.S. Cl.
CPC ............ *A61F 2/07* (2013.01); *A61B 5/02055* (2013.01); *A61M 60/13* (2021.01); (Continued)

(58) Field of Classification Search
CPC .... A61M 1/125; A61M 1/1031; A61M 1/122; A61M 1/1024; A61M 1/1086;
(Continued)

(56) References Cited

U.S. PATENT DOCUMENTS

| | | |
|---|---|---|
| 4,822,345 A | 4/1989 | Danforth |
| 4,886,506 A | 12/1989 | Lovgren et al. |
| | (Continued) | |

FOREIGN PATENT DOCUMENTS

| | | |
|---|---|---|
| AU | 2013205145 A1 | 5/2013 |
| AU | 2013257469 B2 | 3/2016 |
| | (Continued) | |

OTHER PUBLICATIONS

Non-Final Office Action for U.S. Appl. No. 16/242,797 dated Nov. 16, 2021.
(Continued)

*Primary Examiner* — Rex R Holmes
(74) *Attorney, Agent, or Firm* — DORSEY & WHITNEY LLP

(57) ABSTRACT

Apparatus and methods are described for improving renal function of a patient, including mechanically occluding the patient's inferior vena cava downstream of the renal vein ostium to form an upstream region and a downstream region of the inferior vena cava, and mechanically pumping blood through the inferior vena cava from the upstream region to a discharge location in the downstream region while the inferior vena cava is occluded, wherein the blood remains in the inferior vena cava while being mechanically pumped. Other applications are also described.

9 Claims, 45 Drawing Sheets

Related U.S. Application Data continuation of application No. 16/022,445, filed on Jun. 28, 2018, now Pat. No. 10,363,350, which is a continuation of application No. 14/774,081, filed as application No. PCT/IL2014/050289 on Mar. 13, 2014, now Pat. No. 10,039,874.

(60) Provisional application No. 61/914,475, filed on Dec. 11, 2013, provisional application No. 61/779,803, filed on Mar. 13, 2013.

(51) Int. Cl.
| | | |
|---|---|---|
| *A61M 60/135* | (2021.01) | |
| *A61M 60/422* | (2021.01) | |
| *A61M 60/833* | (2021.01) | |
| *A61M 60/411* | (2021.01) | |
| *A61M 60/861* | (2021.01) | |
| *A61M 60/523* | (2021.01) | |
| *A61M 60/237* | (2021.01) | |
| *A61M 60/808* | (2021.01) | |
| *A61M 60/825* | (2021.01) | |
| *A61M 60/13* | (2021.01) | |
| *A61M 60/81* | (2021.01) | |
| *A61M 60/33* | (2021.01) | |
| *A61B 5/0205* | (2006.01) | |
| *A61M 60/148* | (2021.01) | |
| *A61M 60/414* | (2021.01) | |
| *A61M 60/896* | (2021.01) | |

(52) U.S. Cl.
CPC ........ *A61M 60/135* (2021.01); *A61M 60/237* (2021.01); *A61M 60/33* (2021.01); *A61M 60/411* (2021.01); *A61M 60/422* (2021.01); *A61M 60/523* (2021.01); *A61M 60/808* (2021.01); *A61M 60/81* (2021.01); *A61M 60/825* (2021.01); *A61M 60/833* (2021.01); *A61M 60/861* (2021.01); *A61M 60/148* (2021.01); *A61M 60/414* (2021.01); *A61M 60/896* (2021.01); *A61M 2207/00* (2013.01); *A61M 2210/1082* (2013.01); *A61M 2210/12* (2013.01)

(58) Field of Classification Search
CPC ...... A61M 2207/00; A61M 2210/1082; A61M 2210/12; A61B 5/02055; A61F 2/07
See application file for complete search history.

(56) References Cited

U.S. PATENT DOCUMENTS

| | | | |
|---|---|---|---|
| 4,919,647 | A | 4/1990 | Nash |
| 4,954,055 | A | 9/1990 | Raible et al. |
| 5,613,935 | A | 3/1997 | Jarvik |
| 5,713,730 | A | 2/1998 | Nose et al. |
| 5,749,855 | A | 5/1998 | Reitan |
| 5,772,693 | A | 6/1998 | Brownlee |
| 5,876,385 | A | 3/1999 | Ikari et al. |
| 5,964,694 | A | 10/1999 | Siess et al. |
| 6,086,527 | A | 7/2000 | Talpade |
| 6,135,729 | A | 10/2000 | Aber |
| 6,136,025 | A | 10/2000 | Barbut et al. |
| 6,176,848 | B1 | 1/2001 | Rau et al. |
| 6,183,220 | B1 | 2/2001 | Ohara et al. |
| 6,247,892 | B1 | 6/2001 | Kazatchkov et al. |
| 6,482,228 | B1 | 11/2002 | Norred |
| 6,533,716 | B1 | 3/2003 | Schmutz-Rode et al. |
| 6,592,567 | B1 | 7/2003 | Levin et al. |
| 6,616,624 | B1 | 9/2003 | Kieval |
| 6,884,210 | B2 | 4/2005 | Nose et al. |
| 7,004,925 | B2 | 2/2006 | Navia et al. |
| 7,011,620 | B1 | 3/2006 | Siess |
| 7,070,555 | B2 | 7/2006 | Siess |
| 7,144,364 | B2 | 12/2006 | Barbut et al. |
| 7,159,593 | B2 | 1/2007 | Mccarthy et al. |
| 7,201,772 | B2 | 4/2007 | Schwammenthal et al. |
| 7,335,192 | B2 | 2/2008 | Keren et al. |
| 7,341,570 | B2 | 3/2008 | Keren et al. |
| 7,485,104 | B2 | 2/2009 | Kieval |
| 7,717,952 | B2 | 5/2010 | Case et al. |
| 7,744,642 | B2 | 6/2010 | Rittgers et al. |
| 7,762,941 | B2 | 7/2010 | Jarvik |
| 7,766,853 | B2 | 8/2010 | Lane |
| 7,766,892 | B2 | 8/2010 | Keren et al. |
| 7,766,961 | B2 | 8/2010 | Patel et al. |
| 7,780,628 | B1 | 8/2010 | Keren et al. |
| 7,811,221 | B2 | 10/2010 | Gross |
| 7,841,976 | B2 | 11/2010 | McBride et al. |
| 7,914,503 | B2 | 3/2011 | Goodson et al. |
| 7,927,068 | B2 | 4/2011 | McBride et al. |
| 8,007,254 | B2 | 8/2011 | Larose et al. |
| 8,012,121 | B2 | 9/2011 | Goodson et al. |
| 8,079,948 | B2 | 12/2011 | Shifflette |
| 8,221,492 | B2 | 7/2012 | Case et al. |
| 8,235,933 | B2 | 8/2012 | Keren et al. |
| 8,277,470 | B2 | 10/2012 | Demarais et al. |
| 8,376,707 | B2 | 2/2013 | Mcbride et al. |
| 8,449,443 | B2 | 5/2013 | Rodefeld et al. |
| 8,512,262 | B2 | 8/2013 | Gertner |
| 8,538,535 | B2 | 9/2013 | Ariav et al. |
| 8,579,858 | B2 | 11/2013 | Reitan et al. |
| 8,617,239 | B2 | 12/2013 | Reitan |
| 8,684,904 | B2 | 4/2014 | Campbell et al. |
| 8,690,749 | B1 | 4/2014 | Nunez |
| 8,721,516 | B2 | 5/2014 | Scheckel |
| 8,721,517 | B2 | 5/2014 | Zeng et al. |
| 8,727,959 | B2 | 5/2014 | Reitan et al. |
| 8,734,331 | B2 | 5/2014 | Evans et al. |
| 8,734,508 | B2 | 5/2014 | Hastings et al. |
| 8,777,832 | B1 | 7/2014 | Wang et al. |
| 8,849,398 | B2 | 9/2014 | Evans |
| 8,992,163 | B2 | 3/2015 | McBride et al. |
| 9,028,216 | B2 | 5/2015 | Schumacher et al. |
| 9,067,006 | B2 | 6/2015 | Toellner |
| 9,089,634 | B2 | 7/2015 | Schumacher et al. |
| 9,138,518 | B2 | 9/2015 | Campbell et al. |
| 9,162,017 | B2 | 10/2015 | Evans et al. |
| 9,217,442 | B2 | 12/2015 | Wiessler et al. |
| 9,314,558 | B2 | 4/2016 | Er |
| 9,327,067 | B2 | 5/2016 | Zeng et al. |
| 9,339,596 | B2 | 5/2016 | Roehn |
| 9,358,329 | B2 | 6/2016 | Fitzgerald et al. |
| 9,393,384 | B1 | 7/2016 | Kapur et al. |
| 9,402,942 | B2 | 8/2016 | Hastie et al. |
| 9,416,783 | B2 | 8/2016 | Schumacher et al. |
| 9,572,915 | B2 | 2/2017 | Heuring et al. |
| 9,597,205 | B2 | 3/2017 | Tuval |
| 9,675,740 | B2 | 6/2017 | Zeng et al. |
| 9,750,860 | B2 | 9/2017 | Schumacher |
| 9,750,861 | B2 | 9/2017 | Hastie et al. |
| 9,764,113 | B2 | 9/2017 | Tuval et al. |
| 9,771,801 | B2 | 9/2017 | Schumacher et al. |
| 9,895,475 | B2 | 2/2018 | Toellner et al. |
| 9,903,384 | B2 | 2/2018 | Roehn |
| 9,907,891 | B2 | 3/2018 | Wiessler et al. |
| 9,913,937 | B2 | 3/2018 | Schwammenthal et al. |
| 9,964,115 | B2 | 5/2018 | Scheckel |
| 10,039,874 | B2 | 8/2018 | Schwammenthal et al. |
| 10,052,419 | B2 | 8/2018 | Er |
| 10,107,299 | B2 | 10/2018 | Scheckel |
| 10,172,985 | B2 | 1/2019 | Simon et al. |
| 10,179,197 | B2 | 1/2019 | Kaiser et al. |
| 10,196,899 | B2 | 2/2019 | Toellner et al. |
| 10,207,037 | B2 | 2/2019 | Corbett et al. |
| 10,208,763 | B2 | 2/2019 | Schumacher et al. |
| 10,215,187 | B2 | 2/2019 | McBride et al. |
| 10,231,838 | B2 | 3/2019 | Chin et al. |
| 10,245,363 | B1 * | 4/2019 | Rowe ................. A61M 60/148 |
| 10,299,701 | B2 | 5/2019 | Blanton et al. |
| 10,299,918 | B2 | 5/2019 | Tuval |

(56) References Cited

U.S. PATENT DOCUMENTS

| | | |
|---|---|---|
| 10,342,904 B2 | 7/2019 | Schumacher |
| 10,342,906 B2 | 7/2019 | D'Ambrosio et al. |
| 10,413,646 B2 | 9/2019 | Wiessler et al. |
| 10,478,538 B2 | 11/2019 | Scheckel et al. |
| 10,478,539 B2 | 11/2019 | Pfeffer et al. |
| 10,495,101 B2 | 12/2019 | Scheckel |
| 10,557,475 B2 | 2/2020 | Roehn |
| 10,583,231 B2 | 3/2020 | Schwammenthal et al. |
| 10,584,589 B2 | 3/2020 | Schumacher et al. |
| 10,589,012 B2 | 3/2020 | Toellner et al. |
| 10,617,808 B2 | 4/2020 | Hastie et al. |
| 10,662,967 B2 | 5/2020 | Scheckel |
| 10,669,855 B2 | 6/2020 | Toellner et al. |
| 10,765,789 B2 | 9/2020 | Zeng et al. |
| 10,792,406 B2 | 10/2020 | Roehn et al. |
| 10,799,624 B2 | 10/2020 | Pfeffer et al. |
| 10,799,626 B2 | 10/2020 | Siess et al. |
| 10,801,511 B2 | 10/2020 | Siess et al. |
| 10,806,838 B2 | 10/2020 | Er |
| 10,835,653 B2 | 11/2020 | Liebing |
| 10,857,272 B2 | 12/2020 | Liebing |
| 10,864,309 B2 | 12/2020 | McBride et al. |
| 10,865,801 B2 | 12/2020 | McBride et al. |
| 10,874,783 B2 | 12/2020 | Pfeffer et al. |
| 10,881,845 B2 | 1/2021 | Siess et al. |
| 10,894,115 B2 | 1/2021 | Pfeffer et al. |
| 10,898,629 B2 | 1/2021 | Siess et al. |
| 10,907,646 B2 | 2/2021 | Bredenbreuker et al. |
| 10,920,596 B2 | 2/2021 | Toellner et al. |
| 10,926,013 B2 | 2/2021 | Schumacher et al. |
| 10,935,038 B2 | 3/2021 | Siess |
| 10,980,927 B2 | 4/2021 | Pfeffer et al. |
| 11,007,350 B2 | 5/2021 | Tao et al. |
| 11,020,584 B2 | 6/2021 | Siess et al. |
| 11,027,114 B2 | 6/2021 | D'Ambrosio et al. |
| 11,033,727 B2 | 6/2021 | Tuval et al. |
| 11,033,729 B2 | 6/2021 | Scheckel et al. |
| 11,040,187 B2 | 6/2021 | Wiessler et al. |
| RE48,649 E | 7/2021 | Siess |
| 11,116,960 B2 | 9/2021 | Simon et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,168,705 B2 | 11/2021 | Liebing |
| 11,197,690 B2 | 12/2021 | Fantuzzi et al. |
| 11,219,755 B2 | 1/2022 | Siess et al. |
| 11,229,786 B2 | 1/2022 | Zeng et al. |
| 11,253,692 B2 | 2/2022 | Schumacher |
| 11,253,693 B2 | 2/2022 | Pfeffer et al. |
| 11,260,215 B2 | 3/2022 | Scheckel et al. |
| 11,266,824 B2 | 3/2022 | Er |
| 11,268,521 B2 | 3/2022 | Toellner |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,291,824 B2 | 4/2022 | Schwammenthal et al. |
| 11,298,525 B2 | 4/2022 | Jahangir |
| 11,305,105 B2 | 4/2022 | Corbett et al. |
| 11,313,228 B2 | 4/2022 | Schumacher et al. |
| 11,338,124 B2 | 5/2022 | Pfeffer et al. |
| 11,351,358 B2 | 6/2022 | Nix et al. |
| 11,364,373 B2 | 6/2022 | Corbett et al. |
| 11,421,701 B2 | 8/2022 | Schumacher et al. |
| 11,434,922 B2 | 9/2022 | Roehn |
| 11,484,701 B2 | 11/2022 | Schwammenthal et al. |
| 2002/0107536 A1 | 8/2002 | Hussein |
| 2003/0055486 A1 | 3/2003 | Adams et al. |
| 2003/0149473 A1 | 8/2003 | Chouinard et al. |
| 2003/0208097 A1 | 11/2003 | Aboul-Hosn et al. |
| 2004/0064090 A1 | 4/2004 | Keren et al. |
| 2004/0064091 A1 | 4/2004 | Keren et al. |
| 2004/0111006 A1 | 6/2004 | Alferness et al. |
| 2004/0116769 A1 | 6/2004 | Jassawalla et al. |
| 2004/0167415 A1 | 8/2004 | Gelfand et al. |
| 2004/0210236 A1 | 10/2004 | Allers et al. |
| 2004/0219028 A1 | 11/2004 | Demarais et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0055082 A1 | 3/2005 | Ben et al. |
| 2005/0079274 A1 | 4/2005 | Palasis et al. |
| 2005/0119682 A1 | 6/2005 | Nguyen et al. |
| 2005/0137680 A1 | 6/2005 | Ortiz et al. |
| 2006/0062672 A1 | 3/2006 | McBride et al. |
| 2006/0064059 A1 | 3/2006 | Gelfand et al. |
| 2006/0106449 A1 | 5/2006 | Ben |
| 2006/0135961 A1 | 6/2006 | Rosenman et al. |
| 2006/0245959 A1 | 11/2006 | Larose et al. |
| 2007/0100435 A1 | 5/2007 | Case et al. |
| 2007/0162103 A1 | 7/2007 | Case et al. |
| 2007/0208291 A1 | 9/2007 | Patel |
| 2007/0260327 A1 | 11/2007 | Case et al. |
| 2007/0293808 A1 | 12/2007 | Williams et al. |
| 2008/0103591 A1 | 5/2008 | Siess |
| 2008/0114339 A1 | 5/2008 | McBride et al. |
| 2008/0132748 A1 | 6/2008 | Shifflette |
| 2008/0154236 A1 | 6/2008 | Elkins et al. |
| 2008/0183280 A1 | 7/2008 | Agnew et al. |
| 2009/0024195 A1 | 1/2009 | Rezai et al. |
| 2009/0062597 A1 | 3/2009 | Shifflette |
| 2009/0093796 A1 | 4/2009 | Pfeffer et al. |
| 2009/0131785 A1 | 5/2009 | Lee et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0030259 A1 | 2/2010 | Pavcnik et al. |
| 2010/0130810 A1 | 5/2010 | Mohl |
| 2011/0004046 A1 | 1/2011 | Campbell et al. |
| 2011/0106244 A1 | 5/2011 | Ferrari et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |
| 2011/0230949 A1 | 9/2011 | Haverkost et al. |
| 2011/0257462 A1* | 10/2011 | Rodefeld ............ A61M 60/205 600/16 |
| 2011/0264075 A1 | 10/2011 | Leung et al. |
| 2011/0282128 A1 | 11/2011 | Reitan et al. |
| 2011/0282274 A1 | 11/2011 | Fulton |
| 2011/0301662 A1 | 12/2011 | Bar-yoseph et al. |
| 2011/0319906 A1 | 12/2011 | Rudakov et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0116382 A1 | 5/2012 | Ku et al. |
| 2012/0130469 A1 | 5/2012 | Cragg et al. |
| 2012/0172654 A1 | 7/2012 | Bates |
| 2012/0224970 A1 | 9/2012 | Schumacher et al. |
| 2012/0232457 A1* | 9/2012 | Kandarpa ............ A61M 1/3659 604/6.09 |
| 2012/0237357 A1 | 9/2012 | Schumacher et al. |
| 2012/0301318 A1 | 11/2012 | Er |
| 2012/0328460 A1 | 12/2012 | Horvath et al. |
| 2013/0053623 A1 | 2/2013 | Evans et al. |
| 2013/0053732 A1 | 2/2013 | Heuser |
| 2013/0079874 A1 | 3/2013 | Doss et al. |
| 2013/0177409 A1 | 7/2013 | Schumacher et al. |
| 2013/0177432 A1 | 7/2013 | Toellner et al. |
| 2013/0237744 A1 | 9/2013 | Pfeffer et al. |
| 2014/0018840 A1 | 1/2014 | Morgan et al. |
| 2014/0025041 A1 | 1/2014 | Fukuoka et al. |
| 2014/0051908 A1 | 2/2014 | Khanal et al. |
| 2014/0128659 A1* | 5/2014 | Heuring ............... A61M 60/50 600/16 |
| 2014/0275722 A1 | 9/2014 | Zimmermann et al. |
| 2014/0350658 A1 | 11/2014 | Benary et al. |
| 2015/0018597 A1 | 1/2015 | Fierens et al. |
| 2015/0119633 A1 | 4/2015 | Haselby et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |

(56) References Cited

U.S. PATENT DOCUMENTS

| | | |
|---|---|---|
| 2016/0053768 A1 | 2/2016 | Schumacher et al. |
| 2016/0136343 A1 | 5/2016 | Anagnostopoulos |
| 2016/0184500 A1 | 6/2016 | Zeng |
| 2016/0279310 A1 | 9/2016 | Scheckel et al. |
| 2017/0049946 A1 | 2/2017 | Kapur et al. |
| 2017/0071769 A1 | 3/2017 | Mangiardi |
| 2017/0100527 A1 | 4/2017 | Schwammenthal et al. |
| 2017/0197021 A1 | 7/2017 | Nitzan et al. |
| 2018/0126130 A1 | 5/2018 | Nitzan et al. |
| 2018/0149165 A1 | 5/2018 | Siess et al. |
| 2018/0169313 A1 | 6/2018 | Schwammenthal et al. |
| 2018/0303993 A1 | 10/2018 | Schwammenthal et al. |
| 2019/0046702 A1 | 2/2019 | Siess et al. |
| 2019/0175340 A1 | 6/2019 | Tuval |
| 2019/0175806 A1 | 6/2019 | Tuval et al. |
| 2019/0209758 A1 | 7/2019 | Tuval et al. |
| 2019/0239998 A1 | 8/2019 | Tuval et al. |
| 2019/0269840 A1 | 9/2019 | Tuval et al. |
| 2020/0254162 A1 | 8/2020 | Schwammenthal et al. |
| 2020/0288988 A1 | 9/2020 | Goldvasser |
| 2021/0236797 A1 | 8/2021 | D'Ambrosio et al. |
| 2021/0268261 A1 | 9/2021 | Tuval et al. |

FOREIGN PATENT DOCUMENTS

| | | |
|---|---|---|
| CA | 2701809 A1 | 4/2009 |
| CN | 1219136 A | 6/1999 |
| DE | 1033690 B | 7/1958 |
| DE | 10336902 B3 | 8/2004 |
| EP | 1339443 A1 | 9/2003 |
| EP | 1651290 A1 | 5/2006 |
| EP | 1827531 A1 | 9/2007 |
| EP | 1871441 A2 | 1/2008 |
| EP | 2047872 A1 | 4/2009 |
| EP | 2047873 A1 | 4/2009 |
| EP | 2217300 A1 | 8/2010 |
| EP | 2218469 A1 | 8/2010 |
| EP | 2234658 A2 | 10/2010 |
| EP | 2282070 A1 | 2/2011 |
| EP | 2298374 A1 | 3/2011 |
| EP | 2299119 A1 | 3/2011 |
| EP | 2301598 A1 | 3/2011 |
| EP | 2308524 A1 | 4/2011 |
| EP | 2314331 A1 | 4/2011 |
| EP | 2345440 A1 | 7/2011 |
| EP | 2366412 A2 | 9/2011 |
| EP | 2376788 A1 | 10/2011 |
| EP | 2408489 A1 | 1/2012 |
| EP | 2424587 A1 | 3/2012 |
| EP | 2475415 A1 | 7/2012 |
| EP | 2607712 A1 | 6/2013 |
| EP | 2040639 B1 | 2/2014 |
| EP | 2662099 B1 | 9/2014 |
| EP | 2427230 B1 | 12/2014 |
| EP | 2396050 B1 | 1/2015 |
| EP | 2835141 A1 | 2/2015 |
| EP | 2840954 A1 | 3/2015 |
| EP | 2841122 A1 | 3/2015 |
| EP | 2841124 A1 | 3/2015 |
| EP | 2860849 A1 | 4/2015 |
| EP | 2868331 A2 | 5/2015 |
| EP | 2868332 A1 | 5/2015 |
| EP | 2999496 A2 | 3/2016 |
| EP | 3000492 A1 | 3/2016 |
| EP | 3000493 A1 | 3/2016 |
| EP | 3055922 A1 | 8/2016 |
| EP | 3062730 A1 | 9/2016 |
| EP | 3108909 A1 | 12/2016 |
| EP | 3127562 A1 | 2/2017 |
| EP | 3216467 A1 | 9/2017 |
| EP | 3222302 A1 | 9/2017 |
| EP | 3287154 A1 | 2/2018 |
| EP | 3287155 A1 | 2/2018 |
| EP | 3326567 A1 | 5/2018 |
| EP | 3329951 A1 | 6/2018 |
| EP | 3338825 A1 | 6/2018 |
| EP | 3205360 B1 | 8/2018 |
| EP | 3359214 A1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| EP | 3606575 A1 | 2/2020 |
| EP | 3737436 A1 | 11/2020 |
| EP | 3897814 A1 | 10/2021 |
| JP | 2012505038 A | 3/2012 |
| WO | 90/13321 | 11/1990 |
| WO | 1994/01148 A1 | 1/1994 |
| WO | 9744071 A1 | 11/1997 |
| WO | 99/34847 | 7/1999 |
| WO | 2001/083016 A2 | 5/2000 |
| WO | 0107787 A1 | 2/2001 |
| WO | 2002/070039 A2 | 3/2001 |
| WO | 0183016 A2 | 11/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007112033 A2 | 10/2007 |
| WO | 2007127477 A2 | 11/2007 |
| WO | 2008005747 A2 | 1/2008 |
| WO | 2008055301 A1 | 5/2008 |
| WO | 2009010963 A2 | 1/2009 |
| WO | 2009091965 A1 | 7/2009 |
| WO | 2009129481 A1 | 10/2009 |
| WO | 2010133567 A1 | 11/2010 |
| WO | 2010150208 A2 | 12/2010 |
| WO | 2011035926 A1 | 3/2011 |
| WO | 2011047884 A1 | 4/2011 |
| WO | 2011076441 A1 | 6/2011 |
| WO | 2012007141 A1 | 1/2012 |
| WO | 2013032849 A1 | 3/2013 |
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015177793 A2 | 11/2015 |
| WO | 2016185473 A1 | 11/2016 |
| WO | 2017053361 A1 | 3/2017 |
| WO | 2017081561 A1 | 5/2017 |
| WO | 2018033920 A1 | 2/2018 |
| WO | 2018061001 A2 | 4/2018 |
| WO | 2018061002 A1 | 4/2018 |
| WO | 2018078615 A1 | 5/2018 |
| WO | 2018096531 A1 | 5/2018 |
| WO | 2018158636 A1 | 9/2018 |
| WO | 2018172848 A2 | 9/2018 |
| WO | 2018220589 A1 | 12/2018 |
| WO | 2019125899 A1 | 6/2019 |
| WO | 2019138350 A2 | 7/2019 |
| WO | 2019158996 A1 | 8/2019 |
| WO | 2021159147 A1 | 8/2021 |

OTHER PUBLICATIONS

Notice of Allowance for U.S. Appl. No. 15/574,948 dated Nov. 18, 2021.

Corrected Notice of Allowance for U.S. Appl. No. 15/423,368 dated Apr. 17, 2019.

European Search Report for European Application No. 13800935 dated Jan. 12, 2016.

European Search Report for European Application No. 14762232.8 dated Sep. 28, 2016.

Final Office Action for U.S. Appl. No. 14/931,363 dated Jun. 1, 2017.

Final Office Action for U.S. Appl. No. 15/312,034 dated Jan. 17, 2019.

International Search Report and Written Opinion for International Application No. PCT/IL2015/050532 dated Jan. 27, 2016.

(56) References Cited

OTHER PUBLICATIONS

International Search Report and Written Opinion for International Application No. PCT/IL2016/050525 dated Oct. 14, 2016.
International Search Report and Written Opinion for International Application No. PCT/IL2013/050495 dated Nov. 22, 2013.
International Search Report and Written Opinion for International Application No. PCT/IL2014/050289 dated Sep. 11, 2014.
International Search Report and Written Opinion from International Application No. PCT/IL2017/051092 dated Jan. 16, 2018.
International Search Report and Written Opinion from International Application No. PCT/IL2017/051273 dated Apr. 17, 2018.
Invitation to pay additional fees for International Application No. PCT/IL2015/050532 dated Nov. 17, 2015.
Issue Notification for U.S. Appl. No. 14/931,363 dated Feb. 21, 2018.
Issue Notification for U.S. Appl. No. 15/423,368 dated May 8, 2019.
Issue Notification for U.S. Appl. No. 16/022,445 dated Jul. 10, 2019.
Non-Final Office Action for U.S. Appl. No. 14/405,144 dated Feb. 22, 2016.
Non-Final Office Action for U.S. Appl. No. 14/405,144 dated Jul. 14, 2016.
Non-Final Office Action for U.S. Appl. No. 14/567,439 dated Nov. 16, 2016.
Non-Final Office Action for U.S. Appl. No. 14/774,081 dated May 24, 2017.
Non-Final Office Action for U.S. Appl. No. 14/774,081 dated Oct. 12, 2017.
Non-Final Office Action for U.S. Appl. No. 14/931,363 dated Feb. 15, 2017.
Non-Final Office Action for U.S. Appl. No. 14/931,363 dated Oct. 3, 2016.
Non-Final Office Action for U.S. Appl. No. 15/423,368 dated Jun. 6, 2018.
Non-Final Office Action for U.S. Appl. No. 16/022,445 dated Aug. 9, 2018.
Notice of Allowance for U.S. Appl. No. 14/567,439 dated Jun. 2, 2017.
Notice of Allowance for U.S. Appl. No. 14/774,081 dated Apr. 11, 2018.
Notice of Allowance for U.S. Appl. No. 14/931,363 dated Dec. 12, 2017.
Notice of Allowance for U.S. Appl. No. 14/931,363 dated Oct. 12, 2017.
Notice of Allowance for U.S. Appl. No. 15/312,034 dated Jun. 27, 2019.
Notice of Allowance for U.S. Appl. No. 15/423,368 dated Apr. 4, 2019.
Notice of Allowance for U.S. Appl. No. 15/423,368 dated Nov. 13, 2018.
Notice of Allowance for U.S. Appl. No. 16/022,445 dated Mar. 18, 2019.
Office Action for Chinese Application No. 201380037335.4 dated Oct. 17, 2016.
Office Action for Chinese Patent Application No. 201380037335.4 dated Mar. 22, 2017.
Office Action for Chinese Patent Application No. 201380037335.4 dated Sep. 20, 2017.
Office Action for European Application No. 13800935 dated Sep. 30, 2016.
Office Action for Japanese Patent Application No. 2015-562562 dated Jun. 13, 2018.
Office Action for Japanese Patent Application No. 2015562562 dated Oct. 27, 2017.
Restriction Requirement for U.S. Appl. No. 14/567,439 dated Aug. 23, 2016.
Restriction Requirement for U.S. Appl. No. 14/774,081 dated Mar. 9, 2017.
Restriction Requirement for U.S. Appl. No. 14/931,363 dated Jul. 22, 2016.
Restriction Requirement for U.S. Appl. No. 15/888,771 dated Apr. 15, 2019.
U.S. Appl. No. 14/405,144, filed Dec. 2, 2014.
U.S. Appl. No. 14/567,439, filed Dec. 11, 2014.
U.S. Appl. No. 14/774,081, filed Sep. 9, 2015.
U.S. Appl. No. 15/423,368, filed Feb. 2, 2017.
U.S. Appl. No. 16/022,445, filed Jun. 28, 2018.
U.S. Appl. No. 16/273,898, filed Feb. 12, 2019.
U.S. Appl. No. 16/278,323, filed Feb. 18, 2019.
U.S. Appl. No. 16/281,385, filed Feb. 21, 2019.
U.S. Appl. No. 16/345,389, filed Apr. 26, 2019.
U.S. Appl. No. 61/656,244, filed Jun. 6, 2013.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/425,814, filed Nov. 23, 2016.
U.S. Appl. No. 62/401,403, filed Sep. 29, 2016.
Agarwal, et al., "Newer-generation ventricular assist devices.", Best Practice & Research Clinical Anaesthesiology, 26.2, 2012, pp. 117-130.
Alba, et al., "The future is here: ventricular assist devices for the failing heart", Expert review of cardiovascular therapy, 7.9, 2009, pp. 1067-1077.
Burnett, et al., "Renal Interstitial Pressure and Sodium Excretion During Renal Vein Constriction", American Physiological Society, 1980, pp. F279-F282.
Coxworth, "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion and the Association With Renal Impairment in Patients With Cardiac Dysfunction", European Journal of Heart Failure, vol. 9, 2007, pp. 872-878.
Damman, et al., "Increased Central Venous Pressure Is Associated With Impaired Renal Function and Mortality in a Broad Spectrum of Patients With Cardiovascular Disease", Journal of American College of Cardiology, vol. 53, 2009, pp. 582-588.
Doty, et al., "The Effect of Increased Renal Venous Pressure on Renal Function", The Journal of Trauma,, vol. 47(6), Dec. 1999, pp. 1000-1003.
Felker, et al., "Anemia as a Risk Factor and Therapeutic Target in Heart Failure", Journal of the American College of Cardiology, vol. 44, 2004, pp. 959-966.
Firth, et al., "Raised Venous Pressure: A Direct Cause of Sodium Retention in Oedema?", The Lancet, May 7, 1988, pp. 1033-1036.
Forman, et al., "Incidence, Predictors at Admission, and Impact of Worsening Renal Function Among Patients Hospitalized With Heart Failure", Journal of American College of Cardiology, vol. 43, 2004, pp. 61-67.
Fraser, et al., "The use of computational fluid dynamics in the development of ventricular assist devices", Medical engineering & physics, 33.3, 2011, pp. 263-280.
Gomes, et al., "Heterologous valve implantation in the infra-renal vena cava for treatment of the iliac venous valve regurgitation disease", experimental study; Rev Bras Cir Cardiovasc, 17(4), 2002, pp. 367-369.
Haddy, et al., "Effect of Elevation of Intraluminal Pressure on Renal Vascular Resistance", Circulation Research Journal of the American Heart Association, vol. 4, 1956, pp. 659-663.
Heywood, et al., "High Prevalence of Renal Dysfunction and Its Impact on Outcome in 118,465 Patients Hospitalized With Acute Decompensated Heart Failure: A Report From the Adhere Database", Journal of Cardiac Failure, vol. 13, 2007, pp. 422-430.
Hillege, et al., "Renal Function as a Predictor of Outcome in a Broad Spectrum of Patients With Heart Failure", Circulation Journal of the American Heart Association, vol. 113, 2006, pp. 671-678.
Hillege, et al., "Renal Function, Neurohormonal Activation, and Survival in Patients With Chronic Heart Failure", Circulation Journal of the American Heart Association, vol. 102, 2000, pp. 203-210.

(56) References Cited

OTHER PUBLICATIONS

Hsu, et al., "Review of recent patents on foldable ventricular assist devices", Recent Patents on Biomedical Engineering, 5.3, 2012, pp. 208-222.
Ikari, , "The Physics of Guiding Catheter; The Ikari Guiding Catheter in TRI", available at httu:i /www.docstoc.com/docs/148136553/The-[KARI-catheter---anovel-guide-for-TRI--, uploaded on Mar. 8, 2013.
Kafagy, et al., "Design of axial blood pumps for patients with dysfunctional fontan physiology: computational studies and performance testing", Artificial organs, 39.1, 2015, pp. 34-42.
Kang, et al., "Fluid dynamics aspects of miniaturized axial-flow blood pump", Bio-medical materials and engineering, 24.1, 2014, pp. 723-729.
Koochaki, et al., "A new design and computational fluid dynamics study of an implantable axial blood pump", Australasian Physical & Engineering Sciences in Medicine, 36.4, 2013, pp. 417-422.
Lauten, et al., "Heterotopic Transcatheter Tricuspid Valve Implantation: First-In-Man Application of a Novel Approach to Tricuspid Regurgitation", European Heart Journal, (1-7 as printed), Feb. 15, 2011, pp. 1207-1213.
McAlister, et al., "Renal Insufficiency and Heart Failure: Prognostic and Therapeutic Implications From a Prospective Cohort Study", Circulation Journal of the American Heart Association, 109, 2004, pp. 1004-1009.
Mullens, et al., "Elevated Intra-Abdominal Pressure in Acute Decompensated Heart Failure. A Potential Contributor to Worsening Renal Function", Journal of the American College of Cardiology, vol. 51, 2008, pp. 300-306.
Mullens, et al., "Importance of Venous Congestion for Worsening of Renal Function in Advanced Decompensated Heart Failure", Journal of American College of Cardiology, vol. 53, 2009, pp. 589-596.
Mullens, et al., "Prompt Reduction in Intra-Abdominal Pressure Following Large-Volume Mechanical Fluid Removal Improves Renal Insufficiency in Refractory Decompensated Heart Failure", Journal of Cardiac Failure, vol. 14, 2008, pp. 508-514.
Notarius, et al., "Central Venous Pressure During Exercise: Role of Muscle Pump", Canadian Journal of Physiology and Pharmacology, vol. 74(6), 1996, pp. 647-651.
Park, et al., "Nutcracker Syndrome: Intravascular Stenting Approach", Nephrol Dial Transplant, vol. 15, 2000, pp. 99-101.
Reul, et al., "Blood pumps for circulatory support", Perfusion-Sevenoaks, 15.4, 2000, pp. 295-312.
Schmitz-Rode, et al., "An Expandable Percutaneous Catheter Pump for Left Ventricular Support", Journal of the American College of Cardiology, vol. 45, 2005, pp. 1856-1861.
Semple, et al., "Effect of Increased Renal Venous Pressure on Circulatory "Autoregulation" of Isolated Dog Kidneys", Circulation Research Journal of the American Heart Association, vol. 7, 1959, pp. 643-648.
Song, et al., "Axial flow blood pumps", ASAIO journal, 49, 2003, pp. 355-364.
Tang, et al., "Anemia in Chronic Heart Failure: Prevalence, Etiology, Clinical Correlates, and Treatment Options", Circulation Journal of the American Heart Association, vol. 113, 2006, pp. 2454-2461.
Throckmorton, et al., "Design of a protective cage for an intra vascular axial flow blood pump to mechanically assist the failing Fontan", Artificial organs, 33.8, 2009, pp. 611-621.
Thunberg, et al., "Ventricular assist devices today and tomorrow", Journal of cardiothoracic and vascular anesthesia, 24.4, 2010, pp. 656-680.
Timms, , "A review of clinical ventricular assist devices", Medical engineering & physics, 33.9, 2011, pp. 1041-1047.
Uthoff, et al., "Central venous pressure at emergency room presentation predicts cardiac rehospitalization in patients with decompensated heart failure", European Journal of Heart Failure, 12, 2010, pp. 469-476.
Wencker, , "Acute Cardio-Renal Syndrome: Progression From Congestive Heart Failure to Congestive Kidney Failure", Current Heart Failure Reports, vol. 4, 2007, pp. 134-138.
Winton, , "The Control of Glomerular Pressure by Vascular Changes Within the Mammalian Kidney, Demonstrated by the Actions of Adrenaline", Journal of Physiology, vol. 73, Nov. 1931, pp. 151-162.
Winton, , "The Influence of Venous Pressure on the Isolated Mammalian Kidney", Journal of Physiology, vol. 72(1), Jun. 6, 1931, pp. 49-61.
Wood, , "The Mechanism of the Increased Venous Pressure With Exercise in Congestive Heart Failure", Journal of Clinical Investigation, vol. 41(11), 1962, pp. 2020-2024.
Wu, et al., "Design and simulation of axial flow maglev blood pump", International Journal of Information Engineering and Electronic Business, 3.2, 2011, p. 42.
Yancy, et al., "Clinical Presentation, Management, and In-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology, vol. 47(1), 2006, pp. 76-84.
Extended European Search Report for EP Patent Application No. 19212211.7 dated Mar. 31, 2020.
Extended European Search Report for EP Patent Application No. 19215724.6 dated Apr. 1, 2020.
Extended European Search Report for EP Patent Application No. 19216488.7 dated Apr. 1, 2020.
Extended European Search Report for EP Patent Application No. 19216593.4 dated Apr. 6, 2020.
Final Office Action for U.S. Appl. No. 15/574,948 dated Aug. 26, 2020.
Final Office Action for U.S. Appl. No. 15/888,771 dated Apr. 28, 2020.
Non-Final Office Action for U.S. Appl. No. 16/273,898 dated Jun. 18, 2020.
Non-Final Office Action for U.S. Appl. No. 16/278,323 dated May 22, 2020.
U.S. Appl. No. 15/574,948, filed Nov. 17, 2017.
U.S. Appl. No. 16/859,100, filed Apr. 27, 2020.
U.S. Appl. No. 16/859,492, filed Apr. 27, 2020.
Corrected Notice of Allowance for U.S. Appl. No. 15/312,034 dated Feb. 12, 2020.
Issue Notification for U.S. Appl. No. 15/312,034 dated Feb. 19, 2020.
Non-Final Office Action for U.S. Appl. No. 15/574,948 dated Jan. 13, 2020.
Non-Final Office Action for U.S. Appl. No. 16/035,871 dated Jan. 22, 2020.
Notice of Allowance for U.S. Appl. No. 15/312,034 dated Jan. 15, 2020.
Office Action for Chinese Application No. 201810418034.0 and dated Nov. 1, 2019.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/281,264, filed Feb. 21, 2019.
U.S. Appl. No. 16/682,016, filed Nov. 13, 2019.
Extended European Search Report for European Application No. 20179137.3 dated Oct. 9, 2020.
Final Office Action for U.S. Appl. No. 16/273,898 dated Nov. 5, 2020.
International Search Report and Written Opinion from International Application No. PCT/IB2020/054759 dated Nov. 13, 2020.
Invitation to Pay Additional Fees for International Application No. PCT/IB2020/054759 dated Jul. 30, 2020.
Issue Notification for U.S. Appl. No. 16/035,871 dated Dec. 29, 2020.
Issue Notification for U.S. Appl. No. 16/278,323 dated Nov. 24, 2020.
Non-Final Office Action for U.S. Appl. No. 16/273,898 dated Feb. 17, 2021.

(56) References Cited

OTHER PUBLICATIONS

Non-Final Office Action for U.S. Appl. No. 16/281,385 dated Oct. 14, 2020.
Non-Final Office Action for U.S. Appl. No. 16/335,786 dated Sep. 17, 2020.
Non-Final Office Action for U.S. Appl. No. 16/345,389 dated Oct. 26, 2020.
Notice of Allowance for U.S. Appl. No. 16/035,871 dated Aug. 28, 2020.
Notice of Allowance for U.S. Appl. No. 16/035,871 dated Dec. 4, 2020.
Notice of Allowance for U.S. Appl. No. 16/278,323 dated Oct. 29, 2020.
Notice of Allowance for U.S. Appl. No. 16/281,385 dated Mar. 8, 2021.
Notice of Allowance for U.S. Appl. No. 16/335,786 dated Feb. 22, 2021.
Notice of Allowance for U.S. Appl. No. 16/345,389 dated Feb. 16, 2021.
Office Action for Australian Application No. 2020201055 dated Sep. 15, 2020.
Office Action for Chinese Application No. 201810418034.0 dated Aug. 4, 2020.
Office Action for Chinese Application No. 201810418034.0 dated Dec. 24, 2020.
Office Action for Chinese Application No. 201811196500.1 dated Aug. 28, 2020.
Office Action for Chinese Application No. 201910109564.1 dated Feb. 1, 2021.
Office Action for Japanese Application No. 2020-009045 dated Feb. 1, 2021.
Communication for European Application No. 15753493.4 dated Jul. 17, 2019.
Communication Pursuant to Article 94(3) EPC for European Patent Application No. 19216488.7 dated Oct. 19, 2021.
Examination Report for Canadian Application No. 2,948,121 dated Jul. 8, 2021.
International Search Report and Written Opinion from International Application No. PCT/IL2019/050334 dated Jun. 17, 2019.
Issue Notification for U.S. Appl. No. 16/273,898 dated Oct. 13, 2021.
Issue Notification for U.S. Appl. No. 16/281,385 dated Jun. 16, 2021.
Issue Notification for U.S. Appl. No. 16/335,786 dated Jun. 2, 2021.
Issue Notification for U.S. Appl. No. 16/345,389 dated May 26, 2021.
Non-Final Office Action for U.S. Appl. No. 15/888,771 dated Jun. 1, 2021.
Non-Final Office Action for U.S. Appl. No. 15/888,771 dated Oct. 4, 2019.
Non-Final Office Action for U.S. Appl. No. 16/22,445 dated Aug. 9, 2018.
Non-Final Office Action for U.S. Appl. No. 16/682,016 dated Sep. 20, 2021.
Notice of Allowance for U.S. Appl. No. 16/273,898 dated Jun. 30, 2021.
Office Action for Australian Application No. 2015262870 dated Apr. 29, 2019.
Office Action for Australian Application No. 2019202647 dated Jun. 26, 2019.
Office Action for Chinese Application No. 201780072633.5 dated May 26, 2021.
Office Action for Japanese Application No. 2015/562562 dated Jan. 29, 2019.
Office Action for Japanese Application No. 2016/568548 dated Mar. 18, 2019.
Office Action for Japanese Application No. 2020-93277 dated Jun. 23, 2021.
Restriction Requirement for U.S. Appl. No. 16/035,871, dated Sep. 27, 2019.
U.S. Appl. No. 16/750,354, filed Jan. 23, 2020.
U.S. Appl. No. 17/487,145, filed Sep. 28, 2021.
U.S. Appl. No. 61/656,244, filed Jun. 6, 2012.
U.S. Appl. No. 62/412,631, filed Oct. 25, 2016.
U.S. Appl. No. 62/543,540, filed Aug. 10, 2017.
U.S. Appl. No. 62/615,538, filed Jan. 10, 2018.
U.S. Appl. No. 62/665,715, filed May 2, 2018.
U.S. Appl. No. 62/681,868, filed Jun. 7, 2018.
U.S. Appl. No. 62/727,605, filed Sep. 6, 2021.
Final Office Action for U.S. Appl. No. 15/888,771 dated Dec. 9, 2021.
First Examination Report for Indian Application No. 201917018650 dated Dec. 9, 2021.
First Office Action for Japanese Application No. 2019-520097 dated Oct. 26, 2021.
Issue Notification for U.S. Appl. No. 15/574,948 dated Mar. 16, 2022.
Issue Notification for U.S. Appl. No. 16/682,016 dated Mar. 23, 2022.
Issue Notification for U.S. Appl. No. 16/682,269 dated Mar. 23, 2022.
Non-Final Office Action for U.S. Appl. No. 16/682,269 dated Sep. 20, 2021.
Non-Final Office Action for U.S. Appl. No. 16/859,100 dated Apr. 29, 2022.
Notice of Allowance for U.S. Appl. No. 15/574,948 dated Jan. 27, 2022.
Notice of Allowance for U.S. Appl. No. 16/682,016 dated Feb. 23, 2022.
Notice of Allowance for U.S. Appl. No. 16/682,269 dated Feb. 23, 2022.
Issue Notification for U.S. Appl. No. 15/888,771 dated Oct. 12, 2022.
Non-Final Office Action for U.S. Appl. No. 16/859,492 dated Oct. 14, 2022.
Restriction Requirement for U.S. Appl. No. 16/859,492 dated Jul. 28, 2022.
Communication Pursuant to Article 94(3) for European Patent Application No. 20179137.3 dated Nov. 9, 2021.
Examination Report for Canadian Application No. 2,948,121 dated Dec. 15, 2021.
Examination Report for Indian Application No. 201917018650 dated Dec. 9, 2021.
Final Office Action for U.S. Appl. No. 16/859,100 dated Jul. 13, 2022.
Non-Final Office Action for U.S. Appl. No. 15/888,771 dated May 25, 2022.
Notice of Allowance for U.S. Appl. No. 15/888,771 dated Jun. 28, 2022.
Office Action for Japanese Application No. 2019-520097 dated Oct. 26, 2021.
Examination Report for European Application No. 20179137.3 dated Jan. 5, 2023.
Non-Final Office Action for U.S. Appl. No. 17/320,742 dated Dec. 7, 2022.
Non-Final Office Action for U.S. Appl. No. 17/487,145 dated Mar. 1, 2023.
Notice of Allowance for U.S. Appl. No. 16/859,100 dated Mar. 7, 2023.
Notice of Allowance for U.S. Appl. No. 16/859,492 dated Mar. 15, 2023.
Notice of Allowance for U.S. Appl. No. 17/320,742 dated Mar. 22, 2023.
Office Action for Japanese Application No. 2022-31553 dated Dec. 23, 2022.
U.S. Appl. No. 15/312,034, filed Nov. 17, 2016.
U.S. Appl. No. 15/888,771, filed Feb. 5, 2018.
U.S. Appl. No. 18/130,205, filed Apr. 4, 2023.
U.S. Appl. No. 18/130,534, filed Apr. 4, 2023.
U.S. Appl. No. 18/130,698, filed Apr. 4, 2023.
"Compendium of Technical and Scientific Information for the Hemopump Temporary Cardiac Assist System", Johnson & Johnson Interventional Systems, 1988, pp. 1-15.

(56) References Cited

OTHER PUBLICATIONS

Achour, et al., "Mechanical Left Ventricular Unloading Prior to Reperfusion Reduces Infarct Size in a Canine Infarction Model", Catheterization and Cardiovascular Interventions 64, 2005, pp. 182-192.
Butler, et al., "The Hemopump—a New Cardiac Prothesis Device", Reprinted from IEEE Transactions on Biomedical Engineering, vol. 37, No. 2, Feb. 1990, pp. 192-195.
Chan, et al., "Rapid manufacturing techniques in the development of an axial blood pump impeller", Proc. Instn Mech. Engrs vol. 217 Part H: J. Engineering in Medicine, 2003, pp. 469-475.
Dekker, et al., "Efficacy of a New Intraaortic Propeller Pump vs the Intraaortic Balloon Pump", Chest, vol. 123, Issue 6, Jun. 2003, pp. 2089-2095.
Flameng, "Temporary Cardiac Assist with an Axial Pump System", Steinkopff Verlag Darmstadt, 1991, 79 pages.
Frazier, et al., "First Human Use of the Hemopump, a Catheter-Mounted Ventricular Assist Device", Annual of Thoracic Surgeons, vol. 49, 1990, pp. 299-304.
Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.
Gunther, et al., "Experimentelle Radiologie", Life Sciences, Berichte Aus Der Rheinischwestfälischen Technischen Hochschule Aachen Ausgabe Feb. 2002, 9 pages.
Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.
Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.
Roundtree, et al., "The Hemopump Cardiac Assist System: Nursing Care of the Patient", Reprinted from Critical Care Nurse, Apr. 1991.
Scholz, et al., "Mechanical left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.
Siess, "System Analysis and Development of Intravascular Rotation Pumps for Cardiac Assist", Helmholtz-Institute—Chapter 3, Jun. 1998, 17 pages.
Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.
Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.
Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.
Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.
Wampler, "Newspaper Articles", Captain Hemo, 1988, 6 pages.
Wampler, "Newsweek", Captain Hemo, May 16, 1988, 3 pages.
Wampler, "THI Today", Captain Hemo, Summer 1988, 2 pages.
Wampler, "Time Magazine", Captain Hemo, May 1988, 2 pages.
Wampler, et al., "Treatment of Cardiogenic Shock With the Hemopump Left Ventricular Assist Device", Annual of Thoracic Surgery, vol. 52, pp. 560-513, 1991.
Wampler, "U.S. News & World Report", Captain Hemo, pp. 1-2, May 16, 1988.
Examination Report for Australian Application No. 2021225141 dated Oct. 10, 2022.
Extended European Search Report for European Patent Application No. 23174906.0 dated Aug. 21, 2023.
Issue Notification for U.S. Appl. No. 16/859,100 dated Apr. 26, 2023.
Issue Notification for U.S. Appl. No. 16/859,492 dated Apr. 26, 2023.
Issue Notification for U.S. Appl. No. 17/320,742 dated Apr. 26, 2023.
Notice of Acceptance for Australian Application No. 2017364359 dated Nov. 17, 2022.
Office Action for Canadian Application No. 3,039,302 dated Mar. 21, 2023.
Office Action for Canadian Application No. 3,080,800 dated Mar. 21, 2023.
Office Action for Canadian Application No. 3,126,978 dated May 1, 2023.
Office Action for Canadian Application No. 3,137,274 dated Mar. 29, 2023.
U.S. Appl. No. 62/727,605, filed Sep. 6, 2018.
Notice of Allowance for U.S. Appl. No. 17/487,145 dated Aug. 15, 2023.
Notice of Allowance for U.S. Appl. No. 18/130,534 dated Oct. 30, 2023.
Supplemental Notice of Allowance for U.S. Appl. No. 17/487,145 dated Nov. 3, 2023.

* cited by examiner

FIG. 1A
PRIOR ART
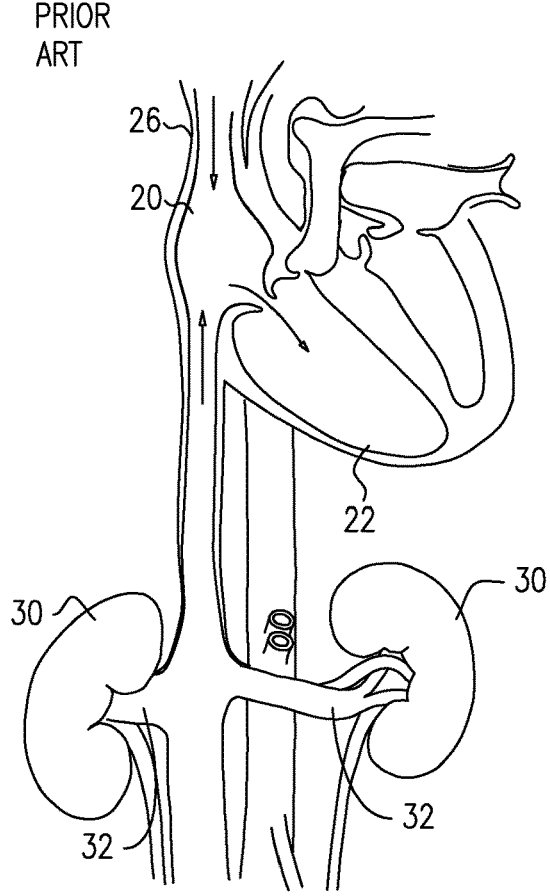
FIG. 1B
PRIOR ART
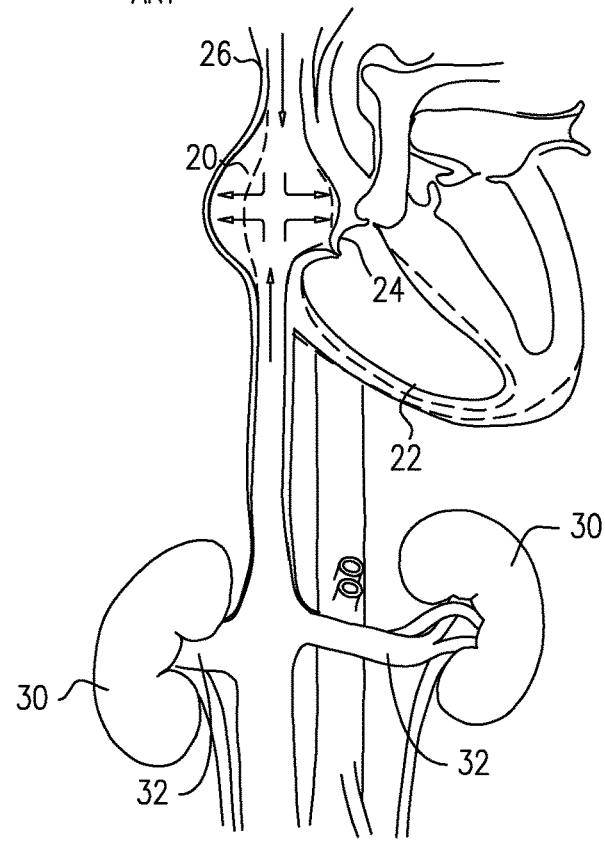
FIG. 1C
PRIOR ART
CV flow velocity
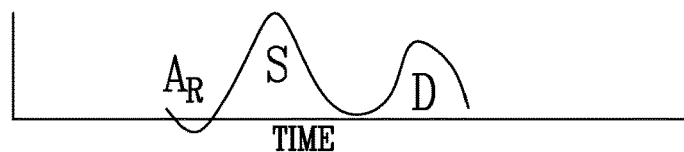
CV pressure
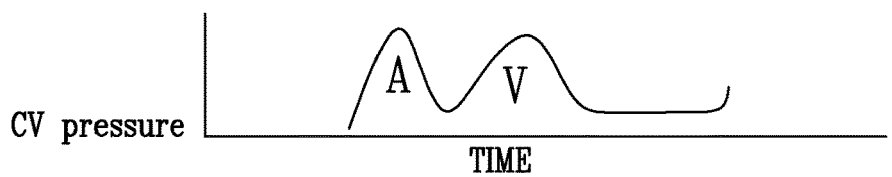
ECG
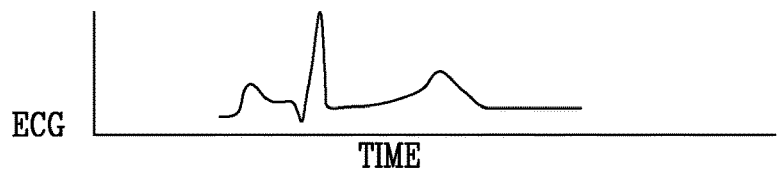

FIG. 2A
PRIOR ART
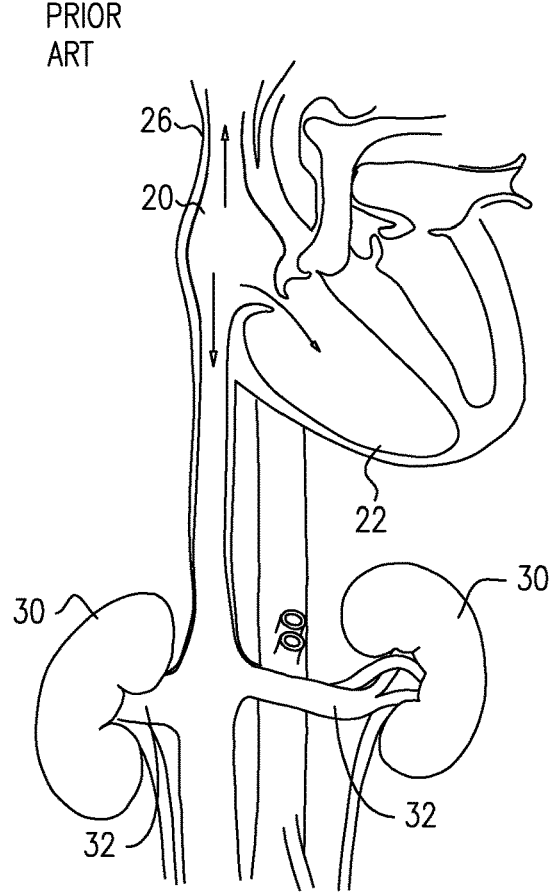
FIG. 2B
PRIOR ART
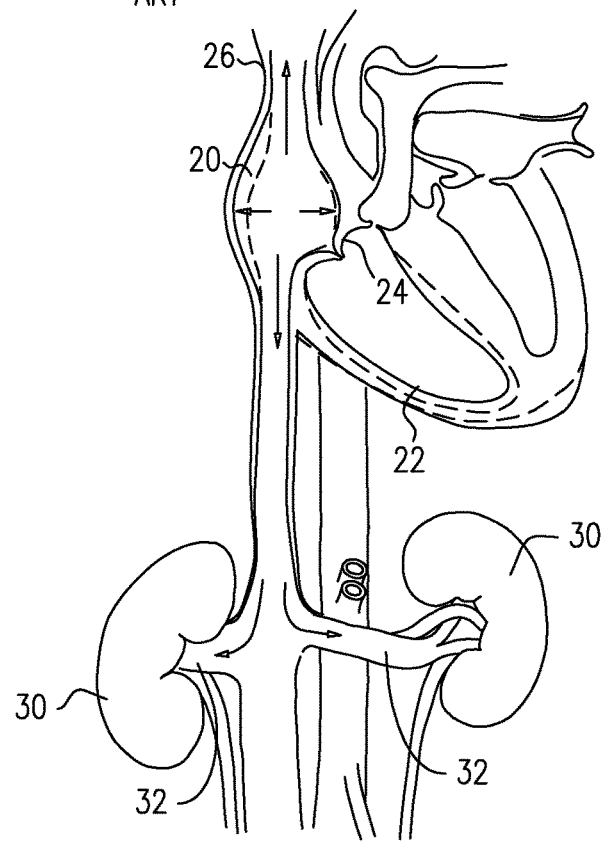
FIG. 2C
PRIOR ART
CV flow velocity
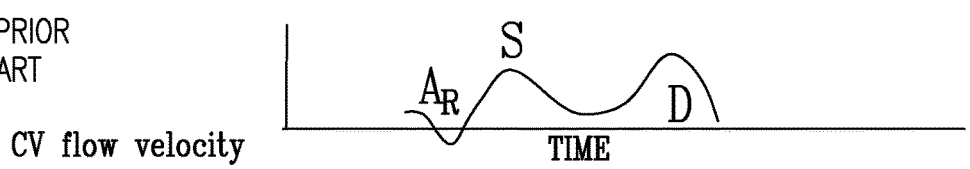
CV pressure
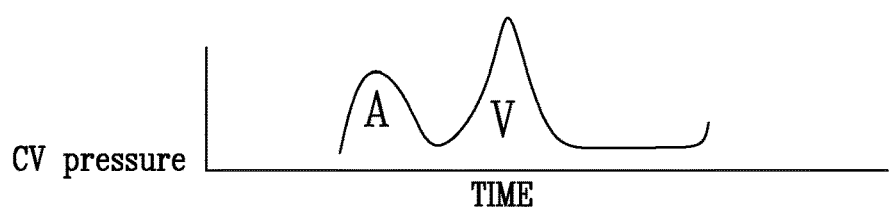
ECG
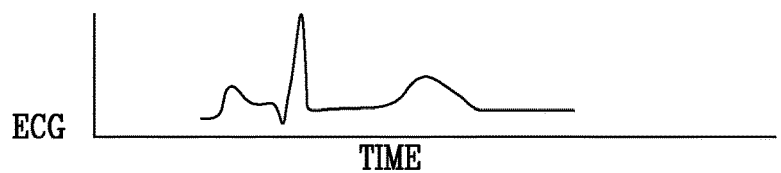

FIG. 3A
PRIOR ART
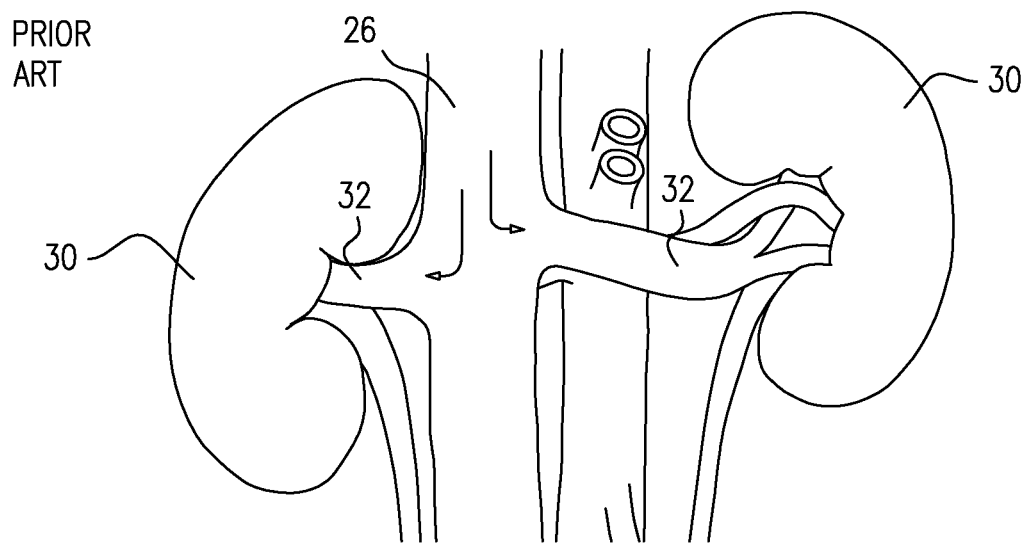
FIG. 3B
PRIOR ART
CV flow velocity
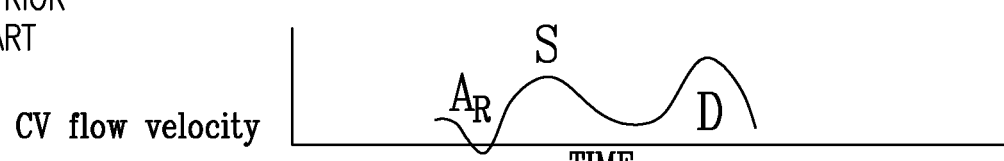
Renal venous pressure
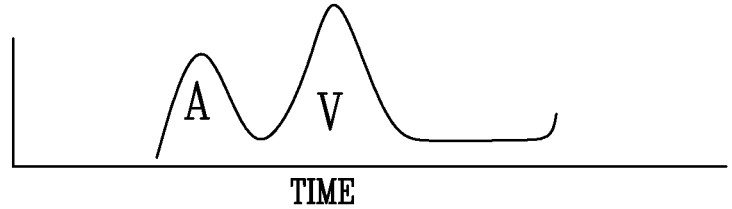
ECG
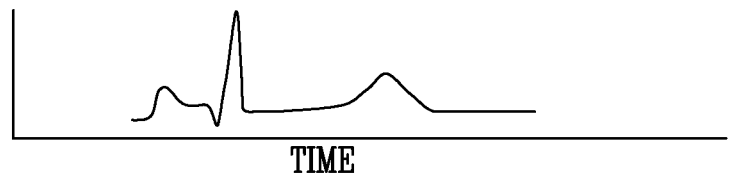

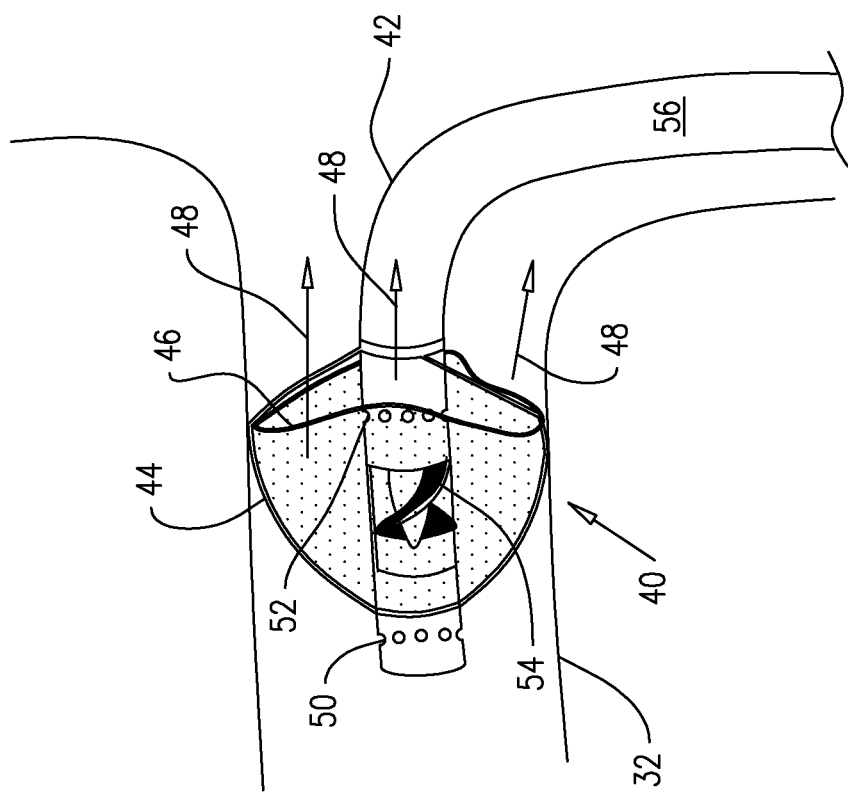

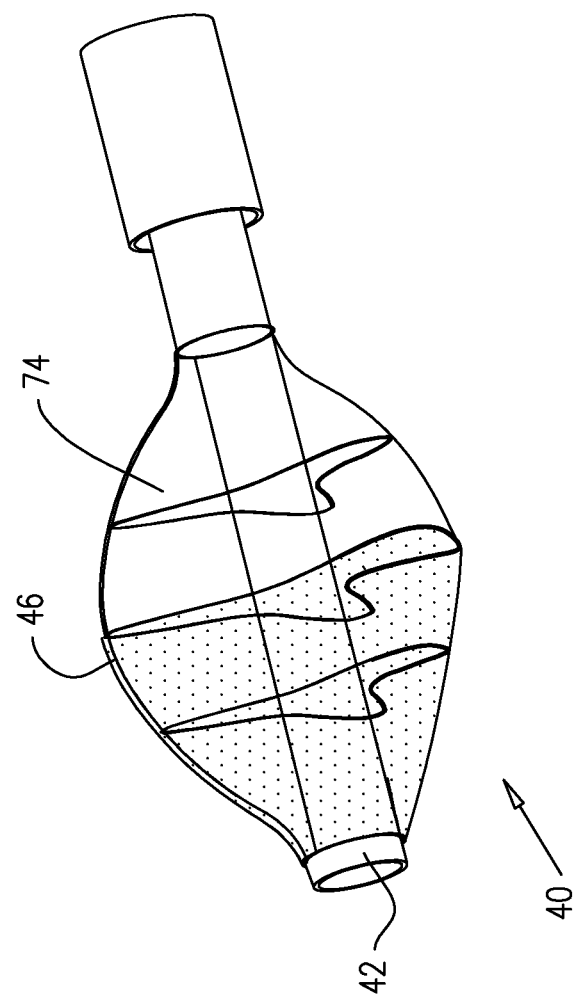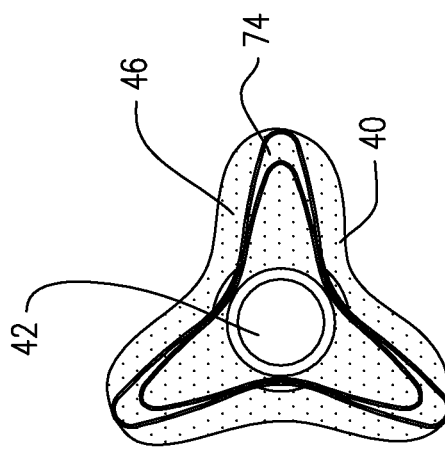

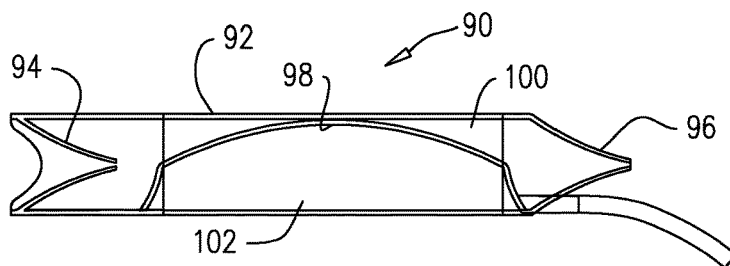
FIG. 9A
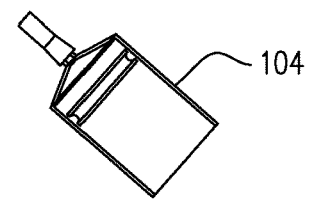
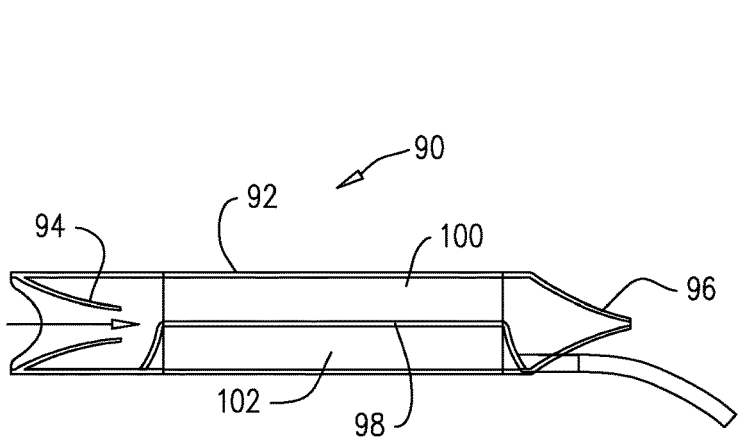
FIG. 9B
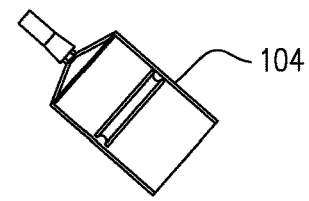
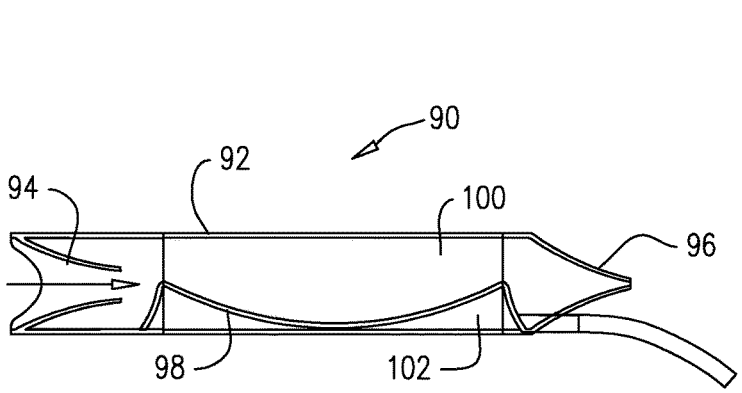
FIG. 9C
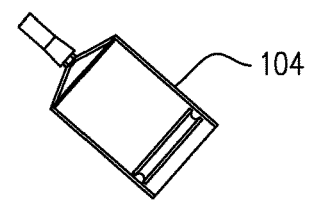
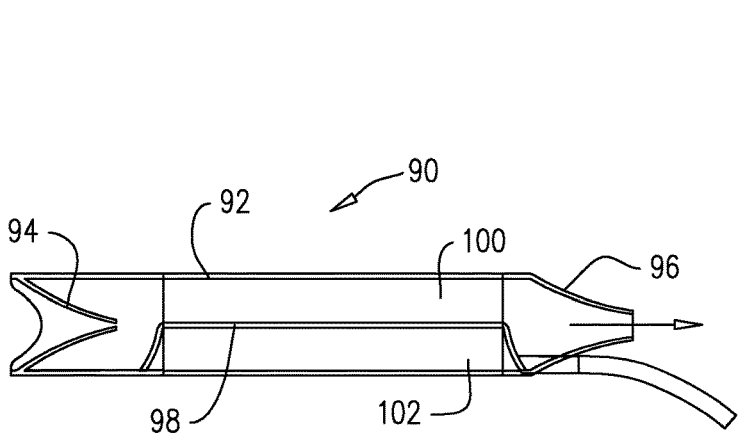
FIG. 9D
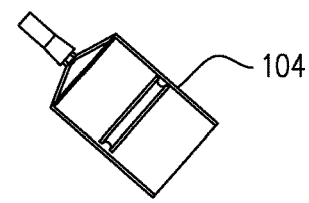

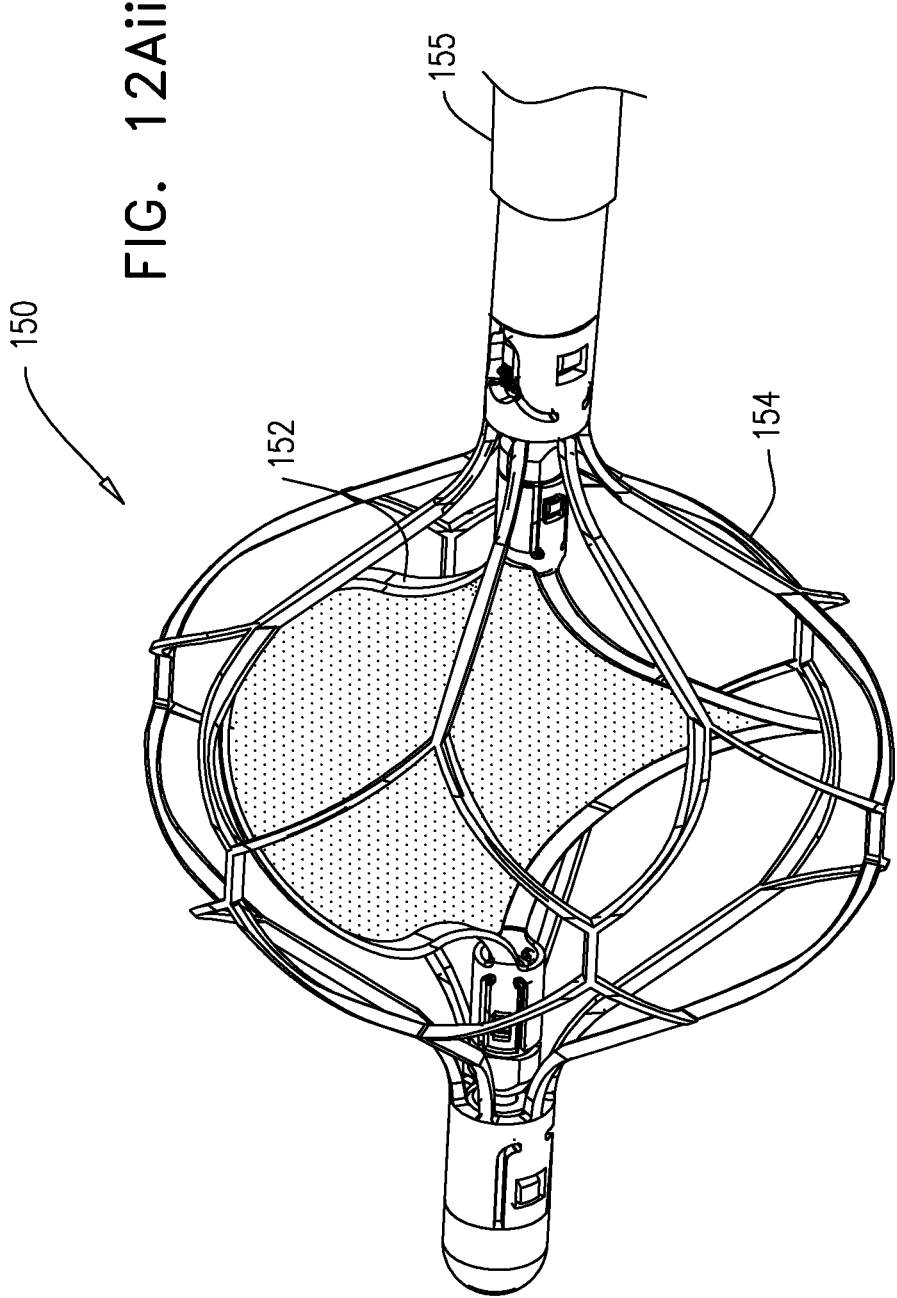
FIG. 12Aii

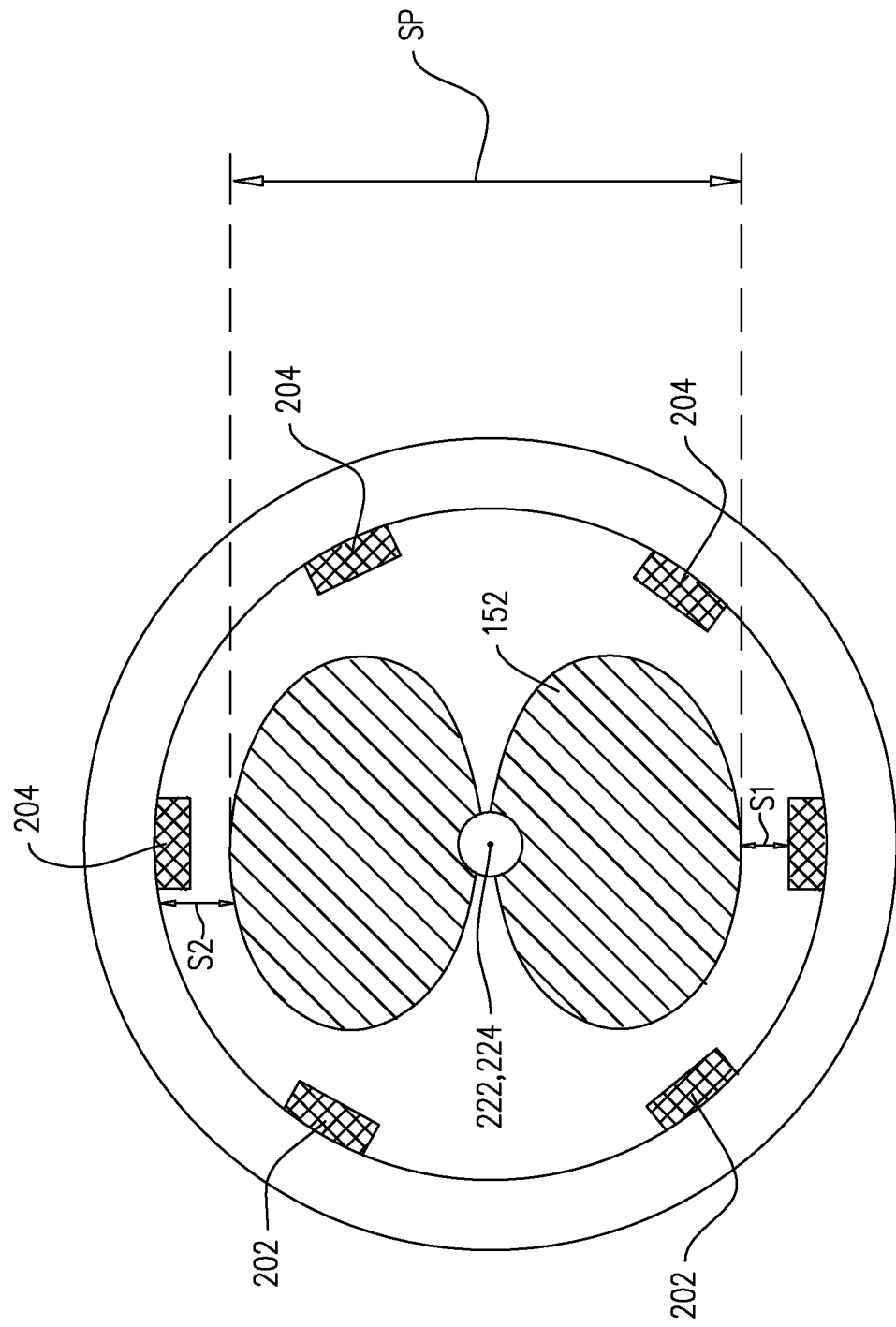

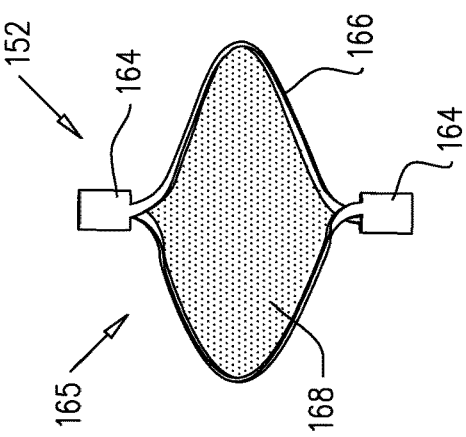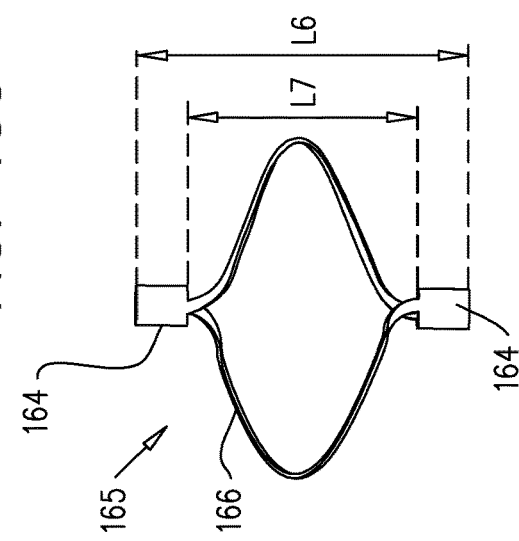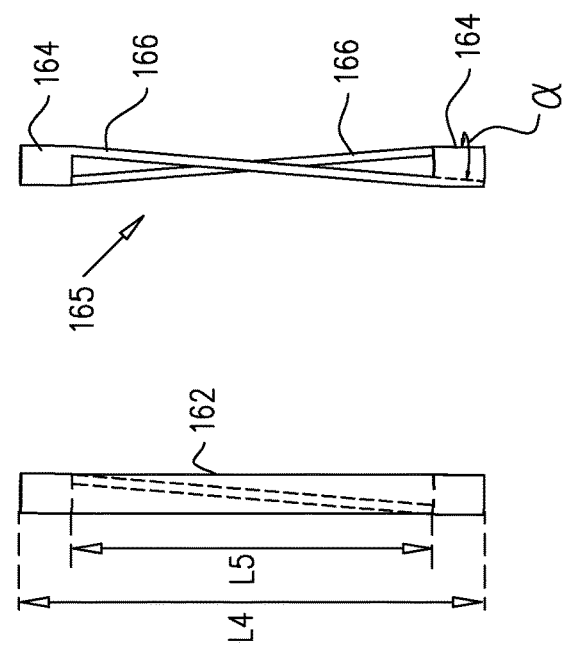
FIG. 13A  FIG. 13B  FIG. 13C  FIG. 13D

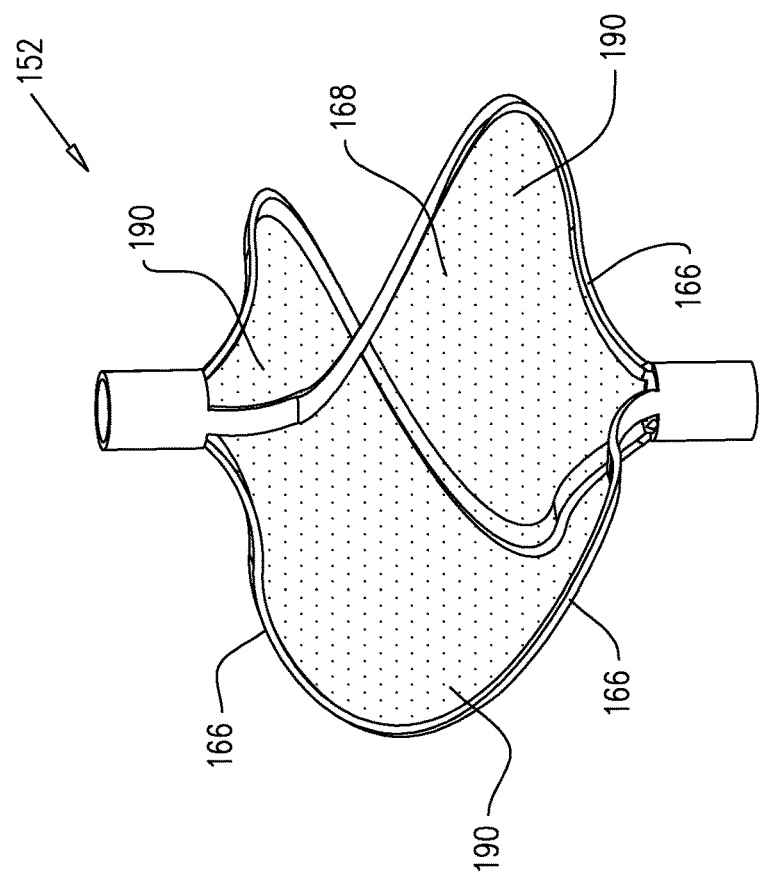
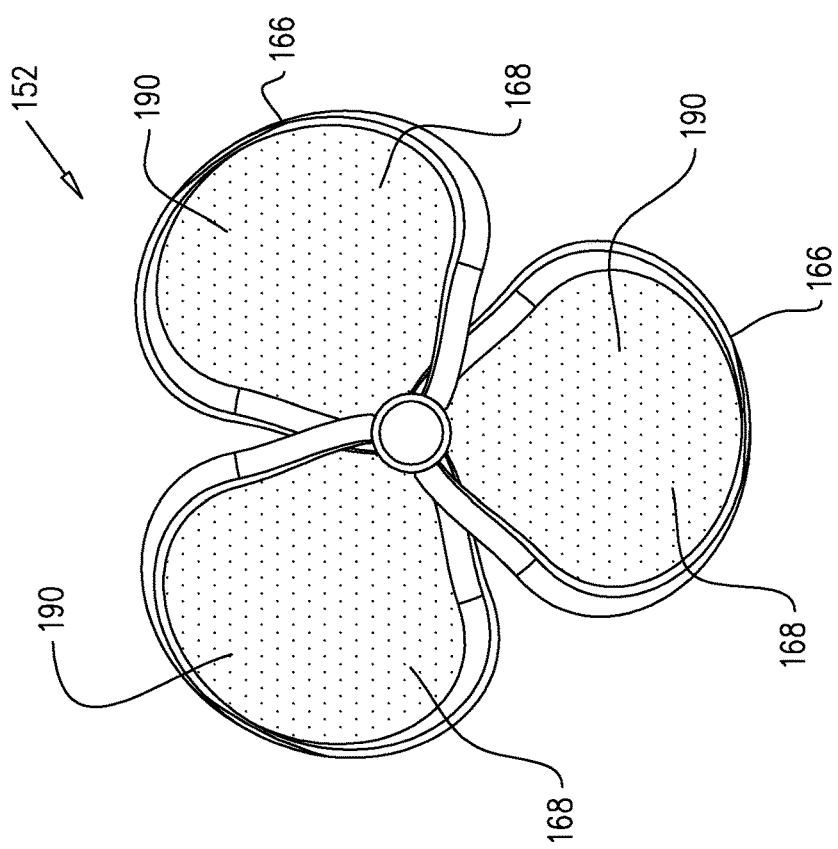

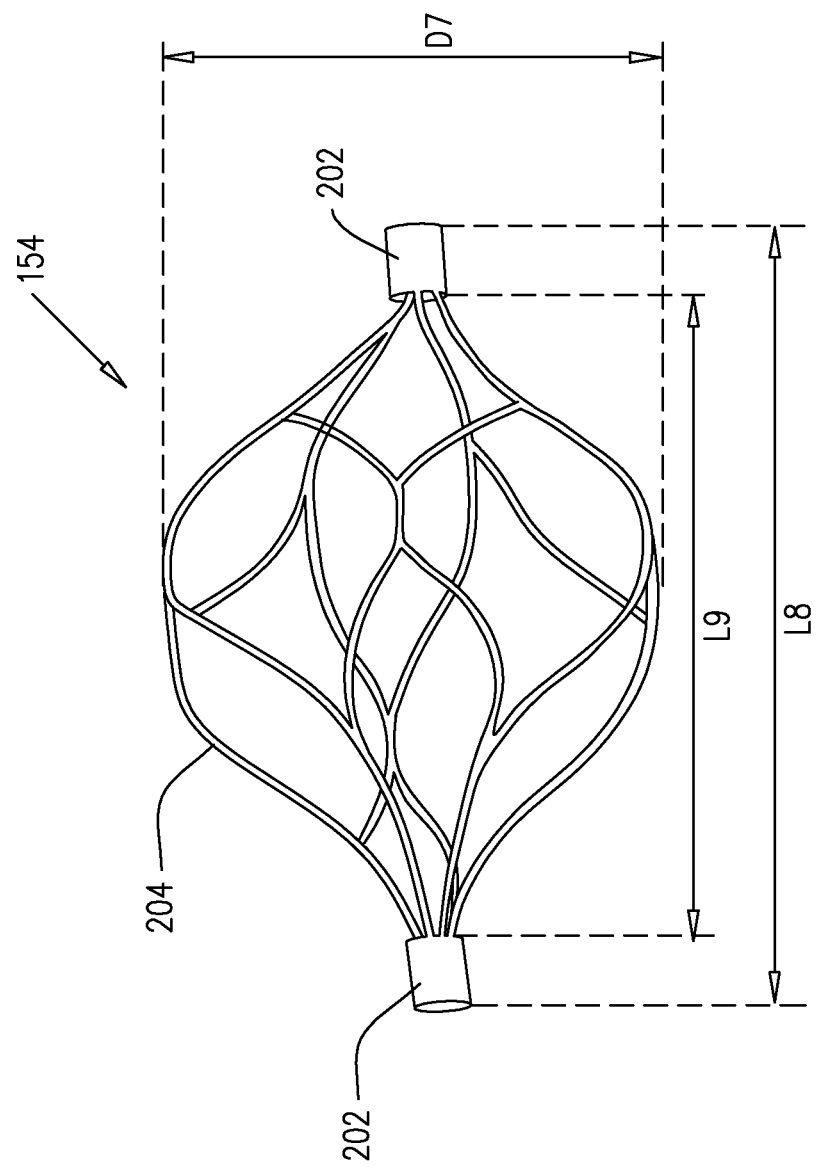

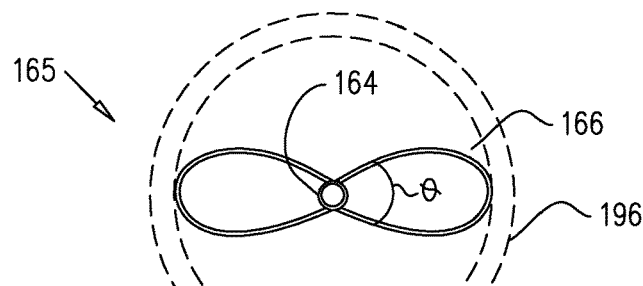
FIG. 18Ai
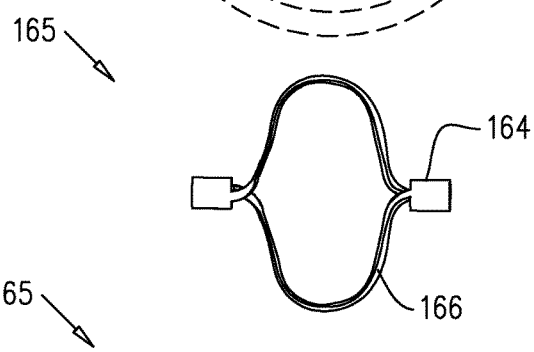
FIG. 18Aii
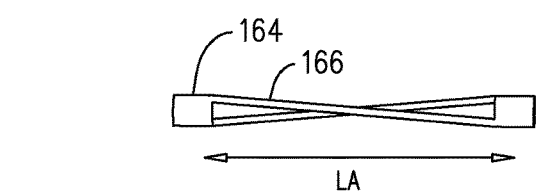
FIG. 18Aiii
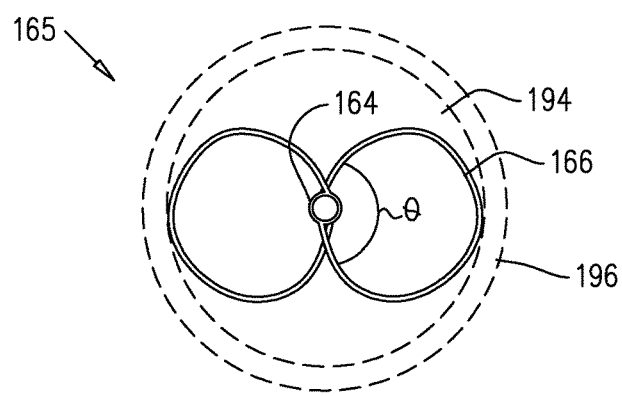
FIG. 18Bi
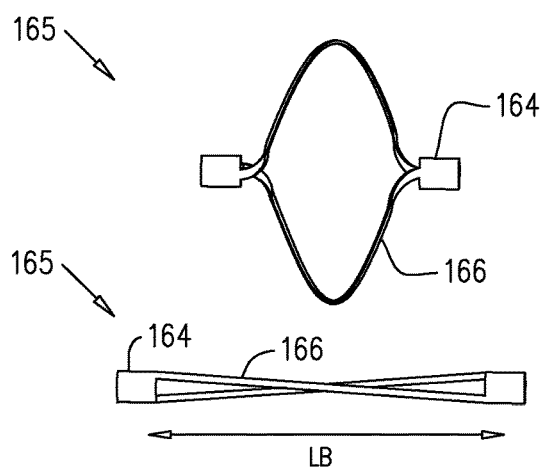
FIG. 18Bii
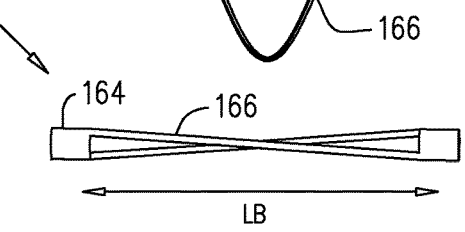
FIG. 18Biii

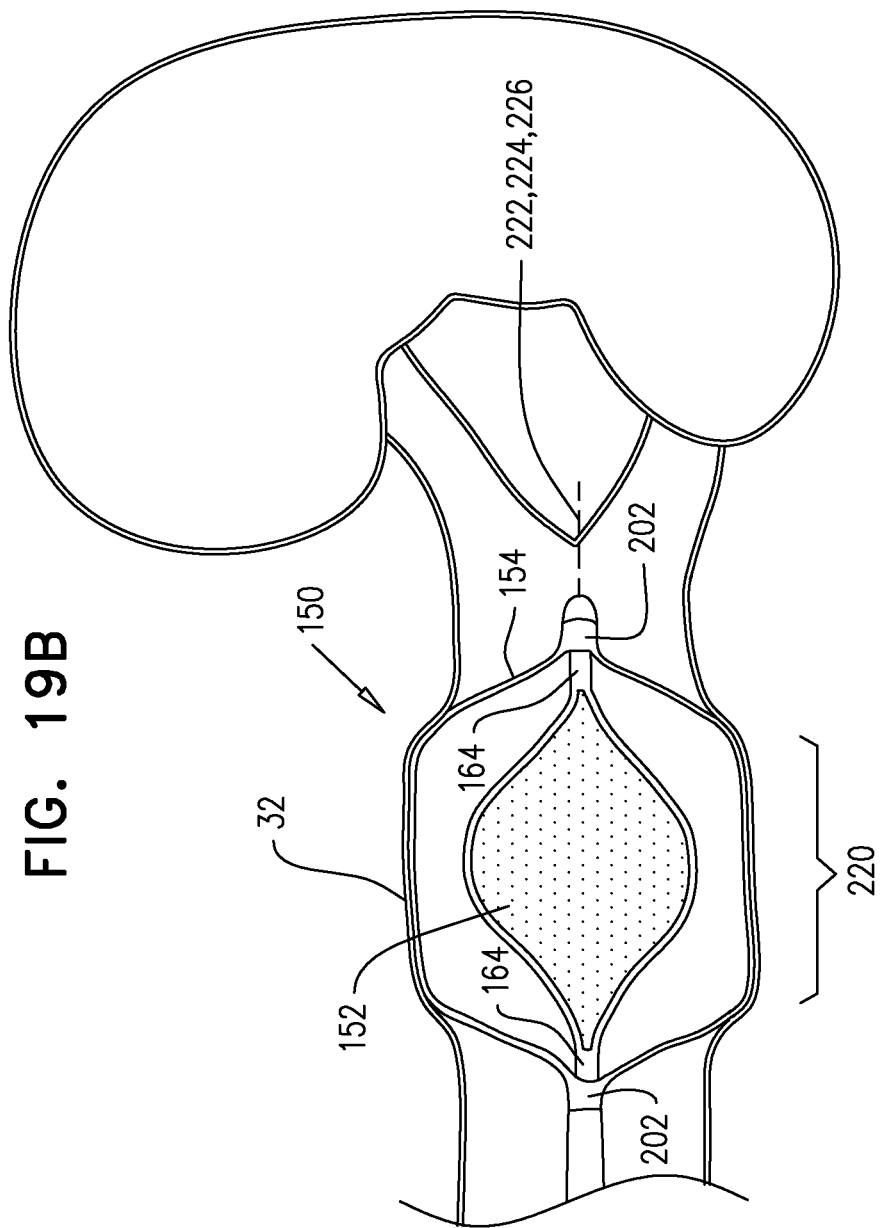

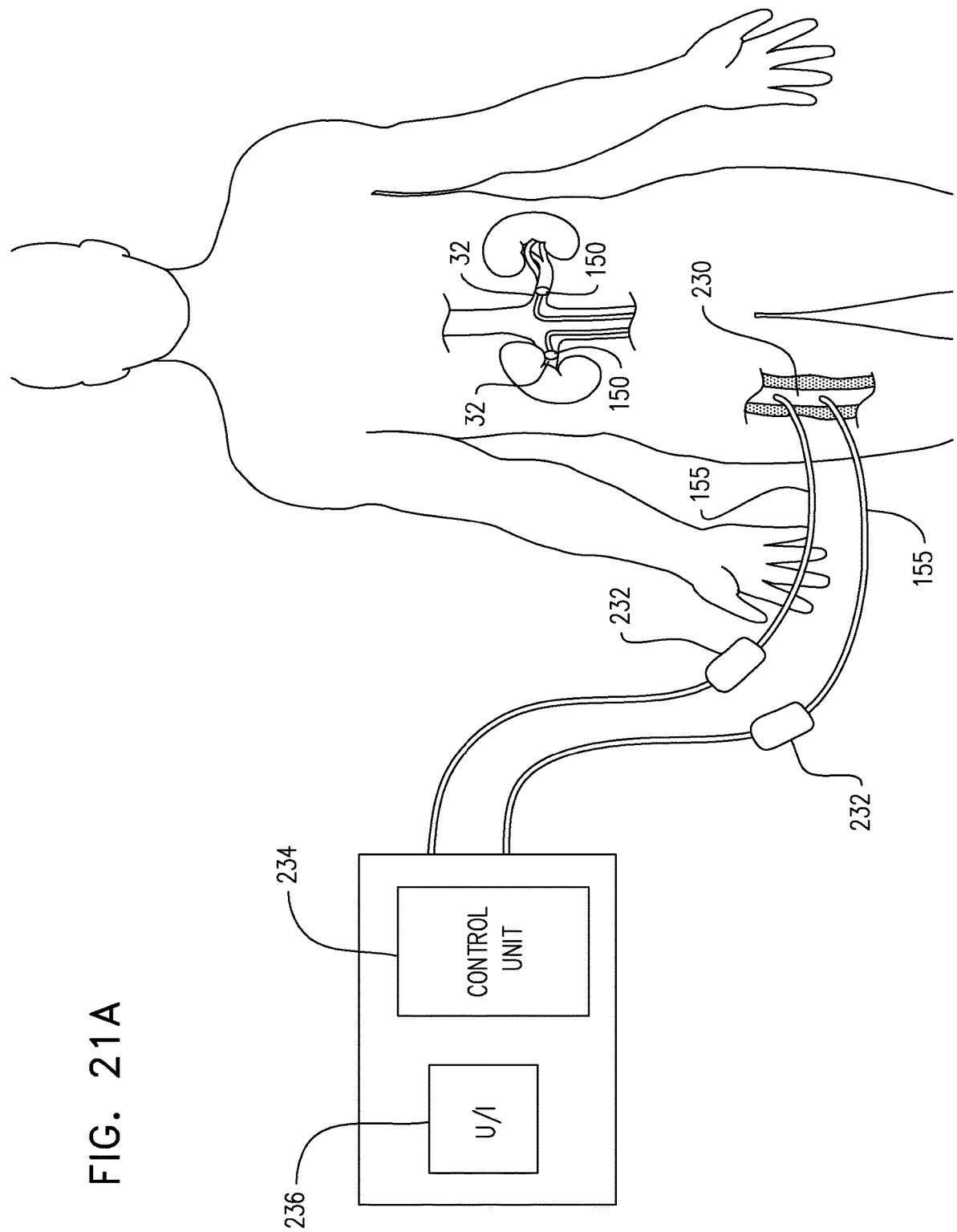

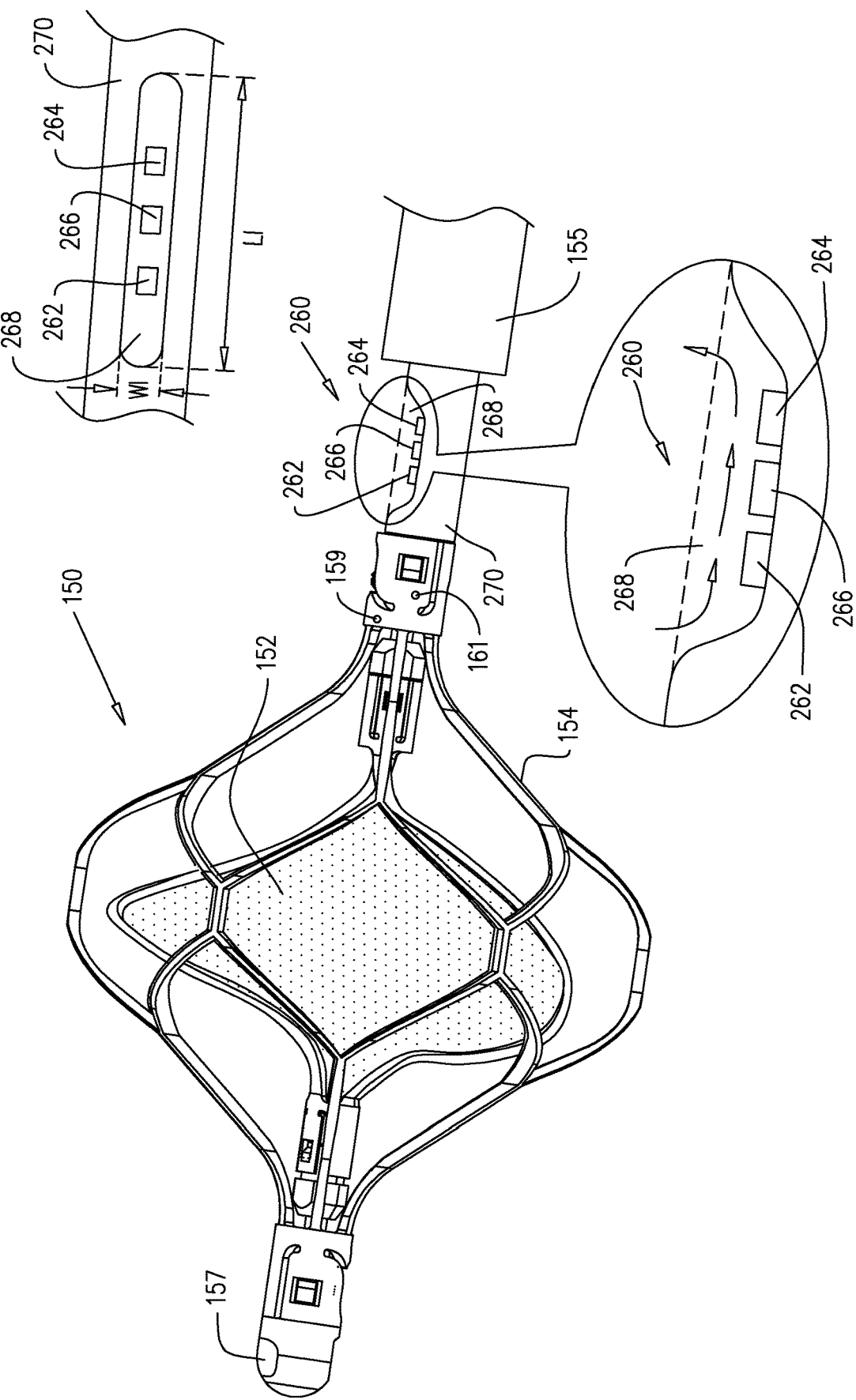

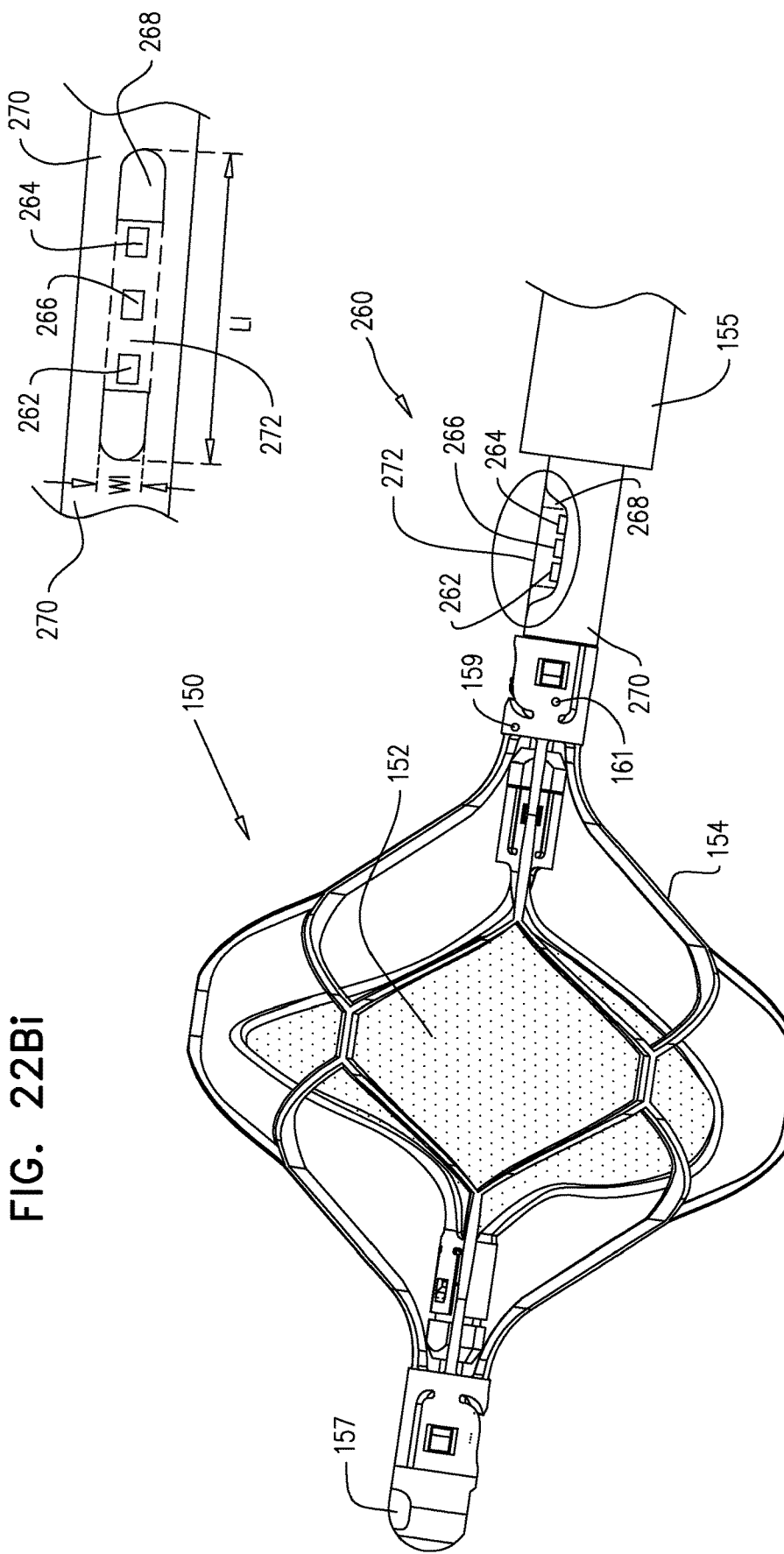

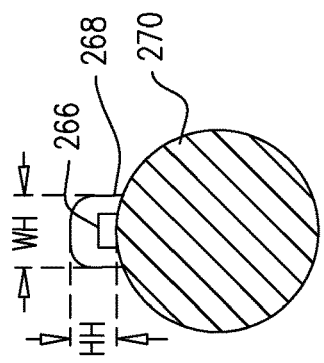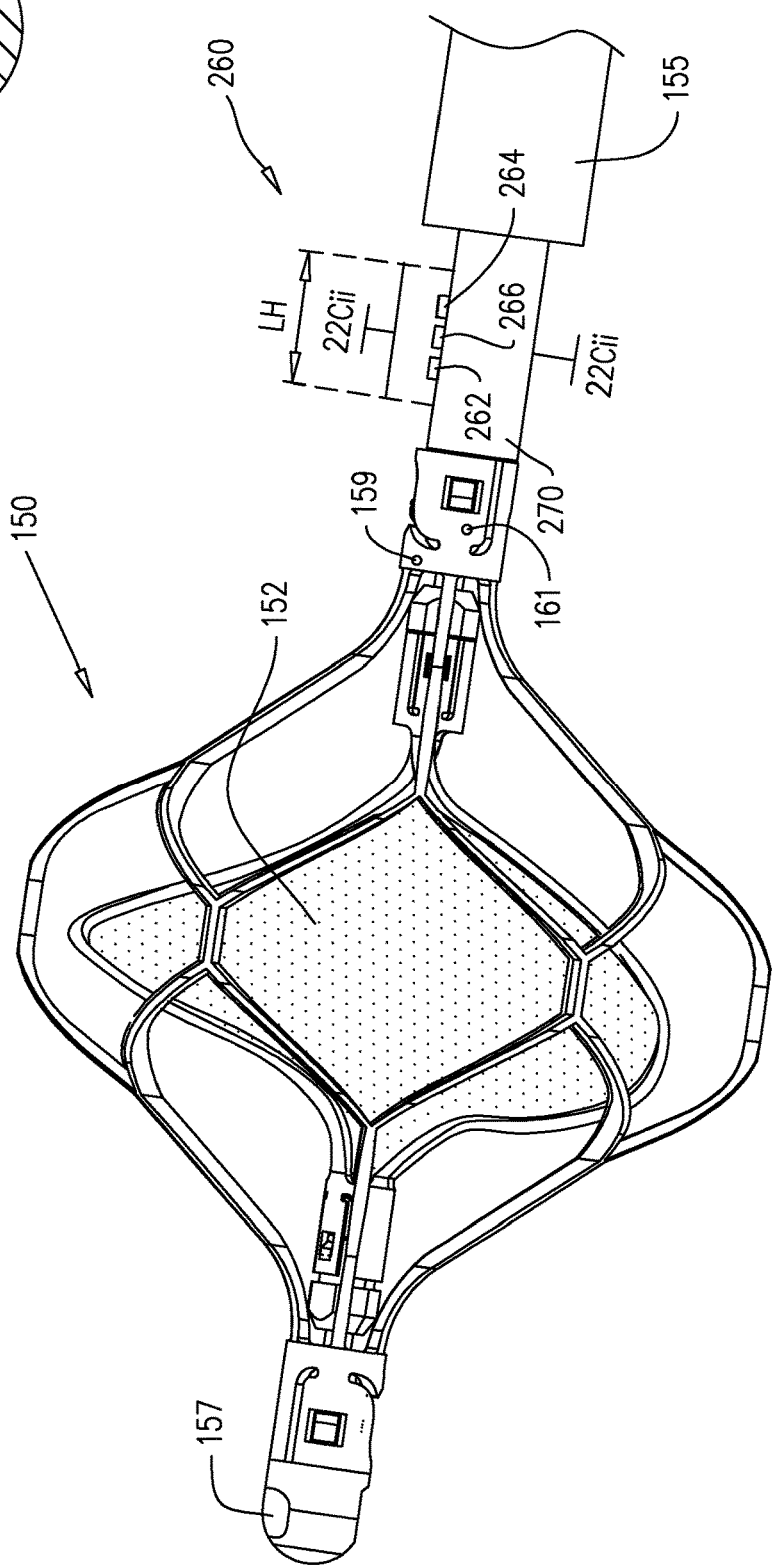

VENA-CAVAL BLOOD PUMP

CROSS-REFERENCES TO RELATED APPLICATIONS

The present application is a continuation of continuation of U.S. patent application Ser. No. 16/278,323 to Schwammenthal (published as US 2019/0175807), filed Feb. 18, 2019, which is continuation of U.S. patent application Ser. No. 16/022,445 to Schwammenthal (issued as U.S. Pat. No. 10,363,350), filed Jun. 28, 2018, which is continuation of U.S. patent application Ser. No. 14/774,081 to Schwammenthal (issued as U.S. Pat. No. 10,039,874), which is the US national phase application of PCT Application No. PCT/IL/2014/050289 to Schwammenthal (published as WO 14/141284), filed Mar. 13, 2014, which claims priority from:

U.S. Provisional Patent Application 61/779,803 to Schwammenthal, filed Mar. 13, 2013, entitled "Renal pump;" and U.S. Provisional Patent Application 61/914,475 to Schwammenthal, filed Dec. 11, 2013, entitled "Renal pump."

The present application is related to International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

All of the above-listed applications are incorporated herein by reference.

FIELD OF EMBODIMENTS OF THE INVENTION

Some applications of the present invention generally relate to medical apparatus. Specifically, some applications of the present invention relate to apparatus and methods associated with placing a pump in one or more of a subject's renal veins.

BACKGROUND

It is common for cardiac dysfunction or congestive heart failure to develop into kidney dysfunction, which in turn, causes congestive heart failure symptoms to develop or worsen. Typically, systolic and/or diastolic cardiac dysfunction causes systemic venous congestion, which gives rise to an increase in renal venous and interstitial pressure. The increase in the pressure causes fluid retention by the body to increase due both to kidney dysfunction and renal neurohormonal activation, both of which typically develop as a result of the increase in renal venous and interstitial pressure. The resulting fluid retention causes congestive heart failure to develop or worsen, by causing a blood volume overload at the heart and/or by increasing systemic resistance. Similarly, it is common for kidney dysfunction and/or renal neurohormonal activation to develop into cardiac dysfunction and/or congestive heart failure. This pathophysiological cycle, in which cardiac dysfunction and/or congestive heart failure leads to kidney dysfunction and/or renal neurohormonal activation, or in which kidney dysfunction and/or renal neurohormonal activation leads to cardiac dysfunction and/or congestive heart failure, each dysfunction leading to deterioration in the other dysfunction, is called the cardio-renal syndrome.

Increased renal venous pressure has been experimentally shown to cause azotemia, and a reduction in glomerular filtration rate, renal blood flow, urine output, and sodium excretion. It has also been shown to increase plasma renin and aldosterone, and protein excretion. Venous congestion may also contribute to anemia via three different pathways: A reduction in the kidney's erythropoietin production, hemodilution by fluid retention, and an inflammatory response leading to a reduced gastro-intestinal iron uptake.

Mechanistically, increased renal venous pressure, may cause intracapsular pressure and, subsequently, interstitial peritubular pressure, to rise. A rise in peritubular pressure may impact tubular function (reduce sodium excretion), as well as diminish glomerular filtration by raising the pressure in the Bowman capsule.

In heart failure patients, increased renal venous pressure may not only result from increased central venous (right atrial) pressure, but also from intraperitoneal fluid accumulations (ascites) exerting direct pressure on the renal veins. Reduction of intraabdominal pressure in heart failure patients by removal of fluid (e.g., via paracentesis, and/or ultrafiltration) has been shown to reduce plasma creatinine levels.

Increased venous return resulting from activation of the "leg muscle pump" during physical activity such as walking may raise systemic venous pressure, particularly in heart failure patients, and may result in reflux into the renal veins.

SUMMARY OF EMBODIMENTS

In accordance with some applications of the present invention, a blood pump that includes an impeller is placed inside a subject's renal vein and the impeller is activated to pump blood from the renal vein to the subject's vena cava, in order to provide acute treatment of a subject suffering from cardiac dysfunction, congestive heart failure, low renal blood flow, high renal vascular resistance, arterial hypertension, and/or kidney dysfunction. For example, the impeller may be placed inside the subject's renal veins for a period of more than one hour (e.g., more than one day), less than one week (e.g., less than four days), and/or between one hour and one week (e.g., between one day and four days).

The pump is typically configured to pump blood in a downstream direction such as to reduce pressure in the renal vein. Typically, due to the reduction in pressure in the renal vein that is caused by the pumping of the blood in the downstream direction, perfusion of the kidney increases. In turn, this may cause pressure in the renal veins to rise relative to the pressure in the renal veins immediately subsequent to initiation of the pumping, due to increased blood flow into the renal vein. Typically, even after perfusion of the kidney increases, the pump is configured to maintain the pressure in the renal vein at a lower value than the pressure in the renal vein before the initiation of the pumping.

Typically, the subject's renal vein is protected from being injured by the impeller, by placing a cage into the renal vein around the impeller, the cage separating a wall of the renal vein from the impeller. For some applications, the cage and the impeller are engaged to one another by an engagement mechanism, such that, in response to the cage becoming radially compressed, the impeller becomes radially compressed and the cage thereby maintains a separation between the wall of the renal vein and the impeller.

In accordance with some applications, a pump and an occlusion element (e.g., a valve) are placed inside the subject's renal veins in order to provide acute treatment of a subject suffering from cardiac dysfunction, congestive heart failure, low renal blood flow, high renal vascular resistance, arterial hypertension, and/or kidney dysfunction. For example, the pump and the occlusion element may be placed inside the subject's renal veins for a period of more than one hour (e.g., more than one day), less than one week (e.g., less than four days), and/or between one hour and one week (e.g., between one day and four days).

The occlusion element is configured to occlude the renal vein at an occlusion site. The pump is configured to pump blood in a downstream direction, from a site that is in fluid communication with the upstream side of the occlusion element to a site that is in fluid communication with a downstream side of the occlusion element. In doing so, the pump reduces pressure in the renal vein. The occlusion element is configured to protect the renal vein from backflow of blood from the vena cava to the renal vein.

Typically, due to the reduction in pressure in the renal vein that is caused by the pumping of the blood in the downstream direction, perfusion of the kidney increases. In turn, this may cause pressure in the renal veins to rise relative to the pressure in the renal veins immediately subsequent to initiation of the pumping, due to increased blood flow into the renal vein. Typically, even after perfusion of the kidney increases, the pump is configured to maintain the pressure in the renal vein at a lower value than the pressure in the renal vein before the initiation of the pumping.

In accordance with some applications of the invention, a blood-impermeable sleeve is placed within the subject's vena cava such that a downstream end of the sleeve is coupled to the wall of the vena cava at a first location that is downstream of all renal veins of the subject, and such that an upstream end of the sleeve is coupled to a wall of the vena cava at a second location that is upstream of all renal veins of the subject. Typically, a coupling structure, e.g., a rigid coupling structure (such as a stent), is configured to couple the upstream and downstream ends of the sleeve to the vena cava.

A pump pumps blood from a location that is exterior to the sleeve to a location that is in fluid communication with the interior of the sleeve (e.g., a location within the vena cava upstream or downstream of the sleeve). Thus, the pump pumps blood out of the subject's renal veins and into the subject's vena cava. The sleeve prevents backflow of blood from the vena cava into the renal veins.

There is therefore provided, in accordance with some applications of the present invention, a method including:

identifying a subject as suffering from a condition selected from the group consisting of: cardiac dysfunction, congestive heart failure, reduced renal blood flow, increased renal vascular resistance, arterial hypertension, and kidney dysfunction; and in response thereto, reducing blood pressure within a renal vein of the subject, by placing an impeller inside the subject's renal vein and activating the impeller to pump blood from the renal vein into a vena cava of the subject.

For some applications, activating the impeller to pump blood from the renal vein into the vena cava includes enhancing a rate of blood flow from the renal vein into the vena cava, without causing a substantial change in a direction of the blood flow relative to a direction of blood flow from the renal vein into the vena cava in an absence of activating the pump.

For some applications, activating the impeller to pump blood from the renal vein into the vena cava includes activating the impeller to pump blood from the renal vein directly into a portion of the vena cava that is adjacent to the renal vein.

For some applications, activating the impeller to pump blood from the renal vein into the vena cava includes activating the impeller to pump blood from the renal vein into the vena cava, without removing blood from a venous system of the subject into a non-venous receptacle.

For some applications, placing the impeller inside the renal vein includes protecting the subject's renal vein from being injured by the impeller, by placing the impeller into the renal vein, with a cage disposed around the impeller, the cage separating an inner wall of the renal vein from the impeller.

For some applications, placing the impeller into the renal vein with the cage disposed around the impeller includes placing the impeller into the renal vein, with the cage disposed around the impeller, the cage and the impeller being engaged to one another by an engagement mechanism, such that in response to the cage becoming radially compressed, the impeller becomes axially elongated such that the cage maintains a separation between the wall of the renal vein and the impeller.

There is further provided, in accordance with some applications of the present invention, apparatus including:

an impeller, including:
an impeller frame that includes proximal and distal end portions and a plurality of helical elongate elements that wind from the proximal end portion to the distal end portion; and
a material that is coupled to the helical elongate elements, such that the helical elongate elements with the material coupled thereto define at least one blade of the impeller.

For some applications, the impeller includes a biocompatible impeller that is configured to be inserted into a blood vessel of a subject.

For some applications, the plurality of elongate elements include a plurality of helical strips.

For some applications, at least one of the helical elongate elements has a variable pitch, the pitch of the at least one of the elongate elements varying along a length of the helical elongate element.

For some applications, the impeller is configured to be placed inside a blood vessel of a subject and to pump blood through the blood vessel by rotating with respect to the blood vessel, the apparatus further including a radially expandable cage configured to be disposed between the impeller and an inner wall of the blood vessel and to separate the blood vessel wall from the impeller.

For some applications, the proximal and distal end portions includes proximal and distal rings.

For some applications, at least one of the proximal and distal end portions defines a notch in an edge thereof, the notch being configured to facilitate coupling of the material to the helical elongate elements.

For some applications, the impeller further includes sutures tied around the helical elongate elements, the sutures being configured to facilitate coupling of the material to the helical elongate elements.

For some applications, the plurality of helical elongate elements includes three helical elongate elements that wind from the proximal end portion to the distal end portion.

For some applications, when the impeller is in a non-constrained configuration thereof, a length of each of the helical elongate elements, measured along a longitudinal axis of the impeller, is greater than 5 mm. For some applications, when the impeller is in the non-constrained configuration thereof, the length of each of the helical elongate elements, measured along a longitudinal axis of the impeller, is less than 14 mm.

For some applications, when the impeller is in a non-constrained configuration thereof, a span of the impeller in a direction perpendicular to a longitudinal axis of the impeller is greater than 8 mm. For some applications, the span of the impeller is greater than 10 mm. For some applications, the span of the impeller is less than 15 mm. For some applications, the span of the impeller is less than 12 mm.

For some applications, the plurality of helical elongate elements includes two helical elongate elements that wind from the proximal end portion to the distal end portion.

For some applications, radii of each of the two helical elongate elements are within 20 percent of one another. For some applications, radii of each of the two helical elongate elements are similar to one another. For some applications, pitches of each of the two helical elongate elements are within 20 percent of one another. For some applications, pitches of each of the two helical elongate elements are similar to one another. For some applications, longitudinal axes of each of the two helical elongate elements are parallel to each other and parallel to a longitudinal axis of the impeller.

For some applications, the material includes a continuous film of material that is supported by the helical elongate elements.

For some applications, each of the helical elongate elements defines more than one eighth of a winding of a helix. For some applications, each of the helical elongate elements defines less than half a winding of a helix.

For some applications:
the helical elongate elements define proximal and distal ends thereof,
the helical elongate elements are configured to support the material between the proximal and distal ends of the helical elongate elements, and
the impeller does not include any additional supporting member for supporting the material between the proximal and distal ends of the helical elongate elements.

For some applications, the impeller is configured such that rotational motion is imparted from the proximal end portion of the impeller to the distal end portion of the impeller substantially solely via the helical elongate elements of the impeller.

For some applications, the impeller, by not including any additional supporting member for supporting the material between the proximal and distal ends of the helical elongate elements, is configured to be radially compressible to a smaller diameter than if the impeller were to include an additional supporting member for supporting the material between the proximal and distal ends of the helical elongate elements.

For some applications, the impeller, by not including any additional supporting member for supporting the material between the proximal and distal ends of the helical elongate elements, is configured to be more flexible than if the impeller were to include an additional supporting member for supporting the material between the proximal and distal ends of the helical elongate elements.

For some applications, the impeller, by not including any additional supporting member for supporting the material between the proximal and distal ends of the helical elongate elements, is configured such that a force that is required to axially elongate the impeller by a given amount is less than would be required if the impeller were to include an additional supporting member for supporting the material between the proximal and distal ends of the helical elongate elements.

There is additionally provided, in accordance with some applications of the present invention, a method, including:
manufacturing an impeller by:
cutting a tube such that the cut tube defines a structure having first and second end portions at proximal and distal ends of the structure, the end portions being connected to one another by a plurality of elongate elements;
causing the elongate elements to radially expand and form helical elongate elements, by axially compressing the structure; and
coupling a material to the helical elongate elements, such that the helical elongate elements with the material coupled thereto define at least one blade of the impeller.

For some applications, cutting the tube includes laser cutting the tube.

For some applications, manufacturing the impeller includes manufacturing a biocompatible impeller that is configured to be inserted into a blood vessel of a subject.

For some applications, cutting the tube includes cutting the tube such that the cut tube defines a structure having first and second end portions at proximal and distal ends of the structure, the end portions being connected to one another by a plurality of strips.

For some applications, causing the elongate elements to radially expand and form helical elongate elements includes causing at least one of the helical elongate elements to have a variable pitch, the pitch of the at least one of the elongate elements varying along a length of the helical elongate element.

For some applications, cutting the tube such that the cut tube defines a structure having first and second end portions at proximal and distal ends of the structure includes cutting the tube such that the cut tube defines a structure having first and second rings at proximal and distal ends of the structure.

For some applications, cutting the tube further includes forming a notch in an edge of at least one of the end portions, the notch being configured to facilitate coupling of the material to the helical elongate elements.

For some applications, the method further includes tying sutures around the helical elongate elements, the sutures being configured to facilitate coupling of the material to the helical elongate elements.

For some applications, cutting the tube includes cutting the tube such that the cut tube defines a structure having first and second end portions at proximal and distal ends of the structure, the end portions being connected to one another by three elongate elements, and causing the elongate elements to radially expand and form helical elongate elements includes causing the elongate elements to form three helical elongate elements.

For some applications, cutting the tube includes cutting the tube such that, in an absence of axial compression being applied to the structure, the structure has a length, measured along a longitudinal axis of the structure, of greater than 15 mm. For some applications, cutting the tube includes cutting the tube such that, in the absence of axial compression being applied to the structure, the length of the structure, measured along the longitudinal axis of the structure, is less than 25 mm. For some applications, cutting the tube includes cutting the tube such that, in an absence of axial compression being applied to the structure, each of the elongate elements has a length, measured along a longitudinal axis of the structure, of greater than 14 mm. For some applications, cutting the tube includes cutting the tube such that, in the absence of axial compression being applied to the structure, the length of each of the elongate elements, measured along the longitudinal axis of the structure, is less than 22 mm.

For some applications, axially compressing the structure includes axially compressing the structure such that the structure defines a length, measured along a longitudinal axis of the structure, of greater than 8 mm. For some applications, axially compressing the structure includes axially compressing the structure such that the length, measured along the longitudinal axis of the structure, is less than 18 mm. For some applications, axially compressing the structure includes axially compressing the structure such that each of the elongate elements defines a length, measured along a longitudinal axis of the structure, of greater than 5 mm. For some applications, axially compressing the structure includes axially compressing the structure such that the length of each of the elongate elements, measured along the longitudinal axis of the structure, is less than 14 mm.

For some applications, axially compressing the structure includes axially compressing the structure such that a span of the structure in a direction perpendicular to a longitudinal axis of the structure is greater than 8 mm. For some applications, axially compressing the structure includes axially compressing the structure such that the span of the structure is greater than 10 mm. For some applications, axially compressing the structure includes axially compressing the structure such that the span of the structure is less than 15 mm. For some applications, axially compressing the structure includes axially compressing the structure such that the span of the structure is less than 12 mm.

For some applications, coupling the material to the helical elongate elements includes dipping at least a portion of the structure into the material, while the material is in a liquid state thereof, and drying the material, while the material is being supported by the helical elongate elements. For some applications, drying the material includes curing the material.

For some applications, cutting the tube includes cutting the tube such that the cut tube defines a structure having first and second end portions at proximal and distal ends of the structure, the end portions being connected to one another by two elongate elements, and causing the elongate elements to radially expand and form helical elongate elements includes causing the elongate elements to form two helical elongate elements.

For some applications, drying the liquid material while the material is being supported by the helical elongate elements includes causing the material to form a continuous film between the helical elongate elements, the continuous film being supported by the helical elongate elements.

For some applications, cutting the tube includes cutting the tube such that the cut tube defines a structure having first and second end portions at proximal and distal ends of the structure, the end portions being connected to one another by two elongate elements, and causing the elongate elements to radially expand and form helical elongate elements includes causing the elongate elements to form two helical elongate elements.

For some applications, causing the elongate elements to form the two helical elongate elements includes causing the elongate elements to form two helical elongate elements both of which originate at the first end portion, and terminate at the second end portion, radii of the helical elongate elements being similar to one another. For some applications, causing the elongate elements to form the two helical elongate elements includes causing the elongate elements to form two helical elongate elements both of which originate at the first end portion, and terminate at the second end portion, radii of the helical elongate elements being within 20 percent of one another.

For some applications, causing the elongate elements to form the two helical elongate elements includes causing the elongate elements to form two helical elongate elements both of which originate at the first end portion, and terminate at the second end portion, pitches of the helical elongate elements being similar to one another. For some applications, causing the elongate elements to form the two helical elongate elements includes causing the elongate elements to form two helical elongate elements both of which originate at the first end portion, and terminate at the second end portion, pitches of the helical elongate elements being within 20 percent of one another.

For some applications, causing the elongate elements to form the two helical elongate elements includes causing the elongate elements to form two helical elongate elements, longitudinal axes of both of the helical elongate elements being parallel to each other and parallel to a longitudinal axis of the impeller.

For some applications, causing the elongate elements to form the two helical elongate elements includes causing the elongate elements to form two helical elongate elements, each of the helical elongate elements defining more than one eighth of a winding of a helix. For some applications, causing the elongate elements to form the two helical elongate elements includes causing the elongate elements to form two helical elongate elements, each of the helical elongate elements defining less than half a winding of a helix.

For some applications, cutting the tube includes cutting the tube such that the cut tube defines a structure having first and second rings at proximal and distal ends of the structure, and such that first and second ends of each of the elongate elements are disposed at an angle from one another with respect to circumferences of the rings, the angle being greater than 50 degrees. For some applications, cutting the tube includes cutting the tube such that the first and second ends of each of the elongate elements are disposed at an angle from one another with respect to circumferences of the rings, the angle being greater than 70 degrees. For some applications, cutting the tube includes cutting the tube such that the first and second ends of each of the elongate elements are disposed at an angle from one another with respect to circumferences of the rings, the angle being greater than 90 degrees.

For some applications, cutting the tube includes cutting the tube such that the cut tube defines a structure having first and second rings at proximal and distal ends of the structure, and such that first and second ends of each of the elongate elements are disposed at an angle from one another with respect to circumferences of the rings, the angle being less than 180 degrees. For some applications, cutting the tube includes cutting the tube such that the first and second ends of each of the elongate elements are disposed at an angle from one another with respect to circumferences of the rings, the angle being less than 150 degrees. For some applications, cutting the tube includes cutting the tube such that the first and second ends of each of the elongate elements are disposed at an angle from one another with respect to circumferences of the rings, the angle being less than 110 degrees.

For some applications, coupling the material to the helical elongate elements includes coupling the material to the elongate elements such that, between the proximal and distal ends of the helical elongate elements, the material is supported by the helical elongate elements, in an absence of any additional supporting member between the proximal and distal ends of the helical elongate elements for supporting the material.

For some applications, coupling the material to the helical elongate elements in the absence of any additional supporting member between the proximal and distal ends of the helical elongate elements for supporting the material includes configuring the impeller such that rotational motion is imparted from the proximal end portion to the distal end portion substantially solely via the helical elongate elements of the impeller.

For some applications, coupling the material to the helical elongate elements in the absence of any additional supporting member between the proximal and distal ends of the helical elongate elements for supporting the material includes configuring the impeller to be radially compressible to a smaller diameter than if the impeller were to include an additional supporting member for supporting the material between the proximal and distal ends of the helical elongate elements.

For some applications, coupling the material to the helical elongate elements in the absence of any additional supporting member between the proximal and distal ends of the helical elongate elements for supporting the material includes configuring the impeller to be more flexible than if the impeller were to include an additional supporting member for supporting the material between the proximal and distal ends of the helical elongate elements.

For some applications, coupling the material to the helical elongate elements in the absence of any additional supporting member between the proximal and distal ends of the helical elongate elements for supporting the material includes configuring the impeller such that a force that is required to axially elongate the impeller by a given amount is less than would be required if the impeller were to include an additional supporting member for supporting the material between the proximal and distal ends of the helical elongate elements.

There is further provided, in accordance with some applications of the present invention, apparatus including:
  an impeller configured, in a radially-expanded configuration thereof, to pump a fluid by rotating;
  a radially expandable cage disposed around the impeller, such that, in radially-expanded configurations of the impeller and the cage, the impeller is separated from an inner surface of the cage; and
  an engagement mechanism configured to engage the impeller with respect to the cage, such that, in response to the cage becoming radially compressed, the engagement mechanism axially elongates the impeller such that the impeller remains separated from the inner surface of the cage.

For some applications:
  the cage and the impeller define axially-elongated configurations thereof, the cage, while in its axially-elongated configuration, being configured to accommodate the impeller inside the cage, while the impeller is in its axially-elongated configuration, and
  the cage includes struts, at least some of the struts including portions thereof that are undulated at least when the cage is in the radially-expanded configuration of the cage,
  a level of undulation of the undulated portions of the struts when the cage is in its radially-expanded configuration being greater than a level of undulation of the undulated portions of the struts when the cage is in its axially-elongated configuration.

For some applications, the engagement mechanism is configured to permit rotation of the impeller, while the cage is maintained in a rotationally fixed position.

For some applications, the engagement mechanism is configured, in response to the cage becoming radially compressed, to axially elongate the impeller, by imparting to the impeller longitudinal motion that is caused by longitudinal motion of the cage.

For some applications, the impeller includes a biocompatible impeller that is configured to be placed inside a blood vessel and to pump blood through the blood vessel by rotating, and the cage is configured to be disposed between the impeller and an inner wall of the blood vessel and to separate the blood vessel wall from the impeller.

For some applications, the cage includes struts that are shaped to define cells, and the cage is configured to separate the blood vessel wall from the impeller even if the blood vessel wall protrudes through a cell of the cage.

For some applications:
  the impeller is coupled to the cage such that a longitudinal axis of the impeller is aligned with a longitudinal axis of the cage, and
  the cage defines a central portion thereof that has a generally cylindrical shape, an outer surface of the cage at the generally cylindrical portion of the cage being parallel to the longitudinal axis of the cage.

For some applications, the impeller is configured to be placed inside a blood vessel and to pump blood through the blood vessel by rotating, and the cage is configured to be disposed between the impeller and an inner wall of the blood vessel and to separate the inner wall of the blood vessel from the impeller.

For some applications, the cage is configured to radially expand inside the blood vessel such that the outer surface of the cage at the generally cylindrical portion of the cage engages the inner wall of the blood vessel, the cage thereby becoming oriented within the blood vessel such that the longitudinal axis of the cage is parallel to a local longitudinal axis of the blood vessel.

There is additionally provided, in accordance with some applications of the present invention, a method including:
  placing inside a blood vessel of a subject:
    an impeller configured, in a radially-expanded configuration thereof, to pump blood through the blood vessel by rotating; and
    a radially-expandable cage disposed around the impeller;
  radially expanding the cage and the impeller inside the blood vessel, such that the impeller is separated from an inner wall of the blood vessel by the cage,
    the impeller being engaged with respect to the cage, such that, in response to the cage becoming radially compressed, the impeller is axially elongated, such that the impeller remains separated from the inner wall of the blood vessel; and
  operating a control unit to pump blood through the blood vessel by rotating the impeller.

For some applications, the blood vessel includes a renal vein, and operating the control unit to pump blood through the blood vessel includes operating the control unit to pump blood away from a kidney of the subject toward a vena cava of the subject.

For some applications, the method further includes operating the control unit to:

measure pressure within the subject's blood vessel at a first location within the blood vessel that is upstream of the impeller, and at a second location within the blood vessel that is downstream of the impeller; and control rotation of the impeller responsively to the pressure measured at the first and second locations.

For some applications:

placing the cage and the impeller inside the blood vessel includes placing the cage and the impeller inside the blood vessel while the cage and the impeller are in axially-elongated configurations thereof, and while the cage, while in its axially-elongated configuration accommodates the impeller inside the cage, while the impeller is in its axially-elongated configuration, the cage includes a cage that defines struts, at least some of the struts including portions thereof that are undulated at least when the cage is in a radially-expanded configuration, and radially expanding the cage includes radially expanding the cage such that a level of undulation of the undulated portions of the struts becomes greater than a level of undulation of the undulated portions of the struts when the cage was in its axially-elongated configuration.

For some applications, operating the control unit to rotate the impeller includes operating the control unit to rotate the impeller, while the cage is maintained in a rotationally fixed position.

For some applications, the cage includes struts that are shaped to define cells, and radially expanding the cage includes separating the blood vessel wall from the impeller even if the blood vessel wall protrudes through a cell of the cage, by radially expanding the cage.

For some applications:

placing the impeller and the cage inside the blood vessel includes placing the impeller and the cage inside the blood vessel, the impeller being coupled to the cage such that a longitudinal axis of the impeller is aligned with a longitudinal axis of the cage, the cage includes a cage that defines a central portion thereof that has a generally cylindrical shape, an outer surface of the cage at the generally cylindrical portion of the cage being parallel to the longitudinal axis of the cage, and radially expanding the cage inside the blood vessel includes radially expanding the cage inside the blood vessel such that the outer surface of the cage at the generally cylindrical portion of the cage engages the inner wall of the blood vessel, the cage thereby becoming oriented within the blood vessel such that a longitudinal axis of the cage is parallel to a local longitudinal axis of the blood vessel.

For some applications:

the blood vessel has a given diameter in an absence of the cage;

radially expanding the cage includes widening a portion of the blood vessel such that a diameter of the portion of the blood vessel is greater than the given diameter; and radially expanding the impeller includes radially expanding the impeller such that a span of the impeller is at least equal to the given diameter.

For some applications, the method further includes operating the control unit to:

measure flow through the blood vessel; and control rotation of the impeller responsively to the measured flow.

For some applications, operating the control unit to measure flow through the blood vessel includes operating the control unit to measure blood flow via a thermal flow sensor that is disposed within a housing, the housing being configured such that blood flow through the housing is substantially in a direction parallel to a local longitudinal axis of the blood vessel.

There is further provided, in accordance with some applications of the present invention apparatus including:

a radially-expandable impeller configured, in a radially-expanded configuration thereof, to pump a fluid by rotating;

a radially-expandable cage disposed around the impeller, such that, in radially-expanded configurations of the impeller and the cage, the impeller is separated from an inner surface of the cage;

the impeller being coupled to the cage such that a longitudinal axis of the impeller is aligned with a longitudinal axis of the cage, and the cage defining a central portion thereof that has a generally cylindrical shape, an outer surface of the cage at the generally cylindrical portion of the cage being parallel to the longitudinal axis of the cage.

For some applications:

the cage and the impeller define axially-elongated configurations thereof, the cage, while in its axially-elongated configuration, being configured to accommodate the impeller inside the cage, while the impeller is in its axially-elongated configuration, and the cage includes struts, at least some of the struts including portions thereof that are undulated at least when the cage is in the radially-expanded configuration of the cage, a level of undulation of the undulated portions of the struts when the cage is in its radially-expanded configuration being greater than a level of undulation of the undulated portions of the struts when the cage is in its axially-elongated configuration.

For some applications:

the impeller defines proximal and distal rings, respectively, at proximal and distal ends thereof, the cage defines proximal and distal rings, respectively, at proximal and distal ends thereof, the impeller is coupled to the cage such that the longitudinal axis of the impeller is aligned with the longitudinal axis of the cage by:

the proximal rings of the impeller and the cage being placed on a first support element such that the proximal rings of the impeller and the cage are aligned with one another, and the distal rings of the impeller and the cage being placed on a second support element such that the distal rings of the impeller and the cage are aligned with one another.

For some applications, the apparatus further includes an engagement mechanism configured to engage the impeller with respect to the cage, such that, in response to the cage becoming radially compressed, the engagement mechanism axially elongates the impeller such that the impeller remains separated from the inner surface of the cage.

For some applications, the engagement mechanism is configured to permit rotation of the impeller, while the cage is maintained in a rotationally fixed position.

For some applications, the engagement mechanism is configured, in response to the cage becoming radially compressed, to axially elongate the impeller, by imparting to the impeller longitudinal motion that is caused by longitudinal motion of the cage.

For some applications, the impeller is a biocompatible impeller that is configured to be placed inside a blood vessel and to pump blood through the blood vessel by rotating, and the cage is configured to be disposed between the impeller and an inner wall of the blood vessel and to separate the blood vessel wall from the impeller.

For some applications, the cage includes struts that are shaped to define cells, and the cage is configured to separate the blood vessel wall from the impeller even if the blood vessel wall protrudes through a cell of the cage.

For some applications, the impeller is a biocompatible impeller that is configured to be placed inside a blood vessel and to pump blood through the blood vessel by rotating, and the cage is configured to be disposed between the impeller and an inner wall of the blood vessel and to separate the blood vessel wall from the impeller.

For some applications, the cage is configured to radially expand inside the blood vessel such that the outer surface of the cage at the generally cylindrical portion of the cage engages the inner wall of the blood vessel, the cage thereby becoming oriented within the blood vessel such that the longitudinal axis of the cage is parallel to a local longitudinal axis of the blood vessel.

There is further provided, in accordance with some applications of the present invention, a method including:
placing inside a blood vessel of a subject:
an impeller configured, in a radially-expanded configuration thereof, to pump blood through the blood vessel by rotating;
a radially-expandable cage disposed around the impeller, the impeller being coupled to the cage such that a longitudinal axis of the impeller is aligned with a longitudinal axis of the cage, and the cage defining a central portion thereof that has a generally cylindrical shape, an outer surface of the cage at the generally cylindrical portion of the cage being parallel to the longitudinal axis of the cage;
radially expanding the cage and the impeller inside the blood vessel, such that:
the impeller is separated from an inner wall of the blood vessel by the cage, and
the outer surface of the cage at the generally cylindrical portion of the cage engages the inner wall of the blood vessel, the cage thereby becoming oriented within the blood vessel such that a longitudinal axis of the cage is parallel to a local longitudinal axis of the blood vessel; and
operating a control unit to pump blood through the blood vessel by rotating the impeller.

For some applications, the method further includes operating the control unit to:
measure pressure within the subject's blood vessel at a first location within the blood vessel that is upstream of the impeller, and at a second location within the blood vessel that is downstream of the impeller; and
control rotation of the impeller responsively to the pressure measured at the first and second locations.

For some applications:
the blood vessel has a given diameter in an absence of the cage;
radially expanding the cage includes widening a portion of the blood vessel such that a diameter of the portion of the blood vessel is greater than the given diameter; and
radially expanding the impeller includes radially expanding the impeller such that a span of the impeller is at least equal to the given diameter.

For some applications, the method further includes operating the control unit to:
measure flow through the blood vessel; and
control rotation of the impeller responsively to the measured flow.

For some applications, operating the control unit to measure flow through the blood vessel includes operating the control unit to measure blood flow via a thermal flow sensor that is disposed within a housing, the housing being configured such that blood flow through the housing is substantially in a direction parallel to the local longitudinal axis of the blood vessel.

There is further provided, in accordance with some applications of the present invention, apparatus including:
a radially-expandable impeller configured, in a radially-expanded configuration thereof, to pump a fluid by rotating; and
a radially-expandable cage disposed around the impeller, such that, in radially-expanded configurations of the impeller and the cage, the impeller is separated from an inner surface of the cage,
the cage and the impeller defining axially-elongated configurations thereof, the cage, while in its axially-elongated configuration, being configured to accommodate the impeller inside the cage, while the impeller is in its axially-elongated configuration,
the cage including struts, at least some of the struts including portions thereof that are undulated at least when the cage is in the radially-expanded configuration of the cage,
a level of undulation of the undulated portions of the struts when the cage is in its radially-expanded configuration, being greater than a level of undulation of the undulated portions of the struts when the cage is in its axially-elongated configuration.

For some applications, for each of the struts that include the undulated portions, the strut is configured such that a ratio of:
a shortest distance from a first longitudinal end of the strut to a second longitudinal end of the strut when the cage is its axially-elongated configuration, to
a shortest distance from the first longitudinal end of the strut to the second longitudinal end of the strut when the cage is its radially-expanded configuration,
is greater than 1.05:1.

For some applications, the ratio is less than 1.4:1. For some applications, the ratio is greater than 1.15:1. For some applications, the ratio is greater than 1.2:1.

For some applications, the apparatus further includes an engagement mechanism configured to engage the impeller with respect to the cage, such that, in response to the cage becoming axially elongated, the impeller is axially elongated such that the impeller remains separated from the inner surface of the cage.

For some applications, the engagement mechanism is configured to permit rotation of the impeller, while the cage is maintained in a rotationally fixed position.

For some applications, the engagement mechanism is configured, in response to the cage becoming axially elongated, to axially elongate the impeller, by imparting to the impeller longitudinal motion that is caused by longitudinal motion of the cage.

For some applications:
the cage and the impeller are biocompatible and are configured to be inserted into a blood vessel, while the impeller is disposed inside the cage, and while the cage and the impeller are in the axially-elongated configurations thereof,
the impeller is configured to radially expand inside the blood vessel and to pump blood through the blood vessel by rotating, and
the cage is configured to radially expand inside the blood vessel and to be disposed between the impeller and an inner wall of the blood vessel such as to separate the inner wall of the blood vessel from the impeller.

For some applications, the struts of the cage are shaped to define cells, and the cage is configured to separate the blood vessel wall from the impeller even if the blood vessel wall protrudes through a cell of the cage.

For some applications:
the impeller is coupled to the cage such that a longitudinal axis of the impeller is aligned with a longitudinal axis of the cage, and
the cage defines a central portion thereof that has a generally cylindrical shape, an outer surface of the cage at the generally cylindrical portion of the cage being parallel to the longitudinal axis of the cage.

For some applications, the impeller is biocompatible and is configured to be placed inside a blood vessel and to pump blood through the blood vessel by rotating, and the cage is configured to be disposed between the impeller and an inner wall of the blood vessel and to separate the inner wall of the blood vessel from the impeller.

For some applications, the cage is configured to radially expand inside the blood vessel such that the outer surface of the cage at the generally cylindrical portion of the cage engages the inner wall of the blood vessel, the cage thereby becoming oriented within the blood vessel such that the longitudinal axis of the cage is parallel to a local longitudinal axis of the blood vessel.

There is additionally provided, in accordance with some applications of the present invention, a method including:
placing inside a blood vessel of a subject:
an impeller configured, in a radially-expanded configuration thereof, to pump blood through the blood vessel by rotating; and
a radially-expandable cage disposed around the impeller, the cage defining struts,
the placing being performed while the cage and the impeller are in axially-elongated configurations thereof, and while the cage, while in its axially-elongated configuration, accommodates the impeller inside the cage, while the impeller is in its axially-elongated configuration;
radially expanding the cage and the impeller inside the blood vessel, such that the cage and the impeller are in radially-expanded configurations thereof, and such that the impeller is separated from an inner wall of the blood vessel by the cage; and
operating a control unit to pump blood through the blood vessel by rotating the impeller,
the cage including struts, at least some of the struts including portions thereof that are undulated at least when the cage is in the radially-expanded configuration of the cage,
radially expanding the cage including radially expanding the cage such that a level of undulation of the undulated portions of the struts becomes greater than a level of undulation of the undulated portions of the struts when the cage was in its axially-elongated configuration.

For some applications, the blood vessel includes a renal vein, and operating the control unit to pump blood through the blood vessel includes operating the control unit to pump blood away from a kidney of the subject toward a vena cava of the subject.

For some applications, the method further includes operating the control unit to:
measure pressure within the subject's blood vessel at a first location within the blood vessel that is upstream of the impeller, and at a second location within the blood vessel that is downstream of the impeller; and
control rotation of the impeller responsively to the pressure measured at the first and second locations.

For some applications:
the blood vessel has a given diameter in an absence of the cage;
radially expanding the cage includes widening a portion of the blood vessel such that a diameter of the portion of the blood vessel is greater than the given diameter; and
radially expanding the impeller includes radially expanding the impeller such that a span of the impeller is at least equal to the given diameter.

For some applications, radially expanding the cage includes radially expanding the cage such that, for each of the struts that include the undulated portions, a ratio of:
a shortest distance from a first longitudinal end of the strut to a second longitudinal end of the strut when the cage is its axially-elongated configuration, to
a shortest distance from the first longitudinal end of the strut to the second longitudinal end of the strut when the cage is its radially-expanded configuration,
is greater than 1.05:1.

For some applications, radially expanding the cage includes radially expanding the cage such that, for each of the struts that include the undulated portions, the ratio is less than 1.4:1. For some applications, radially expanding the cage includes radially expanding the cage such that, for each of the struts that include the undulated portions, the ratio is greater than 1.15:1. For some applications, radially expanding the cage includes radially expanding the cage such that, for each of the struts that include the undulated portions, the ratio is greater than 1.2:1.

For some applications, the method further includes operating the control unit to:
measure flow through the blood vessel; and
control rotation of the impeller responsively to the measured flow.

For some applications, operating the control unit to measure flow through the blood vessel includes operating the control unit to measure blood flow via a thermal flow sensor that is disposed within a housing, the housing being configured such that blood flow through the housing is substantially in a direction parallel to a local longitudinal axis of the blood vessel.

There is further provided in accordance with some applications of the present invention, a method including:
placing a radially expandable structure inside a blood vessel of a subject, the blood vessel having a given diameter in an absence of the radially expandable structure;
widening a portion of the blood vessel such that a diameter of the portion of the blood vessel is greater than the given diameter, by expanding the radially expandable structure inside the portion of the blood vessel;

placing an impeller inside the portion of the blood vessel, the impeller including impeller blades, a span of the impeller blades being at least equal to the given diameter; and operating a control unit to pump blood through the blood vessel by rotating the impeller with respect to the blood vessel.

For some applications, expanding the radially-expandable structure includes expanding a radially-expandable cage that is disposed around the impeller such that the impeller is separated from an inner wall of the blood vessel by the cage.

For some applications, the blood vessel includes a renal vein, and operating the control unit to pump blood through the blood vessel includes operating the control unit to pump blood away from a kidney of the subject toward a vena cava of the subject.

For some applications, the method further includes operating the control unit to:

measure pressure within the subject's blood vessel at a first location within the blood vessel that is upstream of the impeller, and at a second location within the blood vessel that is downstream of the impeller; and control rotation of the impeller responsively to the pressure measured at the first and second locations.

For some applications, the method further includes operating the control unit to:

measure flow through the blood vessel; and control rotation of the impeller responsively to the measured flow.

For some applications, operating the control unit to measure flow through the blood vessel includes operating the control unit to measure blood flow via a thermal flow sensor that is disposed within a housing, the housing being configured such that blood flow through the housing is substantially in a direction parallel to a local longitudinal axis of the blood vessel.

For some applications, widening the portion of the blood vessel includes widening the portion of the blood vessel such that the diameter of the portion of the blood vessel is greater than 105 percent of the given diameter, by expanding the radially expandable structure inside the portion of the blood vessel. For some applications, widening the portion of the blood vessel includes widening the portion of the blood vessel such that the diameter of the portion of the blood vessel is greater than 115 percent of the given diameter, by expanding the radially expandable structure inside the portion of the blood vessel. For some applications, widening the portion of the blood vessel includes widening the portion of the blood vessel such that the diameter of the portion of the blood vessel is less than 125 percent of the given diameter, by expanding the radially expandable structure inside the portion of the blood vessel.

There is further provided, in accordance with some applications of the present invention, apparatus including:

a blood pump configured to pump blood through a blood vessel of a subject, the blood pump including:

an elongate element; and an impeller disposed at a distal end of the elongate element, and configured to pump blood through the blood vessel by rotating;

a thermal flow sensor configured to measure flow of the pumped blood, the thermal flow sensor including an upstream temperature sensor, a heating element and a downstream temperature sensor, disposed sequentially along a portion of a length of the elongate element, the elongate element including a housing that is configured to house the thermal flow sensor, and that is configured such that blood flow through the housing is substantially in a direction parallel to a local longitudinal axis of the blood vessel.

For some applications, the housing includes a portion of an outer surface of the elongate element that is shaped to define an indentation therein, and the upstream temperature sensor, the heating element, and the downstream temperature sensor are disposed sequentially along the indentation.

For some applications, a ratio of a length of the indentation to a width of the indentation is greater than 4:1.

For some applications, the apparatus further includes a cover coupled to the elongate element and disposed such as to cover the thermal sensor.

For some applications, the housing includes a housing disposed on an outer surface of the elongate element, and the upstream temperature sensor, the heating element, and the downstream temperature sensor are disposed sequentially along an inside of the housing.

For some applications, the housing includes a compressible tube disposed on the outer surface of the elongate element.

For some applications, a ratio of a length of the housing to a width of the housing is greater than 4:1. For some applications, a ratio of the length of the housing to a height of the housing is greater than 4:1.

There is additionally provided, in accordance with some applications of the present invention, a method including:

placing into a blood vessel of a subject a blood pump that includes:

an elongate element; and an impeller disposed at a distal end of the elongate element;

operating a control unit to measure flow of the pumped blood, using a thermal flow sensor that includes an upstream temperature sensor, a heating element, and a downstream temperature sensor disposed sequentially along a portion of a length of the elongate element, the elongate element including a housing that is configured to house the thermal flow sensor, and that is configured such that blood flow through the housing is substantially in a direction parallel to a local longitudinal axis of the blood vessel; and operating the control unit to pump blood through the blood vessel by rotating the impeller, at least partially in response to the measured flow.

There is further provided, in accordance with some applications of the present invention, apparatus including:

a pump configured to pump a fluid including:

an elongate element; and an impeller disposed at a distal end of the elongate element, and configured to pump the fluid by rotating;

a thermal flow sensor configured to measure flow of the pumped fluid, the thermal flow sensor including an upstream temperature sensor, a heating element, and a downstream temperature sensor disposed sequentially along a portion of a length of the elongate element, the elongate element including a housing that is configured to house the thermal flow sensor, and that is configured such that flow of the fluid through the housing is substantially in a direction parallel to a local longitudinal axis of the elongate element.

For some applications, the housing includes a portion of an outer surface of the elongate element that is shaped to define an indentation therein, and the upstream temperature sensor, the heating element, and the downstream temperature sensor are disposed sequentially along the indentation.

For some applications, a ratio of a length of the indentation to a width of the indentation is greater than 4:1.

For some applications, the apparatus further includes a cover coupled to the elongate element and disposed such as to cover the thermal sensor.

For some applications, the housing includes a housing disposed on an outer surface of the elongate element, and the upstream temperature sensor, the heating element, and the downstream temperature sensor are disposed sequentially along an inside of the housing.

For some applications, the housing includes a compressible tube disposed on the outer surface of the elongate element.

For some applications, a ratio of a length of the housing to a width of the housing is greater than 4:1. For some applications, a ratio of the length of the housing to a height of the housing is greater than 4:1.

There is further provided, in accordance with some applications of the present invention, a method for use with a plurality of tributary veins that supply a main vein, including:
mechanically isolating blood within the plurality of veins into a compartment that is separated from blood flow within the main vein; and
controlling blood flow from the plurality of veins to the major vein by pumping blood from the compartment to the main vein.

For some applications, the method further includes performing ultrafiltration on the pumped blood.

For some applications,
isolating the plurality of veins includes:
placing into the main vein a blood-impermeable sleeve and a helical support element disposed around the sleeve, and
coupling the sleeve to a wall of the main vein using the helical support element; and
pumping blood from the compartment to the main vein includes guiding a distal portion of a blood pump into the compartment using the helical support element and pumping the blood using the blood pump.

For some applications:
isolating the plurality of veins includes:
placing into the main vein a blood-impermeable sleeve and a helical portion of a blood pump that is disposed around the sleeve and configured to support the sleeve, and
coupling the sleeve to a wall of the main vein; and
pumping blood from the compartment to the main vein includes pumping blood into inlet holes of the blood pump that are defined by the helical portion of the blood pump.

For some applications:
isolating blood within the plurality of veins into a compartment that is separated from blood flow within the main vein includes isolating blood in renal veins of the subject into a compartment that is separated from blood flow within a vena cava of the subject by placing a blood-impermeable sleeve in the subject's vena cava, such that a downstream end of the sleeve is coupled to a wall of the vena cava at a first location that is downstream of all of the renal veins of the subject, and such that an upstream end of the sleeve is coupled to the wall of the vena cava at a second location that is upstream of all the renal veins of the subject; and
pumping blood from the compartment to the main vein includes operating a pump to pump blood from the compartment to a location that is in fluid communication with an interior of the sleeve.

For some applications, pumping blood from the compartment includes drawing blood in a downstream direction through the renal veins.

For some applications, placing the sleeve in the vena cava includes placing the sleeve in the vena cava for less than one week, and operating the pump includes operating the pump for less than one week.

For some applications, the method further includes identifying the subject as a subject suffering from a condition selected from the group consisting of: cardiac dysfunction, congestive heart failure, reduced renal blood flow, increased renal vascular resistance, arterial hypertension, and kidney dysfunction, and operating the pump includes, in response to identifying the subject as suffering from the condition, reducing blood pressure within the subject's renal veins by operating the pump.

For some applications, placing the sleeve in the subject's vena cava includes anchoring the sleeve to the vena cava by causing the vena cava to constrict around at least a portion of the sleeve, by operating the pump.

For some applications, operating the pump to pump blood from the compartment to the location that is in fluid communication with an interior of the sleeve includes operating the pump to pump blood from the compartment to a site of the vena cava that is upstream of the sleeve.

For some applications, operating the pump to pump blood from the compartment to the location that is in fluid communication with an interior of the sleeve includes operating the pump to pump blood from the compartment to a site of the vena cava that is downstream of the sleeve.

For some applications, placing the sleeve in the vena cava includes placing into the vena cava:
a stent shaped to define widened upstream and downstream ends thereof that are widened relative to a central portion of the stent, and
a blood-impermeable sleeve coupled to the stent, the sleeve defining flared upstream and downstream ends thereof that are coupled, respectively, to the widened upstream and downstream ends of the stent; and
coupling the stent to the blood vessel such that:
in response to blood pressure on a first side of at least one of the flared ends of the sleeve being greater than blood pressure on a second side of the at least one flared end of the sleeve, blood flows between an outside of the at least one flared end of the sleeve and an inner wall of the blood vessel, and
in response to blood pressure on the first side of the at least one flared end of the sleeve being less than blood pressure on the second side of the at least one flared end of the sleeve, the at least one flared end of the sleeve occludes blood flow between the outside of the at least one flared end of the sleeve and the inner wall of the blood vessel by contacting the inner wall of the blood vessel.

For some applications, placing the sleeve in the vena cava includes placing into the vena cava:
a sleeve that is shaped to define flared ends thereof, and a narrow central portion between the flared ends, and
a stent shaped to define:
a sleeve-supporting frame that is shaped to define widened ends thereof, and a narrow central portion between the widened ends that is narrower than the widened ends of the stent, the sleeve being coupled to the sleeve-supporting frame of the stent; and a vessel-wall-supporting frame coupled to the narrow central portion of the sleeve-supporting frame and radially protruding from the sleeve-supporting frame.

For some applications, pumping blood from the compartment includes pumping blood from a site between an outside of the sleeve and an inner wall of the vena cava.

For some applications, the method further includes inserting the pump into the compartment via an opening in the sleeve through which the pump is insertable.

For some applications, inserting the pump through the opening includes inserting the pump through an opening having a diameter that is between 2 mm and 10 mm.

For some applications, inserting the pump through the opening includes inserting the pump through the opening such that the opening forms a seal around the pump.

For some applications, the method further includes inserting the pump into the compartment via a pump-accommodating sleeve that protrudes from the sleeve.

For some applications, inserting the pump into the compartment via the pump-accommodating sleeve includes inserting the pump into the compartment via a pump-accommodating sleeve having a diameter that is between 2 mm and 10 mm.

For some applications, inserting the pump into the compartment via the pump-accommodating sleeve includes inserting the pump into the compartment via the pump-accommodating sleeve such that the pump-accommodating sleeve forms a seal around the pump.

There is further provided, in accordance with some applications of the present invention, apparatus, including:

a blood-impermeable sleeve;

at least one support structure configured to couple first and second ends of the sleeve to a blood vessel of a subject; and a pump configured to pump blood from an exterior of the sleeve to a location that is in fluid communication with an interior of the sleeve.

For some applications, the pump is configured to perform ultrafiltration on the blood.

For some applications, the pump is configured to anchor the structure to the blood vessel by causing the blood vessel to constrict around at least a portion of the structure.

For some applications,
the structure includes a stent shaped to define widened ends thereof that are widened relative to a central portion of the stent, and
the sleeve includes a sleeve that is coupled to the stent, the sleeve defining flared ends thereof that are coupled to the widened ends of the stent,
at least one of the flared ends of the sleeve being configured to act as a valve by at least partially separating from widened end of the stent to which it is coupled in response to pressure being applied to the flared end of the sleeve.

For some applications:
the support structure includes a helical support element disposed around the sleeve, and
a distal portion of the blood pump is configured to be guided such as to be disposed around the exterior of the sleeve using the helical support element.

For some applications:
the support structure includes a helical portion of the blood pump that is disposed around the sleeve and configured to support the sleeve, and the pump is configured to pump blood from the exterior of the sleeve by pumping blood into inlet holes of the pump that are defined by the helical portion of the blood pump.

For some applications:
the sleeve is shaped to define flared ends thereof, and a narrow central portion between the flared ends;
the structure includes a stent shaped to define:
a sleeve-supporting frame that is shaped to define widened ends thereof, and a narrow central portion between the widened ends that is narrower than the widened ends of the stent, the sleeve being coupled to the sleeve-supporting frame of the stent; and
a vessel-wall-supporting frame coupled to the narrow central portion of the sleeve-supporting frame and radially protruding from the sleeve-supporting frame.

For some applications, the pump is configured to pump blood from a site between an outside of the sleeve and an inner wall of the blood vessel by being placed between the outside of the sleeve and the vessel-wall-supporting frame.

For some applications, the structure is configured to isolate blood in a renal vein of the subject into a compartment that is separated from blood flow within a vena cava of the subject, by coupling a downstream end of the sleeve to a wall of the vena cava at a first location that is downstream of all renal veins of the subject, and by coupling an upstream end of the sleeve to a wall of the vena cava at a second location that is upstream of all renal veins of the subject.

For some applications, the sleeve is configured to be coupled to the vena cava for less than one week, and the pump is configured to operate for less than one week.

For some applications, the pump is configured to reduce blood pressure within the subject's renal veins by pumping blood.

For some applications, the pump is configured to pump blood from the compartment to a site within the vena cava.

For some applications, the pump is configured to pump blood from the compartment to a site of the vena cava that is upstream of the sleeve.

For some applications, the pump is configured to pump blood from the compartment to a site of the vena cava that is downstream of the sleeve.

For some applications, the sleeve is shaped to define an opening through which the pump is insertable.

For some applications, a diameter of the opening is between 2 mm and 10 mm.

For some applications, the opening is sized such as to form a seal around the pump.

For some applications, the apparatus further includes a pump-accommodating sleeve protruding from the blood-impermeable sleeve, the pump accommodating sleeve being configured to accommodate insertion of the pump therethrough to the exterior of the blood impermeable sleeve.

For some applications, an inner diameter of the pump-accommodating sleeve is between 2 mm and 10 mm.

For some applications, the pump-accommodating sleeve is sized such as to form a seal around the pump.

There is additionally provided, in accordance with some applications of the present invention, a method including:
placing a stent inside a blood vessel at a placement location of the stent; and
at least partially anchoring the stent to the blood vessel at the placement location by causing the blood vessel to constrict around at least a portion of the stent, by applying a suctioning force within the blood vessel.

For some applications, the blood vessel includes a blood vessel having a given diameter at the placement location, and placing the stent inside the blood vessel includes placing inside the blood vessel a stent having a diameter that is less than the given diameter.

For some applications, causing the blood vessel to constrict around at least the portion of the stent includes reducing an extent to which the stent is anchored to the blood vessel by virtue of oversizing of the stent, relative to if the blood vessel were not caused to constrict around at least the portion of the stent.

There is further provided, in accordance with some applications of the present invention, apparatus including:
 a stent configured to be placed inside a blood vessel at a placement location of the stent;
 a pump configured to anchor the stent to the blood vessel at the placement location by causing the blood vessel to constrict around at least a portion of the stent, by applying a suctioning force within the blood vessel.

For some applications, the blood vessel includes a blood vessel having a given diameter at the placement location, and the stent includes a stent having a diameter that is less than the given diameter.

There is additionally provided, in accordance with some applications of the present invention, apparatus including:
 a stent configured to be placed inside a blood vessel, the stent being shaped to define widened ends thereof that are widened relative to a central portion of the stent; and
 a blood-impermeable sleeve coupled to the stent,
  the sleeve defining flared ends thereof that are coupled to the widened ends of the stent,
  at least one of the flared ends of the sleeve being configured to act as a valve by at least partially separating from widened end of the stent to which it is coupled in response to pressure being applied to the flared end of the sleeve.

There is further provided, in accordance with some applications of the present invention, a method including:
 placing into a blood vessel of a subject:
  a stent shaped to define widened upstream and downstream ends thereof that are widened relative to a central portion of the stent, and
  a blood-impermeable sleeve coupled to the stent, the sleeve defining flared upstream and downstream ends thereof that are coupled, respectively, to the widened upstream and downstream ends of the stent; and
 coupling the stent to the blood vessel such that:
  in response to blood pressure on a first side of at least one of the flared ends of the sleeve being greater than blood pressure on a second side of the at least one flared end of the sleeve, blood flows between an outside of the at least one flared end of the sleeve and an inner wall of the blood vessel, and
  in response to blood pressure on the first side of the at least one flared end of the sleeve being less than blood pressure on the second side of the at least one flared end of the sleeve, the at least one flared end of the sleeve occludes blood flow between the outside of the at least one flared end of the sleeve and the inner wall of the blood vessel by contacting the inner wall of the blood vessel.

There is additionally provided, in accordance with some applications of the present invention, apparatus including:
 a blood-impermeable sleeve defining flared ends thereof, and a narrow central portion between the flared ends; and
 a stent configured to be placed inside a blood vessel, the stent being shaped to define:
  a sleeve-supporting frame that is shaped to define widened ends thereof, and a narrow central portion between the widened ends that is narrower than the widened ends of the stent, the sleeve being coupled to the sleeve-supporting frame of the stent; and
  a vessel-wall-supporting frame coupled to the narrow central portion of the sleeve-supporting frame and radially protruding from the sleeve-supporting frame.

For some applications, the apparatus further includes a blood pump, the blood pump being configured to pump blood from between an outside of the sleeve and an inner wall of the blood vessel by being placed between the outside of the sleeve and the vessel-wall-supporting frame.

For some applications, a diameter of the narrow central portion of the sleeve is between 8 mm and 35 mm.

For some applications, a maximum diameter of the flared ends of the sleeve is between 10 mm and 45 mm.

For some applications, a ratio of a maximum diameter of the flared ends of the sleeve, and a diameter of the narrow central portion of the sleeve is between 1.1:1 and 2:1.

For some applications, a maximum diameter of the vessel-wall-supporting frame is between 10 mm and 50 mm.

For some applications, a ratio of a maximum diameter of the wall-supporting frame to a diameter of the narrow central portion of the sleeve-supporting frame is between 1.1:1 and 5:1. For some applications, the ratio is greater than 1.5:1.

For some applications, a length of the sleeve is greater than 6 mm. For some applications, the length of the sleeve is less than 80 mm. For some applications, a length of each one of the flared ends of the sleeve is greater than 3 mm. For some applications, the length of each one of the flared ends of the sleeve is less than 40 mm. For some applications, a length of the narrow central portion of the sleeve is greater than 3 mm. For some applications, the length of the narrow central portion of the sleeve is less than 70 mm.

There is additionally provided, in accordance with some applications of the present invention, a method including:
 placing into a blood vessel of a subject:
  a blood-impermeable sleeve defining flared ends thereof, and a narrow central portion between the flared ends, and
  a stent shaped to define:
   a sleeve-supporting frame that is shaped to define widened ends thereof, and a narrow central portion between the widened ends that is narrower than the widened ends, the sleeve being coupled to the sleeve-supporting frame of the stent; and
   a vessel-wall-supporting frame coupled to the narrow central portion of the sleeve-supporting frame and radially protruding from the sleeve-supporting frame; and
 coupling the stent to the blood vessel such that the vessel-wall-supporting frame of the stent holds open the blood vessel by supporting the wall of the blood vessel, and the sleeve-supporting frame supports the sleeve within the blood vessel.

For some applications, the method further includes pumping blood from a site between an outside of the sleeve and an inner wall of the blood vessel by placing a pump between the outside of the sleeve and the vessel-wall-supporting frame.

For some applications, placing the sleeve into the blood vessel includes placing the sleeve into the blood vessel, a diameter of the narrow central portion of the sleeve being between 8 mm and 35 mm.

For some applications, placing the sleeve into the blood vessel includes placing the sleeve into the blood vessel, a maximum diameter of the flared ends of the sleeve being between 10 mm and 45 mm.

For some applications, placing the sleeve into the blood vessel includes placing the sleeve into the blood vessel, a ratio of a maximum diameter of the flared ends of the sleeve, and a diameter of the narrow central portion of the sleeve being between 1.1:1 and 2:1.

For some applications, placing the stent into the blood vessel includes placing the stent into the blood vessel, a maximum diameter of the vessel-wall-supporting frame being between 10 mm and 50 mm.

For some applications, placing the stent into the blood vessel includes placing the stent into the blood vessel, a ratio of a maximum diameter of the wall-supporting frame to a diameter of the narrow central portion of the sleeve-supporting frame being between 1.1:1 and 5:1. For some applications, placing the stent into the blood vessel includes placing the stent into the blood vessel, the ratio being greater than 1.5:1.

For some applications, placing the sleeve into the blood vessel includes placing the sleeve into the blood vessel, a length of the sleeve being greater than 6 mm. For some applications, placing the sleeve into the blood vessel includes placing the sleeve into the blood vessel, the length of the sleeve being less than 80 mm. For some applications, placing the sleeve into the blood vessel includes placing the sleeve into the blood vessel, a length of each one of the flared ends of the sleeve being greater than 3 mm. For some applications, placing the sleeve into the blood vessel includes placing the sleeve into the blood vessel, the length of each one of the flared ends of the sleeve being less than 40 mm. For some applications, placing the sleeve into the blood vessel includes placing the sleeve into the blood vessel, a length of the narrow central portion of the sleeve being greater than 3 mm. For some applications, placing the sleeve into the blood vessel includes placing the sleeve into the blood vessel, the length of the narrow central portion of the sleeve being less than 70 mm.

There is further provided, in accordance with some applications of the present invention, a method for operating a blood pump disposed inside a blood vessel of a subject, the method including:
  placing an occlusion element in the blood vessel, the occlusion element having an occluding state thereof, in which the occlusion element occludes the blood vessel, and a non-occluding state thereof in which the occlusion element does not occlude the blood vessel;
  drawing blood in a downstream direction from a site that is in fluid communication with an upstream side of the occlusion element;
  pumping blood into a site of the subject's vasculature that is in fluid communication with a downstream side of the occlusion element,
  the pumping of the blood into the subject's vasculature being performed in a manner that maintains the occlusion element in an occluding state thereof, in which state the occlusion element occludes the blood vessel.

For some applications, the method further includes performing ultrafiltration on the blood prior to pumping the blood into the site of the subject's vasculature.

For some applications, placing the occlusion element in the blood vessel includes placing the occlusion element in the blood vessel for less than one week, and pumping the blood includes pumping the blood into the vasculature for less than one week. For some applications, placing the occlusion element in the blood vessel includes placing the occlusion element in the blood vessel for more than one week, and pumping the blood includes pumping the blood into the vasculature for less than one week.

For some applications, the method further includes identifying the subject as a subject suffering from a condition selected from the group consisting of: cardiac dysfunction, congestive heart failure, reduced renal blood flow, increased renal vascular resistance, arterial hypertension, and kidney dysfunction, the blood vessel includes a renal vein of the subject, and drawing blood in the downstream direction from the site that is in fluid communication with the upstream side of the occlusion element includes, in response to identifying the subject as suffering from the condition, reducing blood pressure within the subject's renal vein by drawing the blood in the downstream direction.

For some applications, pumping the blood into the subject's vasculature in the manner that maintains the occlusion element in the occluding state thereof includes pumping the blood into the subject's vasculature such that hydrodynamic pressure of the blood that is pumped into the subject's vasculature maintains the occlusion element in the occluding state thereof.

For some applications, placing the occlusion element in the blood vessel includes placing within the blood vessel a valve having valve leaflets, and pumping the blood into the subject's vasculature such that hydrodynamic pressure of the blood that is pumped into the subject's vasculature maintains the occlusion element in the occluding state thereof includes pumping the blood into the subject's vasculature such that the blood that is pumped into the subject's vasculature directly impacts downstream sides of the valve leaflets.

For some applications, placing the valve within the blood vessel includes placing the valve within the blood vessel such that:
  in response to blood pressure on an upstream side of the valve leaflets exceeding pressure on the downstream side of the valve leaflets, blood flows in an antegrade direction between cusps of the valve leaflets and an inner wall of the blood vessel, and
  in response to blood pressure on the downstream side of the valve leaflets exceeding pressure on the upstream side of the valve leaflets, the valve occludes retrograde blood flow by the cusps of the valve leaflets contacting the inner wall of the blood vessel.

For some applications, pumping the blood into the subject's vasculature such that the blood that is pumped into the subject's vasculature directly impacts downstream sides of the valve leaflets includes reducing blood clots at the valve leaflets, by flushing the valve leaflets.

For some applications, the method further includes pumping an anticoagulation agent into the subject's vasculature together with the blood that is pumped into the subject's vasculature, such that the anticoagulation agent directly impacts the valve leaflets.

For some applications, placing the valve in the blood vessel includes maintaining portions of the valve leaflets in contact with a wall of the blood vessel by inflating a balloon.

For some applications, placing the valve in the blood vessel includes maintaining portions of the valve leaflets in contact with a wall of the blood vessel by expanding portions of a slit tube radially outwardly.

For some applications, pumping the blood such that the blood directly impacts the downstream sides of the valve leaflets includes pumping the blood into the subject's vasculature via holes that are shaped to direct the blood toward the downstream sides of the valve leaflets.

For some applications, pumping the blood such that the blood directly impacts the downstream sides of the valve leaflets includes pumping the blood into the subject's vasculature via a pump catheter that is shaped to define a radial protrusion therefrom that is concavely curved toward a distal end of the catheter, the radial protrusion being configured to direct blood that is pumped into the vasculature toward the valve leaflets.

For some applications, pumping the blood such that the blood directly impacts the downstream sides of the valve leaflets includes pumping the blood into the subject's vasculature via holes that are disposed adjacent to bases of the valve leaflets.

For some applications, pumping the blood such that the blood directly impacts the downstream sides of the valve leaflets includes pumping the blood into the subject's vasculature via holes that are disposed adjacent to a location along lengths of the valve leaflets that is below midway between cusps of the leaflets and bases of the leaflets.

There is further provided, in accordance with some applications of the present invention, apparatus for use with a blood vessel of a subject, the apparatus including:

an occlusion element configured to be placed in the blood vessel, the occlusion element having an occluding state thereof, in which the occlusion element occludes the blood vessel, and a non-occluding state thereof in which the occlusion element does not occlude the blood vessel;

a blood pump configured to:
draw blood in a downstream direction from a site that is in fluid communication with an upstream side of the occlusion element, and
pump blood into the subject's vasculature at a site that is in fluid communication with a downstream side of the occlusion element, the pump being configured to perform the pumping of the blood into the blood vessel in a manner that maintains the occlusion element in the occluding state thereof.

For some applications, the blood pump is configured to perform ultrafiltration of the blood prior to pumping the blood into the subject's vasculature.

For some applications, the occlusion element is configured to be placed in the blood vessel for less than one week, and the pump is configured to pump blood into the vasculature for less than one week. For some applications, the occlusion element is configured to be placed in the blood vessel for more than one week, and the pump is configured to pump blood into the vasculature for less than one week.

For some applications, the pump is configured to perform the pumping of the blood into the subject's vasculature in the manner that maintains the occlusion element in the occluding state thereof, by pumping the blood into the subject's vasculature such that hydrodynamic pressure of the blood that is pumped into the subject's vasculature maintains the occlusion element in the occluding state thereof.

For some applications, the occlusion element includes a valve having valve leaflets, and the pump is configured to pump the blood into the subject's vasculature such that the hydrodynamic pressure of the blood maintains the occlusion element in the occluding state thereof by pumping the blood into the subject's vasculature such that the blood that is pumped into the subject's vasculature directly impacts downstream sides of the valve leaflets.

For some applications, the valve is configured such that:
in response to blood pressure on an upstream side of the valve leaflets exceeding pressure on the downstream side of the valve leaflets, blood flows in an antegrade direction between cusps of the valve leaflets and an inner wall of the blood vessel, and
in response to blood pressure on the downstream side of the valve leaflets exceeding pressure on the upstream side of the valve leaflets, the valve closes by the cusps of the valve leaflets contacting the inner wall of the blood vessel.

For some applications, the pump, by pumping the blood into the subject's vasculature such that the blood that is pumped into the subject's vasculature directly impacts downstream sides of the valve leaflets, is configured to reduce blood clots at the valve leaflets by flushing the valve leaflets.

For some applications, the apparatus is for use with an anticoagulation agent, and the pump is configured to pump the anticoagulation agent into the subject's vasculature together with the blood that is pumped into the subject's vasculature, such that the anticoagulation agent directly impacts the valve leaflets.

For some applications, the apparatus further includes a balloon configured to maintain portions of the valve leaflets in contact with a wall of the blood vessel by being inflated.

For some applications, the apparatus further includes a slit tube configured to be inserted into the blood vessel and to maintain portions of the valve leaflets in contact with a wall of the blood vessel by portions of the slit tube between the slits being expanded radially outwardly.

For some applications, the blood pump is configured to be coupled to the valve, the blood pump includes outlet holes via which the blood is pumped into the subject's vasculature, and the outlet holes are shaped such that when the blood pump is coupled to the valve, the outlet holes direct the blood toward the downstream sides of the valve leaflets.

For some applications, the blood pump is configured to be coupled to the valve, the blood pump includes a blood pump catheter that defines a radial protrusion therefrom that is concavely curved toward a distal end of the catheter, the radial protrusion being configured such that, when the blood pump is coupled to the valve, the radial protrusion directs blood that is pumped into the vasculature toward the valve leaflets.

For some applications, the blood pump is configured to be coupled to the valve, the blood pump includes outlet holes via which the blood is pumped into the subject's vasculature, and the outlet holes are disposed on the blood pump such that, when the blood pump is coupled to the valve, the holes are disposed adjacent to bases of the valve leaflets.

For some applications, the outlet holes are disposed on the blood pump such that, when the blood pump is coupled to the valve, the outlet holes are disposed adjacent to a location along lengths of the valve leaflets that is below midway between cusps of the leaflets and bases of the leaflets.

There is further provided, in accordance with some applications of the present invention, apparatus for use with a blood vessel of a subject, the apparatus including:
a blood pump configured to draw blood in a downstream direction through the blood vessel into the pump; and
a valve including rigid portions thereof, the rigid portions being configured to couple the valve to the blood vessel, the valve being configured to be coupled to a distal portion of the blood pump and to prevent blood from flowing past the valve in a retrograde direction.

For some applications, the valve further includes flexible valve leaflets that are coupled to the rigid portions of the valve.

There is additionally provided, in accordance with some applications of the present invention, a method including:
providing a prosthetic valve that defines valve leaflets; and
placing the valve in a blood vessel such that:
in response to blood pressure on the upstream side of the valve leaflets exceeding pressure on the downstream side of the valve leaflets, blood flows in an antegrade direction between cusps of the valve leaflets and an inner wall of the blood vessel, and
in response to blood pressure on the downstream side of the valve leaflets exceeding pressure on the upstream side of the valve leaflets, the valve closes by the cusps of the valve leaflets contacting the inner wall of the blood vessel.

There is further provided, in accordance with some applications of the present invention, apparatus including:
a prosthetic valve that includes flexible valve leaflets and a rigid valve frame, the valve leaflets being coupled to the valve frame such that:
in response to pressure on a first side of the valve leaflets exceeding pressure on a second side of the valve leaflets, the leaflets open by cusps of the valve leaflets separating from the rigid frame, and
in response to blood pressure on the second side of the valve leaflets exceeding pressure on the first side of the valve leaflets, the valve closes by the cusps of the leaflets contacting the rigid frame.

There is additionally provided, in accordance with some applications of the present invention, apparatus including:
a blood pump, including:
a tube;
first and second unidirectional valves disposed, respectively, at proximal and distal ends of the tube;
a membrane coupled to the inside of the tube such as to partition the tube into a first compartment that is in fluid communication with the valves, and a second compartment that is not in fluid communication with the valves; and
a pumping mechanism configured to pump fluid through the tube by increasing and subsequently decreasing the size of the first compartment by moving the membrane with respect to the tube.

For some applications, the tube includes a stent, and material disposed on the stent.

For some applications, the occlusion element is configured to be placed in a blood vessel for less than one week.

For some applications, one of the valves is configured to prevent backflow of blood from the tube into the blood vessel and a second one of the valves is configured to prevent backflow of blood from the blood vessel into the tube.

For some applications, the blood pump is configured to be placed in a renal vein of a subject and to pump blood in a downstream direction from the renal vein to a vena cava of the subject.

For some applications, the blood pump is configured to occlude backflow of blood from the vena cava to the renal vein.

There is additionally provided, in accordance with some applications of the present invention, a method, including:

coupling a tube to an inner wall of a blood vessel of a subject,
first and second unidirectional valves being disposed, respectively, at proximal and distal ends of the tube, and
a membrane being coupled to the inside of the tube, such as to partition the tube into a first compartment that is in fluid communication with the valves, and a second compartment that is not in fluid communication with the valves; and
operating a pumping mechanism to pump blood through the tube by increasing and subsequently decreasing the size of the first compartment, by moving the membrane with respect to the tube.

For some applications, the tube includes a stent and material disposed on a stent, and coupling the tube to the inner wall of the blood vessel includes coupling the stent and the material to the inner wall of the blood vessel.

For some applications, coupling the tube to the inner wall of the blood vessel includes coupling the tube to the inner wall of the blood vessel for less than one week.

For some applications, operating the pumping mechanism includes operating the pumping mechanism such that one of the valves prevents backflow of blood from the tube into the blood vessel and a second one of the valves prevents backflow of blood from the blood vessel into the tube.

For some applications, coupling the tube to the inner wall of the blood vessel includes coupling the tube to an inner wall of a renal vein of a subject, and operating the pumping mechanism includes pumping blood in a downstream direction from the renal vein to a vena cava of the subject.

For some applications, coupling the tube to the inner wall of the renal vein includes occluding backflow of blood from the vena cava to the renal vein.

For some applications, the method further includes identifying the subject as a subject suffering from a condition selected from the group consisting of: cardiac dysfunction, congestive heart failure, reduced renal blood flow, increased renal vascular resistance, arterial hypertension, and kidney dysfunction, and operating the pump includes, in response to identifying the subject as suffering from the condition, reducing blood pressure within the subject's renal vein by operating the pump to pump blood in the downstream direction from the renal vein to the vena cava.

There is further provided, in accordance with some applications of the present invention, a method including:
operating a blood pump to pump blood in a downstream direction through a first vein, the first vein being a tributary of a second vein and forming a junction with the second vein; and
preventing backflow of blood from the second vein to the first vein by covering an ostium at the junction with an ostium-covering umbrella disposed in the second vein.

For some applications, operating the blood pump includes performing ultrafiltration on the pumped blood.

For some applications, the ostium-covering umbrella includes an ostium-covering umbrella having a diameter of more than 6 mm when in an open configuration, and covering the ostium with the umbrella includes covering the ostium with the umbrella having a diameter of more than 6 mm.

For some applications, operating the blood pump includes causing the ostium-covering umbrella to become sealed against a wall of the second vein surrounding the ostium.

For some applications, the first vein includes a renal vein of the subject, and the second vein includes a vena cava of the subject, and pumping blood in the downstream direction includes pumping blood in a downstream direction from the renal vein toward the vena cava.

For some applications, preventing backflow of blood from the second vein to the first vein includes preventing backflow of blood from the vena cava to the renal vein.

For some applications, the method further includes identifying the subject as a subject suffering from a condition selected from the group consisting of: cardiac dysfunction, congestive heart failure, reduced renal blood flow, increased renal vascular resistance, arterial hypertension, and kidney dysfunction, and operating the pump includes, in response to identifying the subject as suffering from the condition, reducing blood pressure within the subject's renal vein by operating the pump to pump blood in the downstream direction from the renal vein to the vena cava.

There is further provided, in accordance with some applications of the present invention, apparatus for use with a first vein of a subject, the first vein being a tributary of a second vein and forming a junction with the second vein, the apparatus including:
 a catheter configured to be placed in the first vein, a distal end of the catheter being configured to pump blood in a downstream direction through the first vein and into the catheter; and
 an ostium-covering umbrella disposed around the outside of the catheter and configured to be placed within the second vein at the junction such that the umbrella prevents backflow of blood from the second vein to the first vein by the ostium-occluding umbrella covering an ostium at the junction from a location within the second vein.

For some applications, the catheter, by pumping the blood is configured to cause the ostium-covering umbrella to become sealed against a wall of the second vein surrounding the ostium.

For some applications, the ostium-covering umbrella has a diameter of more than 6 mm, when in an open configuration.

For some applications, the first vein includes a renal vein of the subject, and the second vein includes a vena cava of the subject, and the catheter is configured to pump blood by pumping blood in a downstream direction from the renal vein.

For some applications, the ostium-covering umbrella is configured to prevent backflow of blood from the vena cava to the renal vein by the ostium-occluding umbrella covering an ostium at a junction of the renal vein and the vena cava, from a location within the vena cava.

There is further provided, in accordance with some applications of the present invention, apparatus including:
 a catheter;
 a pumping mechanism configured to suction fluid into a distal end of the catheter; and
 an ostium-covering umbrella disposed around the outside of the catheter, the umbrella having a diameter of at least 6 mm when in an open configuration thereof.

For some applications, the diameter of the ostium-covering umbrella is between 10 mm and 20 mm. For some applications, the diameter of the ostium-covering umbrella is between 15 mm and 25 mm.

There is additionally provided, in accordance with some applications of the present invention, a method for measuring flow in a blood vessel including:
 occluding the blood vessel with an occlusion element;
 pumping blood from an upstream side of the occlusion element to a downstream side of the occlusion element;
 measuring blood pressure on the upstream and downstream sides of the occlusion element;
 modulating the pumping such that pressure on the downstream side of the occlusion element is equal to pressure on the upstream side of the occlusion element;
 measuring a flow rate of blood through the pump when the pressure on the downstream side of the occlusion element is equal to pressure on the upstream side of the occlusion element;
 designating the measured flow rate as a baseline flow rate; and
 subsequently, measuring a flow rate of blood through the pump relative to the baseline flow rate.

For some applications, the method further includes, in response to designating the baseline flow rate, designating a baseline measure of vascular resistance of the subject, and subsequently, measuring vascular resistance of the subject relative to the baseline vascular resistance.

The present invention will be more fully understood from the following detailed description of embodiments thereof, taken together with the drawings, in which:

BRIEF DESCRIPTION OF THE DRAWINGS

FIGS. 1A-B are schematic illustrations of a healthy subject's right heart during diastole and systole respectively;

FIG. 1C is a set of graphs showing a healthy subject's central venous flow velocity profile and central venous pressure profile with respect to the subject's ECG cycle;

FIGS. 2A-B are schematic illustrations of the right heart of a subject suffering from congestive heart failure, during diastole and systole respectively;

FIG. 2C is a set of graphs showing the central venous flow velocity profile and central venous pressure profile of the subject suffering from congestive heart failure, with respect to the subject's ECG cycle;

FIG. 3A is a schematic illustration of blood flowing back toward the kidneys of a subject suffering from congestive heart failure;

FIG. 3B is a set of graphs showing the central venous flow velocity profile and renal vein pressure profile of the subject suffering from congestive heart failure, with respect to the subject's ECG cycle;

FIGS. 5A-D are schematic illustrations of an inverted valve disposed around a blood pump catheter, in accordance with some applications of the present invention;

FIGS. 6A-G are schematic illustrations of configurations of the blood pump catheter that are used with the inverted valve, in accordance with some applications of the present invention;

FIGS. 9A-D are schematic illustrations of respective stages of a cycle of operation of the blood pump of FIGS. 8A-B, in accordance with some applications of the present invention;

FIGS. 13A-D are schematic illustrations of respective stages in a method of manufacture of an impeller for a blood pump, in accordance with some applications of the present invention;

FIGS. 16A-B are schematic illustrations of a three-bladed impeller for a blood pump, in accordance with some applications of the present invention;

FIG. 17 is a schematic illustration of a radially-expandable cage for use with an impeller-based blood pump, in accordance with some applications of the present invention FIGS. 18Ai-18Aiii are schematic illustrations of respective views and/or configurations of a frame of an impeller, in accordance with some applications of the present invention;

FIGS. 18Bi-18Biii are schematic illustrations of respective views and/or configurations of a frame of an impeller, the impeller frame of FIGS. 18B1-18Biii being configured to define blades that span a larger transverse area than those of the impeller frame shown in FIGS. 18Ai-18Aiii, in accordance with some applications of the present invention;

FIGS. 19A-B are schematic illustrations of an impeller cage that is shaped to define a generally cylindrical central portion in the absence of any force being applied to the cage, in accordance with some applications of the present invention;

FIG. 21A is a schematic illustration of impeller-based blood pumps inserted into a subject's left and right renal veins via the subject's femoral vein, in accordance with some applications of the present invention;

FIGS. 22Ai-ii, 22Bi-ii, and 22Ci-ii are schematic illustrations of a thermal flow sensor and a housing that houses the thermal flow sensor, in accordance with some applications of the present invention.

DETAILED DESCRIPTION OF EMBODIMENTS

Figure 4A:
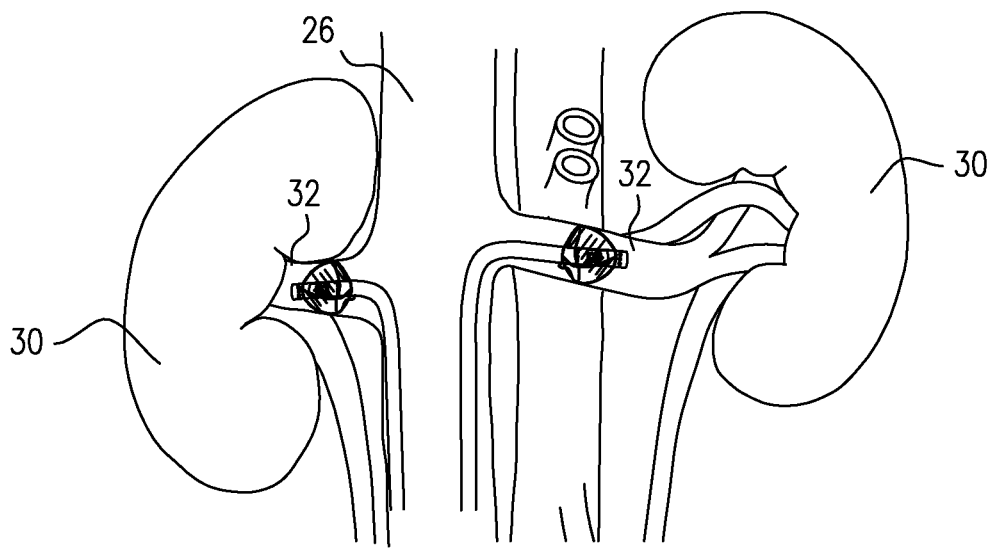
FIG. 4A is a schematic illustration of a pump and an occlusion element placed in left and right renal veins of a subject suffering from congestive heart failure, in accordance with some applications of the present invention.

Reference is now made to FIGS. 1A-B, which are schematic illustrations of a healthy subject's heart during diastole and systole respectively. As shown in FIG. 1A, during diastole, blood flows from the subject's right atrium (RA) 20 to the subject's right ventricle (RV) 22. As shown in FIG. 1B, during systole, the tricuspid valve 24, which separates the right ventricle from the right atrium, closes, as the right ventricle pumps blood toward the subject's lungs. During systolic long-axis contraction of the right ventricle, the right atrium fills with blood from the vena cava 26, the right atrium expanding such as to draw blood into the right atrium.

FIG. 1C is a set of graphs showing the central venous flow velocity profile and central venous pressure profile of a healthy subject with respect to the subject's ECG cycle. The flow velocity profile is characterized by biphasic forward flow, with flow during systole being greater than that during diastole. Typically, there is a small amount of reverse flow AR, during atrial contraction. The central venous pressure profile is characterized by relatively low pressure over the duration of the cardiac cycle, with the A-wave (i.e., the pressure during atrial contraction), typically being greater than the V-wave (i.e., the pressure during systole).

Reference is now made to FIGS. 2A-B, which are schematic illustrations of the heart of a subject suffering from congestive heart failure, during diastole and systole respectively. As shown in FIG. 2A, as with the healthy heart, during diastole, blood flows from the subject's right atrium 20 to the subject's right ventricle 22. As shown in FIG. 2B, during systole, due to right atrial pressure being too high, filling of the subject's right atrium is cut short, causing there to be an increase in pressure in the vena cava 26, as the high atrial pressure is transmitted to the vena cava. In some cases (e.g., in cases of very high right atrial pressure, tricuspid regurgitation, or atrial fibrillation), there may be retrograde flow of blood from the right atrium into the vena cava 26, and/or tributaries of the vena cava, due to the filling of the right atrium being cut short.

FIG. 2C is a set of graphs showing the central venous flow velocity profile and central venous pressure profile of the subject suffering from congestive heart failure, with respect to the subject's ECG cycle. The flow velocity profile is characterized by increased retrograde flow AR at the end of diastole, and by antegrade flow during systole being less than that during diastole. For example, in some subjects there is zero flow, or reverse flow during systole. The central venous pressure profile is characterized by relatively high pressure over the duration of the cardiac cycle with the V-wave being particularly high relative to that of a healthy heart, and relative to the subject's A-wave.

Reference is now made to FIG. 3A, which is a schematic illustration of blood flowing back toward the kidneys 30 of a subject suffering from congestive heart failure, via the subject's left and right renal veins 32. FIG. 3B is a set of graphs showing the central venous flow velocity profile and renal vein pressure profile of the subject suffering from congestive heart failure, with respect to the subject's ECG cycle. It is noted that the graphs shown in FIG. 3B are the same as those shown in FIG. 2C, except that the pressure profile shown in FIG. 3B is that of the renal vein, whereas the pressure profile shown in FIG. 2C is the central venous pressure profile. As shown, typically, in the absence of a device placed in the renal vein (as performed, in accordance with some applications of the present invention), and assuming that the renal vein is at the same height as the central venous system, the renal venous pressure profile is identical to the central venous pressure profile. The renal vein pressure profile is characterized by relatively high pressure over the duration of the cardiac cycle, with the V-wave being particularly high relative to that of a healthy heart.

Reference is now made to FIG. 4A, which is a schematic illustration of a blood pump 34 and an occlusion element 36 placed in left and right renal veins 32 of a subject suffering from congestive heart failure, in accordance with some applications of the present invention. The pump and the occlusion element are typically placed inside the subject's renal veins in order to provide acute treatment of a subject suffering from cardiac dysfunction, congestive heart failure, low renal blood flow, high renal vascular resistance, arterial hypertension, and/or kidney dysfunction. For example, the pump and the occlusion element may be placed inside the subject's renal veins for a period of more than one hour (e.g., more than one day), less than one week (e.g., less than four days), and/or between one hour and one week (e.g., between one day and four days). For some applications, the pump and the occlusion element are chronically placed inside the subject's renal veins in order to provide chronic treatment of a subject suffering from cardiac dysfunction, congestive heart failure, low renal blood flow, high renal vascular resistance, arterial hypertension, and/or kidney dysfunction. For some applications, a course of treatment is applied to a subject over several weeks, several months, or several years, in which the pump and the occlusion element are intermittently placed inside the subject's renal veins, and the subject is intermittently treated in accordance with the techniques described herein. For example, the subject may be intermittently treated at intervals of several days, several weeks, or several months.

The occlusion element is configured to occlude the renal vein at an occlusion site. The pump is configured to pump blood in a downstream direction, from a site that is in fluid communication with the upstream side of the occlusion element to a site that is in fluid communication with a downstream side of the occlusion element. In doing so, the pump reduces pressure in the renal vein. The occlusion element is configured to protect the renal vein from backflow of blood from the vena cava to the renal vein.

Typically, due to the reduction in pressure in the renal vein that is caused by the pumping of the blood in the downstream direction, perfusion of the kidney increases. In turn, this may cause pressure in the renal veins to rise relative to the pressure in the renal veins immediately subsequent to initiation of the pumping, due to increased blood flow into the renal vein. Typically, even after perfusion of the kidney increases, the pump is configured to maintain the pressure in the renal vein at a lower value than the pressure in the renal vein before the initiation of the pumping. For some applications, in addition to lowering the subject's renal vein pressure, and/or increasing perfusion of the subject's kidney, the blood pump performs ultrafiltration on the subject's blood.

It is noted that, for some applications, due to the reduction in pressure in the renal vein that is caused by the pumping of the blood in the downstream direction, the subject's renal vascular resistance decreases, in accordance with physiological mechanisms that are described, for example, in an article by Haddy et al., entitled "Effect of elevation of intraluminal pressure on renal vascular resistance" (Circulation Research, 1956), which is incorporated herein by reference. It is further noted that a treatment of the subject that increases renal perfusion by increasing blood pressure in the subject's renal arteries would typically not effect the aforementioned physiological mechanisms.

Typically, when blood pumps as described herein are used to reduce pressure in the subject's renal veins, it is expected that there will be an improved responsiveness by the subject to administration of diuretics to the subject, due to the reduction in renal venous pressure. Therefore, for some applications, a reduced dosage of diuretics may be administered to the subject relative to a dosage of diuretics that would be administered to the subject in the absence of performing the techniques described herein. Alternatively, a regular dosage of diuretics may be administered to the subject, but the diuretics may have a greater effect on the subject, due to the reduction in renal venous pressure.

High central venous pressure leads to a high level of blood pressure within the heart, which in turn leads to the release of atrial natriuretic peptide (ANP) and B-type natriuretic peptide (BNP) by the subject, both of which act as natural diuretics. Typically, when blood pumps as described herein are used to reduce pressure in the subject's renal veins, there is expected to be an improved responsiveness by the subject to the release of the natural diuretics by the subject, due to the reduction in renal venous pressure. For some applications, since the subject's central venous pressure is not lowered by using the blood pumps described herein, it is expected that the subject will continue to release atrial natriuretic peptide (ANP) and B-type natriuretic peptide (BNP), even while the subject's renal venous pressure is reduced by the use of the blood pumps described herein. Thus, for some applications, using the blood pumps described herein may result in the subject continuing to release atrial natriuretic peptide (ANP) and B-type natriuretic peptide (BNP), as well as resulting in the effectiveness of the aforementioned natural diuretics being greater than the effectiveness of the diuretics in the absence of the use of the blood pumps.

For some applications, pressure and/or flow sensors are disposed at the distal end of the catheter, and the suction pressure that is applied to the renal vein by the pump is modulated in response to feedback from the pressure and/or flow sensors. For example, a first pressure sensor 35 may be disposed on the side of the occlusion element that is closer to the kidney, and a second pressure sensor 37 may be disposed the side of the occlusion element that is closer to the vena cava. When the pumping of the pump is initiated, the flow rate of the pumping is modulated (e.g., automatically modulated, or manually modulated), such as to cause the pressure measured by the first sensor (which is indicative of the pressure in the renal vein) to be equal to the pressure measured by the second sensor (which is indicative of the central venous pressure). When the pressure measured at the first sensor is equal to that measured at the second sensor, the pump control unit interprets the flow rate of the pumping to be indicative of the native blood flow rate from the subject's renal vein to the subject's vena cava, since before the occlusion element were inserted into the renal vein, the renal vein pressure was equal to the central venous pressure. For some applications, the pump control unit designates the aforementioned measured flow rate as a baseline flow rate. Subsequently, when the pump is activated to lower the pressure in the renal vein relative the central venous pressure, the pump control unit measures the flow rate of the pumped blood relative the designated baseline flow rate.

For some applications, a third sensor (e.g., a non-invasive blood pressure sensor, or an invasive blood pressure sensor) is used to measure the subject's arterial blood pressure. As described above, when the pumping of the pump is initiated, the flow rate of the pumping is modulated, such as to cause the pressure measured by the first sensor to be equal to the pressure measured by the second sensor. When the pressure measured at the first sensor is equal to that measured at the second sensor, the pump control unit determines a baseline measure of the subject's renal vascular resistance by measuring the difference between the measured arterial and venous pressures and dividing the difference by the baseline flow rate. Subsequently, when the pump is activated to lower the pressure in the renal vein relative the central venous pressure, the pump control unit measures the current renal vascular resistance (based upon the current difference between the measured arterial and venous pressures and the current flow rate) relative the designated baseline renal vascular resistance.

Figure 4B:
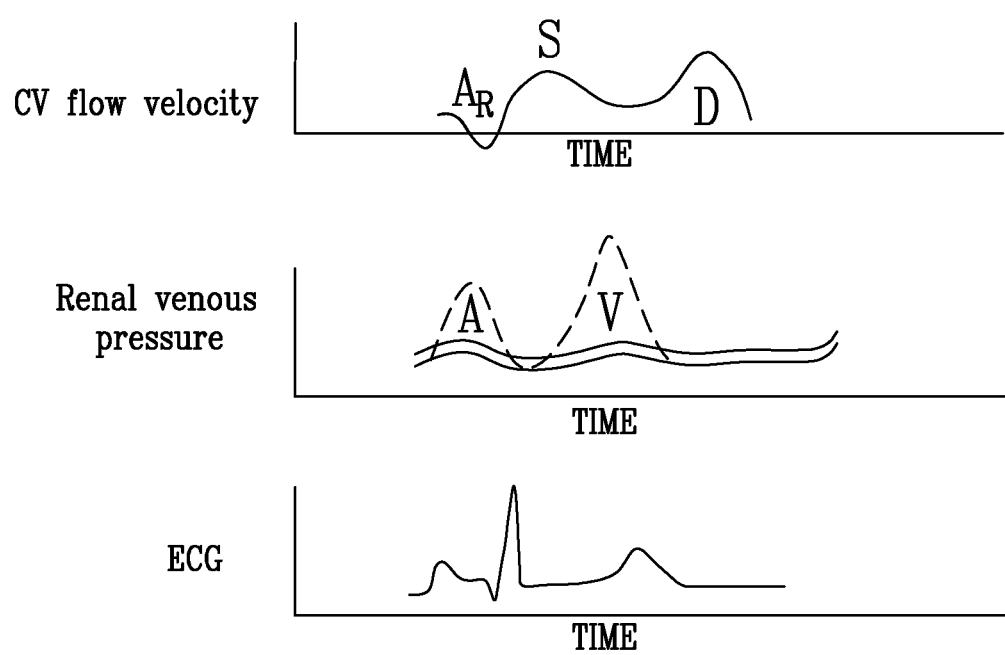
FIG. 4B is a set of graphs showing the central venous flow velocity profile and renal vein pressure profile of the subject suffering from congestive heart failure, with respect to the subject's ECG cycle, subsequent to placement of a blood pump in the subject's left and right renal veins, and activation of the blood pump, in accordance with some applications of the present invention.

FIG. 4B is a set of graphs showing the central venous flow velocity profile and renal vein pressure profile of the subject suffering from congestive heart failure, with respect to the subject's ECG cycle, subsequent to placement of blood pump 34 and occlusion element 36 in the subject's left and right renal veins 32. The renal venous pressure graph shows the original venous pressure profile as a dashed curve, and shows two curves showing the renal venous pressure, subsequent to placement of the pumps and the occlusion elements in the veins, and activation of the pumps. Typically, subsequent to placement of the pumps and the occlusion elements in the veins and activation of the pumps, the height of the venous pressure curve depends on the rate of pumping that the operator applies to the renal veins via the pumps. Therefore, two curves are shown for the renal venous pressure, subsequent to placement of the pumps and the occlusion elements in the veins, and activation of the pumps. As shown, placement of the pumps and the occlusion elements in the veins, and activation of the pumps, typically causes a lowering and flattening of the renal vein pressure profile, even though the subject's central venous pressure is elevated. For some applications, the renal vein pressure profile is not completely flattened, since although the pump applies a constant suction pressure to the renal veins throughout the duration of the subject's cardiac cycle, small cyclical variations in blood pressure are transmitted to the renal veins via the renal capillary system. Alternatively, subsequent to placement of the pumps and the occlusion elements in the veins, and activation of the pumps, the renal vein pressure profile is flattened.

Reference is now made to FIGS. 5A-D, which are schematic illustrations of an inverted valve 40 disposed around a blood pump catheter 42, in accordance with some applications of the present invention. Inverted valve 40 is an example of occlusion element 36 described hereinabove with reference to FIGS. 4A-B, and blood pump catheter 42 is an example of blood pump 34 described hereinabove with reference to FIGS. 4A-B.

Inverted valve 40 typically includes a rigid frame 44, which is configured to anchor the inverted valve to renal vein 32. (In FIGS. 5A-B, inverted valve 40 is shown inside the left renal vein, but the scope of the present invention includes placing inverted valve 40 and blood pump catheter 42 in the right renal vein, and, as is typically the case, placing inverted valve 40 and blood pump catheter 42 in each of the subject's renal veins.) Inverted valve 40 also includes valve leaflets 46. In response to blood pressure on the upstream side of the valve leaflets exceeding pressure on the downstream side of the valve leaflets, the valve leaflets are configured to open by separating from the wall of the blood vessel (and typically by separating from the rigid frame of the valve), such that blood flows in an antegrade direction between cusps of the valve leaflets and an inner wall of the blood vessel. In this sense, the inverted valve is inverted with respect to regular blood vessel valves, the leaflets of which are configured to open by the cusps of the leaflets separating from one another in order to allow blood flow between the leaflets, in response to blood pressure on the upstream side of the valve leaflets exceeding pressure on the downstream side of the valve leaflets. Furthermore, a typical blood vessel valve is disposed within the blood vessel such that the valve leaflets converge toward each other in the downstream direction, whereas, as shown in FIGS. 5A-B, leaflets 46 of valve 40 diverge from each other in the downstream direction.

FIG. 5A shows the inverted valve in an open state, arrows 48 indicating blood flow in an antegrade direction between cusps of the valve leaflets and an inner wall of the renal vein 32. Typically, when inverted valve 40 and blood pump catheter 42 are placed inside the renal vein, and the blood pump catheter is not activated, the valve leaflets will open, such as to permit blood flow from the renal vein to the vena cava, in response to blood pressure within the renal vein exerting pressure on the upstream side of leaflets 46.

Figure 5B:
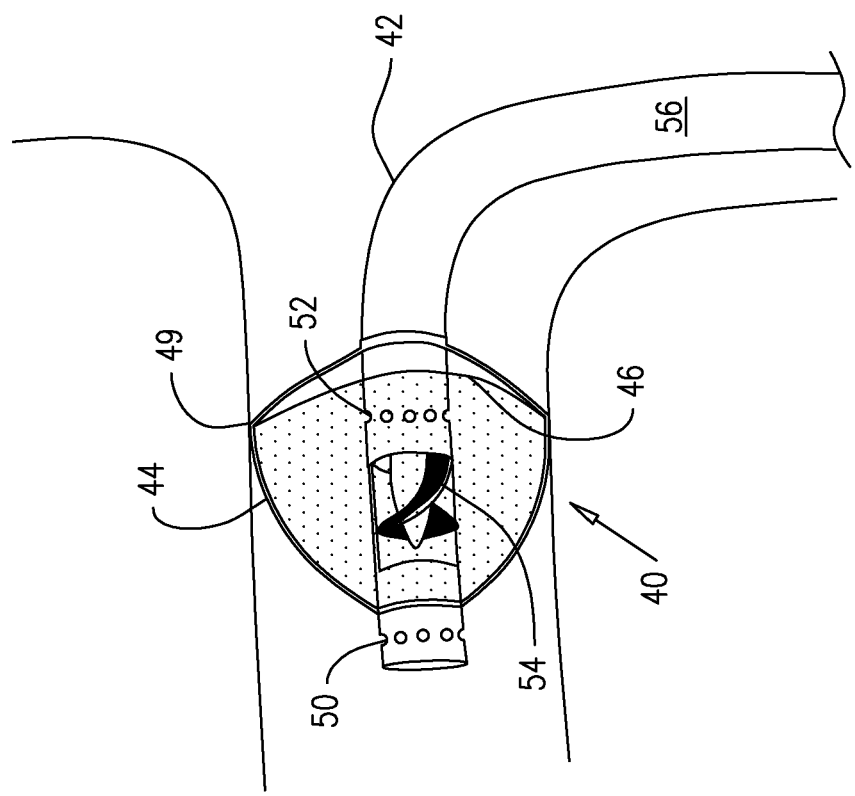

FIG. 5B shows inverted valve 40 in the closed state. As shown, in the closed state of the valve, the valve occludes blood flow from the renal vein to the vena cava, by the cusps of valve leaflets 46 contacting the inner wall of the renal vein at an occlusion site 49. For some applications, in the occluding state of the valve, the cusps of the valve leaflets contact a portion of the rigid frame of the valve. Typically, the valve closes in response to blood pressure on the downstream side of the valve leaflets exceeding pressure on the upstream side of the valve leaflets. When the catheter blood pump is activated, the pump draws blood in a downstream direction from a site that is in fluid communication with the upstream side of the valve, and pumps blood back into the venous system at a site that is in fluid communication with a downstream side of the valve, such as a site within the vena cava or a site within the renal vein. For example, the catheter blood pump may define inlet holes 50, which are in fluid communication with an upstream side of the valve, and through which blood is pumped into the pump, and the catheter blood pump may further define outlet holes 52, which are disposed in fluid communication with the downstream side of the valve, and through which blood is pumped into the renal vein or the vena cava. For some applications, the catheter blood pump pumps blood using an impeller 54 disposed inside a lumen 56 defined by the catheter blood pump, as shown.

For some applications, blood pump catheter 42 is coupled to frame 44 of valve 40 before blood pump catheter 42 and valve 40 are inserted into the subject's body. The pump is coupled to the valve frame such that, upon being placed inside the renal vein, inlet holes 50 are in fluid communication with an upstream side of valve leaflets 46, and outlet holes 52 are disposed in fluid communication with the downstream side of the valve. For some applications, valve 40 and blood pump catheter 42 are inserted into the subject's renal vein separately. For example, the valve may be inserted into the renal vein, and subsequently the blood pump catheter may be inserted through the valve, such that the blood pump catheter becomes coupled to valve frame 44. Alternatively the blood pump catheter may be inserted into the renal vein, and subsequently, the valve may be inserted into the renal vein over the blood pump catheter. Typically, the blood pump catheter and the valve frame define a coupling mechanism that couples the blood pump catheter to the valve frame such that inlet holes 50 are in fluid communication with an upstream side of valve leaflets 46, and such that outlet holes 52 are disposed in fluid communication with the downstream side of the valve.

Typically, blood pump catheter 42 is configured to pump blood into the renal vein in a manner that causes inverted valve 40 to assume an occluding state thereof and/or a manner that maintains inverted valve 40 in an occluding state thereof. For example, the blood pump catheter may be configured to pump blood out of outlet holes 52 in such a manner that blood flowing out of the outlet holes directly impacts the downstream sides of valve leaflets 46, thereby causing the cusps of the leaflets to assume and/or maintain contact with the inner wall of the renal vein. Thus, hydrodynamic pressure of the blood that is pumped into the subject's vasculature causes the cusps of the leaflets to assume and/or maintain contact with the inner wall of the renal vein. For some applications, blood pump catheter is structurally configured to pump blood out of the outlet holes in the aforementioned manner, for example, in accordance with the applications of the present invention described hereinbelow with reference to FIGS. 6B-D. Typically, valve 40 and blood pump catheter 42 are configured such that, in response to blood pump catheter 42 becoming inactive (e.g., due to a loss of power to the pump), valve leaflets 46 will open to allow blood flow from the renal vein to the vena cava, in response to pressure being exerted on the upstream side of the valve leaflets by blood in the subject's renal vein.

As described above, for some applications, blood pump catheter 42 is configured to pump blood out of outlet holes 52 in such a manner that blood flowing out of the outlet holes directly impacts the downstream sides of valve leaflets 46. For some applications, pumping the blood directly against the downstream sides of the valve leaflets has an antithrombogenic effect, by the blood that is pumped against the leaflets flushing the leaflets, and reducing the build-up of blood clots and/or tissue growth on the valve leaflets, relative to if the blood were not pumped directly against the valve leaflets. Alternatively or additionally, the blood pump catheter pumps an anti-coagulation agent directly toward the leaflets together with the blood that is pumped directly toward the leaflets. For some applications, by pumping an anti-coagulation agent directly toward the leaflets, a higher dose of the anticoagulation agent is provided to the leaflets than, for example, if the anticoagulation agent were to be systemically administered to the subject. Thus, the dose of the anticoagulation agent that is administered to the subject may be lowered relative to if the anticoagulation agent were to be systemically administered to the subject, and/or the anticoagulation agent may be more effective at reducing blood clots and/or tissue growth at the leaflets relative to if the anticoagulation agent were to be systemically administered to the subject. For some applications, the valve leaflets define small holes therethrough that are configured to permit the flow of the anticoagulation agent to the upstream sides of the valve leaflets.

In accordance with the description of FIGS. 5A-B, the combination of inverted valve 40 and blood pump catheter 42 is thus configured such that (a) when the blood pump is inactive, the inverted valve opens, in response to pressure exerted on the upstream sides of the valve leaflets by blood in the renal vein, and (b) when the blood pump is active, the pumping of blood into the renal vein on the downstream side of leaflets 46 maintains the valve in an occluding state thereof.

Figure 5C:
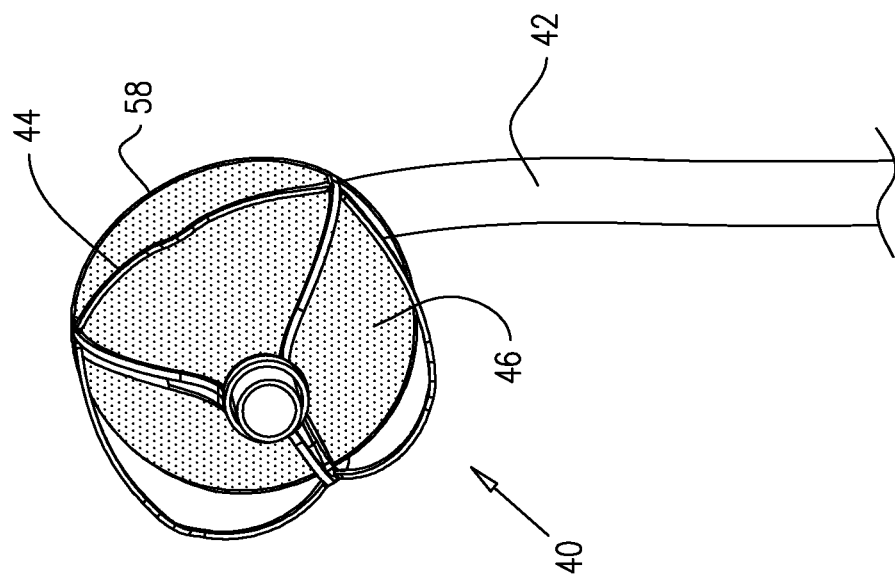
Figure 5D:
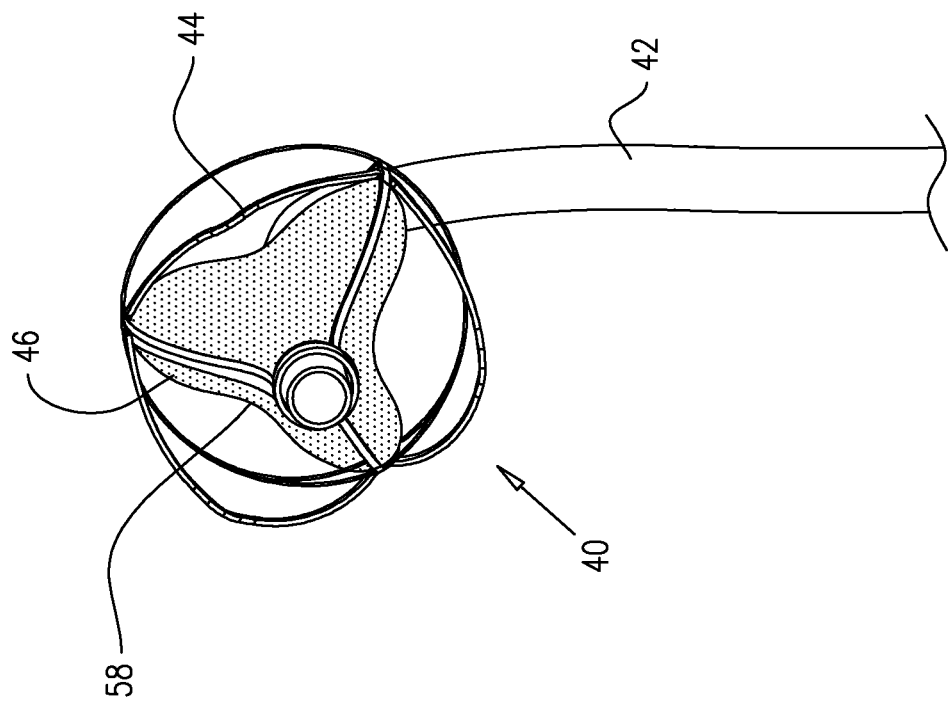

FIGS. 5C-D are schematic illustrations of views of the upstream ends of inverted valve 40 and blood pump catheter 42, when the valve is, respectively, in a non-occluding, and an occluding state thereof. As shown in FIG. 5C, when the valve is in the non-occluding state thereof, cusps 58 of leaflets 46 separate from the valve frame, such as to allow blood flow between the cusps of the valve leaflets and the inner wall of the blood vessel (blood vessel not shown). It is noted that, for some applications, the structure of the valve frame is different from that shown in FIGS. 5C-D. For example, the valve frame may have a structure as shown in FIGS. 5A-B, such that even when the valve is in the occluding state thereof, the cusps of the leaflets are not in direct contact with a portion of the valve frame, but are in contact with the inner wall of the blood vessel.

Reference is now made to FIGS. 6A-G, which are schematic illustrations of configurations of blood pump catheter that 42 are used with inverted valve 40, in accordance with some applications of the present invention.

Figure 6A:
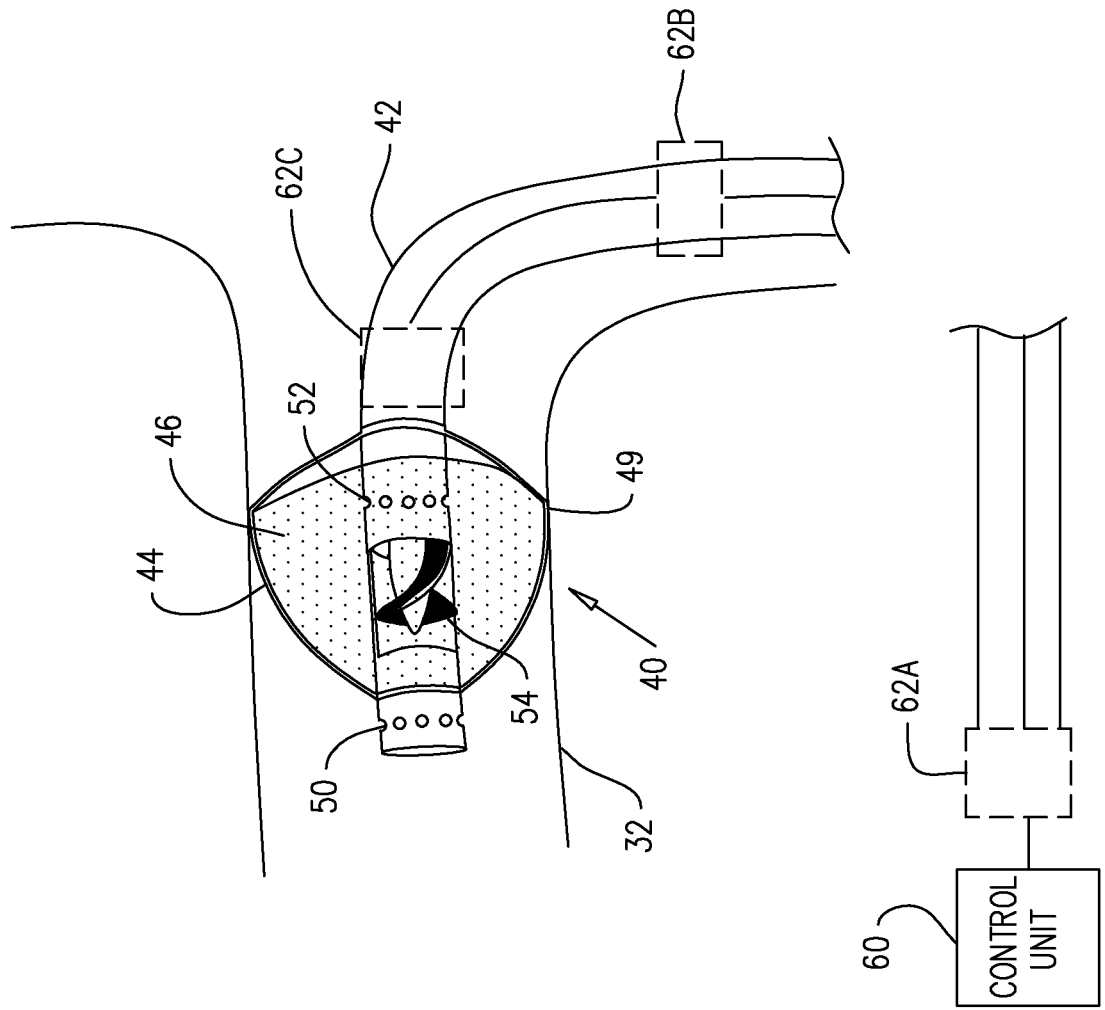

FIG. 6A shows pump control unit 60, which is used to control pumping of blood pump catheter 42. The dashed boxes 62 indicate locations of the blood pump motor, in accordance with respective applications of the invention. For some applications, the blood pump motor is disposed at the location indicated by box 62A, outside of the subject's body, in the vicinity of the pump control unit (e.g., within the same housing as the pump control unit). For some applications, the motor being disposed outside the subject's body allows the use of a smaller diameter catheter for the blood pump catheter than would be required if the motor were to be disposed inside the catheter. Alternatively, the blood pump motor is disposed at the location indicated by box 62B, such that when the distal end of the blood pump catheter is disposed inside renal vein 32, the motor is disposed in the vena cava. For some applications, the motor being disposed in the portion of the catheter that is disposed in the vena cava, allows the distal portion of the catheter that is placed inside the renal vein to be smaller than would be required if the motor were to be disposed inside the distal portion of the catheter. Further alternatively, the blood pump motor is disposed at the location indicated by box 62C, within the distal portion of the catheter that is placed inside the renal vein. For some applications, the blood pump motor is disposed in the vicinity of impeller 54 (e.g., at the location indicated by box 62C) in order for the pump motor to more efficiently impart rotational motion to the impeller, relative to if the blood pump motor were disposed at a greater distance from impeller 54.

Figure 6B:
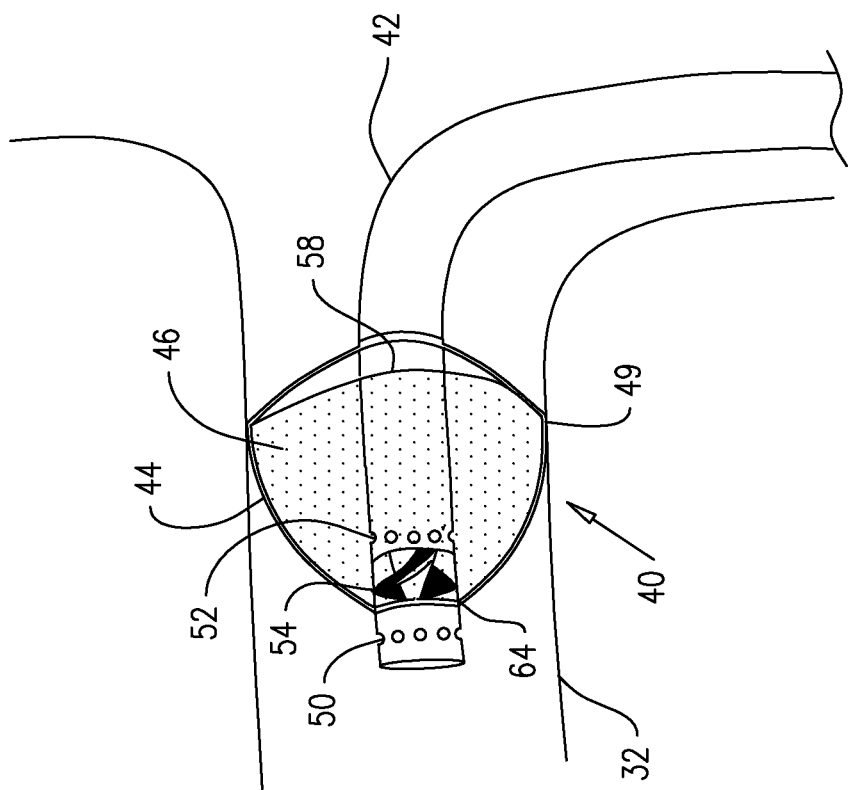
Figure 6C:
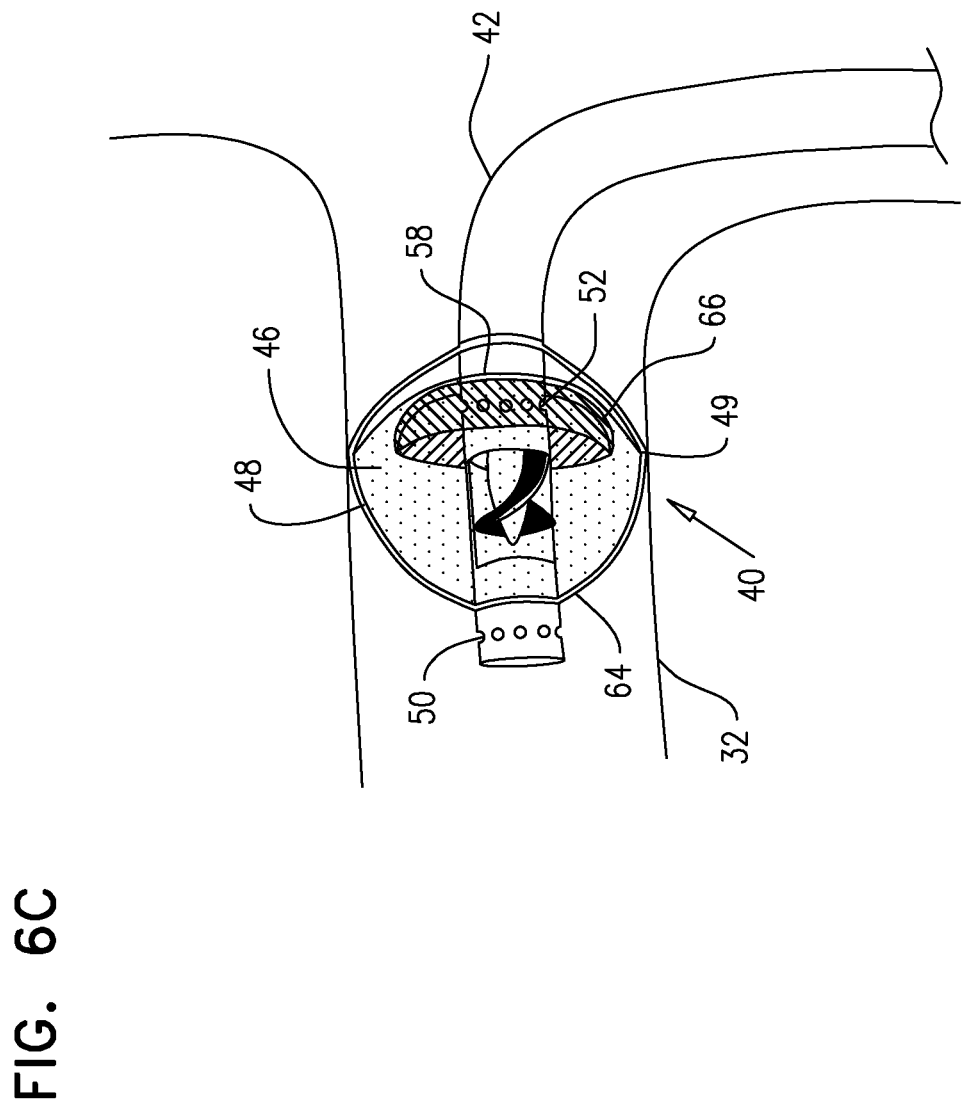
Figure 6D:
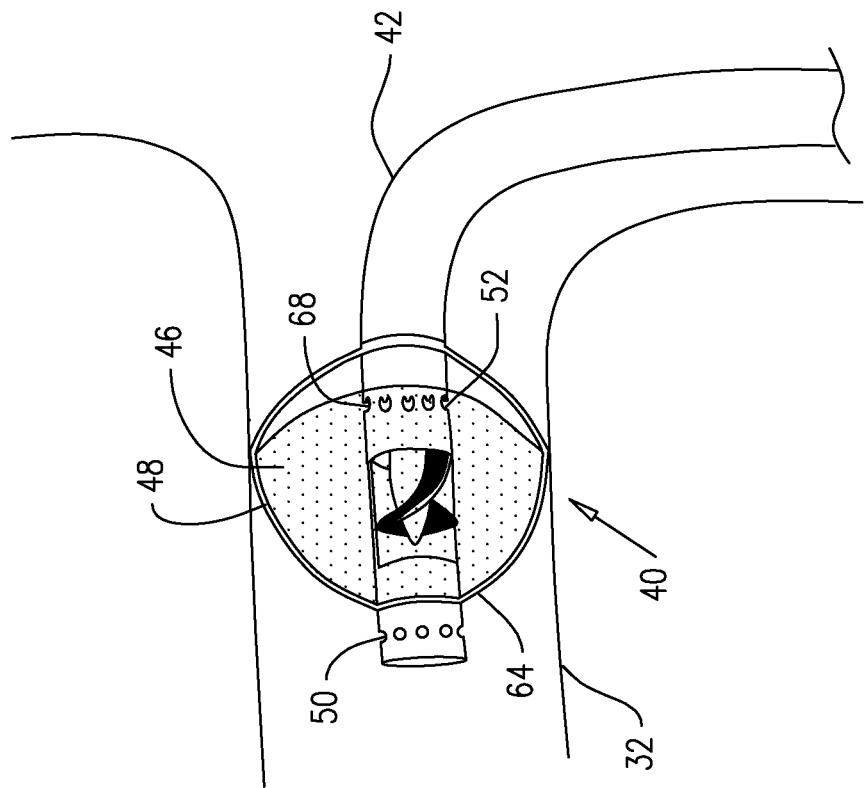

FIGS. 6B-D are schematic illustrations of blood pump catheter 42, the pump being structurally configured to pump blood out of outlet holes 52, in a manner that maintains inverted valve 40 in an occluding state thereof.

As shown in FIG. 6B, for some applications, the outlet holes are located such that when the blood pump catheter is placed through (e.g., coupled to) the valve and inlet holes 50 are disposed in fluid communication with the upstream side of the valve, the outlet holes are disposed adjacent to the bases 64 of valve leaflets 46. For example, the outlet holes of the pump may be disposed adjacent to a location along the length of the valve leaflets that is below midway between cusps 58 of the leaflets and bases 64 of the leaflets. Typically, due to the disposition of the outlet holes with respect to the valve leaflets, blood flowing out of the outlet holes flows against the downstream sides of valve leaflets 46, thereby causing the cusps of the leaflets to maintain contact with the inner wall of the renal vein, i.e., thereby maintaining the valve in an occluding (i.e., closed) state.

For some applications, the blood pump catheter is shaped to define a radial protrusion 66 therefrom that is concavely curved toward a distal end of the catheter, as shown in FIG. 6C. The curvature and disposition of protrusion 66 is typically such that a first end of the protrusion, which is coupled to the catheter, is disposed proximally to outlet holes 52, and the other end of the radial protrusion is disposed distally to the outlet holes. Typically, blood flowing out of the outlet holes is directed toward the downstream sides of valve leaflets 46 by radial protrusion 66, thereby causing the cusps of the leaflets to maintain contact with the inner wall of the renal vein, i.e., thereby maintaining the valve in an occluding (i.e., closed) state.

For some applications, outlet holes 52 are shaped such as to direct blood out of the holes in a distal direction (i.e., toward the upstream end of the catheter pump). For example, as shown in FIG. 6D, surfaces 68 that define the holes may be curved toward the distal end of the pump catheter. Thus, the blood flowing out of the outlet holes is directed toward downstream sides of valve leaflets 46, thereby causing the cusps of the leaflets to maintain contact with the inner wall of the renal vein, i.e., thereby maintaining the valve in an occluding (i.e., closed) state.

Figure 6E:
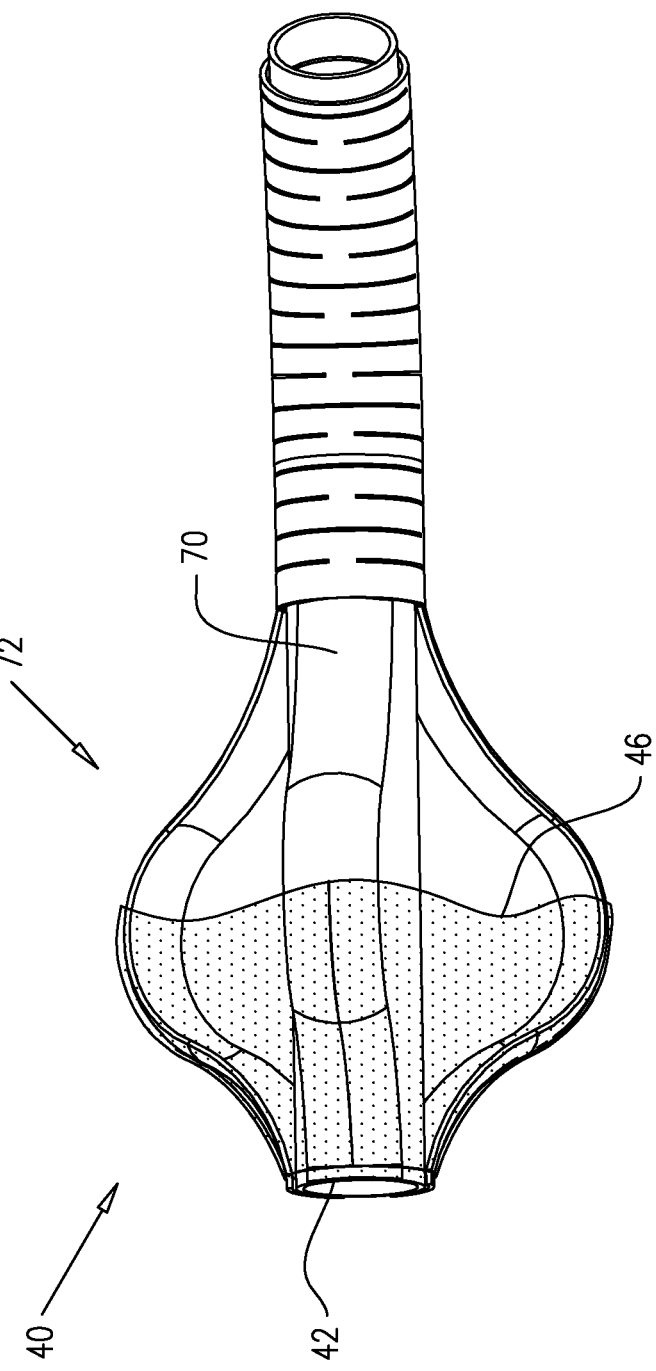

FIGS. 6E-G show support structures that are used to support inverted valve 40 within the renal vein as an alternative to, or in addition to frame 44 (shown in FIGS. 5A-D, for example).

For some applications, valve 40 is a tri-leaflet valve. Alternatively the valve may be a bi-leaflet valve, or may have more than three leaflets. The leaflets are maintained in contact with the renal vein at commissures of the valve leaflets. Between the commissures of the valve leaflets, when the valve is in the occluding state of the valve, the cusps of the valve leaflets contact the renal vein wall, and when the valve is in the non-occluding state of the valve, the cusps of the valve leaflets separate from the renal vein wall, such as to permit blood flow between the valve leaflets and the renal vein wall.

For some applications (shown in FIGS. 5A-D, for example), the leaflets are coupled to valve frame 44 at the commissures of the valve leaflets, and the valve frame maintains the commissures of the valve leaflets in contact with the renal vein wall. Alternatively or additionally, as shown in FIG. 6E, a slit tube 72 is advanced over blood pump catheter 42. The tube is configured such that when the distal end of the tube is pushed toward the distal end of the catheter, the portions of the tube between the slits expand radially outwardly. The radially-expanded portions of the tube are configured to maintain commissures of the valve leaflets in contact with the renal vein wall.

Further alternatively or additionally, a balloon 74 having a star-shaped cross section (e.g., a three-pointed star cross section, as shown) is disposed around the portion of the blood pump catheter 42 that is disposed inside valve 40. Respective views of balloon 74, blood pump catheter 42, and valve 40 are shown in FIGS. 6F-G. For some applications, the three-dimensional shape of balloon 74, when the balloon is in an inflated state thereof, is similar to the shape of a carambola (i.e., a star-fruit). Typically, the balloon is inflated such that at the points of the star of the balloon's cross-section, the balloon maintains the commissures of the valve leaflets in contact with the renal vein wall.

As described hereinabove, typically, inverted valve 40 and blood pump catheter 42 are used to apply an acute treatment to a subject. For example, the inverted valve and the blood pump catheter may be placed inside the subject's renal veins for a period of more than one hour (e.g., more than one day), less than one week (e.g., less than four days), and/or between one hour and one week (e.g., between one day and four days). For some applications, using the slit tube 72 or balloon 74 to maintain the valve commissures in contact with the renal vein wall facilitates removal of the valve from the renal vein, subsequent to the termination of the treatment. For example, in order to remove the valve from the renal vein, the slit tube may be retracted such that the radially-expanded portions of the tube radially constrict, and the valve leaflets are no longer maintained in contact with the renal vein wall, and/or balloon 74 may be deflated such that the valve leaflets are no longer maintained in contact with the renal vein wall.

Figure 7B:
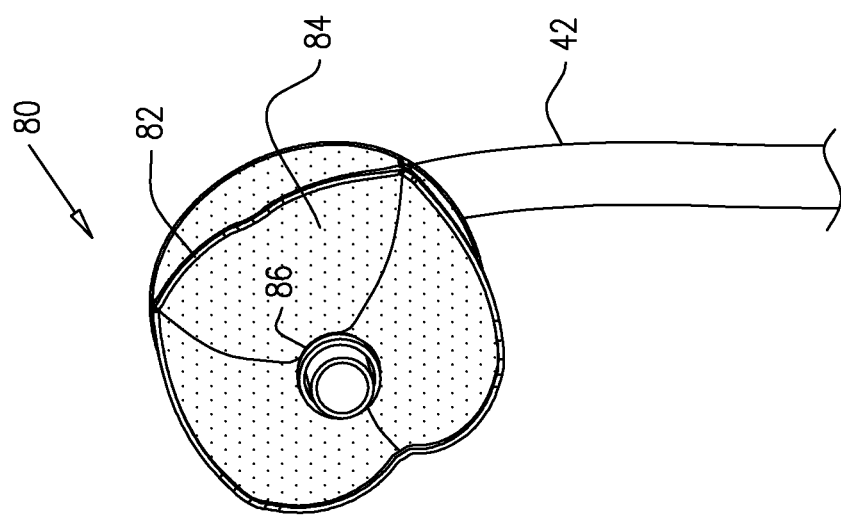
FIGS. 7A-B are schematic illustrations of a blood pump catheter and a non-inverted valve placed in the renal vein, when the non-inverted valve is, respectively, in closed and open states thereof, in accordance with some applications of the present invention.
Figure 7A:
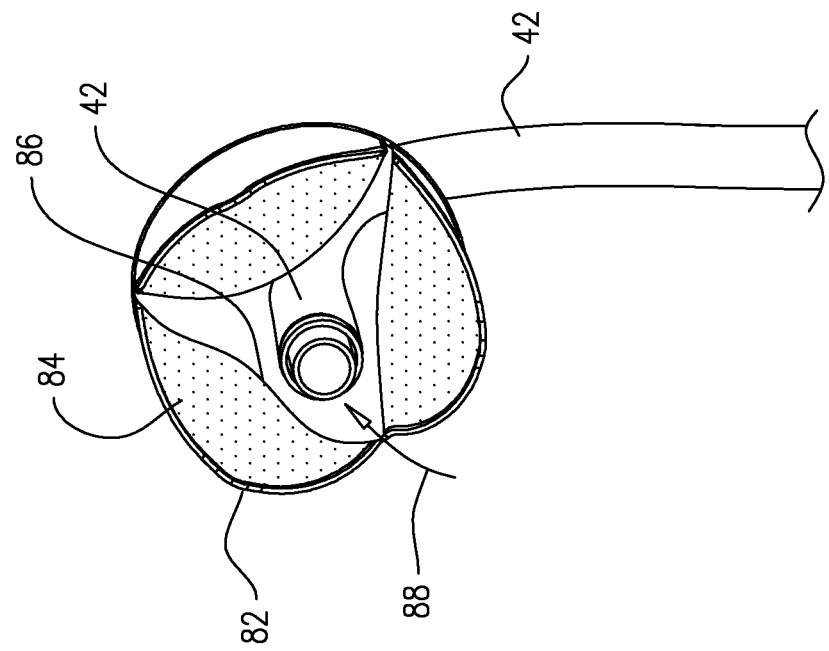

Reference is now made to FIGS. 7A-B, which are schematic illustrations of blood pump catheter 42 and a non-inverted valve 80, when the non-inverted valve is, respectively, in occluding and non-occluding states thereof, in accordance with some applications of the present invention. In some applications, as an alternative to being placed through an inverted valve, blood pump catheter 42 is inserted through a non-inverted valve, as shown in FIGS. 7A-B. Non-inverted valve 80 is an example of occlusion element 36 described hereinabove with reference to FIGS. 4A-B. Non-inverted valve typically includes a rigid frame 82 and valve leaflets 84.

Typically, blood pump catheter 42 is used to pump blood in a downstream direction from a site that is in fluid communication with an upstream side of valve leaflets 84 to a site of the venous system that is in fluid communication with a downstream side of the valve leaflets, such as a site within the vena cava or a site within the renal vein. Valve 80 is configured to prevent backflow of blood by the cusps 86 of the valve leaflets contacting the catheter in response to pressure on the downstream side of the valve leaflets exceeding pressure on the upstream side of the valve leaflets. Valve 80 is further configured, in response to pressure on the upstream side of the valve leaflets exceeding the pressure on the downstream side of the valve leaflets, to allow the flow of blood across the valve, by the cusps of the leaflets separating from the catheter, thereby allowing blood to flow between the leaflets and the blood pump catheter in the direction of arrow 88 (FIG. 7A).

For some applications, initially, a combination of a valve (e.g., an inverted valve, as shown in FIGS. 5A-D, and 6A-G, or a non-inverted valve, as shown in FIGS. 7A-B) and a pump is used to treat the subject. Subsequently (e.g., after a period of more than one hour, less than one week, and/or between one hour and one week), the pump is removed from the subject's renal vein, and the valve is left in place within the renal vein. Even in the absence of the pump, the valve is configured to reduce pressure in the subject's renal vein relative to renal pressure in the subject's renal vein in the absence of the valve, by preventing backflow of blood from the subject's vena cava into the subject's renal vein and permitting the flow of blood from the subject's renal vein to the subject's vena cava. Thus, for some applications, the valve is left inside the renal vein in order to provide chronic treatment to the subject, even after the acute treatment of the subject (using the pump in combination with the valve) has terminated.

Figure 8A:
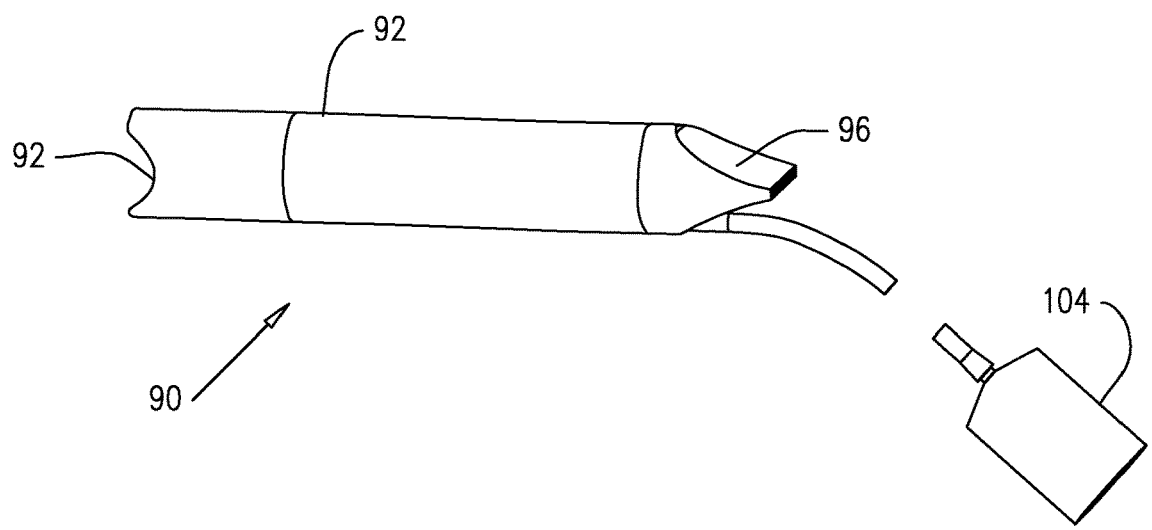
FIGS. 8A-B are schematic illustrations of respective views of a blood pump in accordance with some applications of the present invention.
Figure 8B:
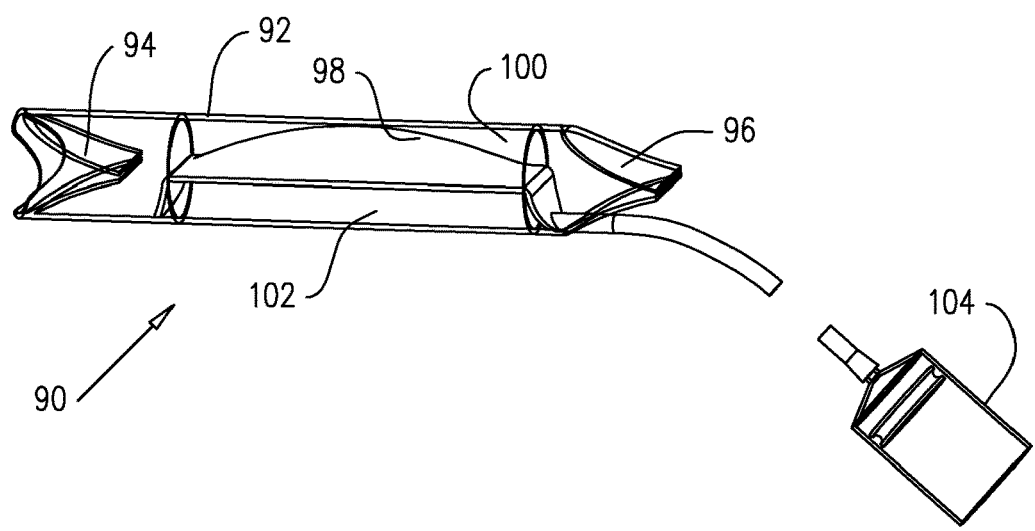

Reference is now made to FIGS. 8A-B, which are schematic illustrations of respective views of a blood pump 90 in accordance with some applications of the present invention. Pump 90 is an example of both occlusion element 36 and pump 34 described hereinabove with reference to FIGS. 4A-B, since pump 90, when placed within the subject's renal vein, is configured to both occlude the renal vein and to pump blood downstream from a site in fluid communication with an upstream side of the pump to a site that is in fluid communication with a downstream side of the pump.

Pump 90 includes an outer tube 92, the outer surface of the tube being configured to be in contact with the inner wall of the renal vein. Typically, outer tube 92 comprises a stent with material (typically, a blood-impermeable material) disposed thereon. First and second unidirectional valves 94 and 96 are disposed at respective ends of the tube, the valves only permitting blood to flow into and out of the tube in the downstream direction. A membrane 98 is coupled to the inside of the tube, such that the membrane partitions the tube into a first compartment 100, which is in fluid communication with the valves, and a second compartment 102, which is not in fluid communication with the valves. A pumping mechanism 104, e.g., an electromagnetically-driven pumping mechanism, cyclically drives the membrane to move with respect to the tube such that the relative sizes of the first and second compartments change.

Reference is now made to FIGS. 9A-D, which are schematic illustrations of respective stages of a cycle of operation of blood pump 90, in accordance with some applications of the present invention. FIG. 9A shows the blood pump at an arbitrary starting point in the cycle of operation of the blood pump, at which point both valve 94 and valve 96 are closed. As shown in the transition from FIG. 9A to FIG. 9B, and FIG. 9B to FIG. 9C, pump mechanism 104 causes membrane 98 to move such that the volume of first compartment 100 increases, e.g., by the pumping mechanism pumping fluid (e.g., air, or saline) out of the second compartment. The increase in the volume of the first compartment causes the pressure inside the first compartment to decrease relative to the pressure on the upstream side of the first valve 94, causing valve 94 to open and blood to be drawn into the first compartment. Subsequently, the pumping mechanism moves the membrane such as to increase the volume of the second compartment, e.g., by pumping fluid into the second compartment, as shown in the transition from FIG. 9C to FIG. 9D, and from FIG. 9D to FIG. 9A. The movement of the membrane causes the volume of the first compartment to decrease, and pressure in the first compartment to increase. The pressure in the first compartment causes valve 94 to close, and causes valve 96 to open and for blood that was inside the first compartment to flow to the downstream side of pump 90.

Reference is now made to FIGS. 10A-D, which are schematic illustrations of a blood-impermeable sleeve 110 configured to occlude blood flow from a subject's vena cava 26 to the subject's renal veins 32, in accordance with some applications of the present invention. Typically, the sleeve is placed within the vena cava such that a downstream end 112 of the sleeve is coupled to the wall of the vena cava at a first location 114 that is downstream of all renal veins of the subject (e.g., left and right renal vein in a typical subject that has two renal veins), and such that an upstream end 116 of the sleeve is coupled to a wall of the vena cava at a second location 118 that is upstream of all renal veins of the subject. Thus, the sleeve isolates the blood in the renal veins into a compartment that is separated from blood flow through the vena cava. Typically, a rigid structure, e.g., a stent 120 as shown, is configured to couple the upstream and downstream ends of the sleeve to the vena cava.

A pump 122 is configured to pump blood from a location that is exterior to sleeve 110 (i.e., from the isolated compartment) to a location that is in fluid communication with the interior of the sleeve (e.g., a location within the vena cava upstream or downstream of the sleeve). Thus, the pump pumps blood out of the subject's renal veins and into the subject's vena cava. The sleeve prevents backflow of blood from the vena cava into the renal veins.

Figure 10A:
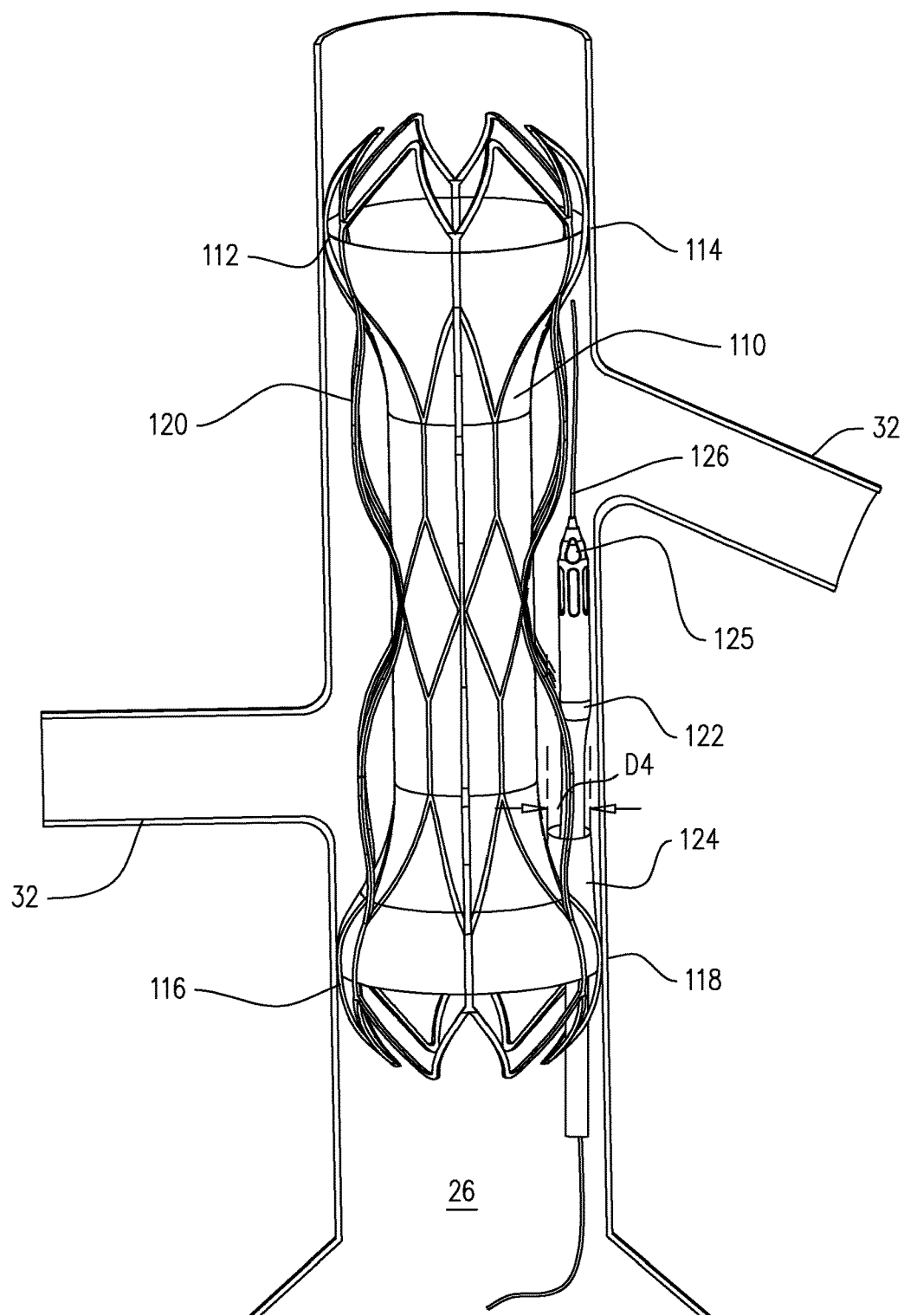
FIGS. 10A-D are schematic illustrations of a sleeve configured to occlude blood flow from a subject's vena cava to the subject's renal veins, in accordance with some applications of the present invention.
Figure 10B:
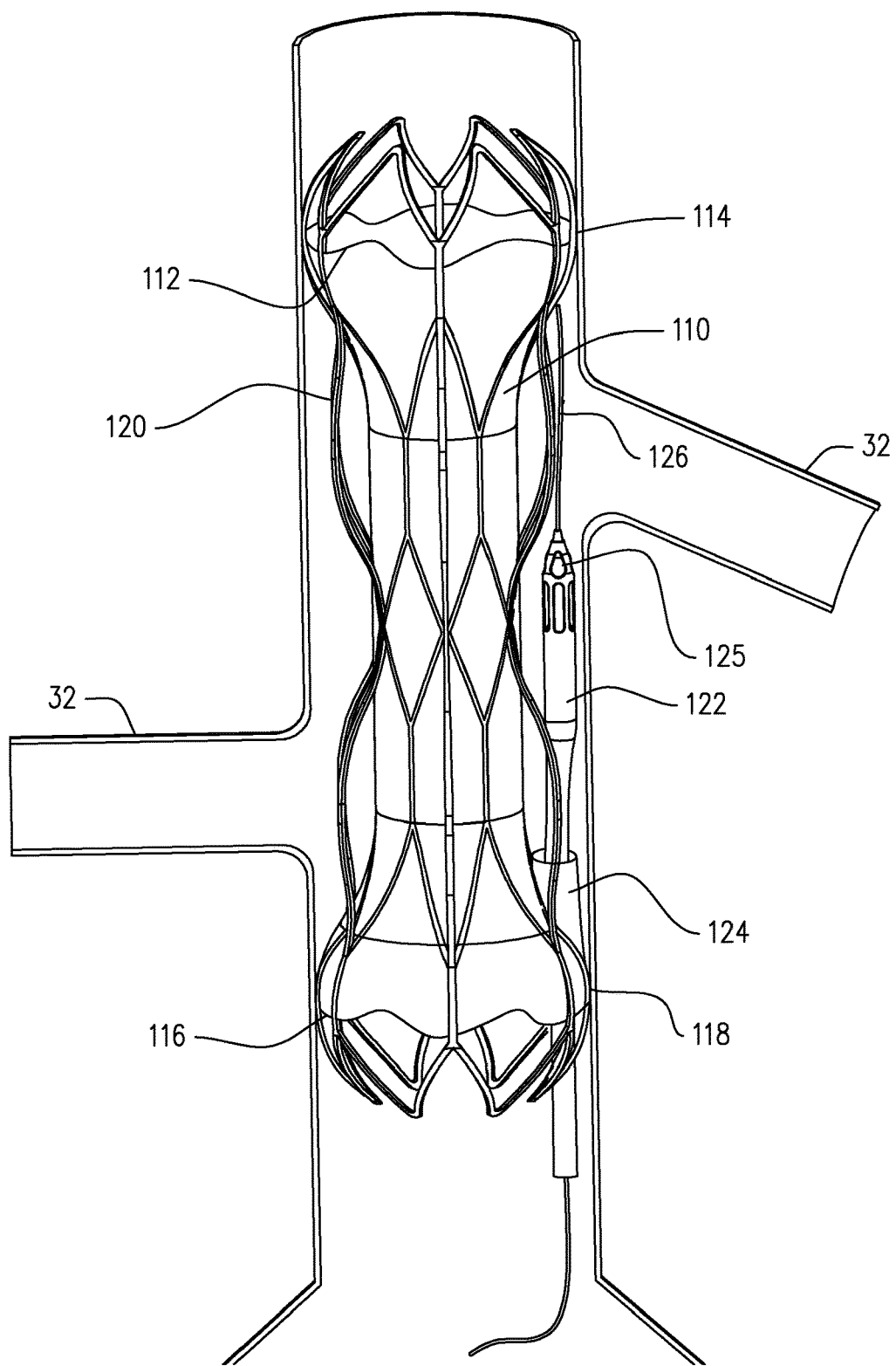

For some applications, as shown, stent 120 defines flared ends thereof. Sleeve 110 also defines flared ends thereof. The flared ends of the sleeve are configured to occlude the flow of blood from the vena cava to the renal veins by contacting the wall of the vena cava, if pressure in the vena cava is greater than or equal to pressure in the renal veins. For some applications, at least one of the flared ends of the sleeve is configured to act as a valve, e.g., by providing blood flow from outside the sleeve to the vena cava in order to relieve pressure and/or an overflow of blood outside the sleeve. In response to blood pressure in the renal veins exceeding blood pressure in the vena cava, the flared end of the sleeve is configured to at least partially separate from the wall of the vena cava, such that blood flows between the outside of the flared end of the sleeve and the inner wall of the vena cava. For some applications, the upstream and the downstream ends of the sleeve are configured to act as a valve in the aforementioned manner, mutatis mutandis. FIG. 10A shows the sleeve when the upstream and downstream ends of the sleeve are closed such as to occlude the flow of blood between the outside of the sleeve and the wall of the vena cava. FIG. 10B shows the sleeve, when the upstream and downstream ends of the sleeve are open, such as to allow the flow of blood from the renal veins to the vena cava, between the outside of the sleeve and the wall of the vena cava.

Figure 10C:
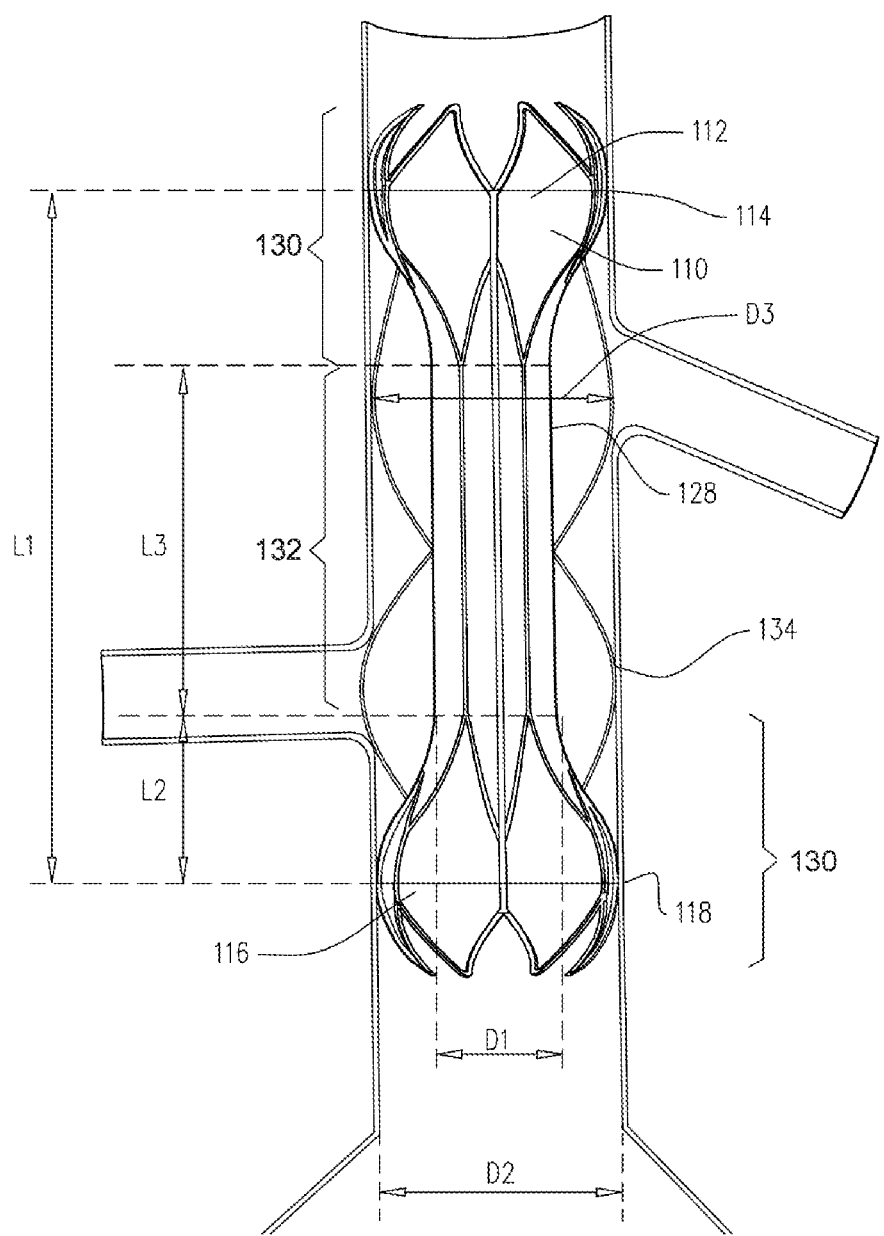
Figure 10D:
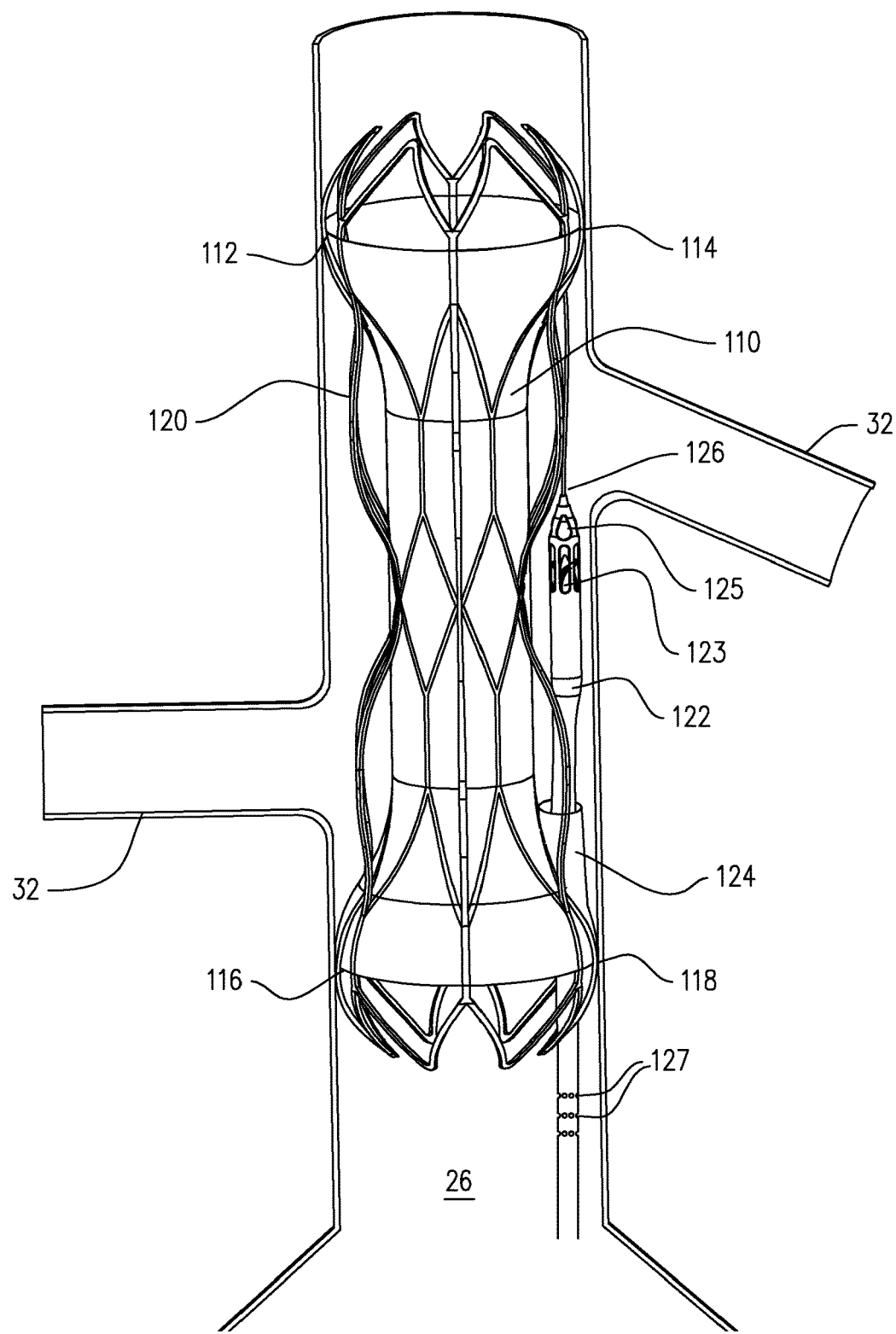

As shown in FIGS. 10A-B and FIG. 10D, for some applications, a pump-accommodating sleeve 124 protrudes from the outside of one of the flared ends of sleeve 110 (e.g., the downstream flared end of sleeve 110, as shown). The pump-accommodating sleeve is shaped such as to facilitate insertion of pump 122 therethrough. The pump-accommodating sleeve is configured to form a seal around the pump, such that there is minimal or zero blood flow between the outside of the pump and the inside of the pump-accommodating sleeve. For some applications (not shown), rather than using pump-accommodating sleeve to form a seal around the outside of the pump, the flared end of the sleeve defines an opening (e.g., a hole) through which the pump is inserted, the opening being sized such that the interface between the outside of the pump and flared distal end of the sleeve is sealed.

It is noted that, although pump-accommodating sleeve is shown protruding from the outside of the flared upstream end of the sleeve, for some applications the pump is inserted through the downstream flared end of the sleeve, and the downstream flared end of the sleeve defines a pump-accommodating sleeve, or a hole through which the pump is inserted. In general, the scope of the present invention includes inserting the blood pumps and the occluding elements that are described herein toward the renal veins by approaching the renal veins via the vena cava, from above the renal veins, or from below the renal veins. For example, the renal veins may be approached through the vena cava from the upstream direction, via the femoral vein, or from the downstream direction, via the jugular vein.

In accordance with respective applications, pump 122 pumps blood into the vena cava at a site that is upstream or downstream of the sleeve. For some applications, the pump pumps the blood into the vena cava at a site that is downstream of the sleeve such as to reduce the flow of blood through the sleeve relative to if the pump were to pump the blood into the vena cava at a site that is upstream of the sleeve. For some applications, it is advantageous to reduce the flow of blood through the sleeve in the aforementioned manner, since the sleeve acts as a resistor to blood flow through the sleeve. As described hereinabove, and as shown for example in FIG. 10D, for some applications, the pump pumps blood into the vena cava at a site that is upstream of the sleeve.

For some applications, sleeve 110 and stent 120 are inserted into the subject's vena cava, while a guidewire 126 is disposed inside pump-accommodating sleeve 124. Subsequent to anchoring sleeve 110 and stent 120 to the vena cava, pump 122 is inserted through the pump-accommodating sleeve, by advancing the pump over the guidewire.

As shown in FIG. 10C, for some applications stent 120 is shaped to define a sleeve-supporting frame 128, which is generally shaped to match the shape of the sleeve. Typically, the sleeve-supporting frame is shaped to define widened ends 130 and a narrow central portion 132 extending between the widened ends, the flared ends extending from the ends of the of narrow central portion. In addition, the stent defines a vessel-wall-supporting frame 134, which is coupled to narrow central portion of the sleeve-supporting frame, and which protrudes radially outwardly from the sides of the narrow central portion of the sleeve-supporting frame.

For some applications, pumping of blood by pump 122 from outside of the sleeve causes the walls of the vena cava to be pulled inwardly. Vessel-wall-supporting frame 134 supports the inner wall of the vena cava, and prevents the inner wall of the vena cava from collapsing around narrow central portion 132 of sleeve-supporting frame 128 of the stent. Typically, during operation of the pump, the pump head, including inlet holes 125 of the pump head, is disposed in the gap between the narrow central portion of the sleeve-supporting frame of the stent (which supports the sleeve) and the vessel-wall-supporting frame (which supports the wall of the vena cava).

As described hereinabove, for some applications, pumping of blood by pump 122 from outside of the sleeve causes the walls of the vena cava to constrict by being pulled inwardly. For some applications, the pump is configured to anchor stent 120 to the vena cava by causing the vena cava to constrict around at least a portion of the stent, by applying a suctioning force to the vena cava. For some applications, a stent that is not substantially oversized with respect to the vena cava, and/or a stent having a diameter that is less than the diameter of the vena cava is anchored to the vena cava by virtue of the vena cava constricting around at least a portion of the stent, due to the suctioning force applied to the vena cava by the pump.

As described hereinabove, typically, sleeve-supporting frame 128 is shaped to generally match the shape of the sleeve. The sleeve and the sleeve-supporting frame define a narrow central portion diameter D1 (FIG. 10C), and a maximum diameter D2 at the ends of the flared distal ends of the sleeve. For some applications, D1 is greater than 8 mm, less than 35 mm, and/or between 8 and 35 mm. For some applications, D2 is greater than 10 mm, less than 45 mm, and/or between 10 and 45 mm. For some applications, a ratio of D2:D1 is greater than 1.1:1, less than 2:1, and/or between 1.1:1 and 2:1. For some applications, a total length L1 of the sleeve is greater than 6 mm, less than 80 mm, and/or between 6 and 80 mm. For some applications, a length L2 of the flared ends of the sleeve (i.e., the length from the location at which the sleeve begins to flare, until the end of the sleeve) is greater than 3 mm, less than 40 mm, and/or between 3 and 40 mm. For some applications, a length L3 of the narrow central portion of the sleeve and the sleeve-supporting frame is greater than 3 mm, less than 70 mm, and/or between 3 and 70 mm.

For some applications, a maximum diameter D3 of vessel-wall-supporting frame 134 of stent 120 is greater than 10 mm, less than 50 mm, and/or between 10 and 50 mm. For some applications, a ratio of D3:D1 is greater than 1.1:1 (e.g., greater than 1.5:1, or greater than 2:1), less than 5:1, and/or between 1.1:1 and 5:1.

For some applications, an inner diameter D4 (FIG. 10A) of pump-accommodating sleeve 124 is greater than 2 mm, less than 10 mm, and/or between 2 and 10 mm. For applications in which sleeve 110 defines an opening through which pump 122 is inserted, the diameter of the opening through which the pump is inserted is typically greater than 2 mm, less than 10 mm, and/or between 2 and 10 mm.

For some applications, pump 122 is generally similar to blood pump catheter 42 described hereinabove, for example with reference to FIGS. 5A-D. For example, as shown in FIG. 10D, the blood pump may include an impeller 123 to pump blood. Blood is drawn into the catheter from the renal veins via inlet holes 125, which are disposed between the outside of the sleeve and the wall of the vena cava, and blood is pumped into the vena cava via outlet holes 127 disposed in the vena cava, for example at a location upstream of the sleeve, as shown in FIG. 10D.

Figure 10E:
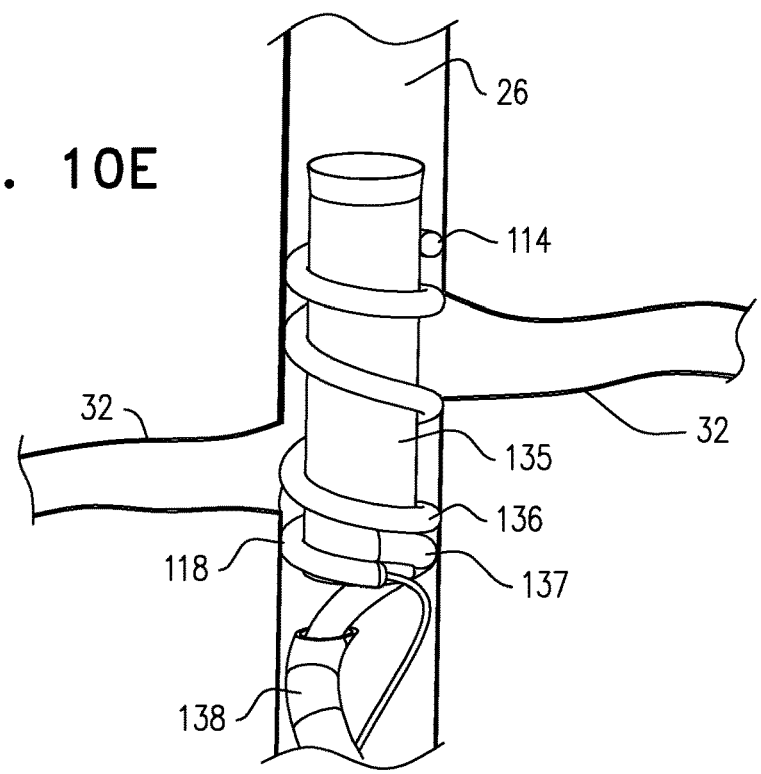
FIGS. 10E-F are schematic illustrations of a sleeve coupled to the vena cava using a helical support element that is configured to occlude blood flow from a subject's vena cava to the subject's renal veins, in accordance with some applications of the present invention.
Figure 10F:
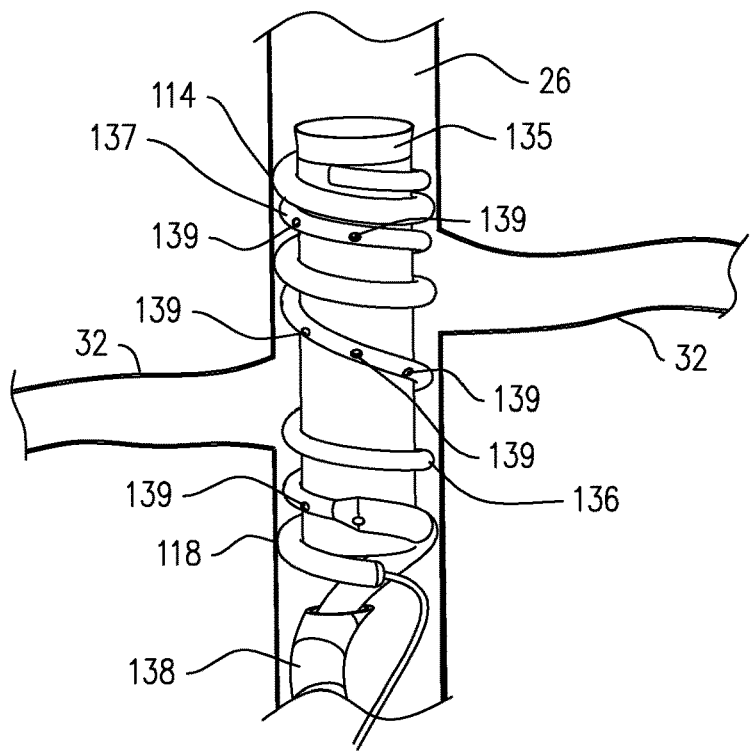

Reference is now made to FIGS. 10E-F, which are schematic illustrations of a blood-impermeable sleeve 135 coupled to vena cava 26 using a helical support element 136 that is configured to occlude blood flow from the subject's vena cava to the subject's renal veins 32, in accordance with some applications of the present invention. In accordance with respective applications the helical support element is an inflatable helical support element (e.g., a helical balloon), or a helical support element that is made from a shape-memory alloy, such as nitinol. Typically, the helical support element becomes coupled to the vena cava such that a downstream end of the helical support element is coupled to the wall of the vena cava at first location 114 that is downstream of all renal veins of the subject (e.g., left and right renal vein in a typical subject that has two renal veins), and such that an upstream end of the helical support element is coupled to a wall of the vena cava at second location 118 that is upstream of all renal veins of the subject. Thus, the helical support element isolates the blood in the renal veins into a compartment outside the sleeve that is separated from blood flow through the vena cava. It is noted that sleeve 135 does not necessarily have flared ends that are configured to occlude blood flow from the vena cava to the renal veins by contacting wall of the vena cava. Rather, as shown, the helical support element may occlude the flow of blood from the vena cava to the renal veins by contacting the wall of the vena cava. Alternatively, sleeve 135 has a generally similar shape to sleeve 110 described hereinabove with reference to FIGS. 10A-D, the sleeve defining flared ends that are configured to contact the wall of the vena cava.

Typically, a blood pump catheter 137 is inserted into the vena cava via a delivery device 138 (FIG. 10F). As shown in the transition from FIG. 10E to FIG. 10F, for some applications, the blood pump catheter is guided into the compartment outside the sleeve by being advanced over the helical support element. For some applications, a distal portion of the blood pump catheter is configured to assume a helical shape automatically upon being advanced out of the delivery device. Alternatively, by being advanced over the helical support element, the distal portion of the blood pump catheter is made to assume a helical shape. Typically, the blood pump catheter defines inlet holes 139 along most of the length (e.g., more than 50 percent, or more than 75 percent of the length) of the distal portion of the blood pump catheter (i.e., the portion of the blood pump catheter that is placed inside the compartment outside the sleeve by being advanced over the helical support element). The blood pump catheter pumps blood out of the compartment outside the sleeve (i.e., out of the renal veins) into the inlet holes. The blood pump typically defines outlet holes (not shown) that are configured to be disposed in the vena cava in fluid communication with the interior of the sleeve (e.g., at a location of the vena cava that is upstream of the sleeve, or a location of the vena cava that is downstream of the sleeve). The pump pumps blood into the vena cava via the outlet holes.

Figure 10G:
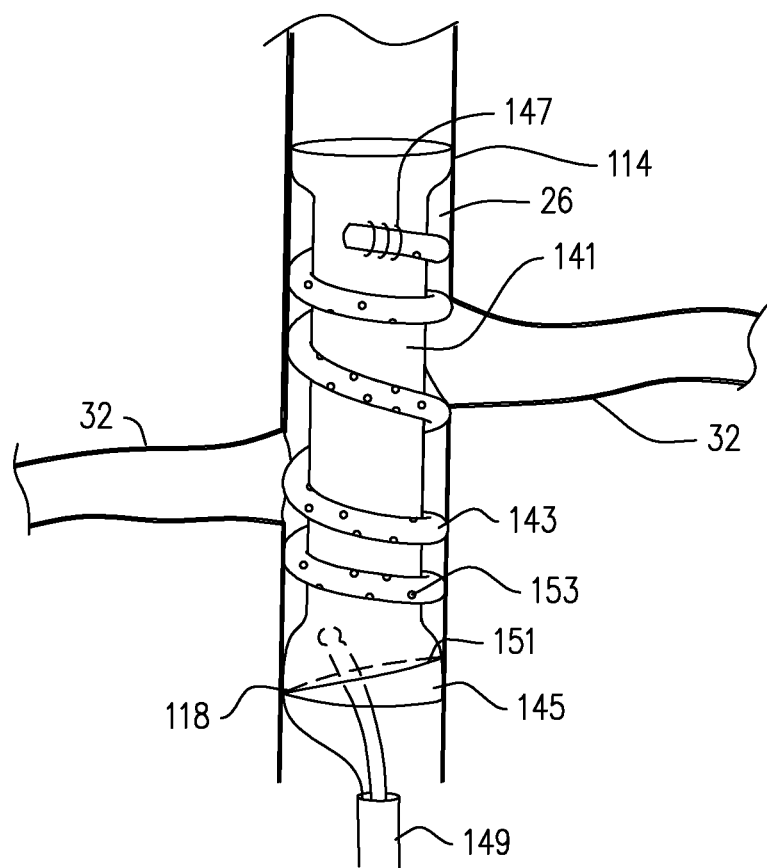
FIG. 10G is a schematic illustration a sleeve coupled to a helical blood pump catheter, the sleeve and the blood pump catheter being configured to occlude blood flow from a subject's vena cava to the subject's renal veins, in accordance with some applications of the present invention.

Reference is now made to FIG. 10G, which is a schematic illustration a blood-impermeable sleeve 141 coupled to a helical blood pump catheter 143, the sleeve and the blood pump catheter being configured to occlude blood flow from the subject's vena cava 26 to the subject's renal veins 32, in accordance with some applications of the present invention. Typically sleeve 141 is shaped to define flared ends 145 thereof, as shown. Typically, sleeve 141 has a generally similar shape to sleeve 110 described hereinabove with reference to FIGS. 10A-D, the sleeve defining flared ends that are configured to contact the wall of the vena cava.

Sleeve 141 and blood pump catheter 143 are inserted into the vena cava via a delivery device 149. A distal end of the catheter 143 (i.e., the end of the catheter that is furthest from an insertion location via which the catheter is inserted into the subject's body) is coupled to a distal end of the sleeve (e.g., a downstream end of the sleeve, as shown) at a coupling location 147. The blood pump catheter is pre-shaped such that, upon being advanced out of the distal end of the insertion device, a distal portion of the catheter assumes a helical shape that is disposed around the outside of the sleeve. Typically, by assuming the helical shape, the distal portion of the catheter axially holds open the sleeve (i.e., prevents the sleeve from collapsing axially). For some applications, a ring 151 made of a shape memory material (such as nitinol) is coupled to the proximal end of the sleeve and is configured to support the proximal end of the sleeve. Typically, the blood pump catheter defines inlet holes 153 along most of the length (e.g., more than 50 percent, or more than 75 percent of the length) of the distal portion of the blood pump catheter (i.e., the helical portion of the blood pump catheter that is disposed around the sleeve). The blood pump catheter pumps blood out from outside the sleeve (i.e., out of the renal veins) into the inlet holes. Typically the sleeve is placed in the vena cava such that a downstream end of the sleeve is coupled to the wall of the vena cava at a first location 114 that is downstream of all renal veins of the subject (e.g., left and right renal vein in a typical subject that has two renal veins), and such that an upstream end of the sleeve is coupled to a wall of the vena cava at a second location 118 that is upstream of all renal veins of the subject. Further typically, the pumping of the blood into the inlet holes causes the vena cava to constrict around the outside of the sleeve such that blood in the renal veins becomes isolated into a compartment outside the sleeve that is separated from blood flow through the vena cava.

The blood pump typically defines outlet holes (not shown) that are configured to be disposed in the vena cava in fluid communication with the interior of the sleeve (e.g., at a location of the vena cava that is upstream of the sleeve, or a location of the vena cava that is downstream of the sleeve). The pump pumps blood into the vena cava via the outlet holes.

It is noted that although in FIGS. 10E-G the blood pump is shown being inserted to outside the sleeve from the upstream end of the sleeve, for some applications the pump is inserted to outside the sleeve from the downstream end of the sleeve. In general, the scope of the present invention includes inserting the blood pumps and the occluding elements that are described herein toward the renal veins by approaching the renal veins via the vena cava, from above the renal veins, or from below the renal veins. For example, the renal veins may be approached through the vena cava from the upstream direction, via the femoral vein, or from the downstream direction, via the jugular vein.

Figure 11A:
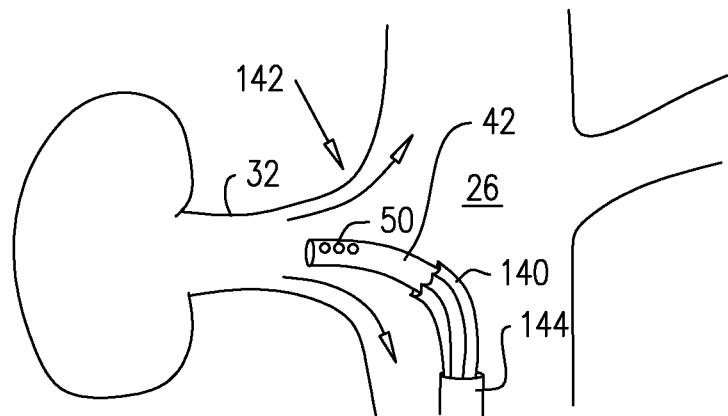
FIGS. 11A-C are schematic illustrations of a blood pump catheter being placed in a subject's renal vein, such that an ostium-covering umbrella disposed around the outside of the catheter covers the ostium at the junction between the subject's vena cava and the renal vein, in accordance with some applications of the present invention.
Figure 11B:
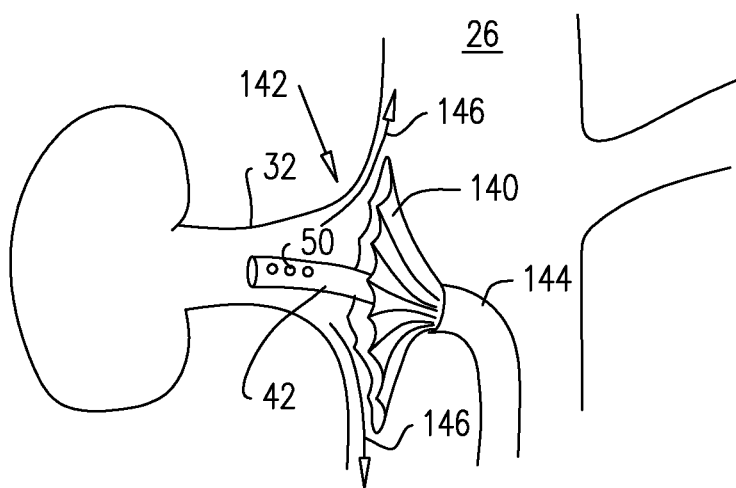
Figure 11C:
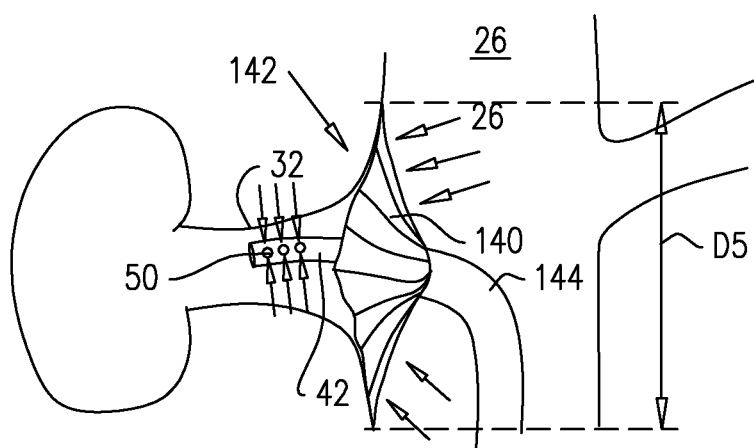

Reference is now made to FIGS. 11A-C, which are schematic illustrations of blood pump catheter 42 being placed in a subject's renal vein 32, such that an ostium-covering umbrella 140 disposed around the outside of the catheter, and disposed within the vena cava, covers an ostium at a junction 142 between the subject's vena cava 25 and the renal vein 32, in accordance with some applications of the present invention. It is noted that although the ostium-covering umbrella is described as an "umbrella," the scope of the present invention includes covering the ostium with any ostium-covering element that is configured to be disposed around the outside of the catheter and that is made of flexible portions (e.g., flexible tissue portions), and rigid support elements that provide shape and structure to the ostium-covering element. Ostium-covering umbrella 140 is an example of occlusion element 36 described hereinabove with reference to FIGS. 4A-B, and blood pump catheter 42 is an example of blood pump 34 described hereinabove with reference to FIGS. 4A-B. (In FIGS. 11A-C, ostium-covering umbrella 140 is shown covering the left renal vein ostium, but the scope of the present invention includes covering the right renal vein ostium with ostium-covering umbrella 140, and, as is typically the case, placing an ostium-covering umbrella at the ostia of the junctions of the vena cava with each of the left and right renal veins.)

As shown in FIGS. 11A-C, blood pump catheter 42 and ostium-covering umbrella 140 are inserted into vena cava 26 via an insertion device 144. During the insertion, the ostium-covering umbrella is typically in a closed state thereof. The blood pump catheter and the ostium-covering umbrella are advanced out of the insertion device, the ostium-covering umbrella opening in response being advanced out of the distal end of the insertion device (FIG. 11B). The ostium-covering umbrella is placed in the vicinity of junction 142. Blood pump catheter is activated to pump blood downstream through the renal vein into inlet holes 50 at the distal end of the blood pump catheter. Typically, due to the suction force of the blood pump, the ostium-covering umbrella is pulled against the walls of the vena cava surrounding the ostium at junction 142 (FIG. 11C).

Typically, ostium-covering umbrella 140 occludes backflow of blood from the vena cava to the renal vein, by being pushed against the walls of the vena cava surrounding the ostium at junction 142, in response to blood flowing from the vena cava to the renal vein. Further typically, while blood pump is active, ostium-covering umbrella occludes blood flow both from the renal vein to the vena cava and from the vena cava to the renal vein, by the ostium-covering umbrella becoming sealed against the walls of the vena cava surrounding the ostium at junction 142, due to the suction force generated by the blood pump. In response to blood pump catheter 42 becoming inactive (e.g., due to a loss of power to the pump), surrounding the ostium at junction umbrella allows blood to flow from the renal vein to the vena cava in the direction of arrows 146 (FIG. 11B), since when the pump is inactive the umbrella is not sealed against the walls of the vena cava surrounding the ostium at junction 142.

For some applications, a diameter D5 of ostium-covering umbrella 140, when the ostium-covering umbrella is in an open state thereof is greater than 5 mm (e.g., greater than 10 mm, or greater than 20 mm), less than 30 (e.g., less than 25 mm, or less than 20 mm), and/or between 5 and 30 mm (e.g., between 10 and 20 mm, or between 15 and 25 mm).

Figure 12A:
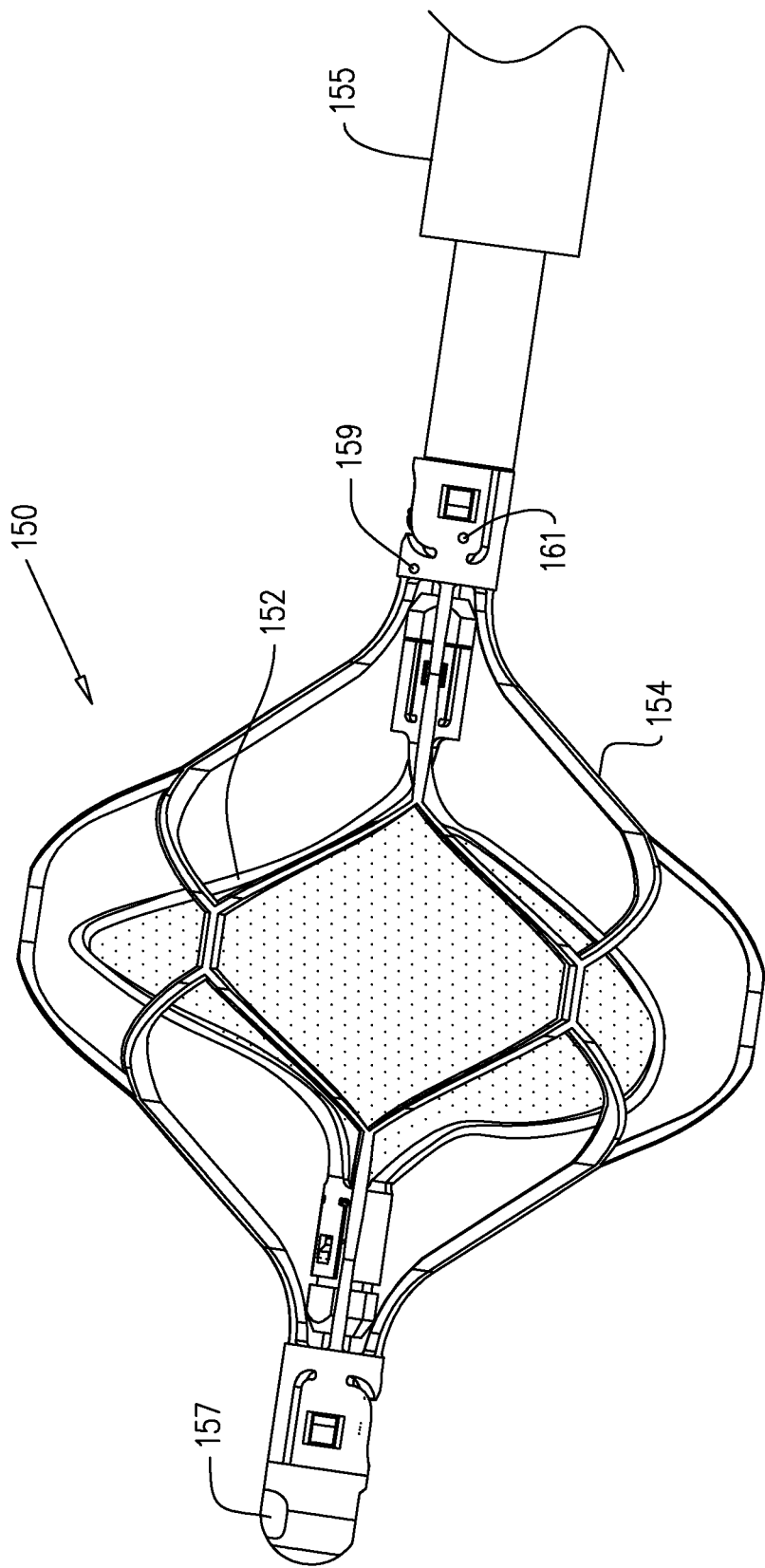
FIGS. 12Ai-ii, and 12B-E are schematic illustrations of a blood pump that includes an impeller disposed inside a radially-expandable cage, in accordance with some applications of the present invention.
Figure 12B:
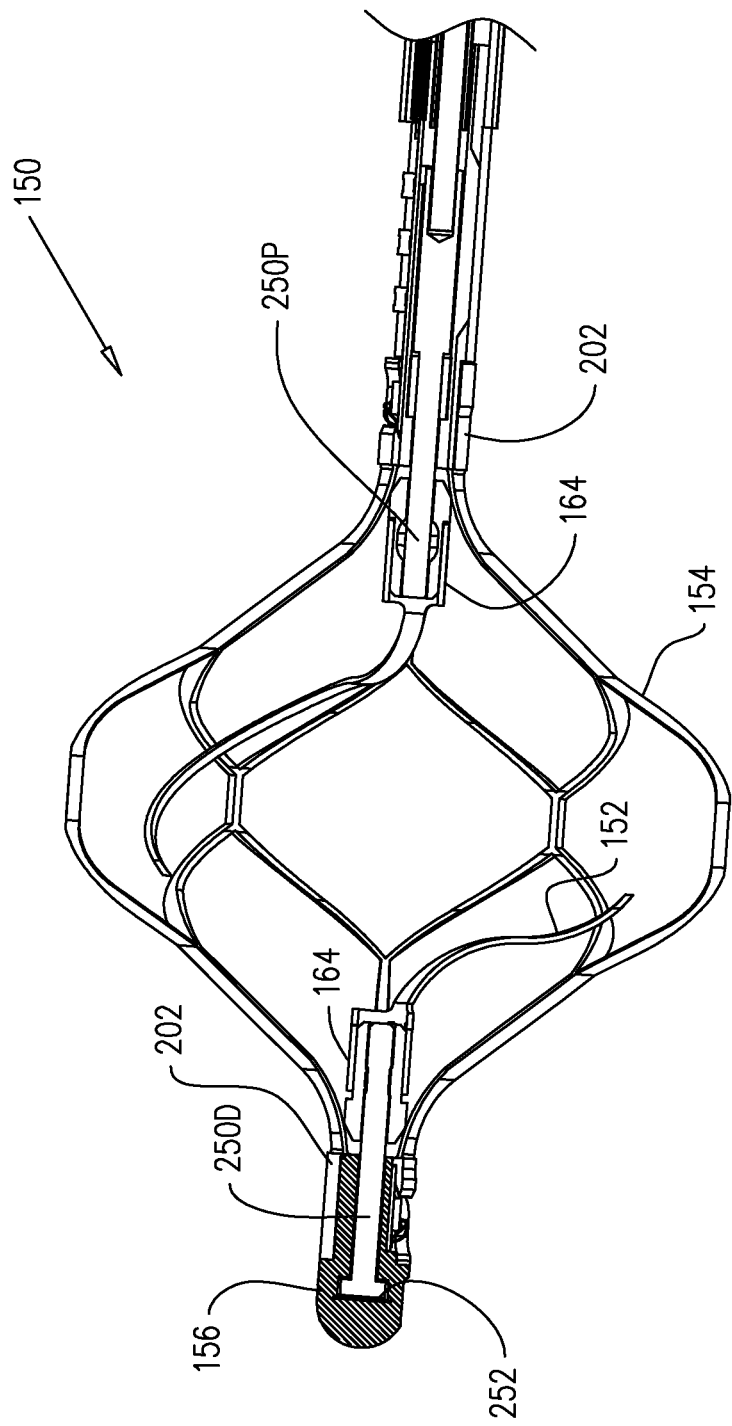
Figure 12C:
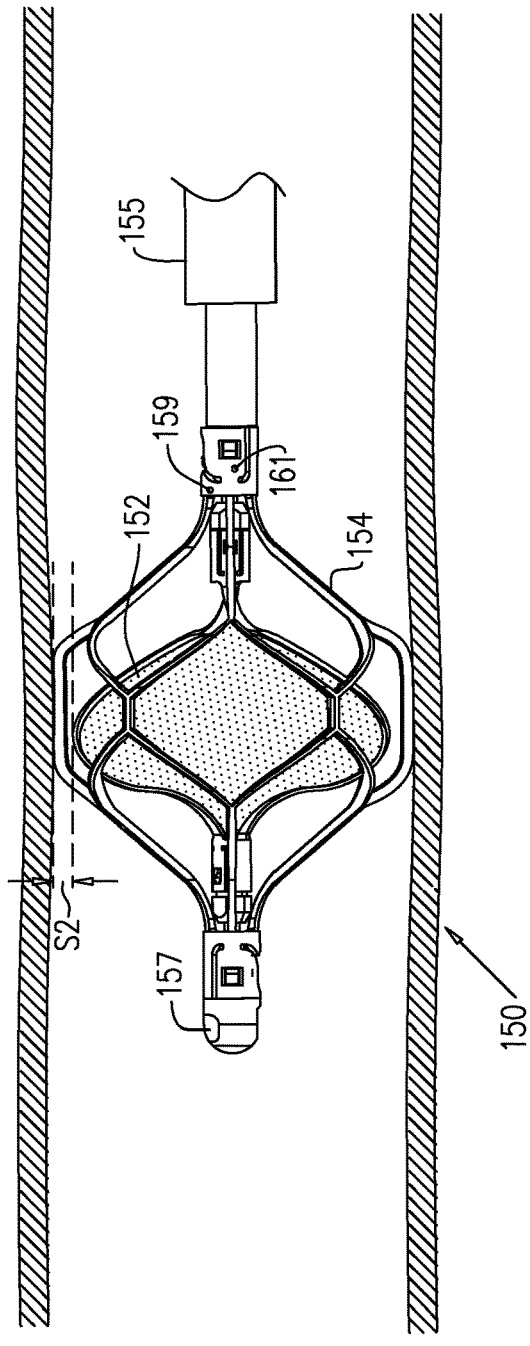
Figure 12D:
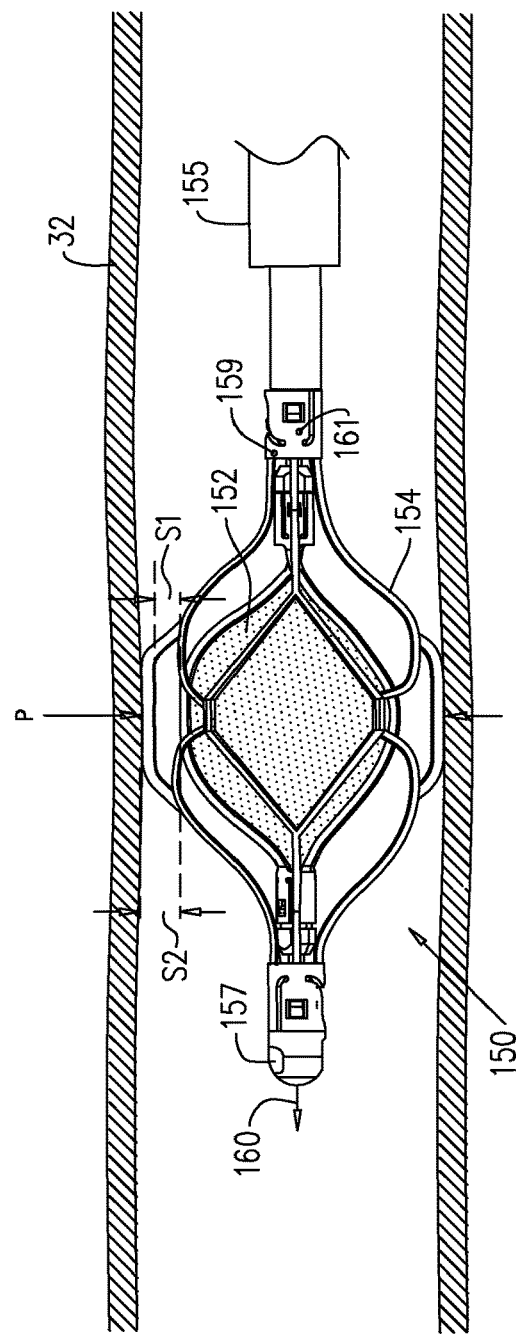

Reference is now made to FIGS. 12Ai-ii and 12-B, which are schematic illustrations of a blood pump 150 that includes an impeller 152 disposed inside a radially-expandable impeller cage 154, in accordance with some applications of the present invention. FIGS. 12Ai and 12Aii show respective views of blood pump 150. Reference is further made to FIGS. 12C-D, which show side views of blood pump 150 disposed inside renal vein 32, when cage 154 is, respectively, in relatively radially-expanded and radially-compressed configurations thereof, in accordance with some applications of the present invention. Reference is also made to FIG. 12E, which shows an end view of impeller 152 combined with a cross-sectional view of struts 204 of cage 154 and a cross-sectional view of renal vein 32, when blood pump 150 is disposed inside renal vein 32, in accordance with some applications of the present invention.

It is noted that the term "impeller" is used herein to denote a bladed rotor, as shown in FIGS. 12Ai-E. When the bladed rotor is placed inside a blood vessel (such as renal vein 32) and rotated, the bladed rotor functions as an impeller, by increasing the flow of blood through the blood vessel, and/or by generating a pressure difference between the upstream end and the downstream end of the impeller.

For some applications, blood pump 150 is placed one or both (or all) of a subject's renal veins and is used to pump blood in a downstream direction through the renal veins toward the vena cava, such as to reduce renal vein pressure, and/or to enhance perfusion of the subject's kidneys.

Blood pump 150 is typically placed inside the subject's renal veins in order to provide acute treatment of a subject suffering from cardiac dysfunction, congestive heart failure, low renal blood flow, high renal vascular resistance, arterial hypertension, and/or kidney dysfunction. For example, the pump may be placed inside the subject's renal veins for a period of more than one hour (e.g., more than one day), less than one week (e.g., less than four days), and/or between one hour and one week (e.g., between one day and four days). For some applications, the pump is chronically placed inside the subject's renal veins in order to provide chronic treatment of a subject suffering from cardiac dysfunction, congestive heart failure, low renal blood flow, high renal vascular resistance, arterial hypertension, and/or kidney dysfunction. For some applications, a course of treatment is applied to a subject over several weeks, several months, or several years, in which the pump is intermittently placed inside the subject's renal veins, and the subject is intermittently treated in accordance with the techniques described herein. For example, the subject may be intermittently treated at intervals of several days, several weeks, or several months.

Typically, the effect of pumping blood through the renal veins of a subject suffering from cardiac dysfunction, congestive heart failure, low renal blood flow, high renal vascular resistance, arterial hypertension, and/or kidney dysfunction is generally similar to that described with reference to FIG. 4B. Namely, the pumping causes a lowering and flattening of the subject's renal vein pressure profile, even though the subject's central venous pressure is elevated. In accordance with the description of FIG. 4B hereinabove, the renal venous pressure graph shows the original venous pressure profile as a dashed curve, and shows two curves showing the renal venous pressure, subsequent to activation of the blood pump. Typically, during pumping of the blood through the renal vein, the height of the venous pressure curve depends on the amount of pumping that the operator applies to the renal vein via the pump, as indicated by the two solid curves shown in FIG. 4B, the curves representing renal venous pressure profiles at respective rates of pumping of blood pump 150. For some applications, as shown, the renal vein pressure profile is not completely flattened, since small cyclical variations in blood pressure are transmitted to the renal veins via the renal capillary system.

Typically, due to the reduction in pressure in the renal vein that is caused by the pumping of the blood in the downstream direction by pump 150, perfusion of the kidney increases. In turn, this may cause pressure in the renal veins to rise relative to the pressure in the renal veins immediately subsequent to initiation of the pumping, due to increased blood flow into the renal vein. Typically, even after perfusion of the kidney increases, the pump is configured to maintain the pressure in the renal vein at a lower value than the pressure in the renal vein before the initiation of the pumping. For some applications, in addition to lowering the subject's renal vein pressure, and/or increasing perfusion of the subject's kidney, the blood pump performs ultrafiltration on the subject's blood.

It is noted that, for some applications, due to the reduction in pressure in the renal vein that is caused by the pumping of the blood in the downstream direction by pump 150, the subject's renal vascular resistance decreases, in accordance with physiological mechanisms that are described, for example, in an article by Haddy et al., entitled "Effect of elevation of intraluminal pressure on renal vascular resistance" (Circulation Research, 1956), which is incorporated herein by reference. It is further noted that a treatment of the subject that increases renal perfusion by increasing blood pressure in the subject's renal arteries would typically not effect the aforementioned physiological mechanisms.

As described hereinabove, typically, when blood pump 150 is used to reduce pressure in the subject's renal veins, it is expected that there will be an improved responsiveness by the subject to administration of diuretics to the subject, due to the reduction in renal venous pressure. Therefore, for some applications, a reduced dosage of diuretics may be administered to the subject relative to a dosage of diuretics that would be administered to the subject in the absence of performing the techniques described herein. Alternatively, a regular dosage of diuretics may be administered to the subject, but the diuretics may have a greater effect on the subject, due to the reduction in renal venous pressure.

High central venous pressure leads to a high level of blood pressure within the heart, which in turn leads to the release of atrial natriuretic peptide (ANP) and B-type natriuretic peptide (BNP) by the subject, both of which act as natural diuretics. Typically, when blood pump 150 is used to reduce pressure in the subject's renal veins, there is expected to be an improved responsiveness by the subject to the release of the natural diuretics by the subject, due to the reduction in renal venous pressure. For some applications, since the subject's central venous pressure is not lowered by using blood pump 150, it is expected that the subject will continue to release atrial natriuretic peptide (ANP) and B-type natriuretic peptide (BNP), even while the subject's renal venous pressure is reduced by the use of the blood pump 150. Thus, for some applications, using blood pump 150 may result in the subject continuing to release atrial natriuretic peptide (ANP) and B-type natriuretic peptide (BNP), as well as resulting in the effectiveness of the aforementioned natural diuretics being greater than the effectiveness of the diuretics in the absence of the use of blood pump 150.

It is noted that, typically, blood pump 150 pumps blood in a manner that enhances the rate of flow of blood flow through the renal veins and into the vena cava, but does not cause a substantial change in the direction of the blood flow relative to the natural direction of flow through the renal veins, or from the renal veins to the vena cava (i.e., relative to blood flow in the absence of pumping by the pump). That is to say that the blood pump pumps blood in the downstream direction through the renal veins and then directly into the portion of the vena cava that is adjacent to the renal veins, rather than, for example, pumping the blood from the renal veins into a different portion of the subject's veins (such as, an upstream location within the vena cava). Further typically, blood pump 150 enhances blood flow through the renal veins without removing blood from the subject's venous system into a non-venous receptacle, such as an artificial lumen of a blood pump.

Typically, cage 154 defines a non-constrained, radially-expanded configuration thereof, which the cage assumes in the absence of any force being applied to the cage, and a radially-compressed configuration, which the cage assumes when the cage is axially elongated. Similarly, typically, impeller 152 defines a non-constrained, radially-expanded configuration thereof, which the impeller assumes in the absence of any force being applied to the impeller, and a radially-compressed configuration, which the impeller assumes when the impeller is axially elongated.

Typically, during insertion of cage 154 and impeller 152 into the subject's renal vein, the cage and the impeller are crimped by axially elongating the cage and the impeller, such that the cage and the impeller become radially compressed. The cage and the impeller are inserted into the renal vein, while the cage and the impeller are maintained in radially-compressed configurations by an insertion device 155, e.g., a catheter. The cage and the impeller are advanced out of the distal end of the insertion device into the renal vein. In response to being advanced out of the distal end of the insertion device, the cage and the impeller automatically radially expand, and axially contract.

Typically, cage 154 is configured to hold open the inner wall of the renal vein and to separate the inner wall of the renal vein from the impeller, such that the renal vein does not become injured by the impeller. Further typically, blood pump 150 includes an engagement mechanism 156 that is configured to engage the impeller with respect to the cage. For example, as shown in FIG. 12B, which shows a cross-sectional view of the impeller and the cage, proximal and distal bearings 250P and 250D are disposed adjacent to the proximal and distal ends of impeller 152, and are configured to impart rotational motion to the impeller. Engagement mechanism 156 is disposed between a ring 202 (described hereinbelow with reference to FIG. 17) disposed at the distal end of the cage and a surface 252 of distal bearing 250P, such that when ring 202 moves distally, the ring pushes the engagement mechanism distally, which, in turn, pushes the distal bearing distally. The distal bearing is coupled to a distal ring 164 (described hereinbelow with reference to FIGS. 13A-D) of the impeller, such that the distal motion of the distal bearing pulls the distal ring of the impeller distally, thereby axially elongating the impeller.

The engagement mechanism thus engages the impeller with respect to the cage such that, in response to the cage becoming radially contracted and axially elongated (e.g., in response to the renal vein exerting radial pressure on the cage), the impeller axially elongates and radially contracts. For example, as shown in the transition from FIG. 12C to FIG. 12D, in response to the renal vein exerting pressure P on cage 154, the cage becomes partially radially compressed, causing the cage to elongate, e.g., by the distal end of the cage moving in the direction of arrow 160. Engagement mechanism 156 causes the impeller to become elongated in response to the cage becoming elongated. The elongation of the impeller causes the impeller to radially contract.

Engagement mechanism 156 is typically configured such that, even at a circumferential location at which a separation Si (FIGS. 12C and 12D) between the impeller and the inner surface of the cage is smallest, a separation between the impeller and the inner surface of the cage is maintained (i.e., impeller and the inner surface of the cage are still separated from each other), even if the cage radially contracts. A fortiori, even at the circumferential location at which a separation S2 between the impeller and the outer surface of the cage is smallest, the engagement mechanism maintains the separation between the impeller and the outer surface of the cage (i.e., impeller and the outer surface of the cage are still separated from each other), even if the cage radially contracts. Since the inner wall of the renal vein is supported by the outer surface of the cage, separation S2 between the impeller and the outer surface of the cage is typically also the separation between the impeller and the inner wall of the renal vein at the location at which the inner wall of the renal vein is closest to the impeller. Thus, the engagement mechanism maintains a separation between the between the impeller and the inner wall of the renal vein, even at the location at which the inner wall of the renal vein is closest to the impeller, and even when the renal vein exerts pressure on the cage such that the cage radially contracts.

It is noted that, in response to the renal vein exerting pressure P on cage 154 and causing the cage to radially contract, separation S1 between the impeller and the inner surface of the cage, and/or separation S2 between the impeller and the outer surface of the cage, may decrease. However, the engagement mechanism is such as to cause the impeller and the inner surface of the cage to remain separated from each other, even if the cage radially contracts. In this manner, the cage protects the renal vein from being injured by the impeller even if the renal vein contracts. It is further noted that, although the inner wall of the renal vein is supported by the outer surface of the cage, the cage typically includes struts that defines cells, and the wall of the renal vein typically can protrude through the cells to inside the cage. By maintaining separation S1 between the impeller and the inner surface of the cage, the engagement mechanism protects the inner wall of the renal vein from the impeller even if the inner wall of the renal vein protrudes to inside the cage.

When blood pump 150 is deployed inside a blood vessel, such as renal vein 32, cage 154 expands against the inner wall of the blood vessel, such that the cage becomes rotationally fixed with respect to the inner wall of the blood vessel. While the cage is rotationally fixed with respect to the wall of the blood vessel, impeller 152 rotates such as to pump blood through the blood vessel. Engagement mechanism 156 is configured to engage the impeller with respect to the cage such that (a) when the cage is radially compressed, the impeller becomes radially compressed, (b) when the cage is axially elongated, the impeller becomes axially elongated, but (c) the impeller is able to rotate, even though the cage is rotationally fixed in position. The engagement mechanism is configured to permit rotation of the impeller even though the cage is rotationally fixed in position, by the engagement mechanism permitting rotation of distal bearing 250D within the engagement mechanism.

Typically, in order to insert the cage and the impeller into the blood vessel, the cage is placed inside insertion device 155 in a crimped configuration. Typically, crimping the cage such that the cage assumes an axially-elongated configuration automatically causes the impeller to assume an axially-elongated configuration, since the engagement mechanism imparts the longitudinal motion of the distal end of the cage to the distal end of the impeller, in the manner described hereinabove.

As shown, for example, in FIG. 12C-D, for some applications, pressure sensors 157 and 159 are disposed on upstream and downstream sides of blood pump 150. When blood pump 150 is disposed inside a renal vein, as shown in FIGS. 12C-D for example, the pressure measured by upstream pressure sensor 157 is indicative of blood pressure upstream of the blood pump in the renal vein, and the pressure measured by downstream pressure sensor 159 is indicative of central venous pressure. For some applications, one or more further sensors 161 are disposed on the blood pump (e.g., on a downstream side of the blood pump, as shown in FIG. 12C-D, or on an upstream side of the blood pump), and are configured to measure one or more additional parameters, such as flow through the renal vein, and/or oxygen-saturation within the renal vein. Alternatively or additionally, a thermal flow sensor is used to measure flow through the renal vein. For example, a thermal flow sensor 260, as described hereinbelow with reference to FIGS. 22Ai-Cii, may be used to measure flow through the subject's renal vein.

FIG. 12E shows an end view of impeller 152 combined with a cross-sectional view of struts 204 of cage 154 and a cross-sectional view of renal vein 32, when blood pump 150 is disposed inside renal vein 32, in accordance with some applications of the present invention. The cross-sectional view of the cage and the renal vein is in a plane that is perpendicular to a longitudinal axis 222 of the cage at a longitudinal location at the center of the longitudinal axis of the cage. Typically, at this location, the diameter of the cage, perpendicular to the longitudinal axis of the cage, is at its maximum. Further typically, at this location a span of the impeller SP, perpendicular to a longitudinal axis 224 of the impeller, is also at its maximum. For some applications, the outer edge of the impeller and the inner surfaces of struts of the cage are minimally separated from one another at this longitudinal location, and the outer edge of the impeller and the outer surfaces of struts of the cage are minimally separated from one another at this longitudinal location.

Since the cage comprises struts 204, which are shaped to define cells, the cage typically allows blood flow therethrough, by allowing blood flow through the cells defines by the cage. As shown in FIG. 12E, typically, when the cage and the impeller assume radially-expanded configurations thereof inside a blood vessel, such as renal vein 32, there is a minimum separation S1 between the outer edge of the impeller and struts 204, and a minimum separation S2 between the outer edge of the impeller and the outer surface of the struts 204 of the cage (which is typically also the minimum separation between the outer edge of the impeller and the inner wall of the blood vessel). Further typically, there is space between blades of the impeller. Typically, even if the impeller is not actively pumping blood through the blood vessel, blood is able to flow through the blood pump by flowing through the cells defined by the cage, and by flowing through the separations between the impeller and the cage, through the separations between the impeller and the blood vessel wall, and/or through the separation between the blades of the impeller.

It is noted that blood pump 150 typically does not include an occlusion element (such as a sealing element) for preventing retrograde flow of blood through the blood pump. For some applications, while blood pump is pumping blood in an antegrade direction, there is some retrograde flow of blood through the separations between the impeller and the cage, through the separations between the impeller and the blood vessel wall, and/or through the separation between the blades of the impeller (e.g., in the vicinity of the center of the impeller). Alternatively or additionally, while blood pump is pumping blood in a downstream direction, there is antegrade flow of blood through the separations between the impeller and the cage, through the separations between the impeller and the blood vessel wall, and/or through the separation between the blades of the impeller (e.g., toward the center of the impeller). Typically, whether the flow of blood through the aforementioned regions is in a retrograde or an antegrade direction, the flow of blood through these regions reduces a likelihood of blood stagnating within these regions.

For some applications, when the impeller is in a non-constrained, radially-expanded configuration thereof (as shown in FIG. 12E), a span SP of the impeller in a direction perpendicular to a longitudinal axis of the impeller is greater than 8 mm, less than 15 mm, and/or between 8 and 15 mm. For example, span SP may be greater than 8 mm, less than 12 mm, and/or between 8 mm and 12 mm. Or, span SP may be greater than 10 mm, less than 15 mm, and/or between 10 mm and 15 mm.

Reference is now made to FIGS. 13A-D, which are schematic illustrations of respective stages of a method of manufacture of impeller (i.e., bladed rotor) 152, in accordance with some applications of the present invention. For some applications, a tube 162 (e.g., a nitinol, a stainless steel, or a plastic tube) is cut (e.g., laser cut) along the dashed lines shown in FIG. 13A, such that the cut tube (FIG. 13B) defines a structure 165 having first and second end portions, e.g., rings 164, at ends of the structures, the rings being connected to each other by a plurality of (e.g., two as shown in FIG. 13B, or more than two) elongate elements 166 (e.g., elongate strips, as shown). The first and second ends of each of the elongate elements are typically disposed at an angle alpha from one another with respect to the circumference of the rings. Typically, angle alpha is greater than 5 degrees (e.g., greater than 50 degrees, greater than 70 degrees, or greater than 90 degrees), less than 360 degrees (e.g., less than 180 degrees, less than 150 degrees, or less than 110 degrees), and/or between 5 and 360 degrees (e.g., between 50 and 180 degrees, between 70 and 150 degrees, or between 90 and 110 degrees).

It is noted that, although elongate elements 166 are described and shown as strips, the scope of the present invention includes using elongate elements having other structures, such as elongate tubular structures, elongate rod structures, etc., mutatis mutandis.

Structure 165 is axially compressed, e.g., by pushing the two rings toward one another, such that elongate elements 166 radially expand, as shown in the transition from FIG. 13B to FIG. 13C. Typically, before the structure is axially compressed (i.e., in the axially elongated configuration of the structure), a length L4 of the structure, measured along the longitudinal axis of the structure, is greater than 15 mm, less than 25 mm, and/or between 15 and 25 mm. Before the structure is axially compressed (i.e., in the axially elongated configuration of the structure), a length L5 of each of the elongate elements, measured along the longitudinal axis of the structure, is greater than 14 mm, less than 22 mm, and/or between 14 and 22 mm. Typically, when impeller 152 is axially elongated, the lengths of impeller 152 and of elongate elements 166, measured along the longitudinal axis of the impeller, are the same as, respectively, lengths L4 and L5. Further typically, when impeller 152 is axially elongated, the lengths of impeller blades, measured along the longitudinal axis of the impeller, are the same as L5.

Typically, the structure is shape set in the axially-compressed state of the structure. Structure 165 forms the frame of the impeller 152. Further typically, in the axially-compressed state of the structure, each of elongate elements 166 of structure 165 forms a helical shape. Each of the helical elongate elements originates from a first one of the end portions (e.g., rings 164) and terminates at the second one of the end portions (e.g., rings 164). The pitches of each of the helical elongate elements are typically within 20 percent of one another, the helical elongate elements typically having the same pitch as one another. For some applications, the pitch of the helical elongate elements varies along the length of the helical elongate elements. The radii of each of the helical elongate elements are typically within 20 percent of one another, and, typically, the helical elongate elements have the same radius as one another. For some applications, the helices defined by the two elongate elements are not symmetrical with respect to one another. The longitudinal axis of each one of the helical elongate elements is typically parallel to the longitudinal axis of the other one of the helical elongate elements, and is typically parallel to the longitudinal axis of the impeller. For some applications, each of the elongate elements defines more than one eighth of a winding of a helix, and/or less than half a winding of a helix, e.g., between one eighth of a winding and half a winding of a helix.

It is noted that although each of the elongate elements is described as being helical, for some applications, the elongate elements do not define precise mathematical helices, but each of the elongate elements defines a generally helical shape in that the elongate element spirals radially outwardly from a first one of end portions (e.g., rings) while extending axially away from the first one of the end portions, and then spirals radially inwardly toward the second one of the end portions while extending axially toward the second one of the end portions.

It is noted that, typically, cutting tube 162 such that angle alpha is as described hereinabove, facilitates the shaping of elongate elements 166 into desired helical shapes. For some applications, the tube is cut such that angle alpha is not as described hereinabove, and nevertheless elongate elements 166 are shaped into desired helical shapes by twisting structure 165, while applying a shape setting treatment to structure 165. Typically, ceteris paribus, cutting tube 162 such that angle alpha is as described hereinabove, facilitates the shaping of elongate elements 166 in desired helical shapes, while reducing stress on elongate elements 166, relative to stress on the elongate elements if the elongate elements are shaped into the desired helical shapes without cutting the tube such that angle alpha is as described hereinabove.

Typically, in the axially-compressed configuration of the structure, a length L6 of the structure, measured along the longitudinal axis of the structure, is greater than 8 mm, less than 18 mm, and/or between 8 and 18 mm. Further typically, in the axially-compressed configuration of the structure, a length L7 of each of the elongate elements, measured along the longitudinal axis of the structure, is greater than 5 mm, less than 14 mm, and/or between 5 and 14 mm. Typically, when impeller 152 is in its non-compressed, radially-expanded configuration, the lengths of impeller 152 and of elongate elements 166, measured along the longitudinal axis of the impeller, are the same as, respectively, lengths L6 and L7. Further typically, when impeller 152 is in its non-constrained, radially-expanded configuration, the lengths of impeller blades, measured along the longitudinal axis of the impeller, are typically the same as L7.

Subsequent to axially compressing structure 165, a material 168 (e.g., a flexible polymeric material, such as silicone, polyurethane, and/or polyester) is coupled to at least a portion of structure 165, e.g., to the helical elongate elements of structure 165. Typically, material 168 is coupled to the portion of structure 165 by structure 165 being dipped into material 168, while material 168 is in a liquid state thereof. For example, structure 165 may be dipped into liquid silicone, a silicone-based elastomer, and/or a different elastomer. Subsequently, the material is dried (e.g., by a curing and/or a polymerization process), such that a film of the material forms that is supported by the helical elongate elements of structure 165. For some applications, techniques are used to facilitate the formation of a film on structure 165 and/or coupling of the material to the helical elongate elements of structure 165, as described hereinbelow. For some applications, during the drying of material 168, structure 165 is rotated about its longitudinal axis, such as to facilitate the formation of a film of material 168 having a uniform thickness. For some applications, material 168 is coupled to structure 165 in a different manner to the above-described manner, e.g., via suturing and/or electrospinning a flexible polymeric material (such as silicone, polyurethane, and/or polyester) to the helical elongate elements of structure 165.

The helical elongate elements 166 with the material coupled thereto define the impeller blade. To form impeller 152 with a single blade, as shown in FIG. 13D, tube 162 is cut to define a structure that defines two helical elongate elements between rings 164. (It is noted that the impeller shown in FIG. 13D may alternatively be described as a two-bladed impeller, each of these elongate elements with the material coupled thereto defining a blade. For example, in the end view of the impeller, shown in FIG. 18Ai, the portions of the impeller on respective sides of ring 164 may each be viewed as blade. Nevertheless, in the context of the present application, an impeller that includes two helical elongate elements, as shown in FIG. 13D, is described as having a single blade.) For some applications, a three-bladed impeller is formed by cutting tube 162 to define a structure that defines three elongate elements between rings 164, such that when the structure is axially compressed the structure defines three helical elongate elements, e.g., as described hereinbelow with reference to FIGS. 16A-B. Alternatively or additionally, an impeller having a different number of blades, e.g., 4-8 blades, is used.

Typically, material 168 is coupled to structure 165 such that the material forms a continuous layer (e.g., a continuous film) between the elongate elements 166. It is further noted that typically material 168 is shaped to form one or more blades, by virtue of the material being supported by helical elongate elements 166 while the material is dried (e.g., by a curing or a polymerization process), and without requiring the use of any instrument, such as a shaping mandrel, that is configured to impart shape to the blades As shown in FIG. 13D, the impeller blade is typically formed of a continuous film of material 168 that is supported by helical elongate elements 166, the helical elongate elements typically forming the outer edges of the blade of the impeller. It is noted that, typically, the impeller does not include an axial support member (such as a shaft) along the axis of the impeller between the proximal and distal ends of the helical elongate elements, for providing support to the film of material. More generally, the impeller typically does not include any support member (such as a shaft) between the proximal and distal ends of the helical elongate elements for providing support to the film of material 168. Thus, typically there is no supporting member that breaks up the continuity of the film of material disposed between the helical elongate elements. Furthermore, rotational motion is imparted from the proximal end portion (e.g., proximal ring 164) of the impeller to the distal end portion (e.g., distal ring 164) of the impeller via the helical elongate elements of the impeller (e.g., substantially solely via the helical elongate elements), and not via an axial support member (such as a shaft).

During insertion of the impeller via insertion device 155 (FIG. 12Ai), the impeller is radially compressed by axially elongating structure 165, such that helical elongate elements 166 become straightened. Typically, the film of material 168 conforms with the shape changes that the helical elongate elements undergo during the axial elongation of structure 165, since there is no additional supporting member providing support to material 168 between the proximal and distal ends of the helical elongate elements. Further typically, ceteris paribus, the lack of an axial support member (such as a shaft) between the proximal and distal ends of the helical elongate elements facilitates radial compression of the impeller such that the maximum diameter of the impeller when the impeller is in a maximally-radially-compressed configuration thereof is less than that of an impeller that is similar in all other aspects, but that includes an axial support member, i.e., the impeller is configured to be radially compressible to a smaller diameter than if the impeller were to comprise an additional supporting member for supporting the material between the proximal and distal ends of the helical elongate elements.

For some applications, ceteris paribus, due to the lack of an axial support member (such as a shaft) between the proximal and distal ends of the helical elongate elements, the impeller is more flexible than an impeller that is similar in all other aspects, but that includes an axial support member (such as a shaft). During the insertion into the renal vein, the impeller and the cage are typically inserted through junctions of blood vessels that form relatively acute angles with each other (e.g., angles of more than 70 degrees), and that are disposed at relatively short distances from one another. For example, the impeller and the cage may be passed through the femoral vein, the iliac vein, into the vena cava, and then into the renal vein. Flexibility of the impeller typically facilitates insertion of the impeller into the renal vein.

Furthermore, ceteris paribus, the lack of an axial support member (such as a shaft) between the proximal and distal ends of the helical elongate elements facilitates axial elongation of the impeller by a given length using less force than would be required to axially elongate by the given length an impeller that includes an axial support member (such as a shaft) between the proximal and distal ends of the helical elongate elements, since axial elongation of an impeller that includes an axial support member would typically require axial elongation of the axial support member (e.g., via axial stretching of the support member). Similarly, ceteris paribus, if a given force is applied to the impeller such as to cause the impeller to axially elongate, the axial elongation of the impeller is greater than the axial elongation that a generally similar impeller that includes an axial support member (such as a shaft) between the proximal and distal ends of the helical elongate elements would undergo.

For some alternative applications of the present invention, material 168 of the impeller itself is molded such as to facilitate the insertion of an axial support member therethrough. For example, an elastomer (such as silicone or a silicone-based elastomer) may be used as material 168, and the elastomer may be molded to form a hollow central lumen therethrough. An axial support member may be coupled to the impeller by being passed through the hollow central lumen defined by the elastomer.

Figure 14A:
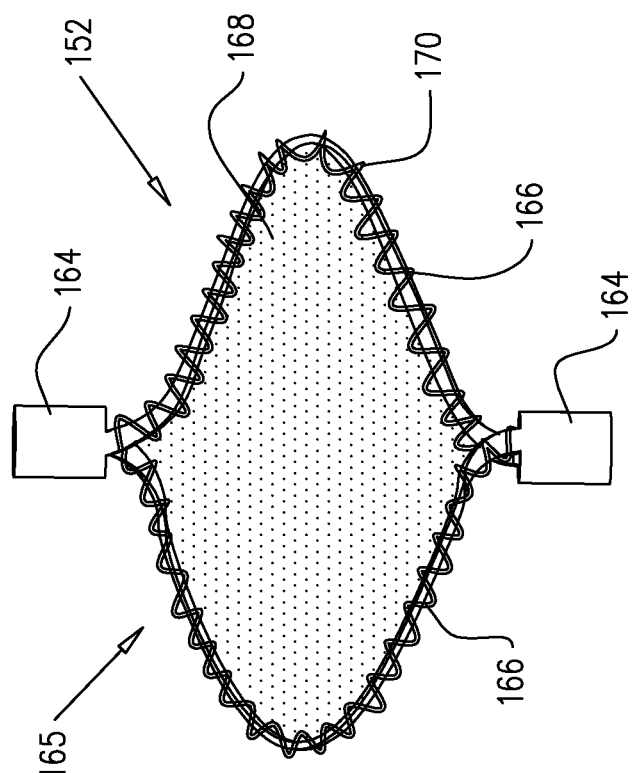
FIGS. 14A-B are schematic illustrations of sutures tied around a portion of a frame of an impeller, in accordance with some applications of the present invention.
Figure 14B:
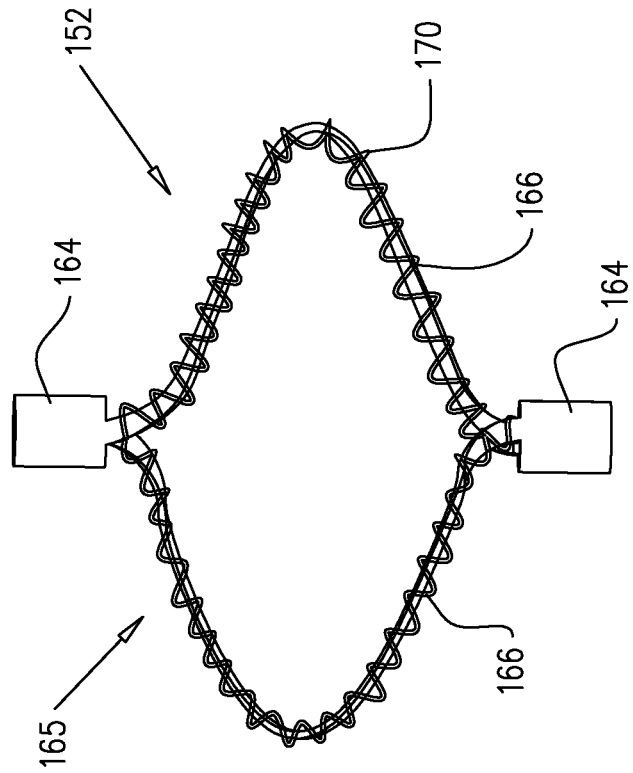
Figure 15:
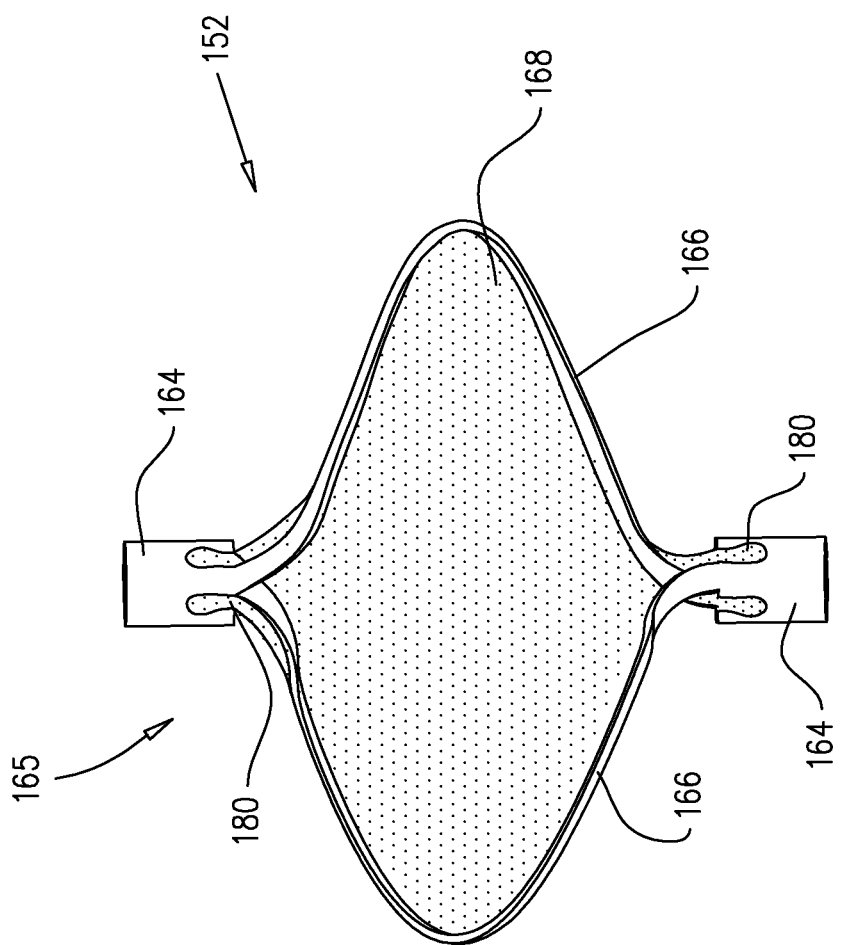
FIG. 15 is a schematic illustration of an impeller for a blood pump, in accordance with some applications of the present invention.

Reference is now made to FIGS. 14A-B, which are schematic illustrations of structure 165 from which impeller 152 is formed, the structure having sutures 170 tied around a portion of the structure, in accordance with some applications of the present invention. Reference is also made to FIG. 15, which is a schematic illustration of an impeller 152, in accordance with some applications of the present invention.

As described hereinabove, typically, material 168 is coupled to at least a portion of structure 165 by structure 165 being dipped into material 168, while material 168 is in a liquid state thereof. For example, structure 165 may be dipped into liquid silicone. Subsequently, the material is dried (e.g., by a curing and/or a polymerization process), such that a film of the material forms that is supported by the helical elongate elements of structure 165. For some applications, in order to facilitate the formation of a film of material 168 on structure 165, and/or in order to facilitate coupling of material 168 to helical elongate elements 166, sutures 170 are tied around a portion of structure 165. For example, the sutures may be tied around helical elongate elements 166 of structure 165, as shown in FIG. 14A, which shows sutures 170 tied around helical elongate elements 166 before material 168 has been coupled to structure 165.

For some applications, the sutures increase the surface area with which material 168 comes into contact, while material 168 is in its liquid state. Alternatively or additionally, the surface of the sutures is more rough and/or porous than that of elongate elements 166 (which are typically made of nitinol). Therefore, material 168 becomes coupled to the sutures with a greater coupling strength than that of the coupling between material 168 and elongate elements 166. For some applications, the sutures act as mediators between a material from which the elongate elements are made, which typically has a relatively high stiffness (and is typically nitinol), and material 168, which is typically an elastomer having a relatively low stiffness. The sutures thereby enhance the strength of the coupling between material 168 and helical elongate elements 166, when the material dries. For some applications, by enhancing the strength of the coupling between material 168 and helical elongate elements 166, the sutures prevent gaps from forming between the material and helical elongate elements 166, during and/or after the drying of material 168. In this manner, the sutures facilitate the formation of a continuous film of material 168 between the helical elongate elements. FIG. 14B shows impeller 152, subsequent to the formation of a film of material 168 on structure 165, the film being supported by helical elongate elements 166 of structure 165.

Alternatively or additionally, in order to facilitate the formation of a film of material 168 on structure 165, the edges of the end portions (e.g., rings 164) of structure 165 that are closest to helical elongate elements 166 define notches 180 therein, as shown in FIG. 15. As described hereinabove, typically, material 168 is coupled to at least a portion of structure 165 by structure 165 being dipped into material 168, while material 168 is in a liquid state thereof. For example, structure 165 may be dipped into liquid silicone. Typically, some of the liquid material enters into notches 180 in the end portions (e.g., rings 164), such that the area of contact between the material and structure is increased relative to if the end portions did not define notches. Thus, the strength of the coupling of the material to structure 165 is strengthened, when the material is subsequently dried.

Reference is now made to FIGS. 16A-B, which are schematic illustrations of impeller 152, the impeller defining three blades 190, in accordance with some applications of the present invention. Typically, impeller 152 is manufactured to have three blades, using a generally similar technique to that described hereinabove with reference to the impeller described with reference to FIGS. 13A-D. However, rather than cutting tube 162 (FIG. 13A) to define two elongate elements 166 (FIG. 13B), tube 162 is cut define three elongate elements. The tube is then axially compressed, such that the elongate elements form three helical shapes, and the tube is shape set in the axially compressed configuration. Material 168 is then coupled to at least a portion of structure 165. Typically, the material is coupled to at least a portion of structure 165 by structure 165 being dipped into material 168, while material 168 is in a liquid state thereof. For example, structure 165 may be dipped into liquid silicone. Typically the material is dried (e.g., by curing, and/or polymerization) onto the helical elongate elements such that the helical elongate elements with the material coupled thereto forms a three-bladed impeller, as shown in FIG. 16A-B.

It is noted that, typically, the three-bladed impeller shown in FIGS. 16A-B does not include an axial support member (such as a shaft) between the proximal and distal ends of the helical elongate elements and along the axis of the impeller, for providing support to material 168. More generally, typically, the impeller does not include a support member (such as a shaft) for providing support to material 168 in addition to the helical elongate elements, between the proximal and distal ends of the helical elongate elements. Furthermore, rotational motion is imparted from the proximal end portion (e.g., proximal ring 164) of the impeller to the distal end portion (e.g., distal ring 164) of the impeller via the helical elongate elements of the impeller (e.g., substantially solely via the helical elongate elements), and not via an axial support member (such as a shaft).

During insertion of the impeller via insertion device 155 (FIG. 12Ai), the impeller is radially contracted by axially elongating the impeller, such that helical elongate elements 166 become straightened. Typically, material 168 conforms with the shape changes that the helical elongate elements undergo during the axial elongation of structure 165, since there is no additional supporting member (such as a shaft) providing support to material 168 between the proximal and distal ends of the helical elongate elements. Further typically, ceteris paribus, the lack of an axial support member (such as a shaft) between the proximal and distal ends of the helical elongate elements facilitates radial compression of the impeller such that the maximum diameter of the impeller when the impeller is in a maximally-radially-compressed configuration thereof is less than that of an impeller that is similar in all other aspects, but that includes an axial support member, i.e., the impeller is configured to be radially compressible to a smaller diameter than if the impeller were to comprise an additional supporting member for supporting the material between the proximal and distal ends of the helical elongate elements.

For some applications, ceteris paribus, due to the lack of an axial support member (such as a shaft) between the proximal and distal ends of the helical elongate elements the impeller is more flexible than an impeller that is similar in all other aspects, but that includes an axial support member (such as a shaft). During the insertion into the renal vein, the impeller and the cage are typically inserted through junctions of blood vessels that form relatively acute angles with each other (e.g., angles of more than 70 degrees), and that are disposed at relatively short distances from one another. For example, the impeller and the cage may be inserted into the renal vein by being passed through the femoral vein, the iliac vein, into the vena cava, and then into the renal vein. Flexibility of the impeller typically facilitates insertion of the impeller into the renal vein.

Furthermore, as described hereinabove, the lack of an axial support member (such as a shaft) between the proximal and distal ends of the helical elongate elements facilitates axial elongation of the impeller by a given length using less force than would be required to axially elongate by the given length an impeller that includes an axial support member (such as a shaft) between the proximal and distal ends of the helical elongate elements. Similarly, ceteris paribus, if a given force is applied to the impeller such as to cause the impeller to axially elongate, the axial elongation of the impeller is greater than the axial elongation that a generally similar impeller that includes an axial support member (such as a shaft) between the proximal and distal ends of the helical elongate elements would undergo.

For some alternative applications of the present invention, material 168 of the impeller itself is molded such as to facilitate the insertion of an axial support member therethrough. For example, an elastomer (such as silicone or a silicone-based elastomer) may be used as material 168, and the elastomer may be molded to form a hollow central lumen therethrough. An axial support member may be coupled to the impeller by being passed through the hollow central lumen defined by the elastomer.

Reference is now made to FIG. 17, which is a schematic illustration of protective cage 154 of blood pump 150, in accordance with some applications of the present invention. Typically, the cage comprises proximal and distal rings 202. Between the proximal and distal rings, the cage comprises struts 204, which are shaped to define cells. For some applications, in a non-compressed, radially-expanded configuration of the cage (i.e., in the absence of any force being applied to the cage), between the proximal and distal rings, the cage defines a generally spherical or ovoid shape, as shown in FIG. 17. Engagement mechanism 156 (FIG. 12B) typically engages the impeller with respect to cage 154 via rings 164 (FIGS. 13A-D) of the impeller, rings 202 of the cage, and distal bearing 250D (FIG. 12B).

For some applications, when cage 154 is in its radially-expanded configuration, a length L8 of the cage, measured along the longitudinal axis of the cage, and including rings 202 of the cage, is greater than 17 mm, less than 26 mm, and/or between 17 and 26 mm. A length L9 of the cage, measured along the longitudinal axis of the cage, and not including rings 202 of the cage, is greater than 12 mm, less than 21 mm, and/or between 12 and 21 mm. For some applications, when the cage is axially elongated, and radially compressed, by being crimped (configuration not shown), the length of the cage, measured along the longitudinal axis of the cage, and including rings 202 of the cage, is greater than 22 mm, less than 35 mm, and/or between 22 and 35 mm. Typically, for such applications, when the cage is axially elongated by being crimped (configuration not shown), the length of the cage, measured along the longitudinal axis of the cage, and excluding rings 202 of the cage is greater than 18 mm, less than 30 mm, and/or between 18 and 30 mm. For some applications, when cage 154 is in its radially-expanded configuration, a diameter D7 of the cage is greater than 8 mm, less than 20 mm, and/or between 8 and 20 mm. For example, diameter D7 may be greater than 8 mm, less than 15 mm, and/or between 8 mm and 15 mm. Or, diameter D7 may be greater than 13 mm, less than 19 mm, and/or between 13 mm and 19 mm.

The cage is typically inserted into a blood vessel (e.g., into the renal vein), while in a crimped configuration thereof (i.e., while the cage is axially elongated and radially compressed with respect to the non-compressed configuration of the cage). As described hereinabove, during insertion of the impeller into the blood vessel, the impeller is radially contracted by axially elongating structure 165, such that helical elongate elements 166 become straightened. Typically, the film of material 168 conforms with the shape changes that the helical elongate elements undergo during the elongation of the impeller. Further typically, during insertion of the blood pump into the blood vessel, impeller 152 is already disposed inside the cage. Thus, during insertion of blood pump 150 into the blood vessel, impeller 152 is disposed inside the cage, while the cage is in a crimped configuration thereof, and while the impeller is in an axially-elongated configuration thereof, in which the helical elongate elements of the impeller are straightened. Typically, in response to being released from the insertion device inside the blood vessel, the cage automatically assumes the non-compressed, radially-expanded configuration of the cage. Similarly, the impeller typically automatically radially expands inside the cage such as to assume a non-compressed, radially-expanded configuration thereof, in response to the cage and the impeller being released from the insertion device.

Reference is now made to FIGS. 18Ai-18Aiii, which are schematic illustrations of examples of structure 165 which forms the frame of impeller 152, in accordance with some applications of the present invention.

As indicated by inner dashed circle 194, which is the same size in both FIG. 18Ai-18Aiii, the impellers shown in each of FIGS. 18Ai and 18Bi rotate such as to encompass a circular area having the same size. Thus, as indicated by outer dashed circle 196, which is the same size in both FIG. 18Ai-18Aiii, the impellers shown in each of FIGS. 18Ai and 18Bi are suitable for being placed inside a blood vessel having a given cross sectional area, such that there a separation between the inner wall of the blood vessel and the impeller, as described hereinabove. (The outer dashed circle is representative of the cross-section of the inner wall of blood vessel into which the impeller is placed.) Despite being suitable for being placed in similarly sized blood vessels, structure 165 of the impeller shown in FIGS. 18Bi-18Biii is configured such that the blades of the impeller formed from the structure span a larger transverse area than the impeller blades formed by structure 165 as shown in FIGS. 18Ai-18Aiii. In other words, when viewed from an end of the impeller (as shown in FIGS. 18Ai and 18Bi), then the blades of the impeller frame shown in FIGS. 18Bi-18Biii span a transverse area (i.e., an area transverse to the axis of the impeller), that is greater than the transverse area that is spanned by the blades of the impeller frame shown in FIGS. 18Ai-18Aiii. Similarly, when viewed from an end of the impeller (as shown in FIGS. 18Ai and 18Bi), then each of the blades of the impeller frame shown in FIGS. 18Bi-18Biii defines an angle theta about the longitudinal axis of the impeller that is less than that defined by each of the blades of the impeller frame shown in FIGS. 18Ai-18Aiii.

Typically, ceteris paribus, for an impeller that is placed inside a blood vessel having a given diameter, the propulsion of blood through the blood vessel at a given rotation rate of the impeller is greater (and, therefore, the efficiency of the impeller is greater), the greater the transverse area of the blood vessel (i.e., the area of the blood transverse to the longitudinal axis of the blood vessel) that the blades of the impeller span. For an impeller as shown in FIGS. 18Ai-iii and 18Bi-iii, the efficiency of the impeller is typically greater, the greater the angle theta defined by the impeller blade about each side of the longitudinal axis of the impeller. Thus, with reference to FIGS. 18Ai-18Aiii and 18Bi-18Biii, ceteris paribus, the impeller shown in FIGS. 18Bi-18Biii would typically pump blood more efficiently than that shown in FIGS. 18Ai-18Aiii. However, as is explained in greater detail hereinbelow, when the impellers are axially elongated, then, ceteris paribus, an impeller that defines blades spanning a larger transverse area, will typically be longer than an impeller that defines blades spanning a smaller transverse area.

It is noted that, for some applications, a single-bladed impeller as described herein is used, and the value of theta (i.e., the angle defined by the blade of the impeller about each side of the longitudinal axis of the impeller) is greater than 5 degrees (e.g., greater than 50 degrees, greater than 70 degrees, or greater than 90 degrees), less than 360 degrees (e.g., less than 180 degrees, less than 150 degrees, or less than 110 degrees), and/or between 5 and 360 degrees (e.g., between 50 and 180 degrees, between 70 and 150 degrees, or between 90 and 110 degrees).

During insertion of blood pump 150 into the blood vessel, impeller 152 is typically disposed inside cage 154, while the cage is in an axially-elongated, crimped configuration thereof, and while the impeller is in an axially-elongated, crimped configuration thereof. Therefore, the length that the impeller defines when the impeller is in its axially-elongated, crimped configuration is typically less than the length of the cage when the cage is in its axially-elongated, crimped configuration. In turn, the dimensions of the cage are limited, since the diameter of the cage in the radially-expanded configuration of the cage is limited based upon the size of the blood vessel into which the blood pump is to be placed.

Figure 18C:
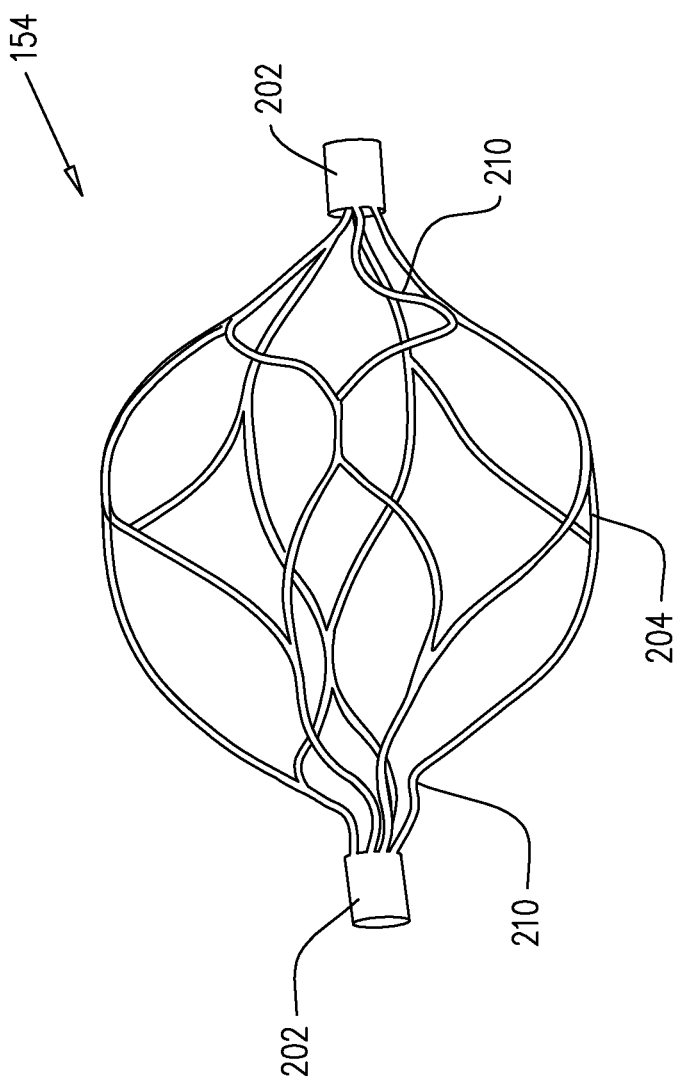
FIG. 18C is a schematic illustration of a radially-expandable cage that includes struts having undulated portions thereof, in accordance with some applications of the present invention.

For some applications, the cage is configured to include struts 204 that are shape set such as to include undulating portions 210, as shown in FIG. 18C (which is described in further detail hereinbelow). Typically, the level of undulation of the undulated portions of the struts of the cage when the cage is in its radially-expanded configuration, is greater than the level of undulation of the undulated portions of the struts when the cage is in its axially elongated configuration. For some applications, by including struts that have undulating portions, a cage that has a given diameter and/or outer profile in its radially-expanded configuration can be elongated to define a greater length when the cage is elongated than a cage having a similar diameter and/or outer profile that does not include struts that have undulating portions. In this manner, the cage (a) is able to accommodate an impeller which in its axially-elongated configuration is longer (and which, in its radially-expanded configuration, therefore defines a larger transverse area), than a cage that did not include struts that have undulating portions would be able to accommodate, but (b) the diameter and/or outer profile of the cage in its radially-expanded configuration is generally similar to the cage that does not include struts that have the undulating portions.

There follows a more detailed description of FIGS. 18Ai-18C.

As described hereinabove, structure 165 of the impeller shown in FIGS. 18Bi-18Biii is configured such that the blades of the impeller formed from the structure span a larger transverse area than the impeller blades formed by structure 165 as shown in FIGS. 18Ai-18Aiii. FIGS. 18Aii and 18Bii show side views of the two examples of structure 165, and FIGS. 18Aiii and 18Biii show views of the examples of structure 165 in the axially-elongated configurations of the structures, in which the helical elongate elements of the structures are straightened. As described hereinabove, during insertion of blood pump 150 into the blood vessel, the impeller is typically in the axially-elongated configuration, as shown in FIGS. 18Aiii and 18Biii. In order for the impeller blades to span a larger transverse area (as shown in FIG. 18Bi), the lengths of elongate elements 166 typically are longer than those of an impeller having blades that span a smaller transverse area (as shown in FIG. 18Ai). Therefore, when the impellers are in the axially-elongated configurations thereof, length LB of impeller shown in FIGS. 18Bi-18Biii is greater than length LA of the impeller shown in FIGS. 18Ai-18Aiii.

Figure 18D:
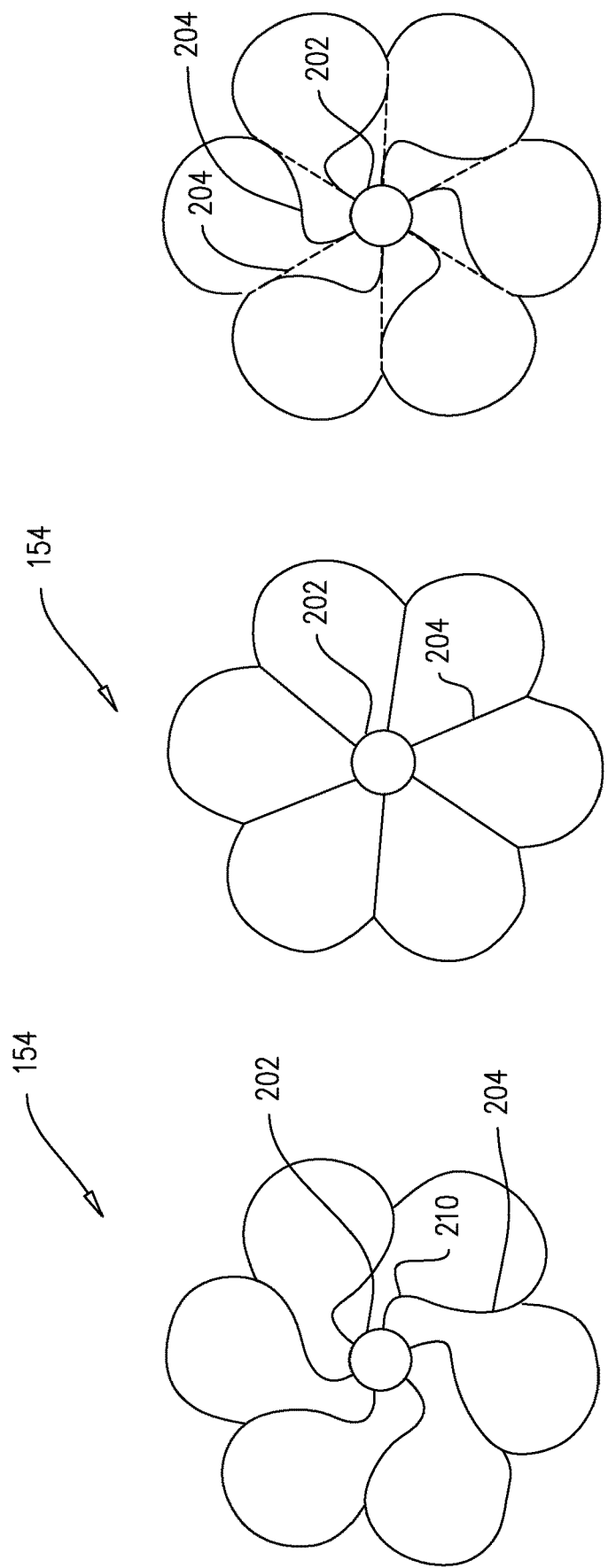
FIG. 18D is a schematic illustration of end views of radially expanded cages, in accordance with some applications of the present invention.

Reference is now made to FIG. 18C, which is a schematic illustration of cage 154 the cage including at least some struts 204 that have undulated portions 210 thereof, in accordance with some applications of the present invention. Reference is also made to FIG. 18D, which is a schematic illustration of end views of radially expanded cages 154, one of which includes struts 204 having undulated portions 210 thereof (the left cage), and the other one of which does not include struts having undulated portions thereof (the middle cage), in accordance with some applications of the present invention. On the right of FIG. 18D, the cage that includes struts having undulated portions thereof is overlaid on the cage that does not include struts having undulated portions thereof, with the struts that include undulated portions shown with solid lines, and the corresponding struts of the second cage that do not include undulated portions being shown with dashed lines. As may be observed in the portion of the FIG. 18D that shows the overlaid cages, the inclusion of undulated portions in some of the struts does not change the outer profile of the cage. However, the undulated portions of the struts add length to the struts, such that, ceteris paribus, the total axially-elongated length of the stent that includes the struts having the undulated portions is greater than the total axially-elongated length of the stent that does not include the struts having the undulated portions.

As described hereinabove, typically, the length of the impeller when the impeller is in its axially-elongated, crimped configuration is less than the length of the cage when the cage is in its axially-elongated, crimped configuration, such that the crimped cage can accommodate the axially-elongated impeller. In turn, the dimensions of the cage are limited, since the diameter of the cage in the radially-expanded configuration of the cage is limited based upon the size of the blood vessel into which the blood pump is to be placed. For cages having structures as shown in FIG. 17, then a cage that has a longer crimped length, typically expands to have a greater maximum diameter inside the blood vessel, which may be undesirable.

For some applications, in order to increase the axially-elongated length of the cage, without increasing the diameter of the cage in the radially-expanded configuration of the cage, a cage as shown FIG. 18C is used. The cage shown in FIG. 18C includes some struts that comprise undulated portions 210. During crimping of the cage, the undulated portions are configured to become at least partially straightened, thereby adding to the crimped length of the cage relative to if portions 210 were not undulated. When the cage radially expands inside the blood vessel, the undulated portions become undulated, but do not add to the diameter of the cage, or otherwise change the outer profile of the cage relative to if the undulated portions were straight. Thus, in general, the extra length that is provided to the cage by the undulated portions when the cage is in a crimped configuration thereof, does not add to the diameter of the cage when the cage expands inside the blood vessel.

As described, during insertion of the cage into the renal vein, the undulated portions of the struts of the cage are at least partially straightened. Upon the cage assuming its radially-expanded configuration inside the renal vein, the level of undulation of the undulated portions of the struts of the cage increases. For some applications, for each of the struts that defines the undulated portions, the strut is configured such that a ratio of:

(a) the shortest distance from a first longitudinal end of the strut to a second longitudinal end of the strut when the cage is its axially-elongated configuration (i.e., when the undulated portion is at least partially straightened), to (b) the shortest distance from the first longitudinal end of the strut to the second longitudinal end of the strut when the cage is its radially-expanded configuration (i.e., when the undulated portion is at the level of undulation to which the strut was shape set), is greater than 1.05:1, e.g., greater than 1.15:1, or greater than 1.2:1.

For some applications, the aforementioned ratio is less than 1.4:1, for example, the ratio may be between 1.05:1 and 1.4:1, between 1.15:1 and 1.4:1, or between 1.2:1 and 1.4:1.

Figure 19A:
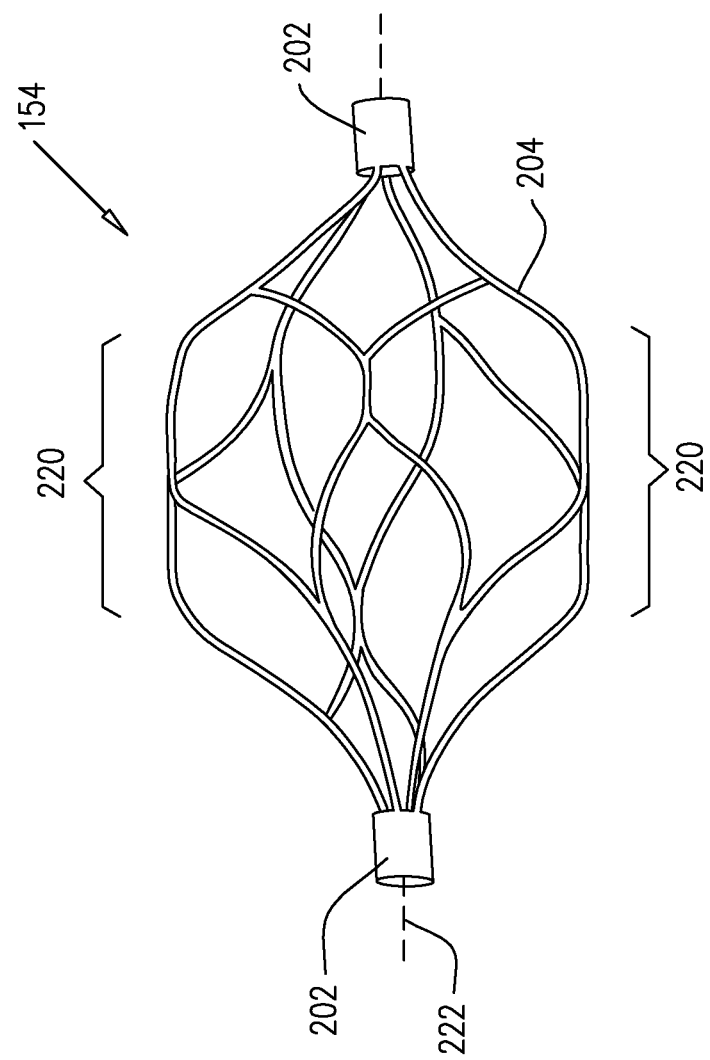

Reference is now made to FIGS. 19A-B, which are schematic illustrations of impeller cage 154, the cage being shaped to define a central portion having a generally cylindrical shape, in the absence of any force being applied to the cage, in accordance with some applications of the present invention. The outer surface of the cage at the generally cylindrical portion of the cage is parallel to longitudinal axis 222 of the cage. FIG. 19A shows the cage by itself, and FIG. 19B shows the cage disposed inside a blood vessel, e.g., renal vein 32.

FIG. 19B shows cage 154, the cage having radially expanded inside the blood vessel (e.g., inside renal vein 32), such that the cage is anchored to the blood vessel. As described hereinabove, impeller 152 of blood pump 150 (FIG. 12Ai) is configured to pump blood axially through the blood vessel, by rotating inside the blood vessel. Typically, in order to for the impeller to efficiently pump blood through the blood vessel, it is desirable that a longitudinal axis 224 of the impeller be aligned with a longitudinal axis 226 of the blood vessel. Further typically, rings 164 of impeller 152 are aligned with rings 202 of cage 154, such that the longitudinal axes of the impeller and the cage are aligned with one another. For example, as shown in FIG. 12B, the longitudinal axes of the impeller and the cage may be aligned with one another by (a) placing the proximal rings of both the impeller and the cage around a first support element (such as proximal bearing 250P), such that the proximal rings of the impeller and the cage are aligned with one another, and (b) placing the distal rings of both the impeller and the cage around a second support element (such as distal bearing 250D), such that the distal rings of the impeller and the cage are aligned with one another.

As shown in FIG. 19B, generally-cylindrical central portion 220 of cage 154, becomes anchored to the blood vessel, such that the longitudinal axis of the cage is aligned with the longitudinal axis of the blood vessel. Since the longitudinal axes of the impeller and the cage are aligned with one another, the generally-cylindrical central portion of the cage causes the impeller to be disposed within the blood vessel such that the longitudinal axis of the impeller is aligned with the longitudinal axis of the blood vessel.

As used in the present application, including in the claims, a "longitudinal axis" of a structure is the set of all centroids of cross-sectional sections of the structure along the structure. Thus the cross-sectional sections are locally perpendicular to the longitudinal axis, which runs along the structure. (If the structure is circular in cross-section, the centroids correspond with the centers of the circular cross-sectional sections.)

Figure 20:
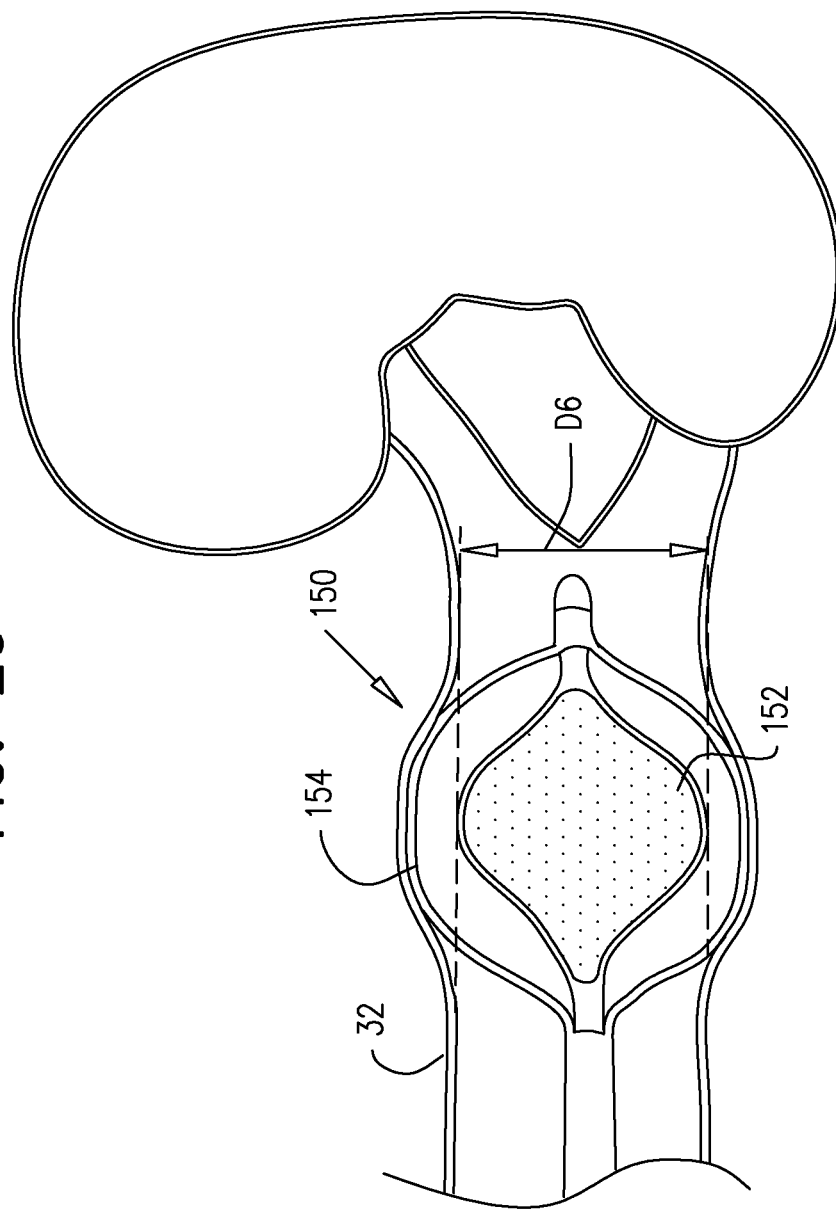
FIG. 20 is a schematic illustration of an impeller cage that is configured to be placed inside a blood vessel, such as to cause the diameter of a portion of the blood vessel to be expanded relative to the diameter of the portion of the blood vessel in the absence of the impeller cage, in accordance with some applications of the present invention.

Reference is now made to FIG. 20, which is a schematic illustration of impeller cage 154, the cage being configured to be placed inside a blood vessel (e.g., renal vein 32), such as to cause the diameter of a portion of the blood vessel to increase relative to the diameter of the blood vessel in the absence of the impeller cage. As shown in FIG. 20, for some applications the cage is configured to expand a blood vessel that has a diameter D6 in the absence of the cage, such that a portion of the blood vessel has a diameter that is greater than D6. For example, the cage may widen the blood vessel, such that, when the blood vessel is widened, the diameter of the blood vessel is more than 105 percent, e.g., more than 110 percent, or more than 115 percent of diameter D6. For some applications, the cage widens the blood vessel, such that, when the blood vessel is widened, the diameter of the blood vessel is less than 125 percent of diameter D6. For example, the widened diameter may be 105-125 percent, 110-125 percent, and/or 115-125 percent, of diameter D6. For some applications, impeller 152 of blood pump 150 is configured to span a diameter that is at least equal to diameter D6 of the blood vessel. Typically, all other factors being equal, the greater the diameter that the impeller spans, the greater the flow rate at which the impeller is able to pump blood through the blood vessel.

Reference is now made to FIG. 21A, which is a schematic illustration of impeller-based blood pumps 150 inserted into a subject's left and right renal veins 32 via the subject's femoral vein 230, in accordance with some applications of the present invention. It is noted that details of blood pump 150 are not shown in FIG. 21A, but the pump is generally as described hereinabove. Typically, the blood pumps are inserted into the left and right renal veins via respective catheters 155, and the catheters are both inserted via the femoral vein. Alternatively (not shown), the blood pumps are inserted via a single catheter that passes from a femoral access point to the subject's vena cava.

Typically, the impellers of the blood pumps 150 are coupled to motors 232, which impart rotational motion to the impellers. In accordance with respective applications, the motors are disposed outside of the subject's body (as shown) or are placed inside the subject's body (not shown). Typically, a control unit 234 and a user interface 236 are disposed outside the subject's body. Further typically, the control unit receives inputs from pressure sensors 157 and 159, which are disposed on upstream and downstream sides of the blood pumps, as described hereinabove with respect to FIG. 12C-D. When blood pump 150 is disposed inside a renal vein (as shown in FIG. 21A, for example), the pressure measured by upstream pressure sensor 157 is indicative of blood pressure upstream of the blood pump, inside the renal vein, and the pressure measured by downstream pressure sensor 159 is indicative of central venous pressure. For some applications, the control unit receives an input from additional sensor 161 (such as a flow sensor and/or an oxygen-saturation sensor), which is disposed on the blood pump (e.g., on a downstream side of the blood pump, as shown in FIG. 12Ai). Alternatively or additionally, the control unit receives an input from a thermal flow sensor, such as thermal flow sensor 260 described hereinbelow with reference to FIGS. 22Ai-Cii.

For some applications, control unit 234 controls rotation of impeller 152, by controlling motor 232, responsively to one or more of the above-described inputs. Typically, user interface 236 displays the subject's current renal venous pressure and central venous pressure, based upon the pressures measured by sensors 157 and 159. Typically, based upon the current values of the subject's renal venous pressure and central venous pressure, a user (such as a healthcare professional) inputs a target value for the subject renal venous pressure, via the user interface. In response thereto, control unit 234 controls the speed of the rotation of the impeller, such that the impeller pumps through the renal vein and toward the vena cava at a flow rate that is such as to reduce the renal venous pressure toward the target level, as indicated by the user. For some applications, in response a signal received from downstream sensor 159 indicating that the central venous pressure is at the target renal venous pressure, the control unit stops the impeller rotating. In general, the control unit typically controls the speed of the rotation of the impeller responsively to inputs from pressure sensors 157 and 159. For some applications, the control unit controls the speed of the rotation of the impeller responsively to an input from additional sensor 161, and/or thermal flow sensor 260 (shown in FIGS. 22Ai-22Cii).

It is noted that a "control unit" as described in the present application, in the description and the claims, includes any type of processor (such as a computer processor) configured to execute the actions described herein. A "user interface"

includes any type of user interface configured to receive inputs from a user and/or to provide outputs to the user. For example, the user interface may include one or more input devices (such as a keyboard, a mouse, a trackball, a joystick, a touchscreen monitor, a touchpad, a voice-command interface, a smartphone, a tablet computer, and/or other types of input devices that are known in the art), and/or one or more output devices (such as a monitor, an audio output device, a smartphone, a tablet computer, and/or other types of output devices that are known in the art).

Figure 21B:
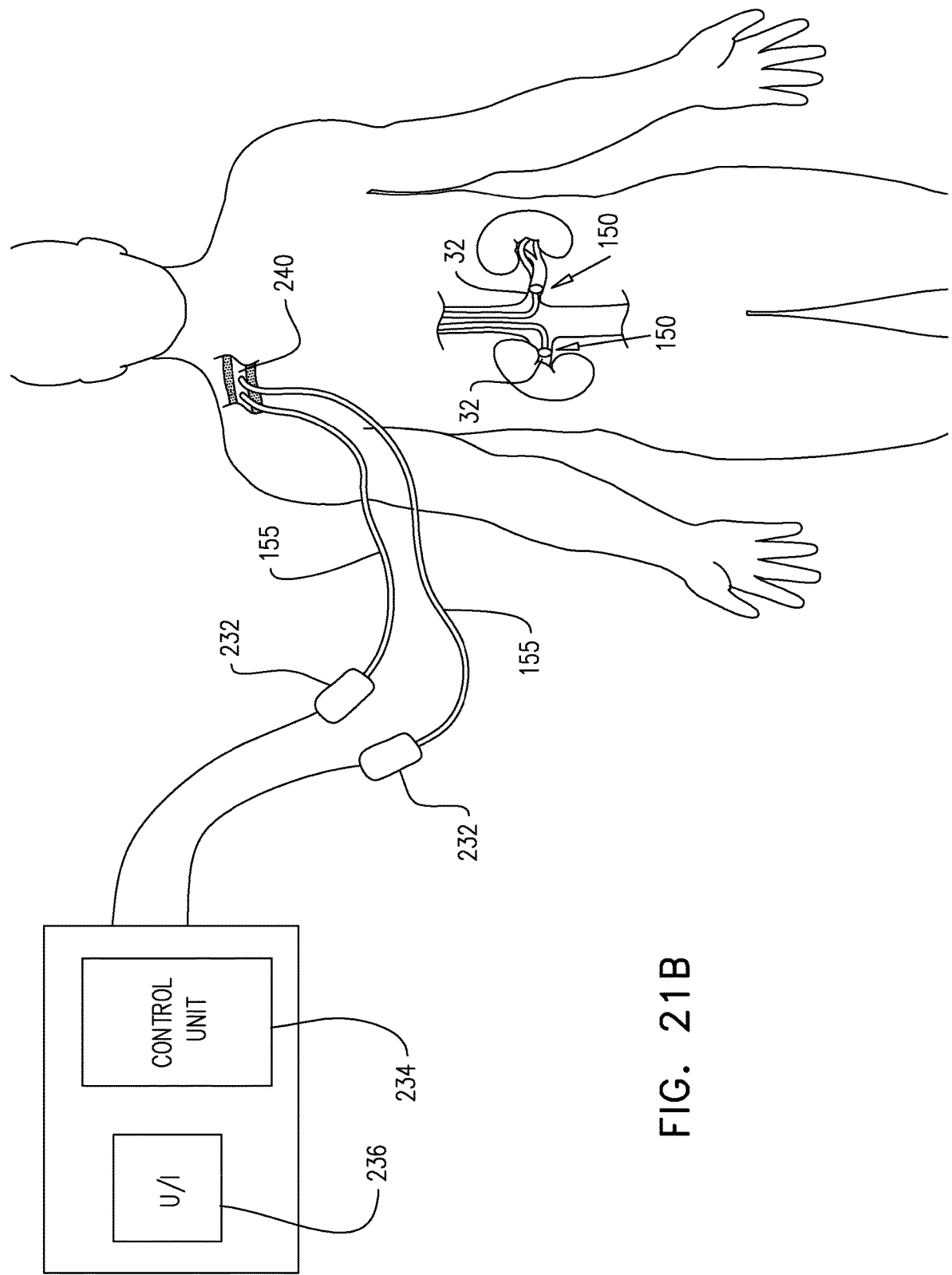
FIG. 21B is a schematic illustration of impeller-based blood pumps inserted into a subject's left and right renal veins via the subject's subclavian vein, in accordance with some applications of the present invention.

Reference is now made to FIG. 21B, which is a schematic illustration of impeller-based blood pumps 150 inserted into a subject's left and right renal veins 32 via the subject's subclavian vein 240, in accordance with some applications of the present invention. It is noted that the details of blood pump 150 are not shown in FIG. 21B, but the pump is generally as described hereinabove. Typically, the blood pumps are inserted into the left and right renal veins via respective catheters, and the catheters are both inserted via the subclavian vein. Alternatively (not shown), the blood pumps are inserted via a single catheter then passes from a subclavian access point to the subject's vena cava. Apart from being inserted into the renal veins via a different vein, blood pumps 150 as shown in FIG. 21B are generally similar to blood pumps 150 as shown in FIG. 21A, in all other respects.

Reference is now made to FIGS. 22Ai-Cii, which are schematic illustrations of a thermal flow sensor 260 for use with blood pump 150, in accordance with some applications of the present invention. The thermal flow sensor typically includes an upstream temperature sensor 262, a downstream temperature sensor 264, and a heating element 266 disposed between the upstream and downstream temperature sensors. As shown by the flow arrows shown in the enlarged drawing of the thermal flow sensor in FIG. 22Ai, blood flows past the upstream temperature sensor to the heating element. The heating element heats the blood, as the blood flows past the heating element. The heated blood then flows to the downstream temperature sensor. The extent to which blood flowing past the downstream temperature sensor has been heated by the heating element is dependent upon the flow rate of the blood. Therefore, the thermal flow sensor measures a change in the temperature of the blood between the upstream and the downstream temperature sensors, and determines the flow of the blood responsively thereto.

As described with reference to FIGS. 21A-B, for some applications, the control unit controls the speed of the rotation of the impeller responsively to an input from thermal flow sensor 260. Typically, it is of interest to measure the component of the blood flow through the renal vein that is in the axial direction, i.e., the axial component of the blood flow that is parallel to the local longitudinal axis of the renal vein, since this determines the rate of flow of blood away from the subject's kidney. However, due to the rotation of the impeller, blood flow downstream of the impeller typically includes components other than the axial component (e.g., rotational and radial components). For some applications, the thermal flow sensor is disposed inside a housing 268 that is configured such that blood flow through housing is substantially in the axial direction, and such that components other than the axial component of the blood flow (e.g., rotational and radial components) are reduced relative to blood flow through the renal vein outside the housing.

Reference is now made to FIGS. 22Ai and 22Aii, which are schematic illustrations of, respectively, a cross-sectional view and a top view of thermal flow sensor 260 and housing 268, in accordance with some applications of the present invention. Typically, impeller 152 and cage 154 of blood pump 150 are disposed at the end of an elongate element 270 (e.g., a tube) of the blood pump. For some applications, elongate element 270 defines an indentation, and the thermal flow sensor is housed inside the indentation, the outer surface of elongate element 270 that defines the indentation thus comprising housing 268. Upstream temperature sensor 262, heating element 266, and downstream temperature sensor 264 are typically disposed sequentially along the length of the indentation, as shown. Typically, the ratio of length LI of the indentation to a width WI of the indentation is greater than 4:1, and/or less 8:1, e.g., between 4:1 and 8:1. The ratio of length LI to width WI is typically such that blood flow through the indentation is substantially in the direction that is parallel to the local longitudinal axis of the renal vein (and that is parallel to the local longitudinal axis of the elongate element), and such that components other than the axial component of the blood flow (e.g., rotational and radial components) are reduced relative to blood flow through the renal vein outside the housing. Since the thermal sensor is housed inside the indentation, the thermal flow sensor measures the blood flow that is substantially in the direction that is parallel to the local longitudinal axis of the renal vein (and that is parallel to the local longitudinal axis of the elongate element).

For some applications (not shown), a single thermistor is used to measure flow, and the single thermistor is placed inside a housing that is typically such that blood flow through the housing is substantially in the direction that is parallel to the local longitudinal axis of the renal vein (and that is parallel to the local longitudinal axis of the elongate element), and such that components other than the axial component of the blood flow (e.g., rotational and radial components) are reduced relative to blood flow through the renal vein outside the housing, e.g., using techniques as described with respect to FIGS. 22Ai-22Cii, mutatis mutandis. For such applications, a ratio of a length of the housing to the width of the housing is typically greater than 1:1, e.g., greater than 4:1, and/or less 8:1, e.g., between 4:1 and 8:1. For such applications, when a housing as shown in FIG. 22Ci-ii is used, the ratio of the length of the housing to the height of the housing is typically greater than 1:1, e.g., greater than 4:1, and/or less 8:1, e.g., between 4:1 and 8:1.

Reference is now made to FIGS. 22Bi and 22Bii, which are schematic illustrations of, respectively, a cross-sectional view and a top view of thermal flow sensor 260 and housing 268, in accordance with some applications of the present invention. Housing 268 as shown in FIGS. 22Bi-22Bii is generally similar to that shown in FIGS. 22Ai-22Aii, except that the thermal sensor shown in FIGS. 22Bi-ii in covered by a cover 272 in addition to being housed inside the indentation in elongate element 270. In other aspects, thermal sensor and housing 268 are generally as described with reference to FIGS. 22Ai-22Aii.

Reference is now made to FIGS. 22Ci-22Cii, which are schematic illustrations of respective cross-sectional views of thermal flow sensor 260 and housing 268, in accordance with some applications of the present invention. For some applications, housing 268, which houses thermal sensor 260, includes a housing, such as a tube, that is coupled to the outer surface of elongate element 270 of blood pump 150. Typically, the housing is compressible, such that the housing may be compressed during insertion of blood pump 150 into the subject's blood vessel via insertion device 155.

Upstream temperature sensor 262, heating element 266, and downstream temperature sensor 264 are typically disposed sequentially along the length of the housing, within the housing, as shown. Typically, the ratio of a length LH of the housing to a width WH of the housing is greater than 4:1, and/or less 8:1, e.g., between 4:1 and 8:1. Further typically, the ratio of a length LH of the housing to a height HH of the housing is greater than 4:1, and/or less 8:1, e.g., between 4:1 and 8:1. The ratios of length LH to width WH, and of length LH to height HH, are typically such that blood flow through the housing is substantially in the direction that is parallel to the local longitudinal axis of the renal vein (and that is parallel to the local longitudinal axis of the elongate element), and such that components other than the axial component of the blood flow (e.g., rotational and radial components) are reduced relative to blood flow through the renal vein outside the housing. Since the thermal sensor is housed inside the indentation, the thermal flow sensor measures the blood flow that is substantially in the direction that is parallel to the local longitudinal axis of the renal vein (and that is parallel to the local longitudinal axis of the elongate element).

It is noted that in FIG. 22Cii, the inside of elongate element 270 is shaded, for illustrative purposes. However, typically, elongate element 270 houses control mechanisms for controlling motion of impeller 152 and cage 154.

Experimental Results

Figure 23:
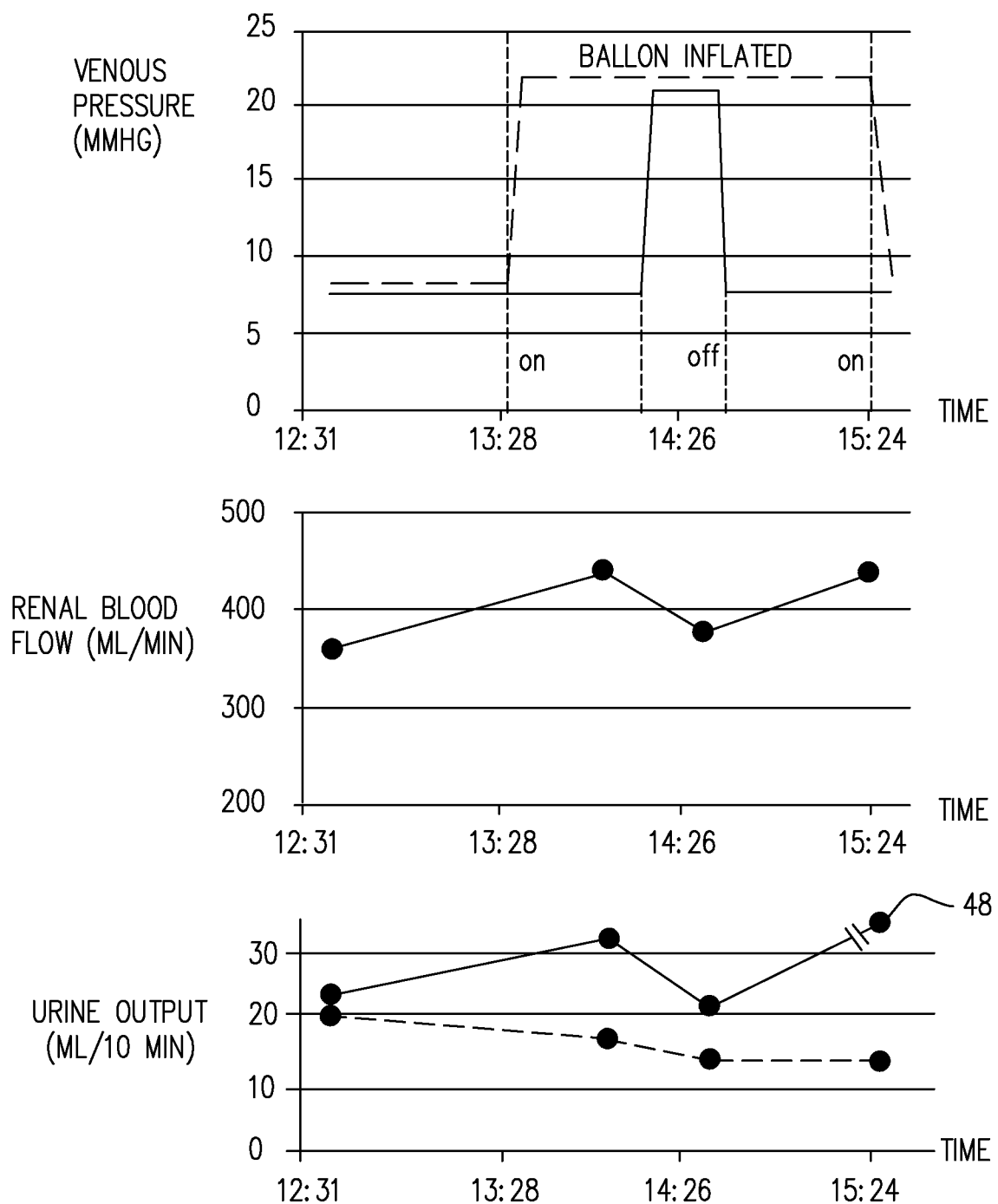
FIG. 23 shows graphs indicating the results of experiments that were performed on a pig, using an impeller-based blood pump, in accordance with some applications of the present invention.

Reference is now made to FIG. 23, which shows graphs indicating the results of experiments that were performed on a healthy pig, using an impeller-based blood pump 150, in accordance with some applications of the present invention. Throughout the experiment, left renal venous pressure of the pig was measured directly using a pressure sensor disposed in the pig's left renal vein. In addition, right renal venous pressure of the pig was measured, using a pressure sensor in the inferior vena cava at the level of the renal vein. Baseline levels of left renal blood flow, and urine output from the left and right kidneys were also measured, and the aforementioned parameters were again measured at certain points in time during the experiment.

A balloon was inflated in the pig's vena cava downstream of the junctions between the vena cava and both left and right renal veins. The balloon was inflated such as to cause an increase in the blood pressure within the pig's vena cava downstream of the renal veins, by partially obstructing blood flow through the vena cava downstream of the renal veins. At the same time as the balloon was inflated inside the pig's vena cava, an impeller-based blood pump, as described herein, was activated to pump blood through the pig's left renal vein, while no assistance was provided to the flow of blood through the pig's right renal vein. While the balloon was still in an inflated state, the blood pump within the left renal vein was temporarily switched off for a period of time, before being switched on again. Subsequently, the balloon within the vena cava was deflated, and the blood pump was switched off.

The top graph in FIG. 23 indicates left renal venous pressure, indicated by the solid curve, and right renal venous pressure, indicated by the dashed curve, as measured during the experiment. It is noted that, in order to more clearly show the left and right renal venous pressure measurements, where the left and right renal venous pressure measurements were identical (e.g., between approximately 12:35 and 13:28), the two curves have been separated slightly. In addition small variations in venous pressure have been ignored. As shown, initially, during the baseline period, the left and right renal venous pressures were similar to one another, at approximately 8 mmHg. Subsequently, at 13:28, the balloon was inflated, and the impeller-based blood pump was activated in the left renal vein. As a result of the balloon being inflated, the pressure in the vena cava rose, and therefore the right renal venous pressure rose to approximately 22 mmHg. Despite the pressure in the vena cava rising, the left renal venous pressure did not increase, due to the pumping of blood through the left renal vein. At approximately 14:10, the blood pump within the left renal vein was switched off, and, as a result, the left renal venous pressure rose to the level of the venous pressure within the vena cava. Subsequently, at approximately 14:40, the pump was switched on again, and, as a result, the pressure in the left renal vein dropped. Subsequently, at 15:24, the balloon was deflated and the venous pressure in the vena cava, and therefore, the right renal venous pressure dropped. These results indicate that an impeller-based blood pump as described herein may effectively reduce renal venous pressure, even if a subject's central venous pressure is elevated.

The middle graph of FIG. 23 shows the renal blood flow as measured in the left renal vein. As shown the baseline value of the left renal blood flow was approximately 360 ml/min. The left renal blood flow was again measured when the balloon had been inflated in the vena cava and the blood pump was operating in the left renal vein. As shown, left renal blood flow had risen to approximately 440 ml/min, due to the pumping of the blood by the blood pump. Subsequently, left renal blood flow was measured while the balloon was inflated within the vena cava, and while the blood pump had been switched off, and the renal blood flow had fallen to approximately 380 ml/min. Subsequently, left renal blood flow was again measured when the blood pump had been switched back on, and the left renal blood flow had again risen to approximately 340 ml/min. These results indicate that an impeller-based blood pump as described herein may effectively increase renal blood flow, even if a subject's central venous pressure is elevated.

It is noted that, for illustrative purposes, changes in renal blood flow between one data point and the next data point are shown on the graph as having occurred at a constant rate. However, the inventors hypothesize that the changes in renal blood flow were substantially due to the blood pump being switched on and off inside the left renal vein, and/or due to inflation of the balloon inside the vena cava, such that most of the changes in the renal blood flow would have occurred, pursuant to the occurrences of the aforementioned events.

The bottom graph of FIG. 23 shows urine output measured at the pig's left kidney (indicated by the solid curve) and right kidney (indicated by the dashed curve) at certain times during the experiment. It is noted that, in general, it is known that the rate of blood flow through the kidney has an effect on the rate of urine output. As shown, when measured during the baseline period, urine production from the left and right kidneys was approximately 21 ml per 10 minutes. Subsequently, urine output was measured at approximately 14:00, while the balloon was inflated inside the vena cava, and while the blood pump was operating inside the left renal vein. As shown, urine output from the left kidney had risen, while urine production from the right kidney had fallen. These results indicate that, even when central venous pressure is elevated, which may lead to reduced urine output (as indicated by the urine output from the right kidney), increasing renal blood flow by pumping blood using a blood pump (as performed within the left renal vein) may increase urine output.

Subsequently, urine output from the left and right kidneys was measured while the balloon was still inflated inside the vena cava, but while the blood pump was switched off, at approximately 14:35. At this point, urine production at the right kidney had continued to fall, while urine output from the left kidney had also fallen. Subsequently, after the blood pump had been switched on again, while the vena cava balloon had still been inflated, the urine output from the right kidney had plateaued at approximately 14 ml per 10 minutes, while the urine output from the right kidney had risen substantially to 48 ml per 10 minutes.

It is noted that, for illustrative purposes, changes in urine production between one data point and the next data point are shown on the graph as having occurred at a constant rate. However, the inventors hypothesize that the changes in urine production were substantially due to the blood pump being switched on and off inside the left renal vein, and/or due to inflation of the balloon inside the vena cava, such that most of the changes in the urine production would have occurred, pursuant to the occurrences of the aforementioned events.

In a further experiment, an impeller-based blood pump as described herein was used to pump blood through the renal vein of a different pig over a continuous period of three hours. During this time period, no incidences of either thrombi, or abnormal levels of hemolysis occurred. This indicates that an impeller-based blood pump as described herein may be used to increase blood flow through a subject's renal vein, thereby reducing pressure in renal vein, without causing a risk of thrombi and/or abnormal levels of hemolysis. It is noted that during the aforementioned experiment, an anticoagulant was administered to the pig. Nevertheless, since in a typically procedure that is performed on a human subject using an impeller-based blood pump as described herein, the subject would be administered an anticoagulant, it is still the case that this result indicates that an impeller-based blood pump as described herein may be used to increase blood flow through a subject's renal vein, thereby reducing pressure in renal vein, without causing a risk of hemolysis and/or thrombi.

In general, in the above-described experiments, as well as in additional experiments that were performed by the inventors of the present application using blood pump 150 in pigs, the following observations were made:

1. Blood pump 150 was smoothly deployed and retrieved within a minute or less.
2. Renal venous pressure was effectively and continuously reduced from about 20 mmHg to a pre-selected target value of 8 mmHg within minimal margins of variation.
3. Elevation of venous pressure in the vena cava caused a drop in urine output, creatinine clearance, and fractional sodium excretion in the untreated kidney, but not in the kidney that was treated using blood pump 150. These results indicate that use of blood pump 150 has a favorable impact on glomerular and tubular renal function.
4. Use of blood pump 150 preserved and restored renal blood flow, urine output, and sodium excretion, even when venous pressure in the vena cava was elevated.
5. Blood pump 150 was successfully operated in a closed-looped mode, under which pressure in the renal vein was kept constant for more than 3 hours.
6. No thrombi were observed on any part of the blood pump, or the catheter.
7. No clinically significant hemolysis was observed over 3 hours of the pump being operated.

It is noted that although some of the pumps and/or occlusion elements described herein are shown as being inserted into a given one of the subject's renal veins, the scope of the present invention includes inserting the pumps and occlusion elements into either a left or right renal vein, or both renal veins of a subject. Furthermore the scope of the present invention includes inserting the pumps and occlusion elements into more than two renal veins of a subject who has more than two renal veins, as is the case with some people.

It is noted that although some of the pumps and/or occlusion elements described herein are shown as being inserted into subject's renal veins, the scope of the present invention includes inserting the pumps and occlusion elements into other blood vessels of a subject, mutatis mutandis. For example, inverted valve 40 (FIGS. 5A-D, and 6A-F) could be placed in a subject's hepatic vein, intestinal vein, or adrenal vein, in order to reduce venous pressure in the vein and/or reduce pressure in an organ from which the vein draws blood (e.g., to reduce liver congestion).

Alternatively or additionally, blood pump 90 (FIGS. 8A-B and 10A-D) could be placed in a subject's hepatic vein, intestinal vein, or adrenal vein, in order to reduce venous pressure in the vein and/or reduce pressure in an organ from which the vein draws blood (e.g., to reduce liver congestion). Or, blood pump 90 could be placed in a fluid-filled chamber inside the brain in order to reduce intracranial pressure by draining cerebrospinal fluid from the chamber. Alternatively or additionally, blood pump 90 could be used as a left ventricular assist device by being placed in the subject's aorta and pumping blood away from the left ventricle. Further alternatively or additionally, blood pump 90 could be placed in the urethra, such as to hold open the subject's prostate, and to drain the subject's bladder.

In general, sleeve 110 (FIGS. 10A-C) may be used to isolate into a separate compartment from blood flow within a main vein, blood that is within a plurality of tributary veins that supply the main vein, and pump 122 may then be used to control the flow of blood from the compartment to the main vein.

For some applications, ostium-covering umbrella 140 (FIGS. 11A-C) is used to cover an ostium at a junction between a subject's hepatic vein, intestinal vein, or adrenal vein and another vein, and blood pump catheter 42 is used to control the flow of blood from the hepatic vein, intestinal vein, or adrenal vein to the other vein, in order to reduce venous pressure in the vein and/or reduce pressure in an organ from which the vein draws blood (e.g., to reduce liver congestion).

For some applications, blood pump 150 (FIGS. 12Ai-E) is placed in an artery that supplies a peripheral limb such as to enhance perfusion of the peripheral limb, for example in order to treat a gangrenous limb. Alternatively or additionally, a blood pump, such as blood pump 150 is placed in an artery, such as the descending aorta in order to propel blood away from the heart, such as to reduce afterload, and/or otherwise improve cardiac function.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

In general, in the specification and in the claims of the present application, the term "downstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is downstream, with respect to the direction of antegrade blood flow through the blood vessel, relative to a different location within the blood vessel. The term "upstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is upstream with respect to the direction of antegrade blood flow through the blood vessel, relative to a different location within the blood vessel.

There is therefore provided the following inventive concepts, in accordance with some applications of the present invention:

Inventive concept 1. A method for use with a plurality of tributary veins that supply a main vein, comprising:
   mechanically isolating blood within the plurality of veins into a compartment that is separated from blood flow within the main vein; and
   controlling blood flow from the plurality of veins to the major vein by pumping blood from the compartment to the main vein.

Inventive concept 2. The method according to inventive concept 1, further comprising performing ultrafiltration on the pumped blood.

Inventive concept 3. The method according to inventive concept 1,
   wherein isolating the plurality of veins comprises:
      placing into the main vein a blood-impermeable sleeve and a helical support element disposed around the sleeve, and
      coupling the sleeve to a wall of the main vein using the helical support element; and
   wherein pumping blood from the compartment to the main vein comprises guiding a distal portion of a blood pump into the compartment using the helical support element and pumping the blood using the blood pump.

Inventive concept 4. The method according to inventive concept 1, wherein:
   isolating the plurality of veins comprises:
      placing into the main vein a blood-impermeable sleeve and a helical portion of a blood pump that is disposed around the sleeve and configured to support the sleeve, and
      coupling the sleeve to a wall of the main vein; and
   pumping blood from the compartment to the main vein comprises pumping blood into inlet holes of the blood pump that are defined by the helical portion of the blood pump.

Inventive concept 5. The method according to any one of inventive concepts 1-4, wherein:
   isolating blood within the plurality of veins into a compartment that is separated from blood flow within the main vein comprises isolating blood in renal veins of the subject into a compartment that is separated from blood flow within a vena cava of the subject by placing a blood-impermeable sleeve in the subject's vena cava, such that a downstream end of the sleeve is coupled to a wall of the vena cava at a first location that is downstream of all the renal veins of the subject, and such that an upstream end of the sleeve is coupled to the wall of the vena cava at a second location that is upstream of all the renal veins of the subject; and
   pumping blood from the compartment to the main vein comprises operating a pump to pump blood from the compartment to a location that is in fluid communication with an interior of the sleeve.

Inventive concept 6. The method according to inventive concept 5, wherein pumping blood from the compartment comprises drawing blood in a downstream direction through the renal veins.

Inventive concept 7. The method according to inventive concept 5, wherein placing the sleeve in the vena cava comprises placing the sleeve in the vena cava for less than one week, and wherein operating the pump comprises operating the pump for less than one week.

Inventive concept 8. The method according to inventive concept 5, further comprising identifying the subject as a subject suffering from a condition selected from the group consisting of: cardiac dysfunction, congestive heart failure, reduced renal blood flow, increased renal vascular resistance, arterial hypertension, and kidney dysfunction, and wherein operating the pump comprises, in response to identifying the subject as suffering from the condition, reducing blood pressure within the subject's renal veins by operating the pump.

Inventive concept 9. The method according to inventive concept 5, wherein placing the sleeve in the subject's vena cava comprises anchoring the sleeve to the vena cava by causing the vena cava to constrict around at least a portion of the sleeve, by operating the pump.

Inventive concept 10. The method according to inventive concept 5, wherein operating the pump to pump blood from the compartment to the location that is in fluid communication with an interior of the sleeve comprises operating the pump to pump blood from the compartment to a site of the vena cava that is upstream of the sleeve.

Inventive concept 11. The method according to inventive concept 5, wherein operating the pump to pump blood from the compartment to the location that is in fluid communication with an interior of the sleeve comprises operating the pump to pump blood from the compartment to a site of the vena cava that is downstream of the sleeve.

Inventive concept 12. The method according to inventive concept 5, wherein placing the sleeve in the vena cava comprises placing in the vena cava:
   a stent shaped to define widened upstream and downstream ends thereof that are widened relative to a central portion of the stent, and
   a blood-impermeable sleeve coupled to the stent, the sleeve defining flared upstream and downstream ends thereof that are coupled, respectively, to the widened upstream and downstream ends of the stent; and
   coupling the stent to the blood vessel such that:
      in response to blood pressure on a first side of at least one of the flared ends of the sleeve being greater than blood pressure on a second side of the at least one flared end of the sleeve, blood flows between an outside of the at least one flared end of the sleeve and an inner wall of the blood vessel, and
      in response to blood pressure on the first side of the at least one flared end of the sleeve being less than blood pressure on the second side of the at least one flared end of the sleeve, the at least one flared end of the sleeve occludes blood flow between the outside of the at least one flared end of the sleeve and the inner wall of the blood vessel by contacting the inner wall of the blood vessel.

Inventive concept 13. The method according to inventive concept 5, wherein placing the sleeve in the vena cava comprises placing into the vena cava:
- a sleeve that is shaped to define flared ends thereof, and a narrow central portion between the flared ends, and
- a stent shaped to define:
  - a sleeve-supporting frame that is shaped to define widened ends thereof, and a narrow central portion between the widened ends that is narrower than the widened ends of the stent, the sleeve being coupled to the sleeve-supporting frame of the stent; and
  - a vessel-wall-supporting frame coupled to the narrow central portion of the sleeve-supporting frame and radially protruding from the sleeve-supporting frame.

Inventive concept 14. The method according to inventive concept 13, wherein pumping blood from the compartment comprises pumping blood from a site between an outside of the sleeve and an inner wall of the vena cava.

Inventive concept 15. The method according to inventive concept 5, further comprising inserting the pump into the compartment via an opening in the sleeve through which the pump is insertable.

Inventive concept 16. The method according to inventive concept 15, wherein inserting the pump through the opening comprises inserting the pump through an opening having a diameter that is between 2 mm and 10 mm.

Inventive concept 17. The method according to inventive concept 15, wherein inserting the pump through the opening comprises inserting the pump through the opening such that the opening forms a seal around the pump.

Inventive concept 18. The method according to inventive concept 5, further comprising inserting the pump into the compartment via a pump-accommodating sleeve that protrudes from the sleeve.

Inventive concept 19. The method according to inventive concept 18, wherein inserting the pump into the compartment via the pump-accommodating sleeve comprises inserting the pump into the compartment via a pump-accommodating sleeve having a diameter that is between 2 mm and 10 mm.

Inventive concept 20. The method according to inventive concept 18, wherein inserting the pump into the compartment via the pump-accommodating sleeve comprises inserting the pump into the compartment via the pump-accommodating sleeve such that the pump-accommodating sleeve forms a seal around the pump.

Inventive concept 21. Apparatus, comprising:
- a blood-impermeable sleeve;
- at least one support structure configured to couple first and second ends of the sleeve to a blood vessel of a subject; and
- a pump configured to pump blood from an exterior of the sleeve to a location that is in fluid communication with an interior of the sleeve.

Inventive concept 22. The apparatus according to inventive concept 21, wherein the pump is configured to perform ultrafiltration on the blood.

Inventive concept 23. The apparatus according to inventive concept 21, wherein the pump is configured to anchor the structure to the blood vessel by causing the blood vessel to constrict around at least a portion of the structure.

Inventive concept 24. The apparatus according to inventive concept 21,
- wherein the structure comprises a stent shaped to define widened ends thereof that are widened relative to a central portion of the stent, and
- wherein the sleeve comprises a sleeve that is coupled to the stent,
  - the sleeve defining flared ends thereof that are coupled to the widened ends of the stent,
  - at least one of the flared ends of the sleeve being configured to act as a valve by at least partially separating from widened end of the stent to which it is coupled in response to pressure being applied to the flared end of the sleeve.

Inventive concept 25. The apparatus according to inventive concept 21, wherein:
- the support structure comprises a helical support element disposed around the sleeve, and
- a distal portion of the blood pump is configured to be guided such as to be disposed around the exterior of the sleeve using the helical support element.

Inventive concept 26. The apparatus according to inventive concept 21, wherein:
- the support structure comprises a helical portion of the blood pump that is disposed around the sleeve and configured to support the sleeve, and
- the pump is configured to pump blood from the exterior of the sleeve by pumping blood into inlet holes of the pump that are defined by the helical portion of the blood pump.

Inventive concept 27. The apparatus according to any one of inventive concepts 21-24, wherein:
- the sleeve is shaped to define flared ends thereof, and a narrow central portion between the flared ends;
- the structure comprises a stent shaped to define:
  - a sleeve-supporting frame that is shaped to define widened ends thereof, and a narrow central portion between the widened ends that is narrower than the widened ends of the stent, the sleeve being coupled to the sleeve-supporting frame of the stent; and
  - a vessel-wall-supporting frame coupled to the narrow central portion of the sleeve-supporting frame and radially protruding from the sleeve-supporting frame.

Inventive concept 28. The apparatus according to inventive concept 27, wherein the pump is configured to pump blood from a site between an outside of the sleeve and an inner wall of the blood vessel by being placed between the outside of the sleeve and the vessel-wall-supporting frame.

Inventive concept 29. The apparatus according to any one of inventive concepts 21-26, wherein the structure is configured to isolate blood in a renal vein of the subject into a compartment that is separated from blood flow within a vena cava of the subject, by coupling a downstream end of the sleeve to a wall of the vena cava at a first location that is downstream of all renal veins of the subject, and by coupling an upstream end of the sleeve to a wall of the vena cava at a second location that is upstream of all renal veins of the subject.

Inventive concept 30. The apparatus according to inventive concept 29, wherein the sleeve is configured to be coupled to the vena cava for less than one week, and wherein the pump is configured to operate for less than one week.

Inventive concept 31. The apparatus according to inventive concept 29, wherein the pump is configured to reduce blood pressure within the subject's renal veins by pumping blood.

Inventive concept 32. The apparatus according to inventive concept 29, wherein the pump is configured to pump blood from the compartment to a site within the vena cava.

Inventive concept 33. The apparatus according to inventive concept 32, wherein the pump is configured to pump blood from the compartment to a site of the vena cava that is upstream of the sleeve.

Inventive concept 34. The apparatus according to inventive concept 32, wherein the pump is configured to pump blood from the compartment to a site of the vena cava that is downstream of the sleeve.

Inventive concept 35. The apparatus according to any one of inventive concepts 21-26, wherein the sleeve is shaped to define an opening through which the pump is insertable.

Inventive concept 36. The apparatus according to inventive concept 35, wherein a diameter of the opening is between 2 mm and 10 mm.

Inventive concept 37. The apparatus according to inventive concept 35, wherein the opening is sized such as to form a seal around the pump.

Inventive concept 38. The apparatus according to any one of inventive concepts 21-26, further comprising a pump-accommodating sleeve protruding from the blood-impermeable sleeve, the pump accommodating sleeve being configured to accommodate insertion of the pump therethrough to the exterior of the blood impermeable sleeve.

Inventive concept 39. The apparatus according to inventive concept 38, wherein an inner diameter of the pump-accommodating sleeve is between 2 mm and 10 mm.

Inventive concept 40. The apparatus according to inventive concept 38, wherein the pump-accommodating sleeve is sized such as to form a seal around the pump.

Inventive concept 41. A method comprising:
placing a stent inside a blood vessel at a placement location of the stent; and
at least partially anchoring the stent to the blood vessel at the placement location by causing the blood vessel to constrict around at least a portion of the stent, by applying a suctioning force within the blood vessel.

Inventive concept 42. The method according to inventive concept 41, wherein the blood vessel includes a blood vessel having a given diameter at the placement location, and wherein placing the stent inside the blood vessel comprises placing inside the blood vessel a stent having a diameter that is less than the given diameter.

Inventive concept 43. The method according to inventive concept 41, wherein causing the blood vessel to constrict around at least the portion of the stent comprises reducing an extent to which the stent is anchored to the blood vessel by virtue of oversizing of the stent, relative to if the blood vessel were not caused to constrict around at least the portion of the stent.

Inventive concept 44. Apparatus comprising:
a stent configured to be placed inside a blood vessel at a placement location of the stent;
a pump configured to anchor the stent to the blood vessel at the placement location by causing the blood vessel to constrict around at least a portion of the stent, by applying a suctioning force within the blood vessel.

Inventive concept 45. The apparatus according to inventive concept 44, wherein the blood vessel includes a blood vessel having a given diameter at the placement location, and wherein the stent comprises a stent having a diameter that is less than the given diameter.

Inventive concept 46. Apparatus comprising:
a stent configured to be placed inside a blood vessel, the stent being shaped to define widened ends thereof that are widened relative to a central portion of the stent; and
a blood-impermeable sleeve coupled to the stent,
the sleeve defining flared ends thereof that are coupled to the widened ends of the stent,
at least one of the flared ends of the sleeve being configured to act as a valve by at least partially separating from widened end of the stent to which it is coupled in response to pressure being applied to the flared end of the sleeve.

Inventive concept 47. A method comprising:
placing into a blood vessel of a subject:
a stent shaped to define widened upstream and downstream ends thereof that are widened relative to a central portion of the stent, and
a blood-impermeable sleeve coupled to the stent, the sleeve defining flared upstream and downstream ends thereof that are coupled, respectively, to the widened upstream and downstream ends of the stent; and
coupling the stent to the blood vessel such that:
in response to blood pressure on a first side of at least one of the flared ends of the sleeve being greater than blood pressure on a second side of the at least one flared end of the sleeve, blood flows between an outside of the at least one flared end of the sleeve and an inner wall of the blood vessel, and
in response to blood pressure on the first side of the at least one flared end of the sleeve being less than blood pressure on the second side of the at least one flared end of the sleeve, the at least one flared end of the sleeve occludes blood flow between the outside of the at least one flared end of the sleeve and the inner wall of the blood vessel by contacting the inner wall of the blood vessel.

Inventive concept 48. Apparatus comprising:
a blood-impermeable sleeve defining flared ends thereof, and a narrow central portion between the flared ends; and
a stent configured to be placed inside a blood vessel, the stent being shaped to define:
a sleeve-supporting frame that is shaped to define widened ends thereof, and a narrow central portion between the widened ends that is narrower than the widened ends of the stent, the sleeve being coupled to the sleeve-supporting frame of the stent; and
a vessel-wall-supporting frame coupled to the narrow central portion of the sleeve-supporting frame and radially protruding from the sleeve-supporting frame.

Inventive concept 49. The apparatus according to inventive concept 48, further comprising a blood pump, the blood pump being configured to pump blood from between an outside of the sleeve and an inner wall of the blood vessel by being placed between the outside of the sleeve and the vessel-wall-supporting frame.

Inventive concept 50. The apparatus according to inventive concept 48, wherein a diameter of the narrow central portion of the sleeve is between 8 mm and 35 mm.

Inventive concept 51. The apparatus according to inventive concept 48, wherein a maximum diameter of the flared ends of the sleeve is between 10 mm and 45 mm.

Inventive concept 52. The apparatus according to inventive concept 48, wherein a ratio of a maximum diameter of the flared ends of the sleeve, and a diameter of the narrow central portion of the sleeve is between 1.1:1 and 2:1.

Inventive concept 53. The apparatus according to inventive concept 48, wherein a maximum diameter of the vessel-wall-supporting frame is between 10 mm and 50 mm.

Inventive concept 54. The apparatus according to any one of inventive concepts 48-53, wherein a ratio of a maximum diameter of the wall-supporting frame to a diameter of the narrow central portion of the sleeve-supporting frame is between 1.1:1 and 5:1.

Inventive concept 55. The apparatus according to inventive concept 54, wherein the ratio is greater than 1.5:1.

Inventive concept 56. The apparatus according to any one of inventive concepts 48-53, wherein a length of the sleeve is greater than 6 mm.

Inventive concept 57. The apparatus according to inventive concept 56, wherein the length of the sleeve is less than 80 mm.

Inventive concept 58. The apparatus according to inventive concept 56, wherein a length of each one of the flared ends of the sleeve is greater than 3 mm.

Inventive concept 59. The apparatus according to inventive concept 58, wherein the length of each one of the flared ends of the sleeve is less than 40 mm.

Inventive concept 60. The apparatus according to inventive concept 56, wherein a length of the narrow central portion of the sleeve is greater than 3 mm.

Inventive concept 61. The apparatus according to inventive concept 60, wherein the length of the narrow central portion of the sleeve is less than 70 mm.

Inventive concept 62. A method comprising:
　placing into a blood vessel of a subject:
　　a blood-impermeable sleeve defining flared ends thereof, and a narrow central portion between the flared ends, and
　　a stent shaped to define:
　　　a sleeve-supporting frame that is shaped to define widened ends thereof, and a narrow central portion between the widened ends that is narrower than the widened ends, the sleeve being coupled to the sleeve-supporting frame of the stent; and
　　　a vessel-wall-supporting frame coupled to the narrow central portion of the sleeve-supporting frame and radially protruding from the sleeve-supporting frame; and
　coupling the stent to the blood vessel such that the vessel-wall-supporting frame of the stent holds open the blood vessel by supporting the wall of the blood vessel, and the sleeve-supporting frame supports the sleeve within the blood vessel.

Inventive concept 63. The method according to inventive concept 62, further comprising pumping blood from a site between an outside of the sleeve and an inner wall of the blood vessel by placing a pump between the outside of the sleeve and the vessel-wall-supporting frame.

Inventive concept 64. The method according to inventive concept 62, wherein placing the sleeve into the blood vessel comprises placing the sleeve into the blood vessel, a diameter of the narrow central portion of the sleeve being between 8 mm and 35 mm.

Inventive concept 65. The method according to inventive concept 62, wherein placing the sleeve into the blood vessel comprises placing the sleeve into the blood vessel, a maximum diameter of the flared ends of the sleeve being between 10 mm and 45 mm.

Inventive concept 66. The method according to inventive concept 62, wherein placing the sleeve into the blood vessel comprises placing the sleeve into the blood vessel, a ratio of a maximum diameter of the flared ends of the sleeve, and a diameter of the narrow central portion of the sleeve being between 1.1:1 and 2:1.

Inventive concept 67. The method according to inventive concept 62, wherein placing the stent into the blood vessel comprises placing the stent into the blood vessel, a maximum diameter of the vessel-wall-supporting frame being between 10 mm and 50 mm.

Inventive concept 68. The method according to any one of inventive concepts 62-67, wherein placing the stent into the blood vessel comprises placing the stent into the blood vessel, a ratio of a maximum diameter of the wall-supporting frame to a diameter of the narrow central portion of the sleeve-supporting frame being between 1.1:1 and 5:1.

Inventive concept 69. The method according to inventive concept 68, wherein placing the stent into the blood vessel comprises placing the stent into the blood vessel, the ratio being greater than 1.5:1.

Inventive concept 70. The method according to any one of inventive concepts 62-67, wherein placing the sleeve into the blood vessel comprises placing the sleeve into the blood vessel, a length of the sleeve being greater than 6 mm.

Inventive concept 71. The method according to inventive concept 70, wherein placing the sleeve into the blood vessel comprises placing the sleeve into the blood vessel, the length of the sleeve being less than 80 mm.

Inventive concept 72. The method according to inventive concept 70, wherein placing the sleeve into the blood vessel comprises placing the sleeve into the blood vessel, a length of each one of the flared ends of the sleeve being greater than 3 mm.

Inventive concept 73. The method according to inventive concept 72, wherein placing the sleeve into the blood vessel comprises placing the sleeve into the blood vessel, the length of each one of the flared ends of the sleeve being less than 40 mm.

Inventive concept 74. The method according to inventive concept 70, wherein placing the sleeve into the blood vessel comprises placing the sleeve into the blood vessel, a length of the narrow central portion of the sleeve being greater than 3 mm.

Inventive concept 75. The method according to inventive concept 74, wherein placing the sleeve into the blood vessel comprises placing the sleeve into the blood vessel, the length of the narrow central portion of the sleeve being less than 70 mm.

Inventive concept 76. A method for operating a blood pump disposed inside a blood vessel of a subject, the method comprising:
　placing an occlusion element in the blood vessel, the occlusion element having an occluding state thereof, in which the occlusion element occludes the blood vessel, and a non-occluding state thereof in which the occlusion element does not occlude the blood vessel;
　drawing blood in a downstream direction from a site that is in fluid communication with an upstream side of the occlusion element;
　pumping blood into a site of the subject's vasculature that is in fluid communication with a downstream side of the occlusion element,
　the pumping of the blood into the subject's vasculature being performed in a manner that maintains the occlusion element in an occluding state thereof, in which state the occlusion element occludes the blood vessel.

Inventive concept 77. The method according to inventive concept 76, further comprising performing ultrafiltration on the blood prior to pumping the blood into the site of the subject's vasculature.

Inventive concept 78. The method according to inventive concept 76, wherein placing the occlusion element in the blood vessel comprises placing the occlusion element in the blood vessel for less than one week, and wherein pumping the blood comprises pumping the blood into the vasculature for less than one week.

Inventive concept 79. The method according to inventive concept 76, wherein placing the occlusion element in the blood vessel comprises placing the occlusion element in the blood vessel for more than one week, and wherein pumping the blood comprises pumping the blood into the vasculature for less than one week.

Inventive concept 80. The method according to inventive concept 76, further comprising identifying the subject as a subject suffering from a condition selected from the group consisting of: cardiac dysfunction, congestive heart failure, reduced renal blood flow, increased renal vascular resistance, arterial hypertension, and kidney dysfunction, wherein the blood vessel includes a renal vein of the subject, and wherein drawing blood in the downstream direction from the site that is in fluid communication with the upstream side of the occlusion element comprises, in response to identifying the subject as suffering from the condition, reducing blood pressure within the subject's renal vein by drawing the blood in the downstream direction.

Inventive concept 81. The method according to any one of inventive concepts 76-80, wherein pumping the blood into the subject's vasculature in the manner that maintains the occlusion element in the occluding state thereof comprises pumping the blood into the subject's vasculature such that hydrodynamic pressure of the blood that is pumped into the subject's vasculature maintains the occlusion element in the occluding state thereof.

Inventive concept 82. The method according to inventive concept 81, wherein placing the occlusion element in the blood vessel comprises placing within the blood vessel a valve having valve leaflets, and wherein pumping the blood into the subject's vasculature such that hydrodynamic pressure of the blood that is pumped into the subject's vasculature maintains the occlusion element in the occluding state thereof comprises pumping the blood into the subject's vasculature such that the blood that is pumped into the subject's vasculature directly impacts downstream sides of the valve leaflets.

Inventive concept 83. The method according to inventive concept 82, wherein placing the valve within the blood vessel comprises placing the valve within the blood vessel such that:
  in response to blood pressure on an upstream side of the valve leaflets exceeding pressure on the downstream side of the valve leaflets, blood flows in an antegrade direction between cusps of the valve leaflets and an inner wall of the blood vessel, and
  in response to blood pressure on the downstream side of the valve leaflets exceeding pressure on the upstream side of the valve leaflets, the valve occludes retrograde blood flow by the cusps of the valve leaflets contacting the inner wall of the blood vessel.

Inventive concept 84. The method according to inventive concept 82, wherein pumping the blood into the subject's vasculature such that the blood that is pumped into the subject's vasculature directly impacts downstream sides of the valve leaflets comprises reducing blood clots at the valve leaflets, by flushing the valve leaflets.

Inventive concept 85. The method according to inventive concept 82, further comprising pumping an anticoagulation agent into the subject's vasculature together with the blood that is pumped into the subject's vasculature, such that the anticoagulation agent directly impacts the valve leaflets.

Inventive concept 86. The method according to inventive concept 82, wherein placing the valve in the blood vessel comprises maintaining portions of the valve leaflets in contact with a wall of the blood vessel by inflating a balloon.

Inventive concept 87. The method according to inventive concept 82, wherein placing the valve in the blood vessel comprises maintaining portions of the valve leaflets in contact with a wall of the blood vessel by expanding portions of a slit tube radially outwardly.

Inventive concept 88. The method according to inventive concept 82, wherein pumping the blood such that the blood directly impacts the downstream sides of the valve leaflets comprises pumping the blood into the subject's vasculature via holes that are shaped to direct the blood toward the downstream sides of the valve leaflets.

Inventive concept 89. The method according to inventive concept 82, wherein pumping the blood such that the blood directly impacts the downstream sides of the valve leaflets comprises pumping the blood into the subject's vasculature via a pump catheter that is shaped to define a radial protrusion therefrom that is concavely curved toward a distal end of the catheter, the radial protrusion being configured to direct blood that is pumped into the vasculature toward the valve leaflets.

Inventive concept 90. The method according to inventive concept 82, wherein pumping the blood such that the blood directly impacts the downstream sides of the valve leaflets comprises pumping the blood into the subject's vasculature via holes that are disposed adjacent to bases of the valve leaflets.

Inventive concept 91. The method according to inventive concept 90, wherein pumping the blood such that the blood directly impacts the downstream sides of the valve leaflets comprises pumping the blood into the subject's vasculature via holes that are disposed adjacent to a location along lengths of the valve leaflets that is below midway between cusps of the leaflets and bases of the leaflets.

Inventive concept 92. Apparatus for use with a blood vessel of a subject, the apparatus comprising:
  an occlusion element configured to be placed in the blood vessel, the occlusion element having an occluding state thereof, in which the occlusion element occludes the blood vessel, and a non-occluding state thereof in which the occlusion element does not occlude the blood vessel;
  a blood pump configured to:
    draw blood in a downstream direction from a site that is in fluid communication with an upstream side of the occlusion element, and
    pump blood into the subject's vasculature at a site that is in fluid communication with a downstream side of the occlusion element, the pump being configured to perform the pumping of the blood into the blood vessel in a manner that maintains the occlusion element in the occluding state thereof.

Inventive concept 93. The apparatus according to inventive concept 92, wherein the blood pump is configured to perform ultrafiltration of the blood prior to pumping the blood into the subject's vasculature.

Inventive concept 94. The apparatus according to inventive concept 92, wherein the occlusion element is configured to be placed in the blood vessel for less than one week, and the pump is configured to pump blood into the vasculature for less than one week.

Inventive concept 95. The apparatus according to inventive concept 92, wherein the occlusion element is configured to be placed in the blood vessel for more than one week, and the pump is configured to pump blood into the vasculature for less than one week.

Inventive concept 96. The apparatus according to any one of inventive concepts 92-95, wherein the pump is configured to perform the pumping of the blood into the subject's vasculature in the manner that maintains the occlusion element in the occluding state thereof, by pumping the blood into the subject's vasculature such that hydrodynamic pressure of the blood that is pumped into the subject's vasculature maintains the occlusion element in the occluding state thereof.

Inventive concept 97. The apparatus according to inventive concept 96, wherein the occlusion element comprises a valve having valve leaflets, and wherein the pump is configured to pump the blood into the subject's vasculature such that the hydrodynamic pressure of the blood maintains the occlusion element in the occluding state thereof by pumping the blood into the subject's vasculature such that the blood that is pumped into the subject's vasculature directly impacts downstream sides of the valve leaflets.

Inventive concept 98. The apparatus according to inventive concept 97, wherein the valve is configured such that:
  in response to blood pressure on an upstream side of the valve leaflets exceeding pressure on the downstream side of the valve leaflets, blood flows in an antegrade direction between cusps of the valve leaflets and an inner wall of the blood vessel, and
  in response to blood pressure on the downstream side of the valve leaflets exceeding pressure on the upstream side of the valve leaflets, the valve closes by the cusps of the valve leaflets contacting the inner wall of the blood vessel.

Inventive concept 99. The apparatus according to inventive concept 97, wherein the pump, by pumping the blood into the subject's vasculature such that the blood that is pumped into the subject's vasculature directly impacts downstream sides of the valve leaflets, is configured to reduce blood clots at the valve leaflets by flushing the valve leaflets.

Inventive concept 100. The apparatus according to inventive concept 97, wherein the apparatus is for use with an anticoagulation agent, and wherein the pump is configured to pump the anticoagulation agent into the subject's vasculature together with the blood that is pumped into the subject's vasculature, such that the anticoagulation agent directly impacts the valve leaflets.

Inventive concept 101. The apparatus according to inventive concept 97, further comprising a balloon configured to maintain portions of the valve leaflets in contact with a wall of the blood vessel by being inflated.

Inventive concept 102. The apparatus according to inventive concept 97, further comprising a slit tube configured to be inserted into the blood vessel and to maintain portions of the valve leaflets in contact with a wall of the blood vessel by portions of the slit tube between the slits being expanded radially outwardly.

Inventive concept 103. The apparatus according to inventive concept 97, wherein the blood pump is configured to be coupled to the valve, wherein the blood pump comprises outlet holes via which the blood is pumped into the subject's vasculature, and wherein the outlet holes are shaped such that when the blood pump is coupled to the valve, the outlet holes direct the blood toward the downstream sides of the valve leaflets.

Inventive concept 104. The apparatus according to inventive concept 97, wherein the blood pump is configured to be coupled to the valve, wherein the blood pump comprises a blood pump catheter that defines a radial protrusion therefrom that is concavely curved toward a distal end of the catheter, the radial protrusion being configured such that, when the blood pump is coupled to the valve, the radial protrusion directs blood that is pumped into the vasculature toward the valve leaflets.

Inventive concept 105. The apparatus according to inventive concept 97, wherein the blood pump is configured to be coupled to the valve, wherein the blood pump comprises outlet holes via which the blood is pumped into the subject's vasculature, and wherein the outlet holes are disposed on the blood pump such that, when the blood pump is coupled to the valve, the holes are disposed adjacent to bases of the valve leaflets.

Inventive concept 106. The apparatus according to inventive concept 105, wherein the outlet holes are disposed on the blood pump such that, when the blood pump is coupled to the valve, the outlet holes are disposed adjacent to a location along lengths of the valve leaflets that is below midway between cusps of the leaflets and bases of the leaflets.

Inventive concept 107. Apparatus for use with a blood vessel of a subject, the apparatus comprising:
  a blood pump configured to draw blood in a downstream direction through the blood vessel into the pump; and
  a valve comprising rigid portions thereof, the rigid portions being configured to couple the valve to the blood vessel, the valve being configured to be coupled to a distal portion of the blood pump and to prevent blood from flowing past the valve in a retrograde direction.

Inventive concept 108. The apparatus according to inventive concept 107, wherein the valve further comprises flexible valve leaflets that are coupled to the rigid portions of the valve.

Inventive concept 109. A method comprising:
  providing a prosthetic valve that defines valve leaflets; and
  placing the valve in a blood vessel such that:
    in response to blood pressure on the upstream side of the valve leaflets exceeding pressure on the downstream side of the valve leaflets, blood flows in an antegrade direction between cusps of the valve leaflets and an inner wall of the blood vessel, and
    in response to blood pressure on the downstream side of the valve leaflets exceeding pressure on the upstream side of the valve leaflets, the valve closes by the cusps of the valve leaflets contacting the inner wall of the blood vessel.

Inventive concept 110. Apparatus comprising:
  a prosthetic valve that comprises flexible valve leaflets and a rigid valve frame, the valve leaflets being coupled to the valve frame such that:
    in response to pressure on a first side of the valve leaflets exceeding pressure on a second side of the valve leaflets, the leaflets open by cusps of the valve leaflets separating from the rigid frame, and
    in response to blood pressure on the second side of the valve leaflets exceeding pressure on the first side of the valve leaflets, the valve closes by the cusps of the leaflets contacting the rigid frame.

Inventive concept 111. Apparatus comprising:
  a blood pump, comprising:
    a tube;
    first and second unidirectional valves disposed, respectively, at proximal and distal ends of the tube;
    a membrane coupled to the inside of the tube such as to partition the tube into a first compartment that is in fluid communication with the valves, and a second compartment that is not in fluid communication with the valves; and a pumping mechanism configured to pump fluid through the tube by increasing and subsequently decreasing the size of the first compartment by moving the membrane with respect to the tube.

Inventive concept 112. The apparatus according to inventive concept 111, wherein the tube comprises a stent, and material disposed on the stent.

Inventive concept 113. The apparatus according to inventive concept 111, wherein the occlusion element is configured to be placed in a blood vessel for less than one week.

Inventive concept 114. The apparatus according to inventive concept 111, wherein one of the valves is configured to prevent backflow of blood from the tube into the blood vessel and a second one of the valves is configured to prevent backflow of blood from the blood vessel into the tube.

Inventive concept 115. The apparatus according to any one of inventive concepts 111-114, wherein the blood pump is configured to be placed in a renal vein of a subject and to pump blood in a downstream direction from the renal vein to a vena cava of the subject.

Inventive concept 116. The apparatus according to inventive concept 115, wherein the blood pump is configured to occlude backflow of blood from the vena cava to the renal vein.

Inventive concept 117. A method, comprising:

coupling a tube to an inner wall of a blood vessel of a subject, first and second unidirectional valves being disposed, respectively, at proximal and distal ends of the tube, and a membrane being coupled to the inside of the tube, such as to partition the tube into a first compartment that is in fluid communication with the valves, and a second compartment that is not in fluid communication with the valves; and operating a pumping mechanism to pump blood through the tube by increasing and subsequently decreasing the size of the first compartment, by moving the membrane with respect to the tube.

Inventive concept 118. The method according to inventive concept 117, wherein the tube includes a stent and material disposed on the stent, and wherein coupling the tube to the inner wall of the blood vessel comprises coupling the stent and the material to the inner wall of the blood vessel.

Inventive concept 119. The method according to inventive concept 117, wherein coupling the tube to the inner wall of the blood vessel comprises coupling the tube to the inner wall of the blood vessel for less than one week.

Inventive concept 120. The method according to inventive concept 117, wherein operating the pumping mechanism comprises operating the pumping mechanism such that one of the valves prevents backflow of blood from the tube into the blood vessel and a second one of the valves prevents backflow of blood from the blood vessel into the tube.

Inventive concept 121. The method according to any one of inventive concepts 117-120, wherein coupling the tube to the inner wall of the blood vessel comprises coupling the tube to an inner wall of a renal vein of a subject, and wherein operating the pumping mechanism comprises pumping blood in a downstream direction from the renal vein to a vena cava of the subject.

Inventive concept 122. The method according to inventive concept 121, wherein coupling the tube to the inner wall of the renal vein comprises occluding backflow of blood from the vena cava to the renal vein.

Inventive concept 123. The method according to inventive concept 121, further comprising identifying the subject as a subject suffering from a condition selected from the group consisting of: cardiac dysfunction, congestive heart failure, reduced renal blood flow, increased renal vascular resistance, arterial hypertension, and kidney dysfunction, wherein operating the pump comprises, in response to identifying the subject as suffering from the condition, reducing blood pressure within the subject's renal vein by operating the pump to pump blood in the downstream direction from the renal vein to the vena cava.

Inventive concept 124. A method comprising:

operating a blood pump to pump blood in a downstream direction through a first vein, the first vein being a tributary of a second vein and forming a junction with the second vein; and preventing backflow of blood from the second vein to the first vein by covering an ostium at the junction with an ostium-covering umbrella disposed in the second vein.

Inventive concept 125. The method according to inventive concept 124, wherein operating the blood pump comprises performing ultrafiltration on the pumped blood.

Inventive concept 126. The method according to inventive concept 124, wherein the ostium-covering umbrella includes an ostium-covering umbrella having a diameter of more than 6 mm when in an open configuration, and wherein covering the ostium with the umbrella comprises covering the ostium with the umbrella having a diameter of more than 6 mm.

Inventive concept 127. The method according to inventive concept 124, wherein operating the blood pump comprises causing the ostium-covering umbrella to become sealed against a wall of the second vein surrounding the ostium.

Inventive concept 128. The method according to any one of inventive concepts 124-127, wherein the first vein includes a renal vein of the subject, and the second vein includes a vena cava of the subject, and wherein pumping blood in the downstream direction comprises pumping blood in a downstream direction from the renal vein toward the vena cava.

Inventive concept 129. The method according to inventive concept 128, wherein preventing backflow of blood from the second vein to the first vein comprises preventing backflow of blood from the vena cava to the renal vein.

Inventive concept 130. The method according to inventive concept 128, further comprising identifying the subject as a subject suffering from a condition selected from the group consisting of: cardiac dysfunction, congestive heart failure, reduced renal blood flow, increased renal vascular resistance, arterial hypertension, and kidney dysfunction, wherein operating the pump comprises, in response to identifying the subject as suffering from the condition, reducing blood pressure within the subject's renal vein by operating the pump to pump blood in the downstream direction from the renal vein to the vena cava.

Inventive concept 131. Apparatus for use with a first vein of a subject, the first vein being a tributary of a second vein and forming a junction with the second vein, the apparatus comprising:

a catheter configured to be placed in the first vein, a distal end of the catheter being configured to pump blood in a downstream direction through the first vein and into the catheter; and an ostium-covering umbrella disposed around the outside of the catheter and configured to be placed within the second vein at the junction such that the umbrella prevents backflow of blood from the second vein to the first vein by the ostium-occluding umbrella covering an ostium at the junction from a location within the second vein.

Inventive concept 132. The apparatus according to inventive concept 131, wherein the catheter, by pumping the blood is configured to cause the ostium-covering umbrella to become sealed against a wall of the second vein surrounding the ostium.

Inventive concept 133. The apparatus according to inventive concept 131, wherein the ostium-covering umbrella has a diameter of more than 6 mm, when in an open configuration.

Inventive concept 134. The apparatus according to any one of inventive concepts 131-133, wherein the first vein includes a renal vein of the subject, and the second vein includes a vena cava of the subject, and wherein the catheter is configured to pump blood by pumping blood in a downstream direction from the renal vein.

Inventive concept 135. The apparatus according to inventive concept 134, wherein the ostium-covering umbrella is configured to prevent backflow of blood from the vena cava to the renal vein by the ostium-occluding umbrella covering an ostium at a junction of the renal vein and the vena cava, from a location within the vena cava.

Inventive concept 136. Apparatus comprising:
a catheter;
a pumping mechanism configured to suction fluid into a distal end of the catheter; and
an ostium-covering umbrella disposed around the outside of the catheter, the umbrella having a diameter of at least 6 mm when in an open configuration thereof.

Inventive concept 137. The apparatus according to inventive concept 136, wherein the diameter of the ostium-covering umbrella is between 10 mm and 20 mm.

Inventive concept 138. The apparatus according to inventive concept 136, wherein the diameter of the ostium-covering umbrella is between 15 mm and 25 mm.

Inventive concept 139. A method for measuring flow in a blood vessel comprising:
occluding the blood vessel with an occlusion element;
pumping blood from an upstream side of the occlusion element to a downstream side of the occlusion element;
measuring blood pressure on the upstream and downstream sides of the occlusion element;
modulating the pumping such that pressure on the downstream side of the occlusion element is equal to pressure on the upstream side of the occlusion element;
measuring a flow rate of blood through the pump when the pressure on the downstream side of the occlusion element is equal to pressure on the upstream side of the occlusion element;
designating the measured flow rate as a baseline flow rate; and
subsequently, measuring a flow rate of blood through the pump relative to the baseline flow rate.

Inventive concept 140. The method according to inventive concept 139, further comprising, in response to designating the baseline flow rate, designating a baseline measure of vascular resistance of the subject, and subsequently, measuring vascular resistance of the subject relative to the baseline vascular resistance.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for improving renal function of a patient, comprising:
using an occluding element that is placed in an inferior vena cava of the patient at a location that is downstream of a renal vein ostium, at least partially mechanically occluding the inferior vena cava of the patient downstream of the renal vein ostium, such as to form a compartment within the inferior vena cava that is isolated from a downstream region of the inferior vena cava that is downstream of the renal vein ostium; and
using a blood pump that is separate from the occluding element, and that is placed in the compartment, mechanically pumping blood through the inferior vena cava from the compartment to a discharge location in the downstream region while the inferior vena cava is at least partially occluded, wherein the blood remains in the inferior vena cava throughout the mechanical pumping of the blood from the compartment to the discharge location.

2. The method of claim 1, wherein mechanically pumping blood comprises placing a catheter-based pump within the compartment.

3. The method of claim 2, wherein placing the catheter-based pump within the compartment comprises placing an impeller pump within the compartment.

4. A method for improving renal function of a patient, comprising:
using an occluding element that is placed in an inferior vena cava of the patient at a location that is downstream of a renal vein ostium, at least partially mechanically occluding the inferior vena cava of the patient downstream of the renal vein ostium, such as to form a compartment within the inferior vena cava that is isolated from a downstream region of the inferior vena cava that is downstream of the renal vein ostium; and
using a blood pump that is separate from the occluding element, and that is placed in the compartment, mechanically pumping blood through the inferior vena cava from the compartment to a discharge location in the downstream region while the inferior vena cava is at least partially occluded, wherein the blood does not leave the inferior vena cava while being mechanically pumped.

5. The method of claim 4, wherein mechanically pumping blood comprises placing a catheter-based pump within the compartment.

6. The method of claim 5, wherein placing the catheter-based pump within the compartment comprises placing an impeller pump within the compartment.

7. A method for improving renal function of a patient, comprising:
using an occluding element that is placed in an inferior vena cava of the patient at a location that is downstream of a renal vein ostium, at least partially mechanically occluding the inferior vena cava of a vasculature of the patient downstream of the renal vein ostium, such as to form a compartment within the inferior vena cava that is isolated from a downstream region of the inferior vena cava that is downstream of the renal vein ostium; and
using a blood pump that is separate from the occluding element, and that is placed in the compartment, mechanically pumping blood through the inferior vena cava from the compartment to a discharge location in the downstream region while the inferior vena cava is at least partially occluded, wherein the blood does not leave the vasculature of the patient while being mechanically pumped.

8. The method of claim 7, wherein mechanically pumping blood comprises placing a catheter-based pump within the compartment.

9. The method of claim 8, wherein placing the catheter-based pump within the compartment comprises placing an impeller pump within the compartment.

* * * * *